(12) United States Patent
Fan et al.

(10) Patent No.: US 12,157,912 B2
(45) Date of Patent: *Dec. 3, 2024

(54) DETERMINISTIC BARCODING FOR SPATIAL OMICS SEQUENCING

(71) Applicant: Yale University, New Haven, CT (US)

(72) Inventors: Rong Fan, Cheshire, CT (US); Yang Liu, New Haven, CT (US); Yanxiang Deng, New Haven, CT (US)

(73) Assignee: Yale University, New Haven, CT (US)

( * ) Notice: Subject to any disclaimer, the term of this patent is extended or adjusted under 35 U.S.C. 154(b) by 462 days.

This patent is subject to a terminal disclaimer.

(21) Appl. No.: 17/036,401

(22) Filed: Sep. 29, 2020

(65) Prior Publication Data

US 2021/0095331 A1 Apr. 1, 2021

Related U.S. Application Data

(60) Provisional application No. 62/908,270, filed on Sep. 30, 2019.

(51) Int. Cl.
| | | |
|---|---|---|
| *C12Q 1/6809* | (2018.01) | |
| *C12Q 1/686* | (2018.01) | |
| *C12Q 1/6869* | (2018.01) | |
| *G01N 33/569* | (2006.01) | |
| *G01N 35/10* | (2006.01) | |
| *G01N 35/00* | (2006.01) | |

(52) U.S. Cl.
CPC .......... *C12Q 1/6809* (2013.01); *C12Q 1/686* (2013.01); *C12Q 1/6869* (2013.01); *G01N 33/56966* (2013.01); *G01N 35/1072* (2013.01); *G01N 2035/00752* (2013.01); *G01N 2458/10* (2013.01)

(58) Field of Classification Search
None
See application file for complete search history.

(56) References Cited

U.S. PATENT DOCUMENTS

| | | |
|---|---|---|
| 9,188,586 B2 | 11/2015 | Fan et al. |
| 9,506,917 B2 | 11/2016 | Fan et al. |
| 10,274,486 B2 | 4/2019 | Fan et al. |
| 2009/0036324 A1 | 2/2009 | Fan |
| 2015/0204862 A1 | 7/2015 | Fan et al. |
| 2015/0204864 A1 | 7/2015 | Fan et al. |
| 2017/0067887 A1 | 3/2017 | Fan et al. |
| 2017/0138942 A1 | 5/2017 | Fan et al. |

FOREIGN PATENT DOCUMENTS

| | | |
|---|---|---|
| WO | WO 2018/064640 A1 | 4/2018 |
| WO | WO 2018/170412 A1 | 9/2018 |

OTHER PUBLICATIONS

Delley et al., Combined aptamer and transcriptome sequencing of single cells. Sci Rep. Feb. 13, 2018;8(1):2919.
Maino et al., A microfluidic platform towards automated multiplexed in situ sequencing. Sci Rep. Mar. 5, 2019;9(1):3542.

(Continued)

*Primary Examiner* — Samuel C Woolwine
(74) *Attorney, Agent, or Firm* — Wolf, Greenfield & Sacks, P.C.

(57) ABSTRACT

Provided herein, in some embodiments, are compositions and methods for producing a molecular expression map of a biological sample using Deterministic Barcoding in Tissue for spatial omics sequencing (DBiT-seq).

23 Claims, 65 Drawing Sheets

Specification includes a Sequence Listing.

(56) References Cited

OTHER PUBLICATIONS

Agasti et al., Photocleavable DNA barcode-antibody conjugates allow sensitive and multiplexed protein analysis in single cells. J Am Chem Soc. Nov. 14, 2012;134(45):18499-502. doi: 10.1021/ja307689w. Epub Nov. 2, 2012.

Asp et al., Spatially Resolved Transcriptomes—Next Generation Tools for Tissue Exploration. Bioessays. Oct. 2020;42(10):e1900221. doi: 10.1002/bies.201900221. Epub May 4, 2020.

Burgess, Spatial transcriptomics coming of age. Nat Rev Genet. Jun. 2019;20(6):317.

Butler et al., Integrating single-cell transcriptomic data across different conditions, technologies, and species. Nat. Biotechnol. 36, 411-420 (2018).

Cao et al., The single-cell transcriptional landscape of mammalian organogenesis. Nature. Feb. 2019;566(7745):496-502. doi: 10.1038/s41586-019-0969-x. Epub Feb. 20, 2019.

Dura et al., scFTD-seq: freeze-thaw lysis based, portable approach toward highly distributed single-cell 3' mRNA profiling. Nucleic Acids Res. Feb. 20, 2019;47(3):e16.

Eng et al., Transcriptome-scale super-resolved imaging in tissues by RNA seqFISH. Nature. Apr. 2019;568(7751):235-239. doi: 10.1038/s41586-019-1049-y. Epub Mar. 25, 2019.

Fan et al., Integrated barcode chips for rapid, multiplexed analysis of proteins in microliter quantities of blood. Nat Biotechnol. Dec. 2008;26(12):1373-8. doi: 10.1038/nbt.1507. Epub Nov. 16, 2008.

Klein et al., Droplet barcoding for single-cell transcriptomics applied to embryonic stem cells. Cell. May 21, 2015;161(5):1187-1201.

Liu et al., High-Spatial-Resolution Multi-Omics Sequencing via Deterministic Barcoding in Tissue. Cell. Dec. 10, 2020;183(6):1665-1681.e18. doi: 10.1016/j.cell.2020.10.026. Epub Nov. 13, 2020.

Lu et al., Highly multiplexed profiling of single-cell effector functions reveals deep functional heterogeneity in response to pathogenic ligands. Proc Natl Acad Sci U S A. Feb. 17, 2015;112(7):E607-15. doi: 10.1073/pnas.1416756112. Epub Feb. 2, 2015.

Navarro et al., ST Pipeline: an automated pipeline for spatial mapping of unique transcripts. Bioinformatics. Aug. 15, 2017;33(16):2591-2593.

Salmen et al., Barcoded solid-phase RNA capture for Spatial Transcriptomics profiling in mammalian tissue sections. Nat Protoc. Nov. 2018;13(11):2501-2534.

Shin et al., Chemistries for patterning robust DNA microbarcodes enable multiplex assays of cytoplasm proteins from single cancer cells. Chemphyschem. Oct. 4, 2010;11(14):3063-9.

Sinicropi et al., Whole transcriptome RNA-Seq analysis of breast cancer recurrence risk using formalin-fixed paraffin-embedded tumor tissue. PLOS One. 2012;7(7):e40092. doi: 10.1371/journal.pone.0040092. Epub Jul. 13, 2012.

Stahl et al., Visualization and analysis of gene expression in tissue sections by spatial transcriptomics. Science. Jul. 1, 2016;353(6294):78-82.

Stoeckius et al., Simultaneous epitope and transcriptome measurement in single cells. Nat Methods. Sep. 2017;14(9):865-868. doi: 10.1038/nmeth.4380. Epub Jul. 31, 2017.

Tang et al., Development and applications of single-cell transcriptome analysis. Nat Methods. Apr. 2011;8(4 Suppl):S6-11.

Vickovic et al., High-definition spatial transcriptomics for in situ tissue profiling. Nat Methods. Oct. 2019; 16(10):987-990. doi: 10.1038/s41592-019-0548-y. Epub Sep. 9, 2019.

Vogel et al., Insights into the regulation of protein abundance from proteomic and transcriptomic analyses. Nat Rev Genet. Mar. 13, 2012;13(4):227-32.

Wang et al., Three-dimensional intact-tissue sequencing of single-cell transcriptional states. Science. Jul. 27, 2018;361(6400):eaat5691. doi: 10.1126/science.aat5691. Epub Jun. 21, 2018.

Wang et al., Multiplexed PCR-Free Detection of MicroRNAs in Single Cancer Cells Using a DNA-Barcoded Microtrough Array Chip. Micromachines (Basel). Mar. 27, 2019;10(4):215.

Zheng et al., Massively parallel digital transcriptional profiling of single cells. Nat Commun. Jan. 16, 2017;8:14049. doi: 10.1038/ncomms14049.

Extended European Search Report mailed Sep. 28, 2023, for Application No. EP 20873248.7.

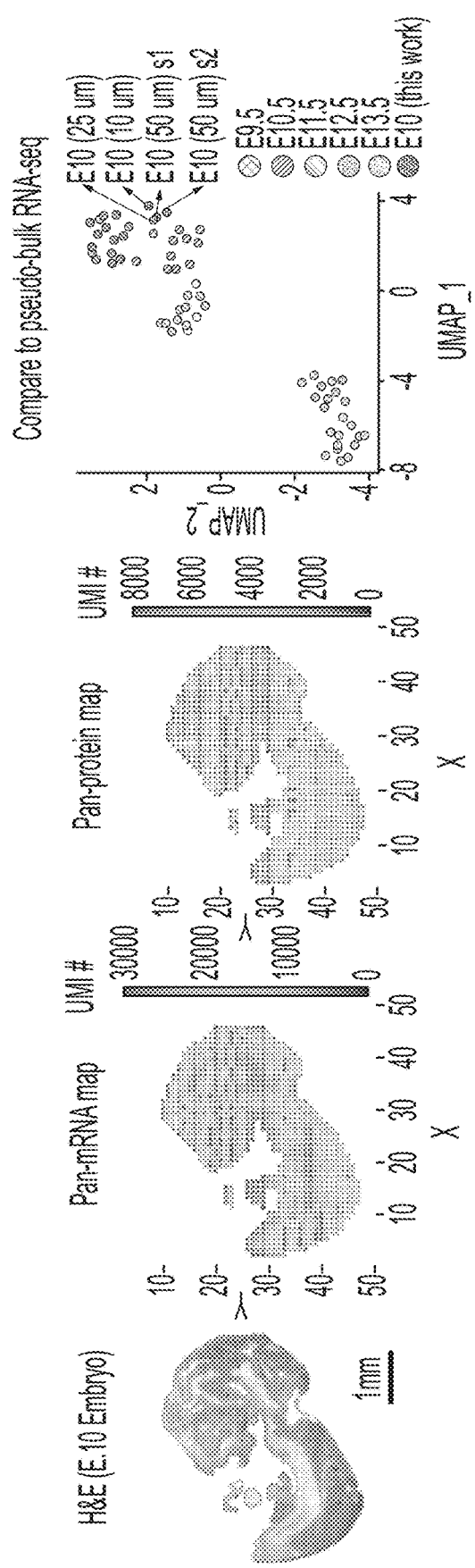
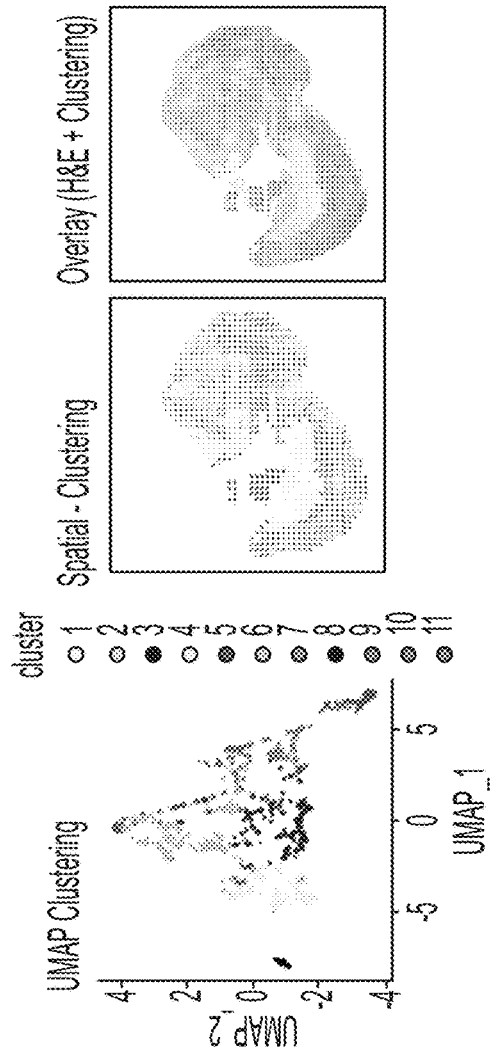
FIG. 8A
FIG. 8B
FIG. 8C

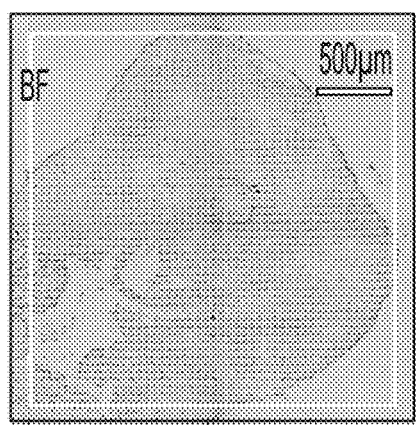
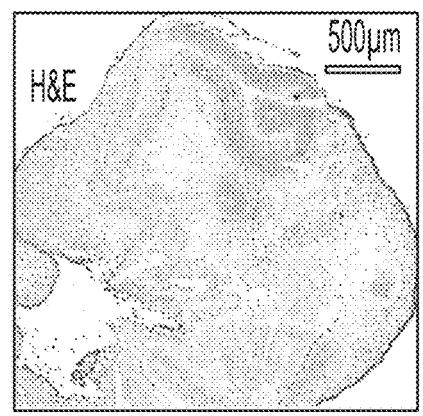
FIG. 9A  FIG. 9B
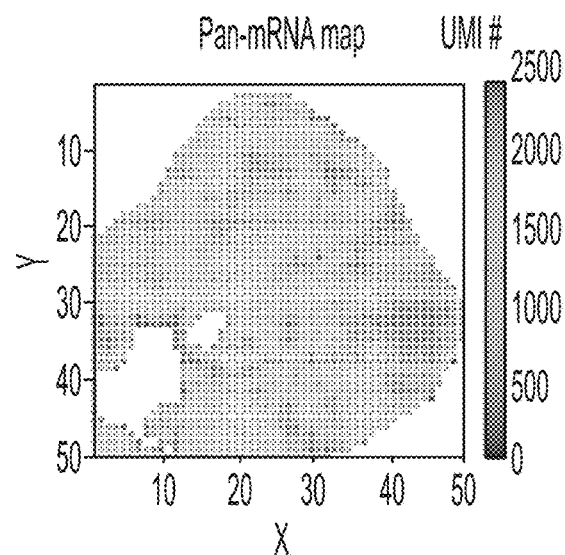
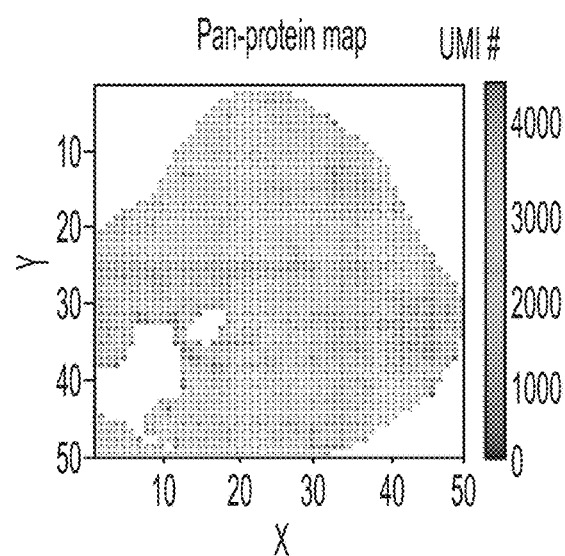
FIG. 9C

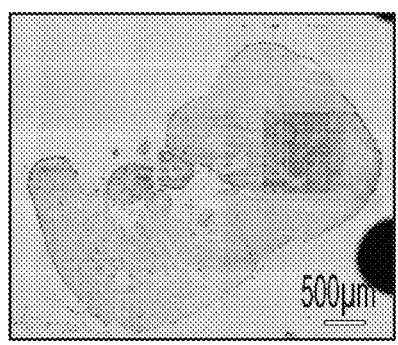
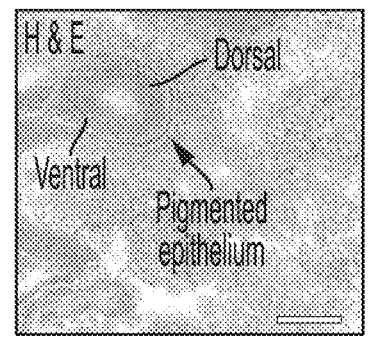
FIG. 10A
FIG. 10B
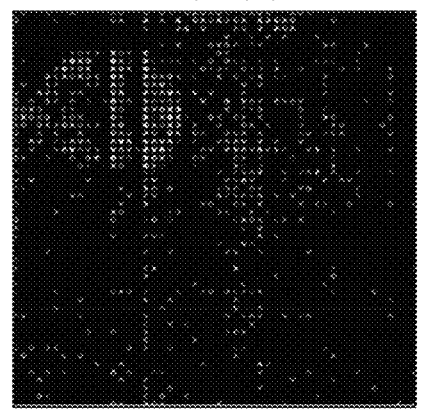
*Pmel / Pax6*
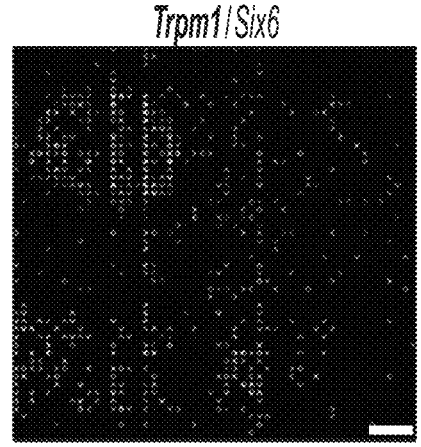
*Trpm1 / Six6*
Normalized UMI counts
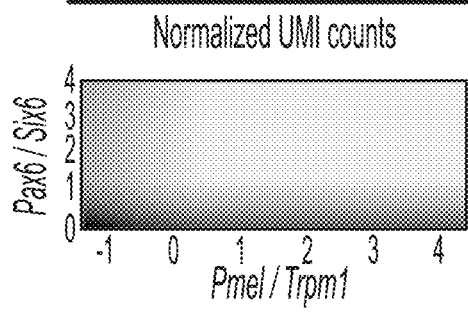
FIG. 10C

- Lymphatic endothelial trajectory
- Pericardium trajectory
- Granule neuron trajectory
- Olfactory ensheathing cell trajectory
- Schwann cell and Enteric glia trajectory 1
- Liver endothelial trajectory
- Lung epithelial trajectory
- Placenta endodermal trajectory
- White blood cell trajectory
- Schwann cell and Enteric glia trajectory 2
- Connective tissue trajectory
- Retina epithelial trajectory
- Olfactory sensory neuron trajectory
- Megakaryocyte trajectory
- Shisa6 positive neuron trajectory
- Inhibitory neuron trajectory
- Primordial germ cell trajectory
- Definitive erythroid trajectory
- Midgut/Hindgut epithelial trajectory
- Chondrocyte trajectory
- Epidermis trajectory
- Stomach epithelial trajectory
- Skeletal muscle trajectory
- PNS glia precursor cell trajectory
- Intermediate mesoderm trajectory
- Olfactory epithelial trajectory
- Branchial arch epithelial trajectory

- Retinal fibroblast trajectory
- Enteric neuron trajectory 2
- Len epithelial trajectory
- Hepatocyte trajectory
- Cholinergic neuron trajectory
- Melanocyte trajectory
- Enteric neuron trajectory 1
- Retina trajectory
- Brain endothelial trajectory
- Apical ectodermal ridge trajectory
- Ganglion neuron trajectory
- Renal epithelial trajectory
- Excitatory neuron trajectory
- Urothelium trajectory
- Auditory epithelial trajectory
- Ependymal cell trajectory
- Arterial endothelial trajectory
- Endocardium trajectory
- Neural epithelial trajectory
- Venous and capillary endothelial trajectory
- primitive erythroid trajectory
- Oligodendrocyte trajectory
- Cardiac muscle trajectory
- Osteoblast trajectory
- Neuron progenitor trajectory
- Limb mesenchyme trajectory
- E10 eye/brain DBit-seq (10μm)

FIG. 10K Continued

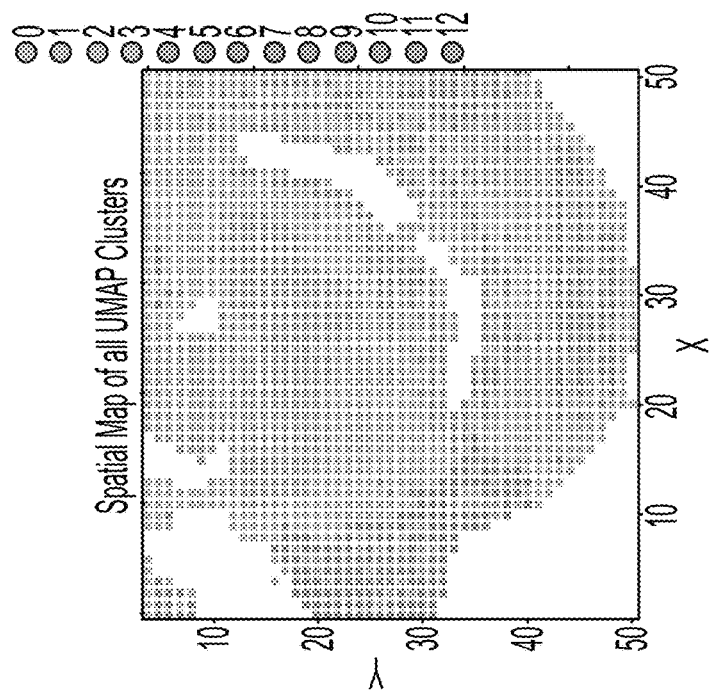
FIG. 12A
FIG. 12C
FIG. 12D
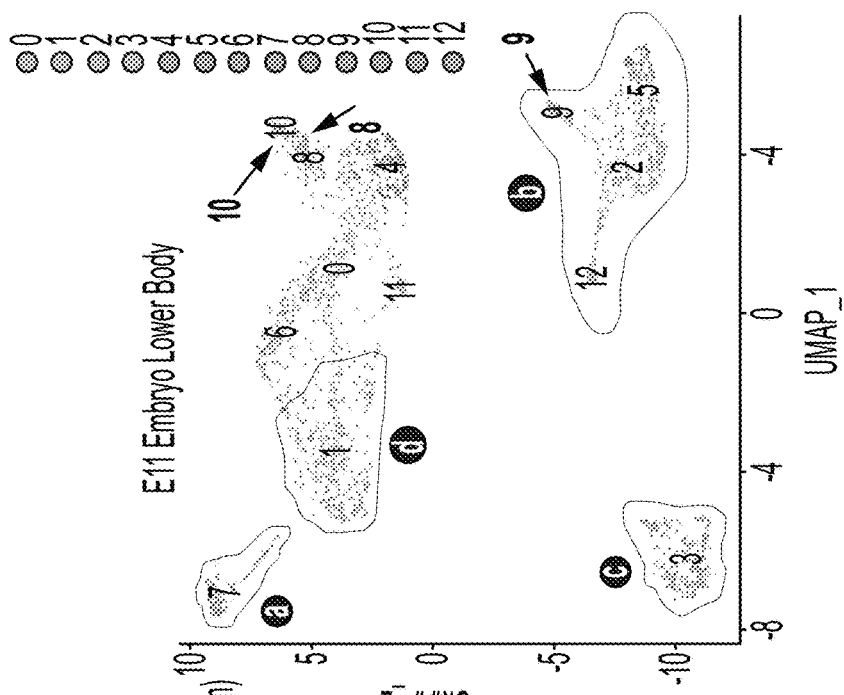
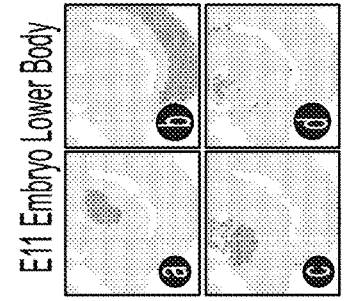
FIG. 12B

```
                              SEQUENCE LISTING

<160> NUMBER OF SEQ ID NOS: 131

<210> SEQ ID NO 1
<211> LENGTH: 15
<212> TYPE: DNA
<213> ORGANISM: Artificial Sequence
<220> FEATURE:
<223> OTHER INFORMATION: Synthetic

<400> SEQUENCE: 1
tgcatgtcat cggtg                                                          15

<210> SEQ ID NO 2
<211> LENGTH: 15
<212> TYPE: DNA
<213> ORGANISM: Artificial Sequence
<220> FEATURE:
<223> OTHER INFORMATION: Synthetic

<400> SEQUENCE: 2
cgcttggacg cttaa                                                          15

<210> SEQ ID NO 3
<211> LENGTH: 15
<212> TYPE: DNA
<213> ORGANISM: Artificial Sequence
<220> FEATURE:
<223> OTHER INFORMATION: Synthetic

<400> SEQUENCE: 3
tggctatgga gcaga                                                          15

<210> SEQ ID NO 4
<211> LENGTH: 15
<212> TYPE: DNA
<213> ORGANISM: Artificial Sequence
<220> FEATURE:
<223> OTHER INFORMATION: Synthetic

<400> SEQUENCE: 4
gatattcagt gcgac                                                          15

<210> SEQ ID NO 5
<211> LENGTH: 15
<212> TYPE: DNA
<213> ORGANISM: Artificial Sequence
<220> FEATURE:
<223> OTHER INFORMATION: Synthetic

<400> SEQUENCE: 5
agtcacctcg aagct                                                          15

<210> SEQ ID NO 6
<211> LENGTH: 15
<212> TYPE: DNA
<213> ORGANISM: Artificial Sequence
<220> FEATURE:
<223> OTHER INFORMATION: Synthetic

<400> SEQUENCE: 6
```

```
gtaacattac tcgtc                                                    15

<210> SEQ ID NO 7
<211> LENGTH: 15
<212> TYPE: DNA
<213> ORGANISM: Artificial Sequence
<220> FEATURE:
<223> OTHER INFORMATION: Synthetic

<400> SEQUENCE: 7
ccgcacctac attag                                                    15

<210> SEQ ID NO 8
<211> LENGTH: 15
<212> TYPE: DNA
<213> ORGANISM: Artificial Sequence
<220> FEATURE:
<223> OTHER INFORMATION: Synthetic

<400> SEQUENCE: 8
gcgcgtttgt gctat                                                    15

<210> SEQ ID NO 9
<211> LENGTH: 15
<212> TYPE: DNA
<213> ORGANISM: Artificial Sequence
<220> FEATURE:
<223> OTHER INFORMATION: Synthetic

<400> SEQUENCE: 9
ttcctttcct acgca                                                    15

<210> SEQ ID NO 10
<211> LENGTH: 15
<212> TYPE: DNA
<213> ORGANISM: Artificial Sequence
<220> FEATURE:
<223> OTHER INFORMATION: Synthetic

<400> SEQUENCE: 10
ttgggcgatt aagaa                                                    15

<210> SEQ ID NO 11
<211> LENGTH: 15
<212> TYPE: DNA
<213> ORGANISM: Artificial Sequence
<220> FEATURE:
<223> OTHER INFORMATION: Synthetic

<400> SEQUENCE: 11
cgtcctagtc attgg                                                    15

<210> SEQ ID NO 12
<211> LENGTH: 15
<212> TYPE: DNA
<213> ORGANISM: Artificial Sequence
<220> FEATURE:
<223> OTHER INFORMATION: Synthetic

<400> SEQUENCE: 12
ttgcttattt ccgca                                                    15

<210> SEQ ID NO 13
<211> LENGTH: 15
<212> TYPE: DNA
<213> ORGANISM: Artificial Sequence
```

```
<220> FEATURE:
<223> OTHER INFORMATION: Synthetic

<400> SEQUENCE: 13
tatgatctgc ccttg                                                15

<210> SEQ ID NO 14
<211> LENGTH: 15
<212> TYPE: DNA
<213> ORGANISM: Artificial Sequence
<220> FEATURE:
<223> OTHER INFORMATION: Synthetic

<400> SEQUENCE: 14
tccggtcact cagta                                                15

<210> SEQ ID NO 15
<211> LENGTH: 15
<212> TYPE: DNA
<213> ORGANISM: Artificial Sequence
<220> FEATURE:
<223> OTHER INFORMATION: Synthetic

<400> SEQUENCE: 15
acttggatgg acact                                                15

<210> SEQ ID NO 16
<211> LENGTH: 15
<212> TYPE: DNA
<213> ORGANISM: Artificial Sequence
<220> FEATURE:
<223> OTHER INFORMATION: Synthetic

<400> SEQUENCE: 16
acccgcgtta gtatg                                                15

<210> SEQ ID NO 17
<211> LENGTH: 15
<212> TYPE: DNA
<213> ORGANISM: Artificial Sequence
<220> FEATURE:
<223> OTHER INFORMATION: Synthetic

<400> SEQUENCE: 17
ccagctcatt caacg                                                15

<210> SEQ ID NO 18
<211> LENGTH: 15
<212> TYPE: DNA
<213> ORGANISM: Artificial Sequence
<220> FEATURE:
<223> OTHER INFORMATION: Synthetic

<400> SEQUENCE: 18
ataagagccc accat                                                15

<210> SEQ ID NO 19
<211> LENGTH: 15
<212> TYPE: DNA
<213> ORGANISM: Artificial Sequence
<220> FEATURE:
<223> OTHER INFORMATION: Synthetic

<400> SEQUENCE: 19
attgttgtca gacca                                                15
```

<210> SEQ ID NO 20
<211> LENGTH: 15
<212> TYPE: DNA
<213> ORGANISM: Artificial Sequence
<220> FEATURE:
<223> OTHER INFORMATION: Synthetic

<400> SEQUENCE: 20
atccgacacg tatta                                                   15

<210> SEQ ID NO 21
<211> LENGTH: 15
<212> TYPE: DNA
<213> ORGANISM: Artificial Sequence
<220> FEATURE:
<223> OTHER INFORMATION: Synthetic

<400> SEQUENCE: 21
ctcagatgcc cttta                                                   15

<210> SEQ ID NO 22
<211> LENGTH: 15
<212> TYPE: DNA
<213> ORGANISM: Artificial Sequence
<220> FEATURE:
<223> OTHER INFORMATION: Synthetic

<400> SEQUENCE: 22
tatagtttcc gccgt                                                   15

<210> SEQ ID NO 23
<211> LENGTH: 22
<212> TYPE: DNA
<213> ORGANISM: Artificial Sequence
<220> FEATURE:
<223> OTHER INFORMATION: Synthetic

<400> SEQUENCE: 23
caagcgttgg cttctcgcat ct                                           22

<210> SEQ ID NO 24
<211> LENGTH: 23
<212> TYPE: DNA
<213> ORGANISM: Artificial Sequence
<220> FEATURE:
<223> OTHER INFORMATION: Synthetic

<400> SEQUENCE: 24
aagcagtggt atcaacgcag agt                                          23

<210> SEQ ID NO 25
<211> LENGTH: 30
<212> TYPE: DNA
<213> ORGANISM: Artificial Sequence
<220> FEATURE:
<223> OTHER INFORMATION: Synthetic

<400> SEQUENCE: 25
cgaatgctct ggcctctcaa gcacgtggat                                   30

<210> SEQ ID NO 26
<211> LENGTH: 32
<212> TYPE: DNA
<213> ORGANISM: Artificial Sequence
<220> FEATURE:
<223> OTHER INFORMATION: Synthetic

```
<400> SEQUENCE: 26
aagcagtggt atcaacgcag agtgaatrgr gg                                   32

<210> SEQ ID NO 27
<211> LENGTH: 70
<212> TYPE: DNA
<213> ORGANISM: Artificial Sequence
<220> FEATURE:
<223> OTHER INFORMATION: Synthetic

<400> SEQUENCE: 27
aatgatacgg cgaccaccga gatctacact agatcgctcg tcggcagcgt cagatgtgta    60
taagagacag                                                            70

<210> SEQ ID NO 28
<211> LENGTH: 88
<212> TYPE: DNA
<213> ORGANISM: Artificial Sequence
<220> FEATURE:
<223> OTHER INFORMATION: Synthetic

<400> SEQUENCE: 28
caagcagaag acggcatacg agattcgcct tagtctcgtg ggctcggaga tgtgtataag    60
agacagcaag cgttggcttc tcgcatct                                        88

<210> SEQ ID NO 29
<211> LENGTH: 88
<212> TYPE: DNA
<213> ORGANISM: Artificial Sequence
<220> FEATURE:
<223> OTHER INFORMATION: Synthetic

<400> SEQUENCE: 29
caagcagaag acggcatacg agatctagta cggtctcgtg ggctcggaga tgtgtataag    60
agacagcaag cgttggcttc tcgcatct                                        88

<210> SEQ ID NO 30
<211> LENGTH: 88
<212> TYPE: DNA
<213> ORGANISM: Artificial Sequence
<220> FEATURE:
<223> OTHER INFORMATION: Synthetic

<400> SEQUENCE: 30
caagcagaag acggcatacg agatttctgc ctgtctcgtg ggctcggaga tgtgtataag    60
agacagcaag cgttggcttc tcgcatct                                        88

<210> SEQ ID NO 31
<211> LENGTH: 88
<212> TYPE: DNA
<213> ORGANISM: Artificial Sequence
<220> FEATURE:
<223> OTHER INFORMATION: Synthetic

<400> SEQUENCE: 31
caagcagaag acggcatacg agatgctcag gagtctcgtg ggctcggaga tgtgtataag    60
agacagcaag cgttggcttc tcgcatct                                        88

<210> SEQ ID NO 32
<211> LENGTH: 40
<212> TYPE: DNA
```

```
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 32
aggccagagc attcgaacgt gatttttttt ttttttttvn                              40

<210> SEQ ID NO 33
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 33
aggccagagc attcgaaaca tcgtttttttt ttttttttvn                             40

<210> SEQ ID NO 34
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 34
aggccagagc attcgatgcc taatttttttt ttttttttvn                             40

<210> SEQ ID NO 35
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 35
aggccagagc attcgagtgg tcatttttttt ttttttttvn                             40

<210> SEQ ID NO 36
<211> LENGTH: 40
```

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 36
aggccagagc attcgaccac tgtttttttt ttttttttvn                           40

<210> SEQ ID NO 37
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 37
aggccagagc attcgacatt ggcttttttt ttttttttvn                           40

<210> SEQ ID NO 38
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 38
aggccagagc attcgcagat ctgtttttttt ttttttttvn                          40

<210> SEQ ID NO 39
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 39
aggccagagc attcgcatca agtttttttt ttttttttvn                           40

<210> SEQ ID NO 40
```

```
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 40
aggccagagc attcgcgctg atctttttttt tttttttttvn                40

<210> SEQ ID NO 41
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 41
aggccagagc attcgacaag ctattttttt tttttttttvn                40

<210> SEQ ID NO 42
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 42
aggccagagc attcgctgta gccttttttt tttttttttvn                40

<210> SEQ ID NO 43
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 43
aggccagagc attcgagtac aagtttttttt tttttttttvn                40
```

```
<210> SEQ ID NO 44
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 44
aggccagagc attcgaacaa ccatttttt ttttttttvn                              40

<210> SEQ ID NO 45
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 45
aggccagagc attcgaaccg agatttttt ttttttttvn                              40

<210> SEQ ID NO 46
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 46
aggccagagc attcgaacgc ttatttttt ttttttttvn                              40

<210> SEQ ID NO 47
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 47
aggccagagc attcgaagac ggatttttt ttttttttvn                              40
```

```
<210> SEQ ID NO 48
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 48
aggccagagc attcgaaggt acattttttt tttttttttvn                           40

<210> SEQ ID NO 49
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 49
aggccagagc attcgacaca gaatttttt tttttttttvn                            40

<210> SEQ ID NO 50
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 50
aggccagagc attcgacagc agatttttt tttttttttvn                            40

<210> SEQ ID NO 51
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 51
aggccagagc attcgacctc caatttttt tttttttttvn                            40
```

```
<210> SEQ ID NO 52
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 52
aggccagagc attcgacgct cgattttttt ttttttttvn                                40

<210> SEQ ID NO 53
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 53
aggccagagc attcgacgta tcattttttt ttttttttvn                                40

<210> SEQ ID NO 54
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 54
aggccagagc attcgactat gcattttttt ttttttttvn                                40

<210> SEQ ID NO 55
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 55
```
aggccagagc attcgagagt caatttttt tttttttttvn                40

<210> SEQ ID NO 56
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 56
aggccagagc attcgagatc gcatttttt tttttttttvn                40

<210> SEQ ID NO 57
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 57
aggccagagc attcgagcag gaatttttt tttttttttvn                40

<210> SEQ ID NO 58
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 58
aggccagagc attcgagtca ctatttttt tttttttttvn                40

<210> SEQ ID NO 59
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 59

-continued aggccagagc attcgatcct gtattttttt ttttttttvn                40

<210> SEQ ID NO 60
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 60
aggccagagc attcgattga ggattttttt ttttttttvn                40

<210> SEQ ID NO 61
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 61
aggccagagc attcgcaacc acattttttt ttttttttvn                40

<210> SEQ ID NO 62
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 62
aggccagagc attcggacta gtattttttt ttttttttvn                40

<210> SEQ ID NO 63
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 63
aggccagagc attcgcaatg gaattttttt ttttttttvn            40

<210> SEQ ID NO 64
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 64
aggccagagc attcgcactt cgattttttt ttttttttvn            40

<210> SEQ ID NO 65
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 65
aggccagagc attcgcagcg ttattttttt ttttttttvn            40

<210> SEQ ID NO 66
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 66
aggccagagc attcgcatac caattttttt ttttttttvn            40

<210> SEQ ID NO 67
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

```
<400> SEQUENCE: 67
aggccagagc attcgccagt tcattttttt ttttttttvn                         40

<210> SEQ ID NO 68
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 68
aggccagagc attcgccgaa gtattttttt ttttttttvn                         40

<210> SEQ ID NO 69
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 69
aggccagagc attcgccgtg agattttttt ttttttttvn                         40

<210> SEQ ID NO 70
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 70
aggccagagc attcgcctcc tgattttttt ttttttttvn                         40

<210> SEQ ID NO 71
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
```

<223> OTHER INFORMATION: n is a, c, g, or t

<400> SEQUENCE: 71
aggccagagc attcgcgaac ttatttttt ttttttttvn                                40

<210> SEQ ID NO 72
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 72
aggccagagc attcgcgact ggatttttt ttttttttvn                                40

<210> SEQ ID NO 73
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 73
aggccagagc attcgcgcat acatttttt ttttttttvn                                40

<210> SEQ ID NO 74
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 74
aggccagagc attcgctcaa tgatttttt ttttttttvn                                40

<210> SEQ ID NO 75
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature

```
<222> LOCATION: (40)..(40)
<223> OTHER INFORMATION: n is a, c, g, or t

<400> SEQUENCE: 75
aggccagagc attcgctgag ccatttttttt tttttttttvn                    40

<210> SEQ ID NO 76
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 76
aggccagagc attcgctggc atatttttttt tttttttttvn                    40

<210> SEQ ID NO 77
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 77
aggccagagc attcggaatc tgatttttttt tttttttttvn                    40

<210> SEQ ID NO 78
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 78
aggccagagc attcgcaaga ctatttttttt tttttttttvn                    40

<210> SEQ ID NO 79
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
```

```
<221> NAME/KEY: misc_feature
<222> LOCATION: (40)..(40)
<223> OTHER INFORMATION: n is a, c, g, or t

<400> SEQUENCE: 79
aggccagagc attcggagct gaattttttt ttttttttvn                                40

<210> SEQ ID NO 80
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 80
aggccagagc attcggatag acattttttt ttttttttvn                                40

<210> SEQ ID NO 81
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-phosphorylation
<220> FEATURE:
<221> NAME/KEY: misc_feature
<222> LOCATION: (40)..(40)
<223> OTHER INFORMATION: n is a, c, g, or t

<400> SEQUENCE: 81
aggccagagc attcggccac atattttttt ttttttttvn                                40

<210> SEQ ID NO 82
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 82
caagcgttgg cttctcgcat ctnnnnnnnn nnaacgtgat atccacgtgc ttgag              55

<210> SEQ ID NO 83
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
```

<220> FEATURE:
<221> NAME/KEY: misc_feature
<222> LOCATION: (23)..(32)
<223> OTHER INFORMATION: n is a, c, g, or t

<400> SEQUENCE: 83
caagcgttgg cttctcgcat ctnnnnnnnn nnaaacatcg atccacgtgc ttgag    55

<210> SEQ ID NO 84
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 84
caagcgttgg cttctcgcat ctnnnnnnnn nnatgcctaa atccacgtgc ttgag    55

<210> SEQ ID NO 85
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 85
caagcgttgg cttctcgcat ctnnnnnnnn nnagtggtca atccacgtgc ttgag    55

<210> SEQ ID NO 86
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 86
caagcgttgg cttctcgcat ctnnnnnnnn nnaccactgt atccacgtgc ttgag    55

<210> SEQ ID NO 87
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)

<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 87
caagcgttgg cttctcgcat ctnnnnnnnn nnacattggc atccacgtgc ttgag      55

<210> SEQ ID NO 88
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 88
caagcgttgg cttctcgcat ctnnnnnnnn nncagatctg atccacgtgc ttgag      55

<210> SEQ ID NO 89
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 89
caagcgttgg cttctcgcat ctnnnnnnnn nncatcaagt atccacgtgc ttgag      55

<210> SEQ ID NO 90
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 90
caagcgttgg cttctcgcat ctnnnnnnnn nncgctgatc atccacgtgc ttgag      55

<210> SEQ ID NO 91
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature

```
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 91
caagcgttgg cttctcgcat ctnnnnnnnn nnacaagcta atccacgtgc ttgag            55

<210> SEQ ID NO 92
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 92
caagcgttgg cttctcgcat ctnnnnnnnn nnctgtagcc atccacgtgc ttgag            55

<210> SEQ ID NO 93
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 93
caagcgttgg cttctcgcat ctnnnnnnnn nnagtacaag atccacgtgc ttgag            55

<210> SEQ ID NO 94
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 94
caagcgttgg cttctcgcat ctnnnnnnnn nnaacaacca atccacgtgc ttgag            55

<210> SEQ ID NO 95
<211> LENGTH: 55
<212> TYPE: DNA
<213> ORGANISM: Artificial Sequence
<220> FEATURE:
<223> OTHER INFORMATION: Synthetic
<220> FEATURE:
```

```
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 95
caagcgttgg cttctcgcat ctnnnnnnnn nnaaccgaga atccacgtgc ttgag      55

<210> SEQ ID NO 96
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 96
caagcgttgg cttctcgcat ctnnnnnnnn nnaacgctta atccacgtgc ttgag      55

<210> SEQ ID NO 97
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 97
caagcgttgg cttctcgcat ctnnnnnnnn nnaagacgga atccacgtgc ttgag      55

<210> SEQ ID NO 98
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 98
caagcgttgg cttctcgcat ctnnnnnnnn nnaaggtaca atccacgtgc ttgag      55

<210> SEQ ID NO 99
<211> LENGTH: 55
<212> TYPE: DNA
<213> ORGANISM: Artificial Sequence
<220> FEATURE:
<223> OTHER INFORMATION: Synthetic
```

```
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 99
caagcgttgg cttctcgcat ctnnnnnnnn nnacacagaa atccacgtgc ttgag      55

<210> SEQ ID NO 100
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 100
caagcgttgg cttctcgcat ctnnnnnnnn nnacagcaga atccacgtgc ttgag      55

<210> SEQ ID NO 101
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 101
caagcgttgg cttctcgcat ctnnnnnnnn nnacctccaa atccacgtgc ttgag      55

<210> SEQ ID NO 102
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 102
caagcgttgg cttctcgcat ctnnnnnnnn nnacgctcga atccacgtgc ttgag      55

<210> SEQ ID NO 103
<211> LENGTH: 55
<212> TYPE: DNA
<213> ORGANISM: Artificial Sequence
<220> FEATURE:
```

<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 103
caagcgttgg cttctcgcat ctnnnnnnnn nnacgtatca atccacgtgc ttgag    55

<210> SEQ ID NO 104
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 104
caagcgttgg cttctcgcat ctnnnnnnnn nnactatgca atccacgtgc ttgag    55

<210> SEQ ID NO 105
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 105
caagcgttgg cttctcgcat ctnnnnnnnn nnagagtcaa atccacgtgc ttgag    55

<210> SEQ ID NO 106
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 106
caagcgttgg cttctcgcat ctnnnnnnnn nnagatcgca atccacgtgc ttgag    55

<210> SEQ ID NO 107
<211> LENGTH: 55
<212> TYPE: DNA
<213> ORGANISM: Artificial Sequence

```
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 107
caagcgttgg cttctcgcat ctnnnnnnnn nnagcaggaa atccacgtgc ttgag      55

<210> SEQ ID NO 108
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 108
caagcgttgg cttctcgcat ctnnnnnnnn nnagtcacta atccacgtgc ttgag      55

<210> SEQ ID NO 109
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 109
caagcgttgg cttctcgcat ctnnnnnnnn nnatcctgta atccacgtgc ttgag      55

<210> SEQ ID NO 110
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 110
caagcgttgg cttctcgcat ctnnnnnnnn nnattgagga atccacgtgc ttgag      55

<210> SEQ ID NO 111
<211> LENGTH: 55
<212> TYPE: DNA
```

```
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 111
caagcgttgg cttctcgcat ctnnnnnnnn nncaaccaca atccacgtgc ttgag        55

<210> SEQ ID NO 112
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 112
caagcgttgg cttctcgcat ctnnnnnnnn nngactagta atccacgtgc ttgag        55

<210> SEQ ID NO 113
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 113
caagcgttgg cttctcgcat ctnnnnnnnn nncaatggaa atccacgtgc ttgag        55

<210> SEQ ID NO 114
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 114
caagcgttgg cttctcgcat ctnnnnnnnn nncacttcga atccacgtgc ttgag        55

<210> SEQ ID NO 115
<211> LENGTH: 55
```

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 115
caagcgttgg cttctcgcat ctnnnnnnnn nncagcgtta atccacgtgc ttgag      55

<210> SEQ ID NO 116
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 116
caagcgttgg cttctcgcat ctnnnnnnnn nncataccaa atccacgtgc ttgag      55

<210> SEQ ID NO 117
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 117
caagcgttgg cttctcgcat ctnnnnnnnn nnccagttca atccacgtgc ttgag      55

<210> SEQ ID NO 118
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 118
caagcgttgg cttctcgcat ctnnnnnnnn nnccgaagta atccacgtgc ttgag      55

<210> SEQ ID NO 119
```

```
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 119
caagcgttgg cttctcgcat ctnnnnnnnn nnccgtgaga atccacgtgc ttgag        55

<210> SEQ ID NO 120
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 120
caagcgttgg cttctcgcat ctnnnnnnnn nncctcctga atccacgtgc ttgag        55

<210> SEQ ID NO 121
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 121
caagcgttgg cttctcgcat ctnnnnnnnn nncgaactta atccacgtgc ttgag        55

<210> SEQ ID NO 122
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 122
caagcgttgg cttctcgcat ctnnnnnnnn nncgactgga atccacgtgc ttgag        55
```

```
<210> SEQ ID NO 123
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 123
caagcgttgg cttctcgcat ctnnnnnnnn nncgcataca atccacgtgc ttgag          55

<210> SEQ ID NO 124
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 124
caagcgttgg cttctcgcat ctnnnnnnnn nnctcaatga atccacgtgc ttgag          55

<210> SEQ ID NO 125
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 125
caagcgttgg cttctcgcat ctnnnnnnnn nnctgagcca atccacgtgc ttgag          55

<210> SEQ ID NO 126
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 126
caagcgttgg cttctcgcat ctnnnnnnnn nnctggcata atccacgtgc ttgag          55
```

<210> SEQ ID NO 127
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 127
caagcgttgg cttctcgcat ctnnnnnnnn nngaatctga atccacgtgc ttgag       55

<210> SEQ ID NO 128
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 128
caagcgttgg cttctcgcat ctnnnnnnnn nncaagacta atccacgtgc ttgag       55

<210> SEQ ID NO 129
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 129
caagcgttgg cttctcgcat ctnnnnnnnn nngagctgaa atccacgtgc ttgag       55

<210> SEQ ID NO 130
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 130
caagcgttgg cttctcgcat ctnnnnnnnn nngatagaca atccacgtgc ttgag       55

```
<210> SEQ ID NO 131
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified with 5'-biotin
<220> FEATURE:
<221> NAME/KEY: misc_feature
<222> LOCATION: (23)..(32)
<223> OTHER INFORMATION: n is a, c, g, or t

<400> SEQUENCE: 131
caagcgttgg cttctcgcat ctnnnnnnnn nngccacata atccacgtgc ttgag          55
```

DETERMINISTIC BARCODING FOR SPATIAL OMICS SEQUENCING

RELATED APPLICATION

This application claims the benefit under 35 U.S.C. § 119(e) of U.S. provisional application No. 62/908,270, filed Sep. 30, 2019, which is incorporated by reference herein in its entirety.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Sep. 29, 2020, is named Y008770152US01-SEQ-HJD and is 40,737 bytes in size.

BACKGROUND

Spatial gene expression heterogeneity plays an essential role in a range of biological, physiological and pathological processes but it remains a scientific challenge to conduct high-spatial-resolution, genome-wide, unbiased biomolecular profiling over a large tissue area.

SUMMARY

The present disclosure provides a platform technology, referred to herein as Deterministic Barcoding in Tissue for spatial omics sequencing (DBiT-seq). This high-spatial resolution (HSR) technology may be used, as described herein, to generate multi-omic maps in intact tissue sections, offering at least the following advantages over current technologies: (1) high spatial resolution; (2) high throughput cell profiling capability; and (3) true-omics sensitivity. The present disclosure demonstrates how to design a microfluidics-based detection system satisfying each of these criteria by utilizing microfluidic chips, for example, as a polynucleotide reagent delivery system. In this modality, downstream spatial reconstruction is enabled by confining reagents labelled with different polynucleotide barcodes to specific spatial regions of the tissue to be mapped. The spatial resolution achieved with the device and methods provided herein are sufficient to distinguish the contributions to analyte profiles (target biomolecules in a region of interest) from single cells (e.g., mammalian cells between 5-20 µm in size). Further, the high-throughput HSR technology provided herein matches the profiling capability of non-spatial techniques, which routinely profile tens of thousands of cells per run. This technology is applicable to sectioned tissue and can be used to map a large area per run in order to map many cells per run. Further still, the HSR technology of the present disclosure can be used to target an entire class of coding RNA molecules, such as messenger RNA (mRNA), and not merely a targeted panel of RNA molecules, which is particularly useful generating transcriptomic maps. Parallel microfluidic channels (10 µm, 25 µm, or 50 µm in width) are used, in some aspects, to deliver molecular barcodes to the surface of a fixed (e.g., formaldehyde or formalin fixed) tissue slide in a spatially confined manner. Crossflow of two sets of barcodes A1-A50 and B1-B50 followed by ligation in situ yields a 2D mosaic of tissue pixels, each containing a unique combination of full barcode AiBj (i=1-50, j=1-50). It permits simultaneous barcoding of mRNAs, proteins, or even other omics on a fixed tissue slide, enabling the construction of a high-spatial-resolution multi-omics atlas by next generation sequencing (NGS). Applying it to mouse embryo tissues revealed all major tissue types in early organogenesis, distinguished brain microvascular networks, discovered new developmental patterning in forebrain, and demonstrated the ability to detect a single-cell-layer of melanocytes lining an optical vesicle and asymmetric expression of RORB and ALDH1A1 within it, presumably associated with the onset of retinal and lens, respectively. Automated feature identification using spatial differential expression further identified dozens of developmental features. DBiT-seq is a highly versatile technology that may become a universal method for spatial barcoding and sequencing of a range of molecular information at a high resolution and the genome scale. It can be readily adopted by biologists with no experience in microfluidics or advanced imaging and could be quickly disseminated for broader impacts in a variety of fields including developmental biology, cancer biology, neuroscience, and clinical pathology.

Some aspects of the disclosure provide a method, comprising: (a) delivering to a region of interest in a fixed section of a mammalian tissue mounted on a substrate a first set of barcoded polynucleotides that bind to nucleic acids of the fixed tissue section, wherein the first set of barcoded polynucleotides is delivered through a first microfluidic device clamped to the region of interest, wherein the first microfluidic device comprises 5-50 variable width microchannels, each having (i) an inlet port and an outlet port, (ii) a width of 50-150 µm at the inlet port and at the outlet port, and (iii) a width of 10-50 µm at the region of interest; (b) delivering to the region of interest reverse transcription reagents to produce cDNAs linked to barcoded polynucleotides of the first set; (c) delivering to the region of interest a second set of barcoded polynucleotides, wherein the second set of barcoded polynucleotides is delivered through a second microfluidic device clamped to the region of interest, wherein the second microfluidic device comprises 5-50 variable width microchannels, each having (i) an inlet port and an outlet port, (ii) a width of 50-150 µm at the inlet port and at the outlet port, and (iii) a width of 10-50 µm at the region of interest, wherein the second microfluidic device is oriented on the region of interest perpendicular to the direction of the microchannels of the first microfluidic device; (d) delivering to the region of interest ligation reagents to join barcoded polynucleotides of the first set to barcoded polynucleotides of the second set; (e) imaging the region of interest to produce a sample image; (f) delivering to the region of interest lysis buffer or denaturation reagents to produce a lysed or denatured tissue sample; and (g) extracting cDNA from the lysed or denatured tissue sample.

Other aspects of the present disclosure provide a method, comprising: (a) delivering to a region of interest in a fixed section of a mammalian tissue mounted on a substrate binder-DNA tag conjugates that comprise (i) a binder molecule that specifically binds to a protein of interest and (ii) a DNA tag, wherein the DNA tag comprises a binder barcode and a polyadenylation (polyA) sequence; (b) delivering to the region of interest a first set of barcoded polynucleotides that bind to nucleic acids of the fixed tissue section, wherein the first set of barcoded polynucleotides is delivered through a first microfluidic device clamped to the region of interest, optionally wherein the first microfluidic device comprises 5-50 variable width microchannels, each having (i) an inlet port and an outlet port, (ii) a width of 50-150 µm at the inlet port and at the outlet port, and (iii) a width of 10-50 µm at the region of interest; (c) delivering to the region of interest reverse transcription reagents to produce cDNAs linked to barcoded polynucleotides of the first set; (d) delivering to the region of interest a second set of barcoded polynucleotides, wherein the second set of barcoded polynucleotides is delivered through a second microfluidic device clamped to the region of interest, optionally wherein the second microfluidic device comprises 5-50 variable width microchannels, each having (i) an inlet port and an outlet port, (i) a width of 50-150 µm at the inlet port and at the outlet port, and (iii) a width of 10-50 µm at the region of interest, wherein the second microfluidic device is oriented on the region of interest perpendicular to the direction of the microchannels of the first microfluidic device; (e) delivering to the region of interest ligation reagents to join barcoded polynucleotides of the first set to barcoded polynucleotides of the second set; (f) imaging the region of interest to produce a sample image; (g) delivering to the region of interest lysis buffer or denaturation reagents to produce a lysed or denatured tissue sample; and (h) extracting cDNA from the lysed or denatured tissue sample.

In some embodiments, the method further comprises sequencing the cDNA to produce cDNA reads.

In some embodiments, the sequencing comprises template switching the cDNAs to add a second PCR handle end sequence at an end opposite from the first PCR handle end sequence, amplifying the cDNAs (e.g., polymerase chain reaction (PCR)), producing sequencing constructs via tagmentation (the initial step in library prep where unfragmented DNA is cleaved and tagged for analysis), and sequencing the sequencing constructs (e.g., via next generation sequencing (NGS)) to produce the cDNA reads.

In some embodiments, the method further comprises constructing a spatial molecular expression map of the tissue section by matching the spatially addressable barcoded conjugates to corresponding cDNA reads.

In some embodiments, the method further comprises identifying the anatomical location of the nucleic acids by correlating the spatial molecular expression map to the sample image.

In some embodiments, the fixed tissue section mounted on a slide is produced by: sectioning a formalin fixed paraffin embedded (FFPE) tissue, optionally into a 5-10 µm section and mounting the tissue section onto a substrate, optionally a poly-L-lysine-coated slide; applying to the tissue section a wash solution, optionally a xylene solution, to deparaffinize the tissue section; applying to the tissue section a rehydration solution to rehydrate the tissue section; applying to the tissue section an enzymatic solution, optionally a proteinase K solution, to permeabilize the tissue section; and applying formalin to the tissue section to post-fix the tissue section.

In some embodiments, the first and/or second microfluidic device is fabricated from polydimethylsiloxane (PDMS).

In some embodiments, the first and/or second microfluidic device comprises 40 to 60, optionally 50 microchannels.

In some embodiments, each microchannel of the first and second microfluidic device has a width of 10 µm and a height of 12-15 µm, a width of 25 µm and height of 17-22 µm, or a width of 50 µm and a height of 20-100 µm.

In some embodiments, delivery of the first set of barcoded polynucleotides is delivered through the first microfluidic device using a negative pressure system and/or delivery of the second set of barcoded polynucleotides is delivered through the second microfluidic device using a negative pressure system.

In some embodiments, the lysis buffer or denaturation reagents are delivered directly to the tissue section, optionally through a hole in a device clamped to the substrate, wherein the hole is positioned directly above the region of interest.

In some embodiments, the barcoded polynucleotides of the first set comprise a ligation linker sequence, a spatial barcode sequence, and a polyT sequence (e.g., ~1-100, e.g., 25, 50, 75, 100 contiguous thymine (T) nucleotides).

In some embodiments, the barcoded polynucleotides of the second set comprise a ligation linker sequence, a spatial barcode sequence, a unique molecular identifier (UMI) sequence, and a first PCR handle end sequence, optionally wherein the first PCR handle end sequence is terminally functionalized with biotin.

In some embodiments, the first and/or second set of barcoded polynucleotides comprises at least 50 barcoded polynucleotides.

In some embodiments, the binder molecule is an antibody, optionally selected from whole antibodies, Fab antibody fragments, F(ab)$_2$ antibody fragments, monospecific Fab$_2$ fragments, bispecific Fab$_2$ fragments, trispecific Fab$_3$ fragments, single chain variable fragments (scFvs), bispecific diabodies, trispecific diabodies, scFv-Fc molecules, and minibodies.

In some embodiments, the nucleic acids of the biological sample are selected from (i) ribonucleic acids (RNAs), optionally messenger RNAs (mRNAs), and (ii) deoxyribonucleic acids (DNAs), optionally genomic DNAs (gDNAs).

In some embodiments, (i) barcoded polynucleotides of the second set are bound to a universal ligation linker, or (ii) the method further comprises delivering to the biological sample a universal ligation linker sequence, wherein the universal ligation linker comprises a sequence complementary to the ligation linker sequence of the barcoded polynucleotides of the first set and comprises a sequence complementary to the ligation linker sequence of the barcoded polynucleotides of the second set.

In some embodiments, the imaging is with an optical or fluorescence microscope.

In some embodiments, the substrate is a microscope slide, optionally a glass microscope slide, optionally poly-amine-coated, and optionally having dimensions of 25 mm×75 mm.

The entire contents of Liu, Y., Yang, M., Deng, Y., Su, G., Guo, C. C., Zhang, D., Kim, D., Bai. Z., Xiao, Y. & Fan. R. *High-Spatial-Resolution Multi-Omics Atlas Sequencing of Mouse Embryos via Deterministic Barcoding in Tissue.* bioRxiv, 788992 (biorxiv.org/content/10.1101/788992v2) (Aug. 3, 2019) is incorporated herein by reference.

BRIEF DESCRIPTION OF THE DRAWINGS

(FIG. 5A) Schematic workflow. A formaldehyde-fixed tissue slide is used as the starting material, which is incubated with a cocktail of antibody-derived DNA tags (ADTs) that recognize a panel of proteins of interest. A custom-designed PDMS microfluidic device with 50 parallel microchannels in the center of the chip is aligned and placed on the tissue slide to introduce the $1^{st}$ set of barcodes A1 to A50 Each barcode is tethered with a ligation linker and an oligo-dT sequence for binding the poly-A tail of mRNAs or ADTs. Then, reverse transcription (RT) is conducted in situ to yield cDNAs which are covalently linked to barcodes A1-A50. Afterwards, this microfluidic chip is removed and another microfluidic chip with 50 parallel microchannels perpendicular to those in the first microfluidic chip is placed on the tissue slide to introduce the 2nd set of DNA barcodes B1-B50. These barcodes contain a ligation linker, a unique molecular identifier (UMI) and a PCR handle. After introducing barcodes B1-B50 and a universal complementary ligation linker through the second microfluidic chip, the barcodes A and B are joined through ligation and then the intersection region of microfluidic channels in the first and second PDMS chips defines a distinct pixel with a unique combination of A and B, giving rise to a 2D array of spatial barcodes AiBj (i=1-50, j=1-50). Afterwards, the second PDMS chip is removed and the tissue remains intact while spatially barcoded for all mRNAs and the proteins of interest. The barcoded tissue is imaged under an optical or fluorescence microscope to visualize individual pixels. Finally, cDNAs are extracted from the tissue slide, template switched to incorporate another PCR handle, and amplified by PCR for preparation of sequencing library via tagmentation. A paired-end sequencing is performed to read the spatial barcodes (AiBj) and cDNA sequences from mRNAs and ADTs. Computational reconstruction of a spatial mRNA or protein expression map is realized by matching the spatial barcodes AiBj to the corresponding cDNA reads using UMIs. The spatial omics map can be correlated to the tissue image taken during or after microfluidic barcoding to identify the spatial location of individual pixels and the corresponding tissue morphology. (FIG. 5B) Schematic of the biochemistry protocol to add spatial barcodes to a tissue slide. Proteins of interest are labeled with antibody DNA tags (ADTs), each of which consists of a unique antibody barcode (15mer, see Table 1) and a poly-A tail. Barcode A1-A50 contains a ligation linker (15mer), a unique spatial barcode Ai(i=1-50, 8mer, see Table 3), and a poly-T sequence (16mer), which detects mRNAs and proteins through binding to poly-A tails. After introducing barcodes A1-A50 to the tissue slide, reverse transcription is conducted in situ to generate cDNAs from mRNAs as well as antibody barcodes. Barcode B1-B50 consists of a ligation linker (15mer), a unique spatial barcode Bj(j=1-50, 8mer, see Table 3), a unique molecular identifier (UMI) (10mer), and a PCR handle (22mer) terminally functionalized with biotin, which facilitates the purification in the later steps using streptavidin-coated magnetic beads. When the barcodes B1-B50 are introduced to the tissue sample that is already barcoded with A1-A50 using an orthogonal microfluidic delivery, a complementary ligation linker is also introduced and initiates the covalent ligation of barcodes A and B, giving rise to a 2D array of spatially distinct barcodes AiBj(i=1-50 and j=1-50). (FIG. 5C) Detailed microfluidic device design (left panel) and barcoding chemistry protocol (right panel). Left panel: fresh frozen tissue sections were first allowed to warm to room temperature for 10 minutes. Then, 4% Formaldehyde was added, and tissue was fixed for 20 minutes at room temperature. After fixation, a cocktail of 22 antibody-DNA tags (ADTs) were added and incubated at 4° C. for 30 minutes. After washing three times with PBS, $1^{st}$ PDMS chip was attached to the glass slide. Barcode A (A1-A50) along with reverse transcription mixture was flowed through each channel. After reverse transcription, the $1^{st}$ PDMS chip was removed and a 2nd PDMS was attached. Ligation solution along with Barcode B (B1-B50) was flowed into each channel. When finished, the 2nd PDMS chip was removed and a PDMS gasket was attached to the glass slide. Lysis solution was added into the gasket and the lysate was collected. cDNA and ADT derived cDNA were extracted using streptavidin coated magnetic beads. Template switch and PCR were then performed. The sequencing library was finally built with standard tagmentation. Right panel: DNA barcode A consists of a poly T region, a barcode region and a ligation region. The poly T region will recognize the poly A tail of mRNA and ADTs. DNA Barcode B consists of a ligation region, a barcode region, a UMI region and a PCR primer handle region. During ligation process, the ligation region will be ligated to the ligation region of barcode A. The cDNA product will then be template-switched. The final product is further amplified by PCR.

(FIG. 7A) Microfluidic device used in DBIT-seq. A series of microfluidic chips were fabricated with 50 parallel microfluidic channels in the center that are 50 μm, 25 μm, or 10 μm in width, respectively. The PDMS chip containing 50 parallel channels is placed directly on a tissue slide and the center region is clamped using two acrylic plates and screws to apply the pressing force in a controlled manner. All 50 inlets are open holes (~2 mm in diameter) capable of holding ~13 μL of solution. Different barcode reagents are pipetted to these inlets and drawn into the microchannels by vacuum applied to the roof cap of the outlets situated on the other side of the PDMS chip. (FIG. 7B) Validation of spatial barcoding using fluorescent DNA probes. The images show parallel lines of Cy3-labelled barcode A (left panel) on the tissue slide defined by the first flow, the square pixels of FITC-labeled barcode B (right panel) corresponding to the intersection of the first and the second flows, and the overlay of both fluorescence colors (middle). Because barcode B is ligated to the immobilized barcode A in an orthogonal direction, it is detectable only at the intersection of the first set (A1-A50) and the second set (B1-B50) of microchannels. Channel width=50 μm. (FIG. 7C) Validation of leak-free flow barcoding using a layer of cells cultured on a glass slide. HUVECs grown on a glass slide were stained by 4',6-diamidino-2-phenylindole (DAPI) during the $1^{st}$ flow and anti-human VE-cadherin during the 2nd flow. As shown in the enlarged figures, fluorescence staining was confined within the channels. Scale bar=20 μm. (FIG. 7D) Confocal microscopy image of a tissue slide stained with fluorescent DNA barcode A. The 3D stacked image shows no leakage between adjacent channels throughput the tissue thickness. Scale bar=20 μm. (FIG. 7E) Validation of spatial barcoding for 10 μm pixels. A tissue slide was subjected to spatial barcoding and the resultant pixels were visualized by optical (upper left) and fluorescent imaging (upper right) of the same tissue sample using FITC-labeled barcode B. Pressing microfluidic channels against the tissue section resulted in a slight deformation of the tissue matrix, which allowed for directly visualizing the topography of individual tissue pixels. Enlarged views (low panels) further show discrete barcoded tissue pixels with 10 µm pixel size. (FIG. 7F) Qualification of the cross-channel diffusion distance, the measured size of pixels, and the number of cells per pixel. Quantitative analysis of the line profile revealed the diffusion of DNA oligomers through the dense tissue matrix is as small as 0.9 µm, which was obtained with the 10 µm-wide microchannels with the application of an acrylic clamp. The measured pixel size agreed with the microchannel size. Using DAPI, a fluorescent dye for nuclear DNA staining, the number of cells in a pixel can be identified. The average cell number is 1.7 in a 10 µm pixel and 25.1 in a 50 µm pixel. (FIG. 7G) Gene and UMI count distribution. DBiT-seq is compared to Slide-seq, ST, and the commercialized ST (Visium) with different spot/pixel sizes. Formaldehyde-fixed mouse embryo tissue slides were used in DBiT-seq. Fresh frozen mouse brain tissues were used in Slide-seq, ST, and Visium.

FIGS. 8A-8I. Spatial multi-omic atlas of whole mouse embryos. (FIG. 8A) Pan-mRNA and pan-protein-panel spatial expression maps (pixel size 50 µm) reconstructed from DBiT-seq, alongside the H&E image from an adjacent tissue section. Whole transcriptome pan-mRNA map correlated with anatomic tissue morphology and density. (FIG. 8B) Comparison to "pseudo bulk" RNA-seq data. Four embryo samples (E10) analyzed by DBiT-seq correctly situated in the UMAP in relation to those analyzed by single-cell RNA-seq (Cao et al., 2019) in terms of the developmental stage (FIG. 8C) Unsupervised clustering analysis and spatial pattern. Left: UMAP showing the clusters of tissue pixel transcriptomes. Middle: spatial distribution of the clusters. Right: overlay of spatial cluster map and tissue image (H&E). Because the H&E staining was conducted on an adjacent tissue section, minor differences were anticipated. (FIG. 8D) Gene Ontology (GO) analysis of all 11 clusters. Selected GO terms are highlighted. (FIG. 8E) Anatomic annotation of major tissue regions based on the H&E image. (FIG. 8F) Correlation between mRNAs and proteins in each of the anatomically annotated tissue regions. The average expression levels of individual mRNAs and cognate proteins are compared. (FIG. 8G) Spatial expression of four individual proteins and cognate mRNA transcripts in a whole mouse embryo. These are Notch 1 (Notch1), CD63 (Cd63), Pan-Endothelial-Cell Antigen (Plvap), and EpCAM (Epcam). Multi-omic DBIT-seq allows for head-to-head comparison of a panel of proteins and the expression of cognate genes. It shows consistence as well as discordance between mRNA and protein for selected pairs, but the spatial resolution is adequate to resolve the fine structures in specific organs. (FIG. 8H) Correlation between mRNAs and proteins in anatomically annotated tissue regions). The average expression levels of individual mRNAs and cognate proteins in each of the thirteen anatomically annotated tissue regions are compared. (FIG. 8I) Comparison to immunofluorescence tissue staining. Pan-endothelial antigen (PECA), which marks the formation of embryonic vasculature, is expressed extensively at this stage (E.10), consistent with the protein and mRNA expression revealed by DBiT-seq. EpCAM, an epithelial marker, already show up but in several highly localized regions, which were also identified by DBiT-seq (both mRNA and protein). P2RY12 is a marker for microglia in CNS, which depicts the spatial distribution of the neural system.

FIGS. 9A-9G. Spatial multi-omics mapping of an embryonic mouse brain. (FIG. 9A) Bright field optical image of the brain region of a mouse embryo (E10) (FIG. 9B) Hematoxylin and eosin (H&E) image of the mouse embryo brain region (E10). It was obtained on an adjacent tissue section. (FIG. 9C) Pan-mRNA and pan-protein-panel spatial expression maps of the brain region of a mouse embryo (E10) obtained with 25 µm pixel size. The spatial pattern of whole transcriptome (pan-mRNA) correlated with cell density and morphology in the tissue. (FIG. 9D) Spatial expression of four individual proteins: CD63, Pan-endothelial cell antigen (PECA), EpCAM (CD326) and MAdCAM-1. Spatial protein expression heatmaps revealed brain tissue region-specific expression and the brain microvascular network. (FIG. 9E) Validation by immunofluorescence staining. Spatial expression of EpCAM and PECA reconstructed from DBiT-seq and the immunofluorescence image of the same proteins were superimposed onto the H&E image for comparison. A highly localized expression pattern of EpCAM is in strong correlation with immunostaining as seen by the line profile. The network of microvasculature revealed by PECA in DBiT-seq is correlated with the immunostaining image. (FIG. 9F) Gene expression heatmap of 11 clusters obtained by unsupervised clustering analysis Top ranked differentially expressed genes are shown in each cluster. (FIG. 9G) Spatial map of clusters 1, 2, 5 and 9. GO analysis identified the major biological processes within each cluster, in agreement with anatomical annotation.

(FIG. 10A) Bright field image of a whole mouse embryo tissue section (E10). Red indicates pan-mRNA signal in a region of interest (ROI) analyzed by DBiT-seq (10 µm pixel size). Scale bar (left panel) 500 µm. Scale bar (right panel) 200 µm.

(FIG. 11A) tSNE plot showing the clustering analysis of DBiT-seq data from all 11 mouse embryo tissue samples. (FIG. 11B) tSNE plot color-coded for different mouse embryo tissue samples. (FIG. 11C) Heatmap of differentially expressed genes in 20 clusters and GO analysis. Select GO terms and top ranked genes are shown for the clusters implicated in muscle system, pigment metabolic system, blood vessel development, neuron development and telencephalon development. (FIG. 11D) UMAP plot showing the cluster analysis result, color-coded for different samples (left) or the developmental stages (right).

FIGS. 12A-12G. Mapping internal organs in a E11 mouse embryo. (FIG. 12A) Enlarged view of UMAP clustering of FIG. 5D with a specific focus on the E11 embryo lower body sample. (FIG. 12B) Spatial expression of four select clusters indicated in FIG. 12A. (FIG. 12C) UMAP showing the clustering analysis of the E11 embryo lower body sample only. The tissue pixels from four major clusters shown in FIG. 6A&B are circled in this UMAP with more sub-clusters identified. (FIG. 12D) Spatial map of all the clusters shown in (FIG. 12C). (FIG. 12E) Cell type annotation (SingleR) using scRNA-seq reference data from E10.5 mouse embryo (Cao et al., 2019). (FIG. 12F) Spatial expression maps of individual genes. (FIG. 12G) Tissue types identified for clusters a, b, c, and d indicated in (A) overlaid onto the tissue image. Major organs such as heart (atrium and ventricle), liver and neutral tube were identified, in agreement with the tissue anatomy. Erythrocyte coagulation was detected by DBiT-seq, for example, within the dorsal aorta and the atrial chamber. Scale bar=250 µm.

(FIG. 13A) Major features identified in a E10 mouse embryo sample (see FIG. 4). It revealed several additional tissue types in addition to eye. Pixel size=10 µm. Scale bar=200 µm. (FIG. 13B) Major features identified in the lower body of a E11 mouse embryo tissue sample (see FIG. 6), which showed a variety of tissue types developed in E11. Pixel size=25 µm. Scale bar=500 µm. (FIG. 13C) Major features identified in the lower body of a E12 mouse embryo sample, which showed more tissue types and developing organs at this embryonic age (E12) Pixel size=50 µm. Scale bar=1 mm.

(FIG. 14A) Fluorescent image of a pre-stained mouse embryo tissue slide. It was stained with DAPI, Phalloidin and P2RY12. Scale bar=200 µm (FIG. 14B) UMI count heatmap generated by DBiT-seq of the same tissue slide pre-stained with fluorescence IHC. (FIG. 14C) Bright filed image of this tissue sample prior to DBiT-seq. (FIG. 14D) Overlap of bright field image with the UMI heatmap. (FIG. 14E) Cell segmentation conducted with Image1 based on the fluorescence image. (FIG. 14F) Overlay of the DBiT-seq pixel grid and the fluorescence image. (FIG. 14G) Fluorescent images of representative pixels. Pixels containing single nuclei can be readily identified. (FIG. 14H) Gene expression pattern of representative pixels from (G).

FIG. 15 depicts the experimental procedure to perform deterministic barcoding in cells (DBIC) to detect and eventually sequence single-cell transcriptome in a massively parallel and deterministic manner, which means each cell to be analyzed by sequencing has a known combination barcode AiBj(i=1-50, j=1-50) and known location on the substrate. Therefore, other cellular characteristics such as cell size, morphology, protein signaling, and migration can be imaged and directly linked to the omics data of the same single cell obtained by sequencing. (1) Hydrodynamic trapping of ~3000 single cells in a microfluidic chip. Then, the cells are fixed with 1% formaldehyde and permeabilized. (2) Flowing through barcode Ai(i=1-50) solutions in the horizontal direction. In order to confirm the flow is leak free, the barcodes introduced to adjacent microchannels were pre-labelled with different color fluorophores. (3) Imaging fluorescently labelled barcodes Ai(i=1-50) that already bind to mRNAs in cells through the hybridization between oligo-dT tag of the barcode A strands and the poly-A tail of mRNAs. (4) This microfluidic chip is removed but cells still remain on the surface of the poly-amine-coated glass slide. Another microfluidic chip is placed on the slide in a way that the microfluidic channels are perpendicular to the first flow direction. Then, barcode Bj(j=1-50) solutions are introduced in a perpendicular direction. Again, the barcode B solutions flowed into adjacent microchannels contain different fluorophores and can be visualized to confirm no leakage. This image shows the fluorescent signals from barcode Bj(j=1-50), confirming successful barcoding of each single cells. Combining barcode Ai and Bj, each cell has a unique and known barcode AiBj(i=1-50 and j=1-50).

(FIG. 16A) Schematic depiction of the workflow to perform spatially resolved assay for chromatin accessibility through orthogonal barcoding of one of the DNAs incorporated in Tn5 enzyme. (FIG. 16B) The tissue image and the fluorescence images showing successful incorporation of barcodes Ai(i=1-50) and barcode Bj(j=1-50), again, in an orthogonal fashion to create a spatial mosaic of barcoded tissue pixels.

(FIG. 17A) Scheme of DBiT-seq on FFPE samples. FFPE tissue blocks stored at room temperature were sectioned into thickness of ~5-7 µm and placed onto a poly-L-lysine coated glass slide. Deparaffinization, rehydration, permeabilization and post-fixation were sequentially completed before attaching the $1^{st}$ PDMS chip. Barcodes A1-A50 were loaded and reverse transcription was carried out inside each channel. After washing, the $1^{st}$ PDMS was removed and a $2^{ad}$ PDMS chip with channels of perpendicular directions was attached on the tissue slide. Ligation reaction mix along with DNA Barcodes B1-B50 were vacuumed through each of the 50 channels and reacted for 30 minutes. Afterwards, the tissue section was lysed completely by Proteinase K and collected for downstream processes, which include template switch, PCR and library preparation. (FIG. 17B) Deparaffinization of a E10 mouse embryo. Tissue section maintained its morphology and tissue features were discernable. (FIG. 17C) Plastic deformation of tissue section after two sequential microfluidic flows of DBIT-seq. (FIG. 17D) Comparison of gene and UMI counts of DBiT-seq on FFPE samples with Slide-seq. Slide-seqV2 and DBIT-seq on Formalin fixed Fresh frozen samples.

(FIG. 18A) Two tissue regions of FFPE mouse embryo were studied using DBIT-seq. One experiment (FFPE-1) covered the head region of the mouse embryo; the other experiment (FFPE-2) covered the mid-body region with small overlap with FFPE-1. Two separate tissue slides were used in this study. (FIG. 18B) UMAP visualization of combined pixels from FFPE-1 and FFPE-2 using Seurat package. Left: UMAP labelled by sample names; right: UMAP labelled by cluster numbers. Totally 10 clusters were identified. (FIG. 18C) Tissue morphology, anatomical annotation, and spatial mapping of the 10 clusters in (FIG. 18B). (FIG. 18D) GO enrichment analysis of above 10 clusters. (FIG. 18E) Comparison to "pseudo bulk" reference data. The aggregated transcriptome profiles of two FFPE samples conform well into data generated from scRNA-seq reference data from mouse embryos ranging from E9.5-E13.5 (Cao et al., 2019).

(FIG. 19A) Integration analysis of FFPE-1 and FFPE-2 with scRNA-seq data from mouse embryos ranging from E9.5-E13.5 (Cao et al., 2019) The two samples conform well in the scRNA-seq data. (FIG. 19B) UMAP of integrated data showing 26 distinct clusters. (FIG. 19C) Cell type annotation for each cluster using cell type information from scRNA-seq data. (FIG. 19D) Spatial map of some representative clusters. (FIG. 19E) Cell types identified in FIG. 8C.

(FIG. 20A) Bright field image of adult mouse aorta. Scale bar is 500 µm. (FIG. 20B) UMI and gene counts map for each pixel. The average UMI count per pixel is ~1828 and gene count is ~664. (FIG. 20C) Clustering with scRNA-seq data. Pixels from aorta sample conform greatly with scRNA-seq reference. (FIG. 20D) Spatial mapping of cell types annotated by integration with scRNA-seq data. The cell types are endothelial cells (ECs), arterial fibroblasts (Fibro), macrophages (Macro), monocytes (Mono), Neurons and vascular smooth muscle cells (VSMCs). (FIG. 20E) Spatial mapping of individual cell types from FIG. 9D.

(FIG. 21A) Bright field image of deparaffinized mouse atrium tissue section and the gene heatmap. (FIG. 21B) Bright field image of deparaffinized mouse ventricle tissue section and the gene heatmap. (FIG. 21C) Clustering of atrium data with reference scRNA-seq data. (FIG. 21D) Spatial distribution of representative annotated cells in atrium. (FIG. 21E) Clustering of ventricle data with reference scRNA-seq data. (FIG. 21F) Spatial distribution of representative annotated cells in ventricle.

DETAILED DESCRIPTION

Figure 1:
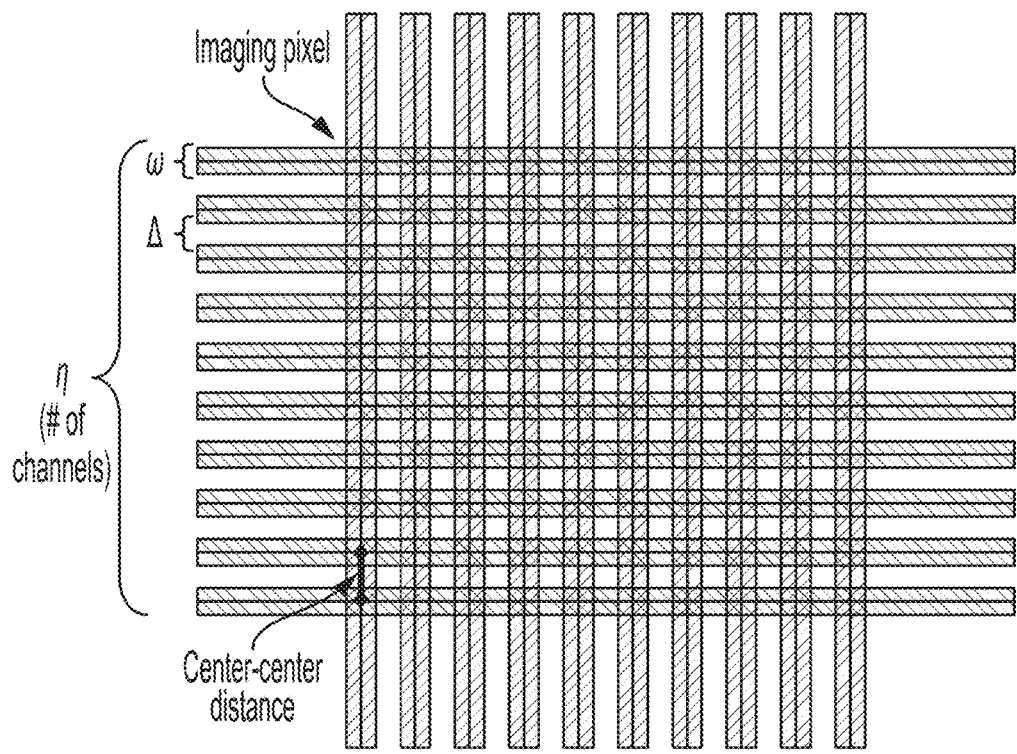
FIG. 1. Spatial parameters for microfluidics-based spatial imaging detectors.

In multicellular systems, cells do not function in isolation but are strongly influenced by spatial location and surroundings (Knipple et al., 1985; Scadden, 2014; van Vliet et al., 2018). Spatial gene expression heterogeneity plays an essential role in a range of biological, physiological and pathological processes (de Bruin et al., 2014; Fuchs et al., 2004; Yudushkin et al., 2007). For example, how stem cells differentiate and give rise to diverse tissue types is a spatially regulated process which controls the development of different tissue types and organs (Ivanovs et al., 2017; Slack, 2008). Mouse embryonic organogenesis begins during the end of the first week right after gastrulation and continues through birth (Mitiku and Baker, 2007). When and how exactly different organs emerge in an early stage embryo is still inadequately understood due to dynamic heterogeneity of tissues and cells during a rapid developmental process. An embryonic organ at this stage could differ substantially in anatomical and molecular definitions as compared to their adult counterparts. In order to dissect the initiation of early organogenesis in the whole embryo context, it is highly desirable to not only identify genome-wide molecular profiles to define emerging cell types but also interrogate their spatial organization in the tissue at a high resolution.

Despite the latest advent of massively parallel single-cell RNA-sequencing (scRNA-seq) (Klein et al., 2015; Macosko et al., 2015) that revealed astonishing cellular heterogeneity in many tissue types, including the dissection of all major cell types in developing mouse embryos from E9 to E14 (Cao et al., 2019; Pijuan-Sala et al., 2019), the spatial information in the tissue context is missing in scRNA-seq data. The field of spatial transcriptomics emerged to address this challenge. Early attempts were all based on multiplexed single-molecule fluorescent in situ hybridization (smFISH) via spectral barcoding and sequential imaging (Pichon et al., 2018. Trcek et al., 2017). It evolved rapidly over the past years from detecting a handful of genes to hundreds or thousands (e.g., seqFISH, MERFISH) (Chen et al., 2015; Lubeck et al., 2014), and recently to the whole transcriptome level (e.g., SeqFISH+) (Eng et al., 2019). However, these methods are technically demanding, requiring high-sensitivity optical imaging systems, sophisticated image analysis process, and a lengthy repeated imaging workflow to achieve high multiplexing (Perkel, 2019). Moreover, they are all based upon a finite panel of probes that hybridize to known mRNA sequences, limiting their potential to discover new sequences and variants. Fluorescent in situ sequencing methods (e.g., FISSEQ, STARmap) (Lee et al., 2015; Wang et al., 2018) were additionally reported but the number of detectable genes is limited, and their workflow resembles sequential FISH, again requiring a lengthy, repeated, and technically demanding imaging process.

It is highly desirable to develop new methods for high-spatial-resolution, unbiased, genome-scale molecular mapping in intact tissues, which does not require sophisticated imaging but can instead capitalize on the power of high-throughput Next Generation Sequencing (NGS). This year, a method called Slide-seq was reported that utilizes a self-assembled monolayer of DNA-barcoded beads on a glass slide to capture mRNAs released from a tissue section placed on top. It demonstrated spatial transcriptome sequencing at a 10 µm resolution (Rodriques et al., 2019). A similar method, called HDST, used 2 µm beads in a microwell array chip to further increase the nominal resolution (Vickovic et al., 2019). However, these emergent NGS-based methods have the following limitations: (a) the way to decode the array of DNA-barcoded beads is through manual sequential hybridization or SOLID sequencing, similar to seqFISH, again requiring a lengthy and repeated imaging process; (b) the number of detected genes from the 10 µm resolution Slide-seq data is very low (~150 genes/pixel) and thus, it can hardly visualize the spatial expression of individual genes in a meaningful way even if the collective gene sets can locate major cell types; (c) these methods, including a previously reported low-spatial-resolution (~150 µm) approach (Stahl et al., 2016), are all based upon the same mechanism-"barcoded solid-phase RNA capture" (Salmen et al., 2018) (they require newly sectioned tissues to be carefully transferred to the bead or spot array and lysed to release mRNAs; although the mRNAs are presumably captured only by the beads right underneath, the lateral diffusion of free mRNAs is unavoidable; and (d) all these genome-scale methods are technically demanding and difficult to use in most biology laboratories. Finally, it is not obvious how these methods can be extended to other omics measurements and how easy researchers from other fields can adopt them. Therefore, high-spatial-resolution omics is still a scientific challenge but also an opportunity that, if fully realized and democratized, will shift the paradigm of research in many fields of biology and medicine. Current methods are either technically impractical or fundamentally limited by the approaches themselves for enabling wide-spread adoption.

Inspired by how molecular barcoding of individual cells in isolated droplets or microwells served as a universal sample preparation method (Dura et al., 2019; Klein et al., 2015; Macosko et al., 2015) to barcode single cells for massively parallel sequencing of mRNAs, DNAs, or chromatin states, the inventors sought to develop a universal method to spatially barcode tissues, forming a large number of barcoded tissue pixels each containing a distinct molecular barcode. Similarly, the barcoded mRNAs or proteins in the tissue pixels can be retrieved, pooled, and amplified for NGS sequencing but, in this case, to generate a spatial omics atlas. The inventors have previously developed microfluidic channel-guided deposition and patterning of DNAs or antibodies on a substrate for multiplexed protein assay (Lu et al., 2013; Lu et al., 2015). Building on this technology, they have designed a microfluidic channel-guided delivery technique for high-resolution spatial barcoding.

The present disclosure provides a fundamentally new technology for spatial omics-microfluidic Deterministic Barcoding in Tissue for spatial omics sequencing (DBIT-seq). A microfluidic chip with parallel channels (10, 25 or 50 µm in width) is placed directly against a fixed tissue slide, and in some embodiments clamped only to the region of interest using a particular clamping force, to introduce oligo-dT tagged DNA barcodes A1-A50 that bind mRNAs and initiate in situ reverse transcription. This step results in stripes of barcoded cDNAs in the tissue section. Afterwards, the first chip is removed and another microfluidic chip is placed perpendicular to the first flow direction to introduce a second set of DNA barcodes B1-B50, which are ligated at the intersection to form a 2D mosaic of tissue pixels, each of which has a distinct combination of barcodes Ai and Bj(i=1-50, j=1-50) Then, the tissue is lysed and spatially barcoded cDNAs are retrieved, pooled, template-switched, amplified by PCR, and subjected to tagmentation to prepare a library for NGS sequencing. Proteins can be co-measured by applying a cocktail of antibody-derived DNA tags (ADTs) to the fixed tissue slide prior to flow barcoding, similar to Ab-seq or CITE-seq (Shahi et al., 2017; Stoeckius et al., 2017).

Using DBiT-seq, the data provided herein has demonstrated high-spatial-resolution co-mapping of whole transcriptome and a panel of 22 proteins in mouse embryos. It faithfully detected all major tissue types in early organogenesis. The spatial gene expression and protein atlas further identifies a differential pattern in embryonic forebrain development and microvascular networks. The 10 µm-pixel resolution can detect a single-cell-layer of melanocytes lining around an optical vesicle and discovered asymmetric gene expression within it, which has not been observed previously. DBiT-seq does not require any DNA spot microarray or decoded DNA-barcoded bead array. It works for an existing fixed tissue slide, not requiring newly prepared tissue sections that are necessary for other methods (Rodriques et al., 2019; Stahl et al., 2016). It is highly versatile allowing for the combining of different reagents for multiple omics measurements to yield a spatial multi-omics atlas. The inventors envision that this may become a universal approach to spatially barcode a range of molecular information including DNAs, epigenetic states, non-coding RNAs, protein modifications, or combined. The microfluidic chip is directly clamped onto the region of interest on the tissue slide and the barcode flow step requires no experience in microfluidic control. Reagent dispensing is similar to pipetting into a microliter plate. Thus, DBiT-seq is potentially a platform technology that can be readily adopted by researchers from a wide range of biological and biomedical research fields.

HSR Microfluidic-Based Systems

To achieve high spatial resolution in a biological context, a detector (e.g., microfluidic device) should profile single cells and resolve spatial features small enough to meaningfully image patterns in the spatial arrangement of single cells and groups of cells.

Single-Cell Resolution. A detector can profile single cells if the detectors pixels are of approximately equal or smaller size than the cells. Given mammalian cell sizes that range from approximately 5-20 microns (µm) in length, this entails utilizing a detector with pixels of approximately the same length. Although cell sizes vary within samples, and some cells may be larger and some smaller than detector pixels with a constant size, the inventors have found that by combining optical imaging with digital spatial reconstruction they can select those pixels that circumscribe a single cell in order to achieve true single-cell resolution, even if only for subset of a reconstructed image.

Imaging Multicellular Motifs. In addition to profiling individual cells, it is also useful to consider the ability of an imaging detector to resolve spatial features as being determined by the center-center distance between imaging pixels. This perspective becomes more relevant when examining structures or motifs comprising groups of cells rather than individual cells, such as developing organoids in mouse embryos, as shown in the Examples provided herein.

The standard criterion used in data processing in both the time and spatial domains is the Nyquist Criterion, which dictates that given a center-center distance of a certain number of microns, a detector can faithfully reproduce imaged spatial features only down to approximately twice that center-center distance. Given mammalian cell sizes that range from approximately 5-20 µm and that typically neighbor each other face-to-face, features of cell neighborhoods should vary over distances equal to one or more cell lengths. Thus, to resolve these features, a the HSR detector provided herein, in some embodiments, includes pixels with center-center distance between pixels of not more than several cell lengths, e.g., 10-50 µm.

Imaging systems with pixel sizes and center-center distances much larger than these values cannot profile single cells or resolve features characteristic of cells or multicellular features and therefore do not display HSR. For example, a detector with pixels with size of 1 millimeter would probe distance scales of size 1-2 mm or larger and would not resolve single cells or multicellular features. As the present disclosure described elsewhere herein, pixels much smaller than this range (e.g., less than one micron) result in unsuitable detectors because their mappable area becomes extremely small and logistical tasks (including reagent loading and delivery) become impractical to carry out. The inventors have found that there is a critical range for high-throughput HSR detection with channel width and pitch (near the region of interest) between approximately 2.5-50 μm, for example.

Microfluidic Devices

Microfluidic devices (e.g., chips) may be used, in some embodiments, to deliver barcoded polynucleotides to a biological sample in a spatially defined manner. A system based on crossed microfluidic channels, such as those described here, have several key parameters that largely determine the spatial resolution and mappable area of the device. These include (1) the number of microfluidic channels (η/eta); (2) the microchannel width (ω/omega), measured in microns, i.e., the width of the open space in each microfluidic channel (tissue beneath these open spaces is imaged); and (3) microchannel pitch (Δ/delta), measured in microns, i.e., the width of the closed space between the end of one channel and the start of another channel (tissue beneath these closed spaces is not imaged). See the Examples for a further discussion of key challenges and solutions associated with the device parameters.

Device Parameters

The microfluidic devices provided herein include multiple microchannels characterized by a certain width, depth, and pitch. Surprisingly, the present disclosure demonstrates critical ranges for several microchannel parameters, required to achieve high spatial resolution at the single-cell level.

FIG. 1 depicts an exemplary detection scheme comprising two microfluidic devices. The first device flows reagents left to right and is drawn as a series of rows. The second device flows reagents from top to bottom and is drawn as a series of columns. The pixels of the detector comprise the overlap areas between the two sets of shapes, and as can be seen in the drawing such a geometry endows the squares with edge length w microns. As an illustrative example, assume a detection scheme that utilizes microfluidic devices with η=50, ω=10 microns, and Δ=10 microns. Referring to FIG. 1, this detector will feature pixels that are squares with edge length 10 microns, and the distance between squares in the horizontal and vertical directions is equal to 20 microns. This means it can profile single cells that are approximately 10 microns or larger and resolve spatial features (e.g., characteristics of cell neighborhoods) that are 40 microns or larger. As we have seen in this example, independently of some details of the embodiment, such microfluidic-based detectors will display certain performance characteristics determined by the design and the design parameters. These include the following: (1) the ability to profile individual cells; (2) minimum length scale of spatial feature reproduction; and (3) the size of the mappable area.

These performance characteristics exert tension upon one another and therefore cannot be chosen independently. For example, it is possible to design a device with arbitrarily fine spatial resolution by decreasing ω and Δ, even down to nanometer scale, as has been reported elsewhere. However, doing so would not result in a practical detector for examining tissue sections at single-cell resolution, as the mappable area of the device would be correspondingly small (see, e.g., FIG. 2). On the other hand, drastically increasing the mappable area of the device by increasing w and A to very large values such as 1-2 mm (which has also been reported) would result in extremely coarse spatial resolution unsuitable for high spatial resolution imaging. Thus there is a tradeoff between these design parameters that must be navigated to achieve a detector with both high spatial resolution and mappable area appropriately large for addressing the needs of the research community in investigating tissue samples with spatial features as small as cells but cell neighborhoods that can vary in biologically meaningful ways over distances of hundreds of microns.

Figure 2:
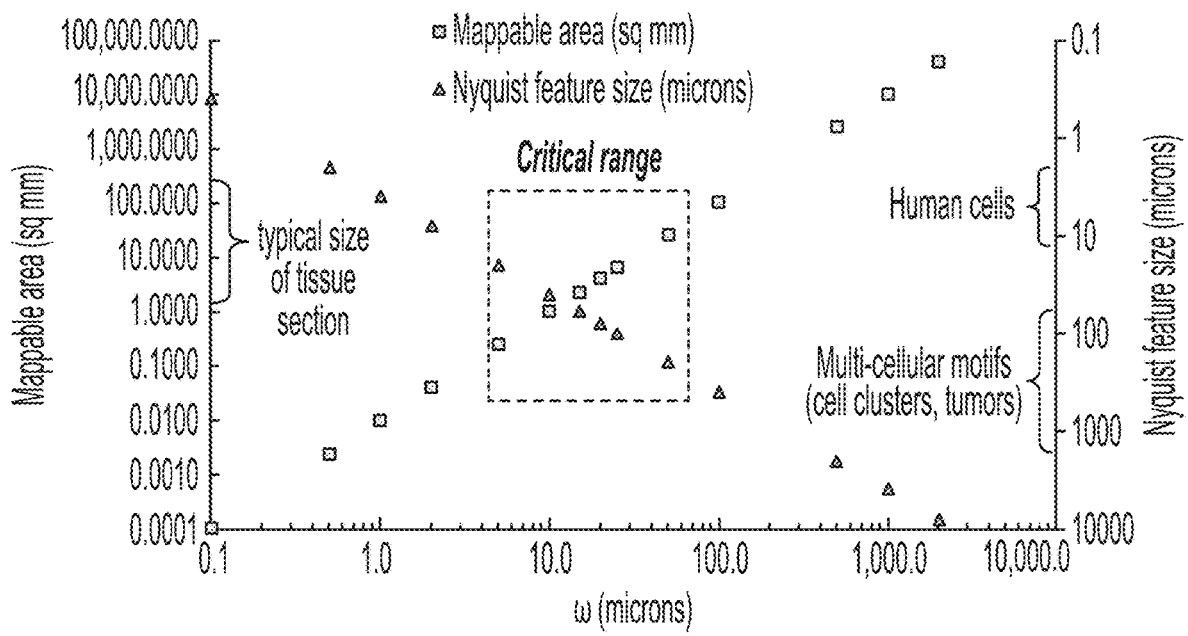
FIG. 2. Graph depicting device performance v. channel width. This image depicts the tradeoff between spatial resolution and mappable area in microfluidic detectors compared to biological benchmarks. It is assumed that the tissue has been mounted on a standard 25 mm×75 mm microscope slide, as is standard practice in pathology and there is room therefore for approximately 50 inlets, outlets, and associated channel routing area.

One contributing factor to this tension is the fact that in a single-layer microfluidic device n, the number of channels, cannot be increased without limit. This is because each channel must be fed by inlets and lead to an outlet and must approach and recede from the region of interest without intersecting other channels on the same device. The inventors have found that it is possible to fit approximately 50 inlet and outlet ports while ensuring the device is still practical to fabricate and fill with reagents by hand. FIG. 2 shows the performance characteristics for 50 channel devices with various microchannel widths. It is also assumed in this example that the channel width and spacing (parameters ω and Δ) are equal. Clearly, even if it were practical to create nano-channels with width down to 100 nanometers, such a device would assay a tiny portion of a tissue section, which range in size from 600 microns (for some tumor cores) to centimeters (for human biopsies, e.g. whole-tumor sections). On the other extreme, devices have been reported utilizing macro-channels with up to 2 mm in width. While these could map out a large area (much larger than most tissue sections), they do not do so at high spatial resolution.

Number of microchannels. In some embodiments, a first set of barcoded polynucleotides is delivered through a first microfluidic chip that comprises parallel microchannels positioned on a surface of the biological sample. In some embodiments, a first microfluidic chip comprises at least 5, at least 10, at least 20, at least 30, at least 40, or at least 50 parallel microchannels. In some embodiments, a first microfluidic chip comprises 5, 10, 20, 30, 40, or 50 parallel microchannels. In some embodiments, a first microfluidic chip comprises 5 to 100 parallel microchannels (e.g., 5-10, 5-25, 5-50, 5-75, 10-25, 10-50, 10-75, 10-100, 25-0, 25-27, 25-100, 50-75, or 50-100 parallel microchannels). In some embodiments, a second set of barcoded polynucleotides is delivered through a second microfluidic chip that comprises parallel microchannels that are positioned on the biological sample perpendicular to the direction of the microchannels of the first microfluidic chip. In some embodiments, a second microfluidic chip comprises at least 5, at least 10, at least 20, at least 30, at least 40, or at least 50 parallel microchannels. In some embodiments, a second microfluidic chip comprises 5, 10, 20, 30, 40, or 50 parallel microchannels. In some embodiments, a second microfluidic chip comprises 5 to 100 parallel microchannels (e.g., 5-10, 5-25, 5-50, 5-75, 10-25, 10-50, 10-75, 10-100, 25-0, 25-27, 25-100, 50-75, or 50-100 parallel microchannels).

Microchannel width. Data in accordance with the present disclosure has shown that while microchannels having a width of 5 μm could be reproducibly manufactured via soft lithographic techniques, for example, dimensions this small were prone to blockage and/or tissue section impaction. The data shows that the highest resolution was achieved with microchannels having a width of at least 10 μm. Thus, in some embodiments, a microchannel has a width of at least 10 μm (e.g., at least 15 μm, at least 20 μm, at least 25 μm, at least 30 μm, at least 35 μm, at least 40 μm, or at least 50 μm). In some embodiments, a microchannel has a width of 10 μm, 15 μm, 20 μm, 25 μm, 30 μm, 35 μm, 40 μm, or 50 μm. In some embodiments, a microchannel has a width of 10 μm to 150 μm (e.g., 10-125 μm, 10-100 μm, 25-150 μm, 25-125 μm, 25-100 μm, 50-150 μm, 50-125 μm, or 50-100 μm).

Figure 3:
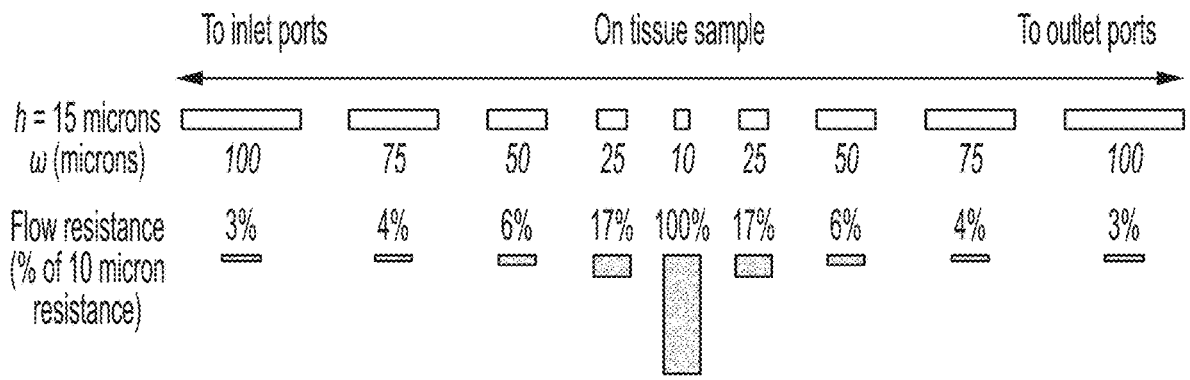
FIG. 3. Example schedule for dynamically altering microchannel width. Dynamically altering microchannel width in the 10 µm device reduces the incidence of blockages due to dust and to reduce overall device flow resistance per unit length (estimated via resistance proportional to $12/(1-0.63 h\omega))(1/h^3\omega)))$. Drastically larger channel cross sections reduce flow resistance, enabling gentle vacuum pulling and therefore less chance of tissue damage or clogged channels. Other schedules are possible, following the general principle that channels should stay as wide as possible for as long as possible.

Variable width. Early data showed that microchannel devices with microchannels having constant width, e.g., same width along the length of the microchannel, were often vulnerable to blockage by particulate (e.g., dust), impacting flow or the application of negative pressure, with such errors occurring more frequently on devices with narrower microchannels (e.g. ~10 µm). To overcome this complication, the present disclosure provides variable width microchannels having a width at the outlet and inlet ports that is greater than (e.g., at least 10% greater than, e.g., 10-50% greater than, e.g., 10%, 15%, 20%, 25%, 30%, 35%, 40%, 45%, or 50% greater than) the width of the microchannel near/at the region of interest (e.g., wide near the inlet and outlet ports, with width gradually reducing as the channel approaches the region of interest-FIG. 3).

Variable channel width also eases fluid flow through the microfluidic channels. In microchannels with a rectangular cross-section, hydrodynamic resistance per unit length is proportional to an amount approximated by the formula $12/(1-0.63\, h\omega)\, (1/h^3\omega)$, where h represents the channel height (shown as the vertical dimension in FIG. 3). This formula was used to generate the approximate relative flow resistance values shown in FIG. 3. For example, a 50 µm device features 100 µm channels which shrink to 50 µm only near the region of interest. As another example, a 25 µm device's channels shrink to 100, 50, and then 25 µm near the region of interest. As yet another example, a 10 µm device's channels range from 100, 50, 25, and then 10 µm near the region of interest.

In some embodiments, a microchannel has a width of 50 µm to 150 µm near the inlet and outlet ports and a width of 10 µm to 50 µm near the region of interest. For example, a microchannel may have a width of 100 µm near the inlet and outlet ports and width of 50 µm near the region of interest. As another example, a microchannel may have a width of 100 µm near the inlet and outlet ports and width of 25 µm near the region of interest. As yet another example, a microchannel may have a width of 100 µm near the inlet and outlet ports and width of 10 µm near the region of interest. In some embodiments, a microchannel has a width of 50, 60, 70, 80, 90, 100, 110, 120, 130, 130, 140, or 150 µm near the inlet and outlet ports. In some embodiments, a microchannel has a width of 10, 20, 30, 40, or 50 µm near the region of interest.

Microchannel height. Data in accordance with the present disclosure has also shown that the most stable and least error-prone microfluidic devices, at least those manufactured from PDMS, have microchannel heights approximately equal (e.g., within 10%) to the microchannel width. In some embodiments, a microchannel has a height of at least 10 µm (e.g., at least 15 µm, at least 20 µm, at least 25 µm, at least 30 µm, at least 35 µm, at least 40 µm, or at least 50 µm). In some embodiments, a microchannel has a height of 10 µm, 15 µm, 20 µm, 25 µm, 30 µm, 35 µm, 40 µm, or 50 µm). In some embodiments, a microchannel has a height of 10 µm to 150 µm (e.g., 10-125 µm, 10-100 µm, 25-150 µm, 25-125 µm, 25-100 µm, 50-150 µm, 50-125 µm, or 50-100 µm). These heights have been tested and shown to be enough to provide clearance above dust or tissue blockages, for example, and low enough to provide the required rigidity and to prevent deformation of the channel during clamping and flow.

In some embodiments, a microchannel has a width of 10 µm and a height of 12-15 µm. In other embodiments, a microchannel has a width of 25 µm and a height of 17-22 µm. In yet other embodiments, a microchannel has a width of 50 µm and a height of 20-100 µm.

Microchannel pitch. The pitch is the distance between microchannels of a microfluidic device (e.g., chip). In some embodiments, the pitch of a microfluidic device is at least 10 µm (e.g., at least 15 µm, at least 20 µm, at least 25 µm, at least 30 µm, at least 35 µm, at least 40 µm, or at least 50 µm). In some embodiments, the pitch of a microfluidic device is at 10 µm, 15 µm, 20 µm, 25 µm, 30 µm, 35 µm, 40 µm, or 50 µm. In some embodiments, the pitch of a microfluidic device is at 10 µm to 150 µm (e.g., 10-125 µm, 10-100 µm, 25-150 µm, 25-125 µm, 25-100 µm, 50-150 µm, 50-125 µm, or 50-100 µm).

Negative Pressure Systems

Many microfluidics platforms utilize positive pressure via syringe pumps, peristaltic pumps, and other types of positive pressure pumps whereby fluid is pumped from a reservoir into the device. Generally, a connection is made to interface the reservoir/pump assembly with the microfluidic device; often this takes the form of tubes terminating in pins that plug into inlet ports on the device. However, this type of system requires laborious and time-consuming fine-tuning of the assembly process associated with several drawbacks. For example, if the pins are inserted insufficiently deep into the inlet wells or the pin diameter is too small relative to the ports, then upon activation of the pumps, fluid pressure will eject the tube from the port. As another example, if the pins are inserted excessively deep into the wells, then upon activation of the pumps, fluid pressure will separate the microfluidic device from the glass substrate, resulting in leakage. While epoxying pins into ports and/or bonding the microfluidic device to the substrate via plasma bonding or thermal bonding might address the foregoing drawbacks, these strategies are make it difficult to disassemble the system in a non-destructive way, resulting in component loss and are impractical when the substrate contains sensitive material, such as a tissue section, and/or antibodies.

The methods and devices provided herein, by contrast, overcome the drawbacks associated with existing microfluidic platforms by using, in some embodiments, a negative pressure system that utilizes a vacuum to pull liquid through the device from the back, rather than positive pressure to push it through the device from the front. This has several advantages, including, for example, (i) reducing the risk of leakage by pulling together the device and substrate and (ii) increasing efficiency and ease of use—the vacuum can be applied to all outlet ports, unlike pins, which must be inserted individually into each inlet port. Using a negative pressure system saves several hours per run of fine-tuning and pin assembly.

Thus, in some embodiments provided herein, the barcoded polynucleotides are delivered to a region of interest through a microfluidic device (e.g., chip) using negative pressure (vacuum). In some embodiments, delivery of a first set of barcoded polynucleotides is delivered through a first microfluidic device using a negative pressure system. In some embodiments, delivery of a second set of barcoded polynucleotides is delivered through a second microfluidic device using a negative pressure system.

Inlet and Outlet Ports

Data in accordance with the present disclosure has further shown that microfluidic devices having a common outlet port are vulnerable to backflow of reagents into the region of interest through incorrect microchannels, particularly during device disassembly. Such backflow can result in incorrect addressing of target molecules, resulting in an incorrect reconstruction of a spatial map of target molecules performed in later steps of the methods (e.g., after sequencing). To limit the possibility of reagent backflow, the microfluidic devices provided herein, in some embodiments, include microchannels that each have its own inlet port and outlet port. For example, a microchannel device having 50 microchannels has 50 inlet ports and 50 outlet ports. This device design eliminates backflow. Thus, this design has reduced the rate of reconstruction errors (e.g., crosstalk events) by at least 90% (at least 95%, at least 98%, or 100%).

Inlet wells. Initial microfluid device designs employed small (1 mm) inlet wells without filters and long stretches of small cross-section channels. This posed several challenges. First, punching PDMS, for example, creates small particulate debris, sometimes of similar size to the microfluidic channel cross section. This debris when streamed to the region of interest often caused blockages and flow restrictions. By including filter components with openings ~10 microns in front of every inlet well, these kinds of errors were drastically reduced.

Inlet filters. Second, the extremely small (1 mm diameter) inlet well footprints posed great difficulty in accurately punching holes to provide for reagent delivery into the inlets. It was difficulty to pipette reagents into the inlet holes as well. By increasing the hole diameter from 1 mm to 1.85 mm, it was possible to greatly facilitate chip fabrication and reagent loading.

Microchannel length. Thirdly, with initial microfluidic designs, the length of the portion of channels with the smallest cross-sections were too long, resulting in drastically increased flow resistance. By increasing the length of the portion of the channels with large cross section (e.g., 50-100 microns) and reducing the length of the portions with small cross section (e.g., 10-25 microns) we were able to more reliably flow reagents at lower vacuum pressures.

Figure 4:
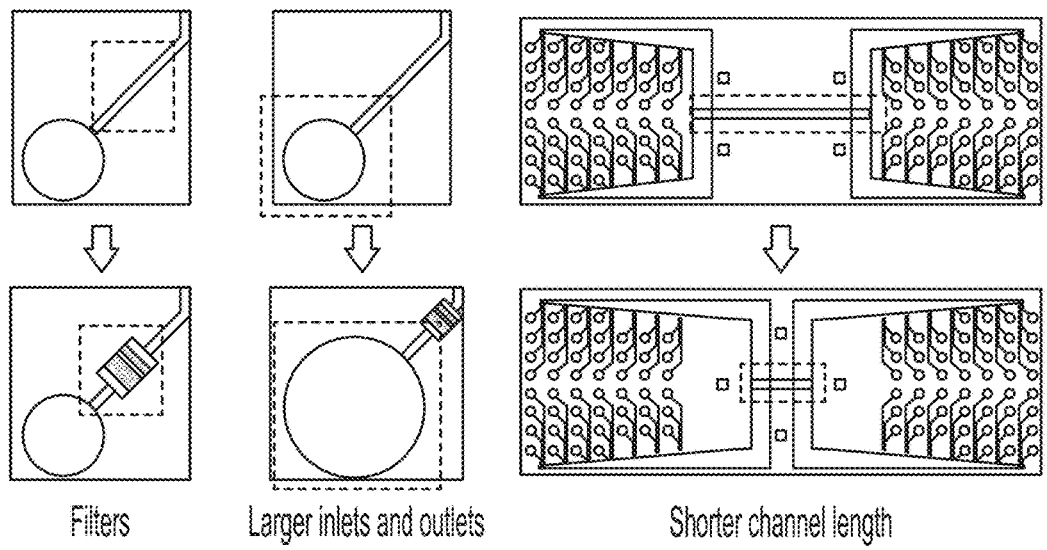
FIG. 4. Three design innovations which greatly improved device performance and reduced failure rates.

FIG. 4 depicts these three design innovations that greatly improved device performance and reduced failure rates.

Clamping

Figure 7A:
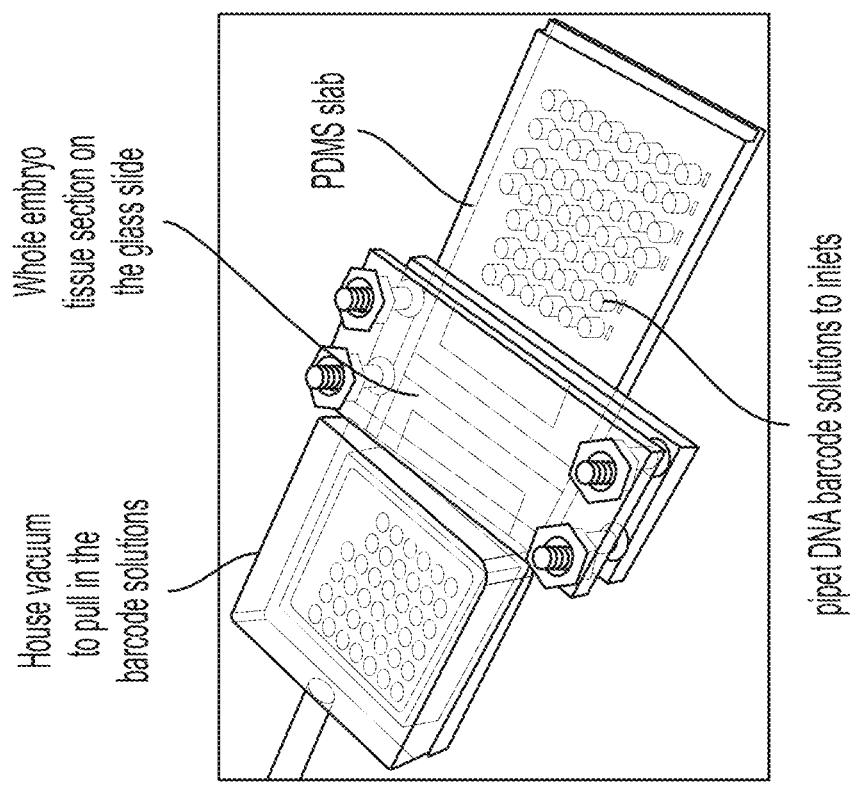
FIGS. 7A-7G. Validation of DBiT.
Figure 7B:
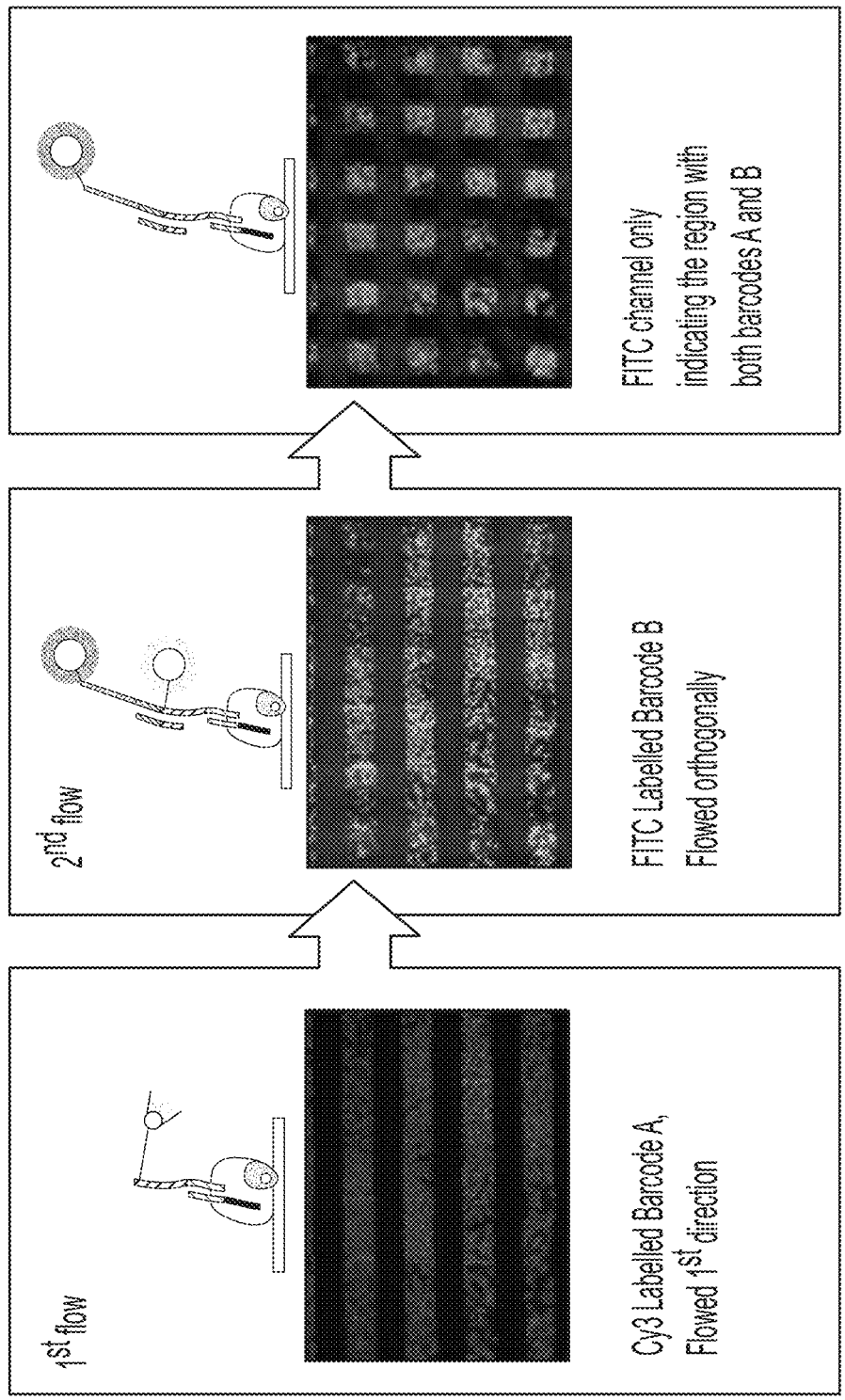
Figure 7E:
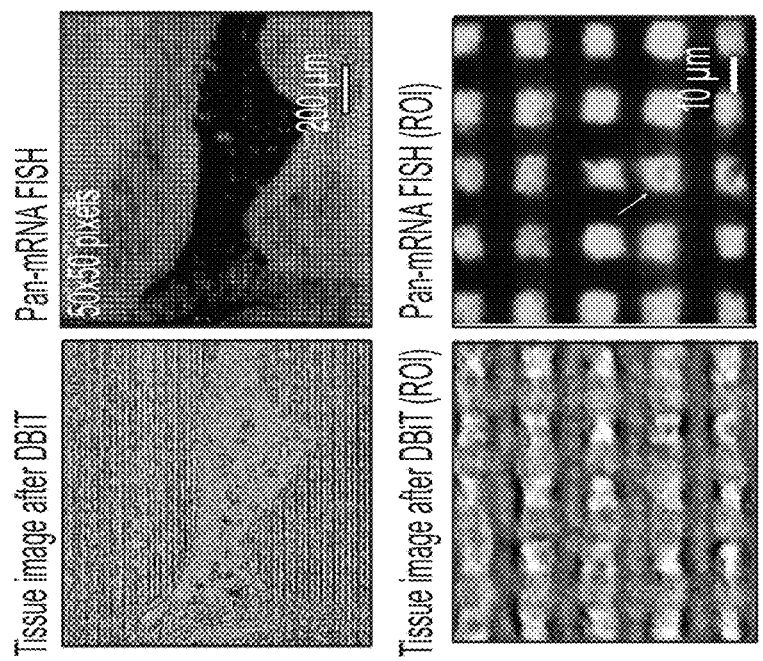
Figure 7D:
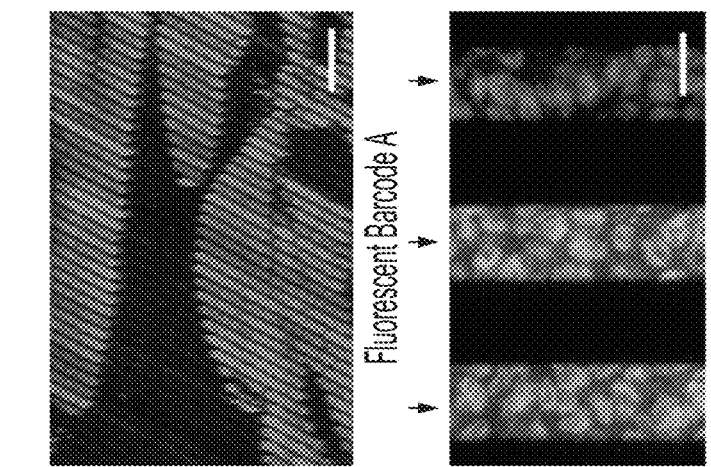
Figure 7C:
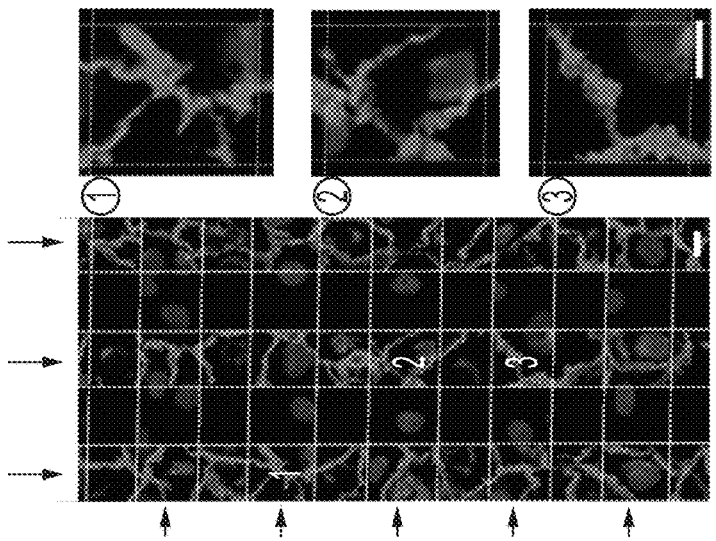
Figure 7F:
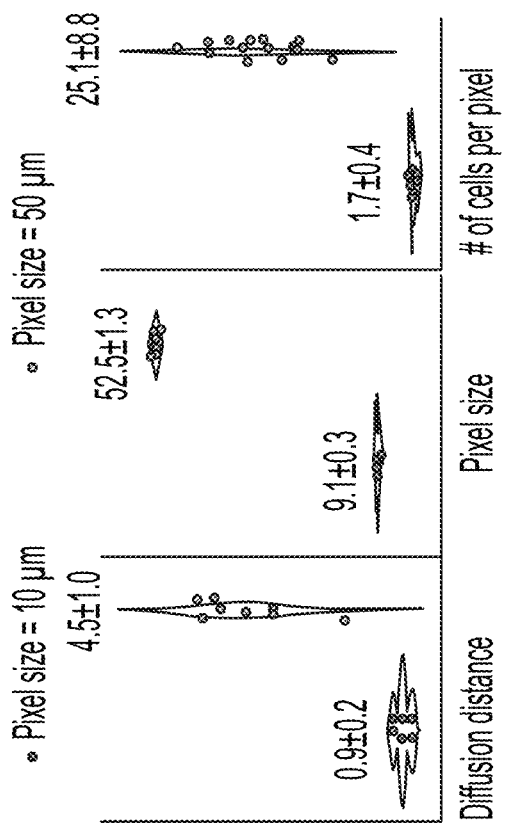

During initial experiments used to test the microfluidic devices and methods provided herein, frequent leakage of reagents occurred between channels on the region of interest, as evidence by fluorescent dye analyses (sec. e.g., Example 4, FIG. 7F). Convention clamping mechanisms proved cumbersome and introduced difficulties in addressing inlet and outlet ports. To address the issues identified, a new clamping mechanism was developed, which combines specific clamping parameters including localized clamping and specific clamping forces. A range of clamping forces was investigated—in some instances, the clamping force was insufficient to prevent leaks, and in other cases the clamping force was so great that flow was significantly reduced or even stopped entirely in some or all microchannels. Without being bound by theory, it was though that the was due to the channel cross section being deformed by the clamping force, reducing the cross-sectional area and making the channels more vulnerable to blockages due, for example, either to dust or the tissue occupying the entire microchannel.

Surprisingly, clamping the microfluidic device to the substrate in a localized manner, only above the region of interest, with a clamping force in the range of 5 to 50 newtons of force reduced leakage of reagents. In some embodiments, the clamping force is 5 to 50 newtons of force or 5 to 100 newtons of force (e.g., 5-75, 5-50, 5-25, 10-100, 10-75, 10-50, 10-25, 25-100, 25-75, 25-50, 50-100, 50-75, or 75-100 newtons of force, such as 5, 10, 15, 20, 25, 30, 35, 40, 45, 50, 55, 60, 65, 70, 75, 80, 85, 90, 95, or 100 newtons of force).

Microfluid chips, in some embodiments, are fabricated from polydimethylsiloxane (PDMS). Other substrates may be used.

Samples

In some embodiments, a sample is a biological sample. Non-limiting examples of biological samples include tissues, cells, and bodily fluids (e.g., blood, urine, saliva, cerebrospinal fluid, and semen). The biological sample may be adult tissue, embryonic tissue, or fetal tissue, for example. In some embodiments, a biological sample is from a human or other animal. For example, a biological sample may be obtained from a murine (e.g., mouse or rat), feline (e.g., cat), canine (e.g., dog), equine (e.g., horse), bovine (e.g., cow), leporine (e.g., rabbit), porcine (e.g., pig), hircine (e.g., goat), ursine (e.g., bear), or piscine (e.g., fish). Other animals are contemplated herein.

In some embodiments, a biological sample is fixed, and thus is referred to as a fixed biological sample. Fixation (e.g., tissue fixation) refers to the process of chemically preserving the natural state of a biological sample, for example, for subsequent histological analysis. Various fixation agents are routinely used, including, for example, formalin (e.g., formalin fixed paraffin embedded (FFPE) tissue), formaldehyde, paraformaldehyde and glutaraldehyde, any of which may be used herein to fix a biological sample. Other fixation reagents (fixatives) are contemplated herein. In some embodiments, the fixed tissue is FFPE tissue.

In some embodiments, the biological sample is a tissue. In some embodiments, the biological sample is a cell. A biological sample, such as a tissue or a cell, in some embodiments, is sectioned and mounted on a surface, such as a slide (e.g., a glass microscope slide, such as a polylysine-coated glass microscope slide). In such embodiments, the sample may be fixed before or after it is sectioned. In some embodiments, the fixation process involves perfusion of the animal from which the sample is collected. In some embodiments, the fixation process involves formalin fixation followed by paraffin embedding.

Molecules of Interest

The molecules of interest in a biological sample may be any molecules present in the sample. Non-limiting examples include polynucleotides, polypeptides (e.g., protein), peptides, lipids, and carbohydrates. Examples of polynucleotides include, but are not limited to, DNA and RNA, such as messenger RNA (mRNA). Examples of polypeptides include, but are not limited to, proteins. The molecules of interest may be, for example, receptors, ligands, cytokines, growth hormones, growth factors, transcription factors, and enzymes. Other molecules of interest are contemplated herein.

Binder-DNA Tag Conjugates

Barcoding a molecule of interest present in a biological sample, in some embodiments, includes the use of binder-DNA tag conjugates, which include (i) a binder molecule that specifically binds to a molecule of interest (e.g., an antibody) and (ii) a DNA tag (e.g., a contiguous stretch of nucleotides), wherein the DNA tag comprises a binder barcode and a poly A sequence (e.g., at least 50, at least 100, ~1-100, e.g., 25-100, 50-100, or 75-100 contiguous adenine (A) nucleotides).

A binder molecule is any molecule that can bind to a molecule of interest, such as a polynucleotide, polypeptide, lipid, and/or carbohydrate, for a period of time sufficient to withstand the barcoding methods described herein (e.g., to produce the cDNA used for the sequencing reads). In some embodiments, the binder molecule is an antibody. Non-limiting examples of antibodies include whole antibodies, Fab antibody fragments, F(ab')$_2$ antibody fragments, monospecific Fab$_2$ fragments, bispecific Fab$_2$ fragments, trispecific Fab$_3$ fragments, single chain variable fragments (scFvs), bispecific diabodies, trispecific diabodies, scFv-Fc molecules, and minibodies. Other binder molecules include ligands (e.g., to detect receptor molecules of interest) and receptors (e.g., to detect ligand molecules of interest). Other molecules that bind polynucleotides, polypeptides, peptides, lipids, and/or carbohydrates are contemplated herein.

Barcoded Polynucleotides

Figure 5A:
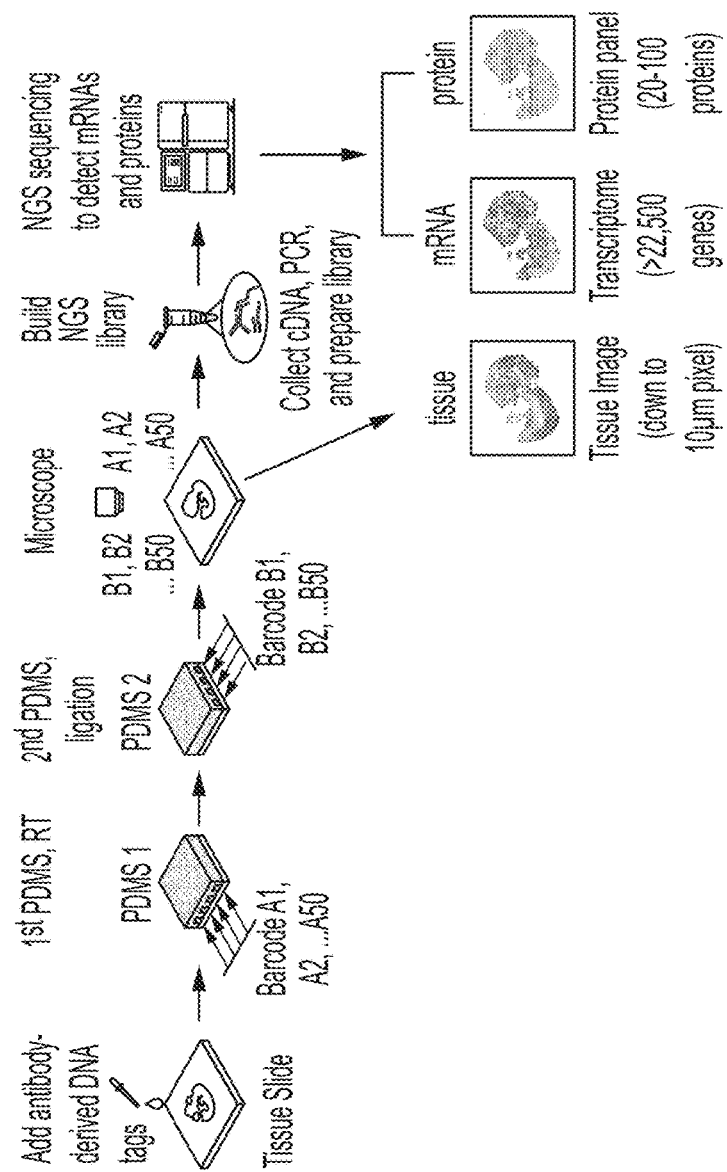
FIGS. 5A-5C. Design of the DBIT-seq platform.
Figure 5A:
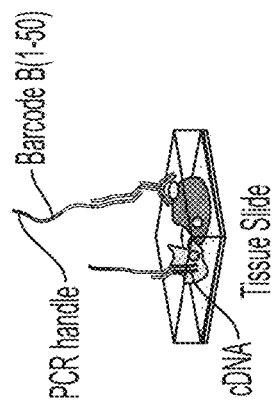
Figure 5A:
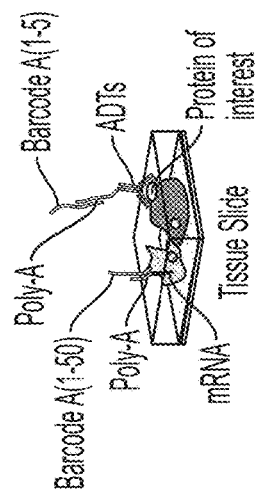
Figure 5B:
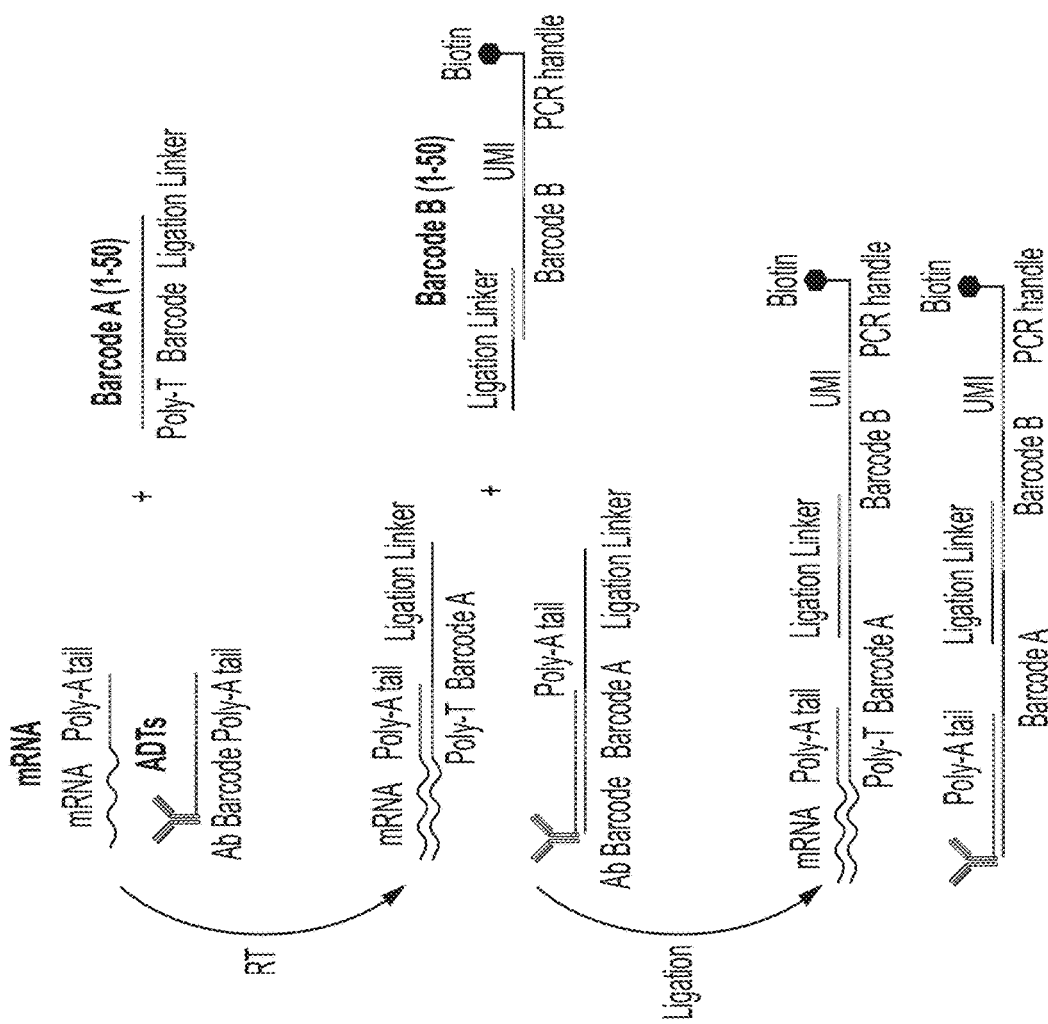

A non-limiting example of the barcoded polynucleotides (e.g., barcoded DNA) of the present disclosure is shown in FIG. 5B. In some embodiments, barcoded polynucleotides (e.g., of a first set of barcoded polynucleotides) include a ligation linker sequence, a spatial barcode sequence, and a polyT sequence. In some embodiments, barcoded polynucleotides (e.g., of a second set of barcoded polynucleotides) include a ligation linker sequence, a spatial barcode sequence, a unique molecular identifier (UMI) sequence, and a first PCR handle end sequence. In some embodiments, a PCR handle end sequence is terminally functionalized with biotin.

A ligation linker sequence is any sequence complementary to a sequence of a universal ligation linker, as provided herein. The length of a ligation linker sequence may vary. For example, a ligation linker sequence may have a length of 5 to 50 nucleotides (e.g., 5 to 40, 5 to 30, 5 to 20, 5 to 10, 10 to 50, 10 to 40, 10 to 30, or 10 to 20 nucleotides). In some embodiments, a ligation linker sequence may have a length of 5, 10, 15, 20, 25, 30, 35, 40, 45, or 50 nucleotides. Longer ligation linker sequences are contemplated herein. In some embodiments, a ligation linker sequence of a barcoded polynucleotide of one set (e.g., a first set) differ (e.g., have a different composition of nucleotides and/or a different length) from a ligation linker sequence of a barcoded polynucleotide of another set (e.g., a second set).

A barcode sequence is a unique sequence that can be used to distinguish a barcoded polynucleotide in a biological sample from other barcoded polynucleotides in the same biological sample. A spatial barcode sequence is a barcode sequence that is associated with a particular location in a biological sample (e.g., a tissue section mounted on a slide). The concept of "barcodes" and appending barcodes to nucleic acids and other proteinaceous and non-proteinaceous materials is known to one of ordinary skill in the art (see, e.g., Liszczak G et al. *Angew Chem Int Ed Engl.* 2019 Mar. 22; 58 (13): 4144-4162). Thus, it should be understood that the term "unique" is with respect to the molecules of a single biological sample and means "only one" of a particular molecule or subset of molecules of the sample. Thus, a "pixel" (also referred to as a "patch) comprising a unique spatially addressable barcoded conjugate (or a unique subset of spatially addressable barcoded conjugates) is the only pixel in the sample that includes that particular unique barcoded polynucleotide (or unique subset of barcoded polynucleotides), such that the pixel (and any molecule(s) within the pixel) can be identified based on that unique barcoded conjugate (or a unique subset of barcoded conjugates).

For example, as shown in FIG. 5A, the polynucleotides of subset A1 (of Barcode A) are coded with a specific barcode sequence, while the polynucleotides of subsets A2, A3, A4, etc. are each coded with a different barcode sequence, each barcode specific to the subset. Likewise, the polynucleotides of subset B1 (of Barcode B) are coded with a specific barcode sequence, while the polynucleotides of subsets B2, B3, B4, etc. are each coded with a different barcode sequence, each barcode specific to the subset. Thus, each overlapping patch, which includes a unique combination of Barcode A subsets and Barcode B subsets, contains a unique composite barcode (Barcode A+Barcode B). For example, an overlapping pixel (patch) containing A1+B1 barcodes is uniquely coded relative to its neighboring overlapping patches, which contain A2+B1 barcodes, A1+B2 barcodes, A2+B2 barcodes, etc.

The length of a spatial barcode sequence may vary. For example, a spatial barcode sequence may have a length of 5 to 50 nucleotides (e.g., 5 to 40, 5 to 30, 5 to 20, 5 to 10, 10 to 50, 10 to 40, 10 to 30, or 10 to 20 nucleotides). In some embodiments, a spatial barcode sequence may have a length of 5, 10, 15, 20, 25, 30, 35, 40, 45, or 50 nucleotides. Longer spatial barcode sequences are contemplated herein.

A poly T sequence is simply a contiguous sequence of thymine (T) residues. Likewise, a poly A sequence is simply a contiguous sequence of adenine (A) residues. The length of a polyT or polyA sequence may vary. For example, a polyT or poly A sequence may have a length of 5 to 50 nucleotides (e.g., 5 to 40, 5 to 30, 5 to 20, 5 to 10, 10 to 50, 10 to 40, 10 to 30, or 10 to 20 nucleotides). In some embodiments, a polyT or poly A sequence may have a length of 5, 10, 15, 20, 25, 30, 35, 40, 45, or 50 nucleotides. Longer polyT or poly A sequences are contemplated herein.

As is known in the art, unique molecular identifiers (UMI) are molecular (e.g., DNA or RNA) tags that are typically used to detect and quantify unique mRNA transcripts (see, e.g., Islam S et al. *Nat Methods* 2014 February; 11 (2): 163-6; Smith T et al. *Genome Res.* 2017 March; 27 (3): 491-499; and Liu D *Peer J.* 2019 Dec. 16:7: e8275). In some embodiments, the UMI is a barcode sequence. For example, the UMI may a degenerate nucleotide sequence having a length of 5 to 50 nucleotides (e.g., 5 to 40, 5 to 30, 5 to 20, 5 to 10, 10 to 50, 10 to 40, 10 to 30, or 10 to 20 nucleotides), which may be used to distinguish a barcoded polynucleotide or a spatially addressable barcoded conjugate from other polynucleotides (e.g., other barcoded polynucleotides and/or conjugates) in a biological sample. In some embodiments, a UMI may have a length of 5, 10, 15, 20, 25, 30, 35, 40, 45, or 50 nucleotides.

Universal Ligation Linkers

Also provided herein are universal ligation linkers, which may be a polynucleotide, for example, that includes (i) a first nucleotide sequence that is complementary to and/or binds to the linker sequence of the barcoded polynucleotides of a first set of barcoded polynucleotides, and (ii) a second nucleotide sequence that is complementary to and/or binds to the linker sequence of the barcoded polynucleotides of a second set of barcoded polynucleotides. The purpose of the universal ligation linkers is to serve as a bridge to join barcoded polynucleotides from two different sets (e.g., the first set comprising a ligation linker sequence, a spatial barcode sequence, and a polyT sequence and the second set comprising a ligation linker sequence, a spatial barcode sequence, a unique molecular identifier (UMI) sequence, and a first PCR handle end sequence). The length of a universal ligation linker may vary. For example, a universal ligation linker may have a length of 10 to 100 nucleotides (e.g., 10 to 90, 10 to 80, 10 to 70, 10 to 60, 10 to 50, 10 to 40, 10 to 30, 10 to 20, 20 to 100, 20 to 90, 20 to 80, 20 to 70, 20 to 60, 20 to 50, 20 to 40, or 20 to 30 nucleotides). In some embodiments, a universal ligation linker may have a length of 10, 15, 20, 25, 30, 35, 40, 45, 50, 55, 60, 65, 70, 75, 80, 85, 90, 95, or 100 nucleotides. Longer universal ligation linkers are contemplated herein.

The universal ligation linkers are typically added to a biological sample following the delivery of the second set of barcoded polynucleotides, although, in some embodiments, universal ligation linkers are annealed to the barcoded polynucleotides of the second set prior to delivery of the second set.

Methods

In some embodiments, the methods comprise delivering to a biological tissue a first set of barcoded polynucleotides. A first set may include any number of barcoded polynucleotides. In some embodiments, a first set include 5 to 1000 barcoded polynucleotides. For example, a first set may comprise 5 to 900, 5 to 800, 5 to 700, 5 to 600, 5 to 500, 5 to 400, 5 to 300, 5 to 200, 5 100, 10 to 1000, 10 to 900, 10 to 800, 10 to 700, 10 to 600, 10 to 500, 10 to 400, 10 to 300, 10 to 200, 20 to 1000, 20 to 900, 20 to 800, 20 to 700, 20 to 600, 20 to 500, 20 to 400, 20 to 300, 20 to 200, 50 to 1000, 50 to 900, 50 to 800, 50 to 700, 50 to 600, 50 to 500, 50 to 400, 50 to 300, or 50 to 200 barcoded polynucleotides. More than 1000 barcoded polynucleotides in a first set are contemplated herein.

Data has shown that permeabilization facilitates access to cytoplasmic analytes such as mRNA. However, introducing a permeabilization step prior to delivering the first set of barcoded polynucleotides, for example, through the first microfluidic device, resulted in increasing the rate at which reagents diffuse through the tissue matrix, including through the tissue directly beneath the walls of the device. This led to drastically increased leakage of reagents from microchannel to microchannel beneath the microchannel walls, leading to reconstruction errors. By modifying the protocol to introduce permeabilization agents after applying the first microfluidic device, thereby only increasing the rate of diffusion of reagents through tissue directly beneath microfluidic microchannels (and not microchannel walls), the rate of crosstalk failure events we was drastically reduced in each of the devices tested (10, 25, and 50 micron channel devices). Thus, in some embodiments, the methods comprise delivering to a biological tissue permeabilization reagents (e.g., detergents such as Triton-X 100 or Tween-20). In some embodiments, the methods comprise delivering to a biological tissue a first set of barcoded polynucleotides, and then delivering to the biological tissue permeabilization reagents.

In some embodiments, the methods comprise producing cDNAs linked to barcoded polynucleotides of the first set. In some embodiments, the methods comprise exposing the biological sample to a reverse transcription reaction. Methods of producing cDNA are known and an example protocol is provided herein.

In some embodiments, the methods comprise delivering to the biological sample a second set of barcoded polynucleotides. A second set may include any number of barcoded polynucleotides. In some embodiments, a second set include 5 to 1000 barcoded polynucleotides. For example, a first set may comprise 5 to 900, 5 to 800, 5 to 700, 5 to 600, 5 to 500, 5 to 400, 5 to 300, 5 to 200, 5 100, 10 to 1000, 10 to 900, 10 to 800, 10 to 700, 10 to 600, 10 to 500, 10 to 400, 10 to 300, 10 to 200, 20 to 1000, 20 to 900, 20 to 800, 20 to 700, 20 to 600, 20 to 500, 20 to 400, 20 to 300, 20 to 200, 50 to 1000, 50 to 900, 50 to 800, 50 to 700, 50 to 600, 50 to 500, 50 to 400, 50 to 300, or 50 to 200 barcoded polynucleotides. More than 1000 barcoded polynucleotides in a second set are contemplated herein.

In some embodiments, the methods comprise joining barcoded polynucleotides of the first set to barcoded polynucleotides of the second set. In some embodiments, the methods comprise exposing the biological sample to a ligation reaction, thereby producing a two-dimensional array of spatially addressable barcoded conjugates bound to molecules of interest, wherein the spatially addressable barcoded conjugates comprises a unique combination of barcoded polynucleotides from the first set and the second set. Ligation methods are known and an example protocol is provided herein.

In some embodiments, the methods comprise imaging the biological sample to produce a sample image. An optical microscope or a fluorescence microscope, for example, may be used to image the sample.

cDNA Extraction

In some embodiments, the methods comprise extracting cDNAs from the biological sample. Nucleic acid extractions methods are known and an example protocol is provided herein. Unexpectedly, however, simply lysing the entire biological sample, in some embodiments, introduces complications into downstream processes. For example, because the first and second stage flow patterns intersect in regions outside the region of interest as well as in regions inside the region of interest, lysing the entire tissue section or regions larger than the region of interest results, in some instances, in incorrect spatial reconstruction following sequencing. The presence of intersections outside of the region of interest results in target analytes tagged with a valid spatial address, however the location no longer matches the reconstructed address, resulting in spatial reconstruction errors. Another complication results from the high viscosity of the lysis buffer, which makes it difficult to constrain the buffer to the region of interest.

To address the complications above, the present disclosure provides a custom-built clamp with an opening positioned directly over the region of interest, which enables targeted delivery of the lysis buffer (or other extraction reagent) to the region of interest. In addition, experimental data demonstrated that the clamping pressure of the device (e.g., 10-100 newtons of force), in some instances, determined, at least in part, the extend of lysis buffer leakage from tissue sample.

Sequencing

The methods provided herein, in some embodiments, include a sequencing step. For example, next generation sequencing (NGS) methods (or other sequencing methods) may be used to sequence the molecules identified within a region of interest. See, e.g., Goodwin S et al. *Nature Reviews Genetics* 2016; 17: 333-351, incorporated herein by reference. In some embodiments, the methods comprise preparing an NGS library in vitro. Thus, in some embodiments, the methods comprise sequencing the cDNAs to produce cDNA reads. Other sequencing methods are known, and an example protocol is provided herein.

In some embodiments, the sequencing comprises template switching the cDNAs to add a second PCR handle end sequence at an end opposite from the first PCR handle end sequence, amplifying the cDNAs, producing sequencing constructs via tagmentation, and sequencing the sequencing constructs to produce the cDNA reads. Template-switching (also known as template-switching polymerase chain reaction (TS-PCR)) is a method of reverse transcription and polymerase chain reaction (PCR) amplification that relies on a natural PCR primer sequence at the polyadenylation site, also known as the poly(A) tail, and adds a second primer through the activity of murine leukemia virus reverse transcriptase (see, e.g., Petalidis L. et al. *Nucleic Acids Research.* 2003:31 (22): e142). Tagmentation refers to a modified transposition reaction, often used for library preparation, and involves a transposon cleaving and tagging double-stranded DNA with a universal overhang. Tagmentation methods are known.

In some embodiments, the methods comprise constructing a spatial molecular expression map of the biological sample by matching the spatially addressable barcoded conjugates to corresponding cDNA reads. In some embodiments, the methods comprise identifying the location of the molecules of interest by correlating the spatial molecular expression map to the sample image. Examples of these methods steps are described above and in the Examples section.

Compositions

Also provided herein are intermediate compositions produced during the methods of constructing a molecular expression map of a biological sample, for example. In some embodiments, such compositions comprise a biological sample comprising messenger ribonucleic acids (mRNAs) comprising a poly A tail and/or proteins linked to binder-DNA tag conjugates. In some embodiments, the compositions comprise spatially addressable barcoded conjugates comprising a PCR handle sequence, a universal molecular identifier (UMI) sequence, a first spatial barcode sequence, a ligation linker sequence, a second spatial barcode sequence, and a polyT sequence, wherein the spatially addressable barcoded conjugates are bound to the mRNAs and/or proteins through hybridization of the poly A and polyT sequences. In some embodiments, the compositions comprise a polynucleotide comprising a universal complementary ligation linker sequence bound to the ligation linker sequence of (b).

Kits

Also provided herein are kits for producing a molecular expression map of a biological sample, for example. In some embodiments, the kits comprise a first set of barcoded polynucleotides that comprise a ligation linker sequence, a spatial barcode sequence, and a polyT sequence. In some embodiments, the kits comprise a second set of barcoded polynucleotides that comprise a ligation linker sequence, a spatial barcode sequence, a unique molecular identifier (UMI) sequence, and a first PCR handle end sequence, optionally wherein the first PCR handle end sequence is terminally functionalized with biotin. In some embodiments, the kits comprise a polynucleotide comprising a universal complementary ligation linker sequence capable of binding to the ligation linker sequences of the barcoded polynucleotides of the first and second sets.

In some embodiments, the kits comprise a collection of binder-DNA tag conjugates that comprises (i) a binder molecule that specifically binds to a molecule of interest and (ii) a DNA tag that comprises a binder barcode and a poly A sequence.

In some embodiments, the kits comprise at least one reagent selected from tissue fixation reagents, reverse transcription reagents, ligation reagents, polymerase chain reaction reagents, template switching reagents, and sequencing reagents.

In some embodiments, the kits comprise tissue slides (e.g., glass slides).

In some embodiments, the kits comprise at least one microfluidic chip that comprises parallel microchannels.

ADDITIONAL EMBODIMENTS

The present disclosure provides the following additional embodiments:
1. A method for producing a molecular expression map of a biological sample, the method comprising: (a) barcoding molecules of interest in a biological sample by delivering to the biological sample spatially addressable barcoded conjugates; and (b) producing a molecular expression map of the biological sample by imaging the sample, sequencing the spatially addressable barcoded conjugates, and correlating sequences of the spatially addressable barcoded conjugates to an image of the sample.
2. The method of paragraph 1, wherein the biological sample is a fixed biological sample.
3. The method of paragraph 1 or 2, wherein the biological sample comprises a cell, optionally a population of cells, and/or a tissue.
4. The method of any one of paragraphs 1-3 wherein the molecules of interest are selected from ribonucleic acids (RNAs), optionally messenger RNAs (mRNAs), deoxyribonucleic acids (DNAs), optionally genomic DNAs (gDNAs), and proteins.
5. The method of any one of paragraphs 1-4, comprising delivering to the biological sample binder-DNA tag conjugates that comprise (i) a binder molecule that specifically binds to a molecule of interest and (ii) a DNA tag, wherein the DNA tag comprises a binder barcode and a poly A sequence.
6. The method of paragraph 5, wherein the binder molecule is an antibody.
7. The method of paragraph 6, wherein the antibody is selected from whole antibodies, Fab antibody fragments. F(ab')$_2$ antibody fragments, monospecific Fab$_2$ fragments, bispecific Fab$_2$ fragments trispecific Fab$_3$ fragments, single chain variable fragments (scFvs), bispecific diabodies, trispecific diabodies, scFv-Fc molecules, and minibodies.
8. The method of any one of paragraphs 1-7, comprising delivering to the biological tissue a first set of barcoded polynucleotides.
9. The method of paragraph 8, wherein the barcoded polynucleotides of the first set comprise a ligation linker sequence, a spatial barcode sequence, and a polyT sequence.
10. The method of paragraph 8 or 9, wherein the first set of barcoded polynucleotides is delivered through a first microfluidic chip that comprises parallel microchannels positioned on a surface of the biological sample.
11. The method of paragraph 10, wherein the first microfluidic chip comprises at least 10, at least 20, at least 30, at least 40, or at least 50 parallel microchannels.
12. The method of any one of paragraphs 8-11, further comprising producing cDNAs linked to barcoded polynucleotides of the first set by exposing the biological sample to a reverse transcription reaction.
13. The method of paragraph 12 further comprising delivering to the biological sample a second set of barcoded polynucleotides.
14. The method of paragraph 13, wherein the barcoded polynucleotide of the second set comprise a ligation linker sequence, a spatial barcode sequence, a unique molecular identifier (UMI) sequence, and a first PCR handle end sequence, optionally wherein the first PCR handle end sequence is terminally functionalized with biotin.
15. The method of paragraph 13 or 14, wherein (i) barcoded polynucleotides of the second set are bound to a universal ligation linker, or (ii) the method further comprises delivering to the biological sample a universal ligation linker sequence, wherein the universal ligation linker comprises a sequence complementary to the ligation linker sequence of the barcoded polynucleotides of the first set and comprises a sequence complementary to the ligation linker sequence of the barcoded polynucleotides of the second set.

16. The method of any one of paragraphs 13-15, wherein the second set of barcoded polynucleotides is delivered through a second microfluidic chip that comprises parallel microchannels that are positioned on the biological sample perpendicular to the direction of the microchannels of the first microfluidic chip.

17. The method of paragraph 16, wherein the second microfluidic chip comprises at least 10, at least 20, at least 30, at least 40, or at least 50 parallel microchannels.

18. The method of any one of paragraphs 13-17 further comprising joining barcoded polynucleotides of the first set to barcoded polynucleotides of the second set by exposing the biological sample to a ligation reaction, thereby producing a two-dimensional array of spatially addressable barcoded conjugates bound to molecules of interest, wherein the spatially addressable barcoded conjugates comprises a unique combination of barcoded polynucleotides from the first set and the second set.

19. The method of paragraph 18 further comprising imaging the biological sample to produce a sample image.

20 The method of paragraph 19, wherein the imaging is with an optical or fluorescence microscope.

21. The method of any one of paragraphs 18-20 further comprising extracting cDNAs from the biological sample.

22. The method of paragraph 21 further comprising sequencing the cDNAs to produce cDNA reads.

23. The method of paragraph 22, wherein the sequencing comprises template switching the cDNAs to add a second PCR handle end sequence at an end opposite from the first PCR handle end sequence, amplifying the cDNAs, producing sequencing constructs via tagmentation, and sequencing the sequencing constructs to produce the cDNA reads.

24. The method of paragraph 22 or 23 further comprising constructing a spatial molecular expression map of the biological sample by matching the spatially addressable barcoded conjugates to corresponding cDNA reads.

25. The method of paragraph 24 further comprising identifying the location of the molecules of interest by correlating the spatial molecular expression map to the sample image.

26. A composition comprising:
   (a) a biological sample comprising messenger ribonucleic acids (mRNAs) comprising a polyA tail and/or proteins linked to binder-DNA tag conjugates, wherein the conjugates comprises (i) a binder molecule that specifically binds to a molecule of interest and (ii) a DNA tag that comprises a binder barcode and a poly A sequence; and
   (b) spatially addressable barcoded conjugates comprising a PCR handle sequence, a universal molecular identifier (UMI) sequence, a first spatial barcode sequence, a ligation linker sequence, a second spatial barcode sequence, and a polyT sequence, wherein the spatially addressable barcoded conjugates are bound to the mRNAs and/or proteins through hybridization of the poly A and polyT sequences.

27. The composition of paragraph 26 further comprising a polynucleotide comprising a universal complementary ligation linker sequence bound to the ligation linker sequence of (b).

28. A kit comprising:
   (a) a first set of barcoded polynucleotides that comprise a ligation linker sequence, a spatial barcode sequence, and a polyT sequence; and
   (b) a second set of barcoded polynucleotides that comprise a ligation linker sequence, a spatial barcode sequence, a unique molecular identifier (UMI) sequence, and a first PCR handle end sequence, optionally wherein the first PCR handle end sequence is terminally functionalized with biotin; and
   a polynucleotide comprising a universal complementary ligation linker sequence capable of binding to the ligation linker sequence of (a) and (b).

29. The kit of paragraph 28 further comprising a collection of binder-DNA tag conjugates that comprises (i) a binder molecule that specifically binds to a molecule of interest and (ii) a DNA tag that comprises a binder barcode and a poly A sequence.

30. The kit of paragraph 28 or 29, further comprising at least one reagent selected from tissue fixation reagents, reverse transcription reagents, ligation reagents, polymerase chain reaction reagents, template switching reagents, and sequencing reagents.

31. The kit of any one of paragraphs 28-30, further comprising tissue slides.

32. The kit of any one of paragraphs 28-31, further comprising at least one microfluidic chip that comprises parallel microchannels.

EXAMPLES

We developed a completely new technology for high-resolution (~10 μm) spatial omics sequencing. All early attempts towards spatial transcriptomics were all based on multiplexed fluorescent in situ hybridization (Chen et al., 2015; Eng et al., 2019; Lubeck et al., 2014; Perkel, 2019). Recently, a major breakthrough in the field arises from the use of high throughput next generation sequencing (NGS) to reconstruct spatial transcriptome maps (Rodriques et al., 2019; Stahl et al., 2016), which is unbiased, genome-wide, and presumably easier to adopt by a wider range of biological and biomedical research community. The core mechanism of these NGS-based methods to achieve spatial transcriptomics is through a method called "barcoded solid-phase RNA capture" (Trcek et al., 2017), which uses a DNA barcode spot array such as ST seq (Stahl et al., 2016) or a barcoded bead array such as Slide-seq (Rodriques et al., 2019) to capture mRNAs from a freshly sectioned tissue slice placed on top and lysed to release mRNAs. These approaches are still technically demanding, requiring a lengthy and sophisticated step to decode the beads, while the mRNA capture efficiency and the number of dateable genes per pixel at the 10 μm size level is markedly below optimal. Additionally, it is not obvious how they can be extended for other omics measurements. Herein, spatial DBIT-seq is a fundamentally different approach. Tissue does not need to be lysed to release mRNAs and is compatible with existing 2.5 formaldehyde-fixed tissue slides. It is highly versatile and easy to operate. It uses, in some embodiments, only a simple microchannel device and a set of reagents. Conduct sophisticated sequential hybridization or SOLID sequencing is not required to decode beads before experiments. This stand-alone device is highly intuitive to use with no need for any microfluidic handling system and thus can be readily adopted by biologists who have no microfluidics training.

With this technology, we conducted the spatial multi-omics atlas (proteins and mRNAs) sequencing of whole mouse embryos and generated numerous new insights. Major tissue types in a mouse embryo could be identified during early organogenesis stages. Spatial protein and gene expression atlas revealed a differential pattern in embryonic forebrain defined by MAdCAM1 expression. Reconstructed spatial protein expression map can readily resolve brain microvasculature networks, which are barely distinguishable in tissue histology images. We further demonstrated the ability to resolve a single-cell layer of melanocytes lining around the optical vesicle and discovered an asymmetric gene expression pattern between Rorb and Aldh1a1 within the optical vesicle that may contribute to the subsequent development of retina and lens, respectively. DBiT-seq demonstrated not only high spatial resolution but also high quality of sequencing data with a much higher genome coverage and a greater number of genes detected per 10 µm pixel when compared to Slide-seq. This improvement enabled us to visualize the spatial expression of individual genes whereas the Slide-seq data are too sparse to query individual genes in a meaningful way.

Thanks to the versatility of our technology, we can readily combine multiple omics on the same pixel. As demonstrated in this work, we simultaneously measured whole mRNA transcriptome and a panel of 22 protein markers, allowing for comparing individual proteins and mRNAs for their spatial expression patterns. We demonstrated the use of high-quality spatial protein expression data to guide the tissue region-specific transcriptome analysis for differential gene expression and pathway analyses, leading to the new approach for mechanistic discovery that one type of omics data cannot readily provide. Moreover, DBIT has the capability to become a universal sample preparation step to enable high-spatial-resolution mapping of many other molecular information. For example, it can be applied to barcode DNA sequences for high-spatial-resolution Assay for Transposase-Accessible Chromatin (ATAC) (Chen et al., 2016) and potentially for detecting chromatin modifications via in-tissue Cut-Run (Skene and Henikoff, 2017) followed by DBIT.

This spatial barcoding approach is not limited to tissue specimens but also applicable to single cells dispensed on a substrate to perform deterministic barcoding for massively parallel transcriptome, proteome, or epigenome sequencing. In this way, a variety of cellular assays such as cell migration, morphology, signal transduction, drug responses, etc. can be done before hand and linked to the omics data, enabling direct correlation of single-cell omics to live cell functions in every single cell. This may further address a long-standing problem in the field of single-cell RNA sequencing—the unavoidable perturbation of cellular states including protein and mRNA expression during trypsinization and single-cell suspension preparation.

Like any other emerging technologies, DBiT-seq has limitations. First, although it is close to single-cell level mapping, it does not resolve single cells. However, due to the unique capability of DBiT-seq to obtain precisely matched tissue image from the same tissue slide, we believe molecular imaging such as immunohistochemistry (IHC) or fluorescent in situ hybridization (FISH) can be perform to outline the boundaries of individual cells, which could help identify how many and which cells are in each pixel. A large database of IHC or FISH on the same type of tissue is used to train a machine learning (ML) neural network to predict the spatial expression in individual cells based on tissue histology. Then, the trained neural network can be applied to DBiT-seq and matched histology image to computationally reconstruct single-cell spatial gene or protein expression atlas. Second, there is a theoretical resolution limit. Based on our validation data, this limit is ~2 µm, which is challenging to perform using microfluidic DBIT. However, we are optimistic to push it down to ~5 µm, in which most pixels containing 1 or less than one cell. Third, current DBiT-seq approach relies on a 50×50 orthogonal barcoding array, which yields a 1 mm mappable area at the 10 µm pixel size. But this can be readily expanded by increasing the number of barcode reagents to 100×100 or even 200×200 to cover a larger area of mappable region. Fourth, with the current DBiT device, in some embodiments, the tissue section is placed relatively in the center of the slide (in a 10 mm×10 mm region). Many banked tissue slides contain tissue sections on different locations of the slide. To solve this problem, a microfluidic device with a large-sized reagent delivery handle chip bonded onto a small flow barcoding chip can be fabricated such that the footprint required to attach the microfluidic flow barcoding region to the slide is much smaller and can be aligned the tissue section anywhere on the slide.

In summary, we report on an enabling and versatile technology referred to herein as microfluidic deterministic barcoding in tissue (DBIT) to perform high-resolution spatial barcoding to simultaneously measure, for example, mRNA transcriptome and a panel of proteins on a fixed tissue slide at high spatial resolution (10 µm), in an unbiased manner, and at the genome-wide scale. DBiT-seq is a fundamentally different approach for spatial omics and has the potential to become a universal method for mapping a range of molecular information (proteins, transcriptome, and epigenome). The potential impacts could be broad and far-reaching in many different fields of basic and translational research including embryology, neuroscience, cancer and clinical pathology.

Example 1. DBiT-Seq Workflow

Figure 5C:
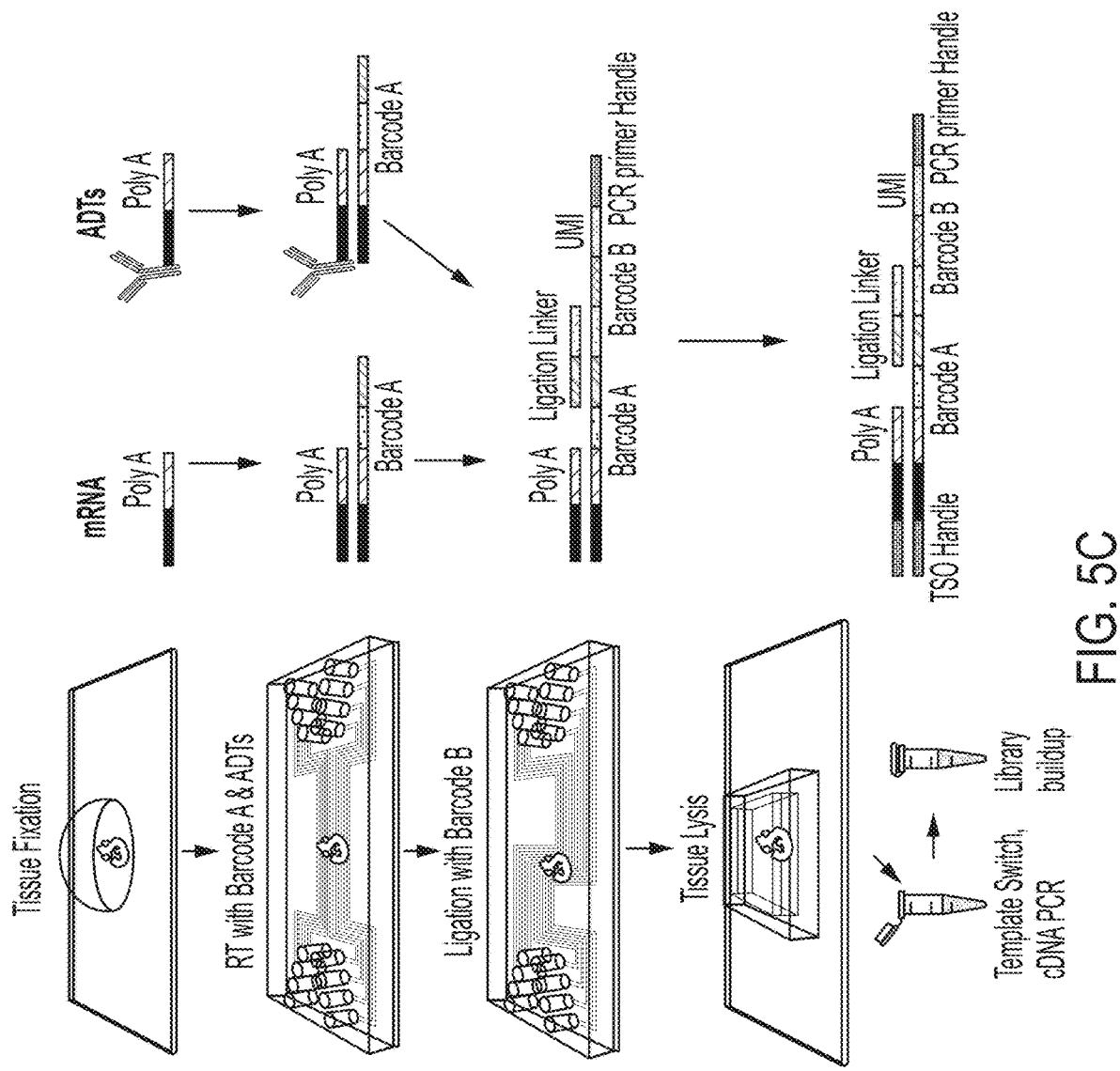

The workflow of DBiT-seq is described in FIG. 5A. It does not require a newly microtomed tissue section to start with as a standard tissue slide that has already been fixed and banked is compatible with our approach. If a frozen tissue section were the starting material, it can be transferred to a poly-L-lysine coated slide, fixed with formaldehyde, and stored in −80° C. until use. A polydimethylsiloxane (PDMS) microfluidic chip containing parallel microchannels (down to 10 µm in width) is placed on the tissue slide to introduce a set of DNA barcode solutions (FIG. 5C). Each barcode is composed of an oligo-dT sequence for binding mRNAs and a distinct barcode $A_i$(i=1 to 50). Reverse transcription is conducted during the first flow for in situ synthesis of cDNAs that immediately incorporate barcodes A1-A50. Then, this PDMS chip is removed and another PDMS chip is placed on the same tissue with the microchannels perpendicular to those in the first flow barcoding. Next, a second set of barcodes $B_j$(j=1 to 50) are flowed in to initiate in situ ligation that occurs only at the intersections, resulting in a mosaic of tissue pixels, each of which has a distinct combination of barcodes $A_i$ and $B_j$(i=1 to 50 and j=1 to 50). The tissue slide being processed is imaged during each flow as well as after both flows such that the exact tissue region comprising each pixel can be identified unambiguously. To perform multi-omic measurements of proteins and mRNAs, the tissue slide is first stained with a cocktail of antibody-derived tags (ADTs) (Stoeckius et al., 2017) prior to microfluidic flow barcoding. The ADTs have a polyadenylated tail that allows for detecting proteins using a workflow similar to detecting mRNAs. After forming a spatially barcoded tissue mosaic, cDNAs are collected, template-switched, and PCR amplified to make a sequencing library. Using 100×100 pair-ended NGS sequencing, we can detect spatial barcodes ($A_iB_j$, i=1-200, j=1-200) of all pixels and the corresponding transcripts and proteins to computationally reconstruct a spatial expression atlas. It is worth noting that unlike other methods, DBIT permits the same tissue slide being imaged with microfluidic channels to precisely locate the pixels and perform correlative analysis of tissue morphology and omics at high resolution and high accuracy.

Example 2. Barcode Design and Chemistry

The key elements of DNA barcodes and the chemistry to perform DBIT is described in FIG. 5B. To detect proteins of interest, the tissue is firstly labeled with ADTs, each of which consists of a unique antibody barcode (15mer, see Table 1) and a poly-A tail. Barcode A contains a 15mer ligation linker, a unique spatial barcode Ai(i=1-50, 8mer, see Table 3), and a 16mer poly-T sequence, which binds mRNAs and ADTs through binding to poly-A tail. After permeabilization, DNA barcodes A1-A50 are flowed in along with a reverse transcriptase mixture and reverse transcription is conducted in situ to generate cDNAs as well as incorporate barcode A in the tissue stripes within individual microchannels. Barcode B consists of a 15mer ligation linker, a unique spatial barcode Bj(j=1-50, 8mer, see Table 3), a 10mer unique molecular identifier (UMI), and a 22mer PCR handle terminally functionalized with biotin, which is used later to perform cDNA purification with streptavidin-coated magnetic beads. During the second flow to introduce barcodes B1-B50, a complementary ligation linker and the T4 ligase are also introduced to initiate in situ ligation of barcodes A and B only at the intersections of two flow, which completes the deterministic barcoding of a tissue slide and yields a mosaic of tissue pixels with distinct barcodes in each of the 50×50=2,500 pixels. This chemistry is versatile and can be readily expanded to a larger array (e.g., 100×100=10,000) of pixels or extended to other omics measurement by changing the binding chemistry from poly-T to, for example, spicing-site specific sequences.

Example 3. Enabling Microfluidic Devices with HSR

To explore enabling HSR using the microfluidic devices described here, we experimented with values for ω and Δ of 10, 25 and 50 microns. Here we review the key challenges we faced in enabling devices with these parameters, and the solutions we invented to overcome them.

Aspect ratios. We experimented with a wide range of aspect ratios for the 10, 25, and 50 μm devices. Though those skilled in the art will recognize that microchannels can typically display a wide range of widths and heights, it turns out that only aspect ratios within a certain band perform well when being clamped onto tissue (which is necessary for various reasons; see below).

Figure 6:
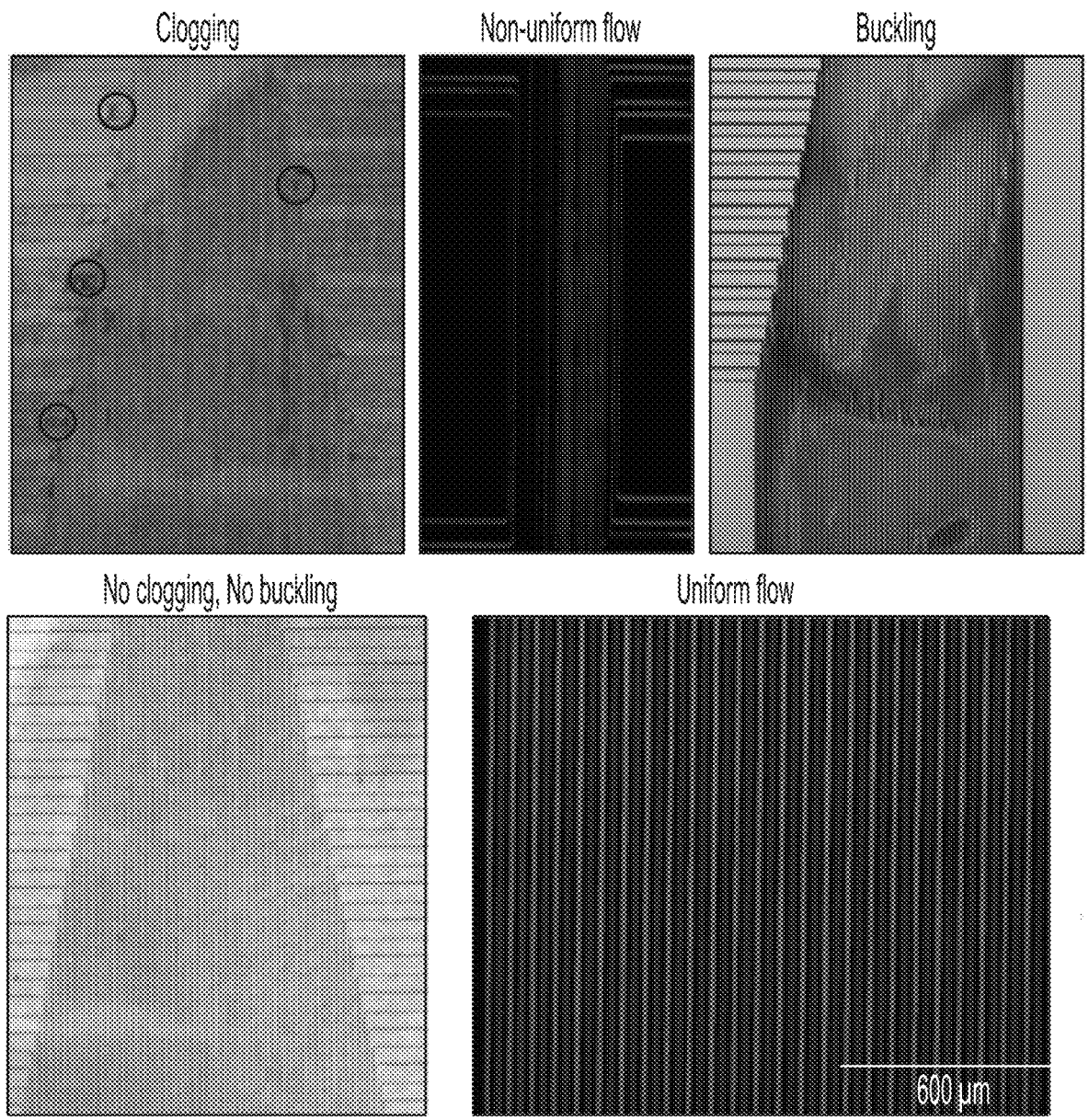
FIG. 6. Microfluidic device designs for HSR. Top-various failure modes induced by incorrect choice of channel aspect ratios. Bottom-successful flow resulting from proper choice of channel aspect ratios.

Because the microfluidic devices described here include open spaces (channels) followed by solid layers of PDMS (walls), the walls may be thought of as pillars or columns, with width equal to Δ, the channel pitch, and height equal to the depth of the mold from which the PDMS device was molded. For the SU-8 molds we used to create our devices, heights typically range from a few microns to a hundred microns. However, we found that for each choice of Δ, choosing a height that was too small resulted in channels that clogged very easily (see FIG. 6, top left and top middle panels). This is due to the tissue itself being forced into the channel during clamping and stopping or selectively restricting flow. This can be avoided by utilizing very large heights. However, this results in the channel walls being unstable and then buckling during clamping (see FIG. 6, top right panel). We tested a range of values for the channel heights that achieve the results shown in the bottom panels of FIG. 6, by creating channels that are deep enough to avoid clogging, but with walls stable enough to avoid buckling.

| Channel and wall width (microns) | Minimum functioning height (microns) | Maximum functioning height (microns) |
| --- | --- | --- |
| 10 | 12 | 15 |
| 25 | 17 | 22 |
| 50 | 20 | 100 |

Example 4. Microfluidic Device for the DBiT Process

The PDMS microfluidic chip design in this example includes 50 parallel microchannels in the center which are connected to the same number of inlet and outlets on two sides of the PDMS slab. It is made of silicone rubber, which is sticky to the glass slide surface and can be placed on the tissue slide to introduce solution without noticeable leakage if no positive pressure is applied. To further assist the assembly, a simple clamp is used to hold the PDMS firmly against the slide at the tissue specimen region (FIG. 7A). The inset (inlet) holes which are ~2 mm in diameter and 4 mm in depth allow the ~5 μL of barcode reagents to be directly pipetted with no need for any microfluidic handling setup. The outlet holes are roofed with a global cover connected to a house vacuum to pull the reagents from the insets (inlets) into the tissue region. It takes several seconds to pull the solution from inlets through outlets for a 50 μm microfluidic chip and up to 3 min for a 10 μm microfluidic chip. After flow barcoding, the microfluidic chip is sonicated and rinsed with 0.5M NaOH solution and DI water for reuse. Thus, this device requires no sophistic microfluidic control systems, can be readily assembled by a scientist with no experience in microfluidics, and the workflow is readily adoptable in a conventional biology laboratory.

Example 5. Evaluation of DBIT Using Fluorescent In Situ Hybridization (FISH)

Although no noticeable leakage was observed between microchannels during the vacuum driven flow barcoding, it is unclear if the DNA barcode solutions could diffuse through the tissue matrix and result in cross-contamination. The diffusion distance in an aqueous solution decreases substantially with the increase of molecular size, which was utilized to perform diffusion-limited reagent exchange in microfluidics for multiple chemistry reactions. We hypothesize that the diffusion through a dense matrix is even more restricted. A validation experiment was designed to monitor our workflow step by step using fluorescent probes and to evaluate the effect of diffusion underneath the microchannel walls (FIGS. 7B and 7C, and data not shown). We conjugated barcodes A (1-50) with fluorophore Cy3 and barcodes B (1-50) with fluorophore FITC, and then imaged the tissue during and after DBIT at a 50 μm pixel resolution. The first flow is supposed to yield stripes of Cy3 signal corresponding to barcodes A hybridized in situ to tissue mRNAs. We observed distinct stripe pattern with no visually noticeable diffusion between stripes. The second flow adds barcodes B only to the intersections, yielding isolated squares of FITC signal, which is exactly our observation (FIG. 7B). Due to autofluorescence of tissue excited by blue light (488 nm), the faint fluorescence appears in between squares but the average intensity is an order of magnitude lower. We also used a layer of human umbilical vein endothelial cells (HUVECs)

grown on a glass slide and fixed with formaldehyde to mimic a thin "tissue" section (FIG. 1D), which had a higher surface roughness and served as a stringent model to evaluate the leakage across microchannels. Small molecule dye DAPI (4',6-diamidino-2-phenylindole, staining for nuclear DNA) and fluorophore-labeled anti-human VE-Cadherin (staining for endothelial cell-cell junction, red) were used in the first and the second flow, respectively. When a microchannel wall cut through one cell or one nucleus, fluorescence signal was observed only in the half within the microchannel (FIG. 7C and data not shown). To evaluate the possibility of DNA diffusion through the tissue matrix underneath the microchannel wall, a 3D fluorescence confocal image was collected, which confirmed negligible leakage signal throughout the tissue section thickness (FIG. 7D). These images were taken when using a 50 μm device without clamp. To evaluate the feasibility of reducing to 10 μm flow barcoding, we performed a full DBiT using fluorescent barcodes B with FITC and observed a clean pattern of fluorescence pixels (FIG. 7E and data not shown). Interestingly, this pan-mRNA FISH signal in each tissue pixel is not uniform but can reflect the underlying cell morphology. As mentioned above, our approach allows for the imaging of the same tissue slide during and after flow barcoding. We found that the clamping step compressed the tissue underneath the microchannel walls and led to localized plastic deformation. As a result, the light field optical image of the tissue region processed by cross-flow barcoding show imprinted topological patterns with readily distinguishable tissue pixels, which can be used to assist the correlation of tissue histology with spatial omics sequencing data. The compressed tissue region underneath the microchannel walls has a higher matrix density and may further reduce the diffusion distance. We used the fluorescence intensity line profile (FIG. 7E) to calculate the half-peak-width-intensity increase, which represents a quantitative measure of the "diffusion" distance between microchannels. It turned out to only 0.9±0.2 μm for 10 μm flow channels operated with clamp and 4.5±1 μm for 50 μm flow channels without clamp (FIG. 7F). Thus, we speculate the theoretical limit of DBiT spatial resolution can be as good as ~2 μm.

Example 6. Evaluation of DBiT-Seq Data Quality

Figure 7G:
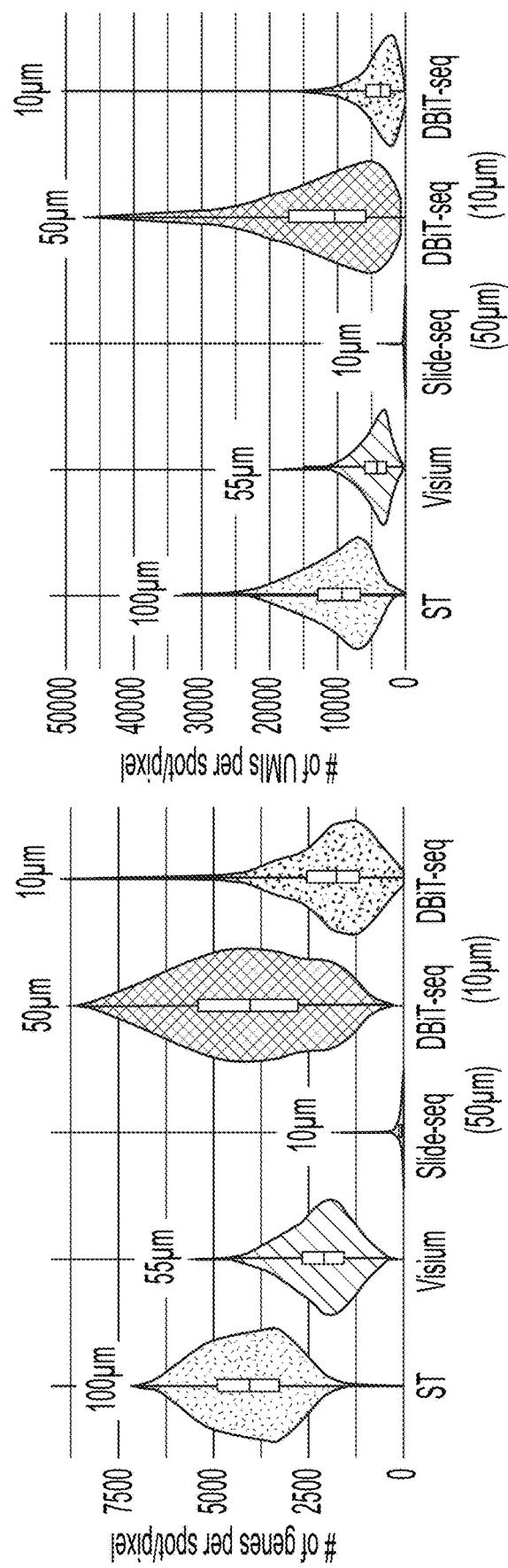

The PCR amplicons were analyzed for cDNA size distribution, which peaks at 900-1100 bp for a sample fixed right after preparation (data not shown). A frozen tissue section slide left at room temperature for 24 hours or longer led to significant degradation and the shift of the main peak to ~350 bp. However, after fixation and flow barcoding, it still resulted in usable sequencing data for quantification of gene expression. A HiSeq pair-ended (100×100) sequencing was conducted to identify spatial barcodes and the expression of proteins and mRNAs on each pixel. The alignment was done using DropSeq tools Macosko et al., 2015) to extract UMI, Barcode A and Barcode B, from Read 2. The processed read was trimmed, mapped against the mouse genome (GRCh38), demultiplexed annotation (Gencode release M11) using the Spatial Transcriptomics pipeline reported previously (Navarro et al., 2017). With that, similar to scRNA-seq quality evaluation, we calculated the total number of transcripts reads (UMIs) per pixel and the total number of genes detected (FIG. 7G and data not shown). Compared with the literature data from Slide-seq (Rodriques et al., 2019) and the low resolution Spatial Transcriptomics (ST) sequencing data (Stahl et al., 2016), our data from a 10 μm DBiT-seq experiment was able to detect 22.969 genes in total and 2,068 genes per pixel. In contrast. Slide-seq, which has the same pixel size (10 μm), detected ~150 genes per pixel (spot). It is worth pointing out that this significant improvement in data quality allows DBIT-seq to directly visualize the expression pattern of individual genes but Slide-seq could not do that in a meaningful way due to data sparsity. The number of UMIs or genes per pixel detected by low-resolution ST method is similar to our approach but the size of the pixel in ST is ~100-150 μm, which is ~100× larger in area. This marked increase in data quality is presumably attributed to the uniqueness in flow barcoding method that does not require a tissue lysis step to release mRNAs and avoids the loss of released mRNAs because of their lateral diffusion into the solution phase. Although it has long been recognized that retrieving mRNAs from fixed tissue specimens for NGS sequencing has decreased yield due to degradation, recent studies showed that the quality of mRNAs in tissue remains largely intact but rather, it is the tissue lysis and RNA retrieval step that leads to the degradation and the consequential poor recovery.

Example 7. Whole Mouse Embryo Spatial Multi-Omics Atlas Mapping

Figures 8D, 8E:
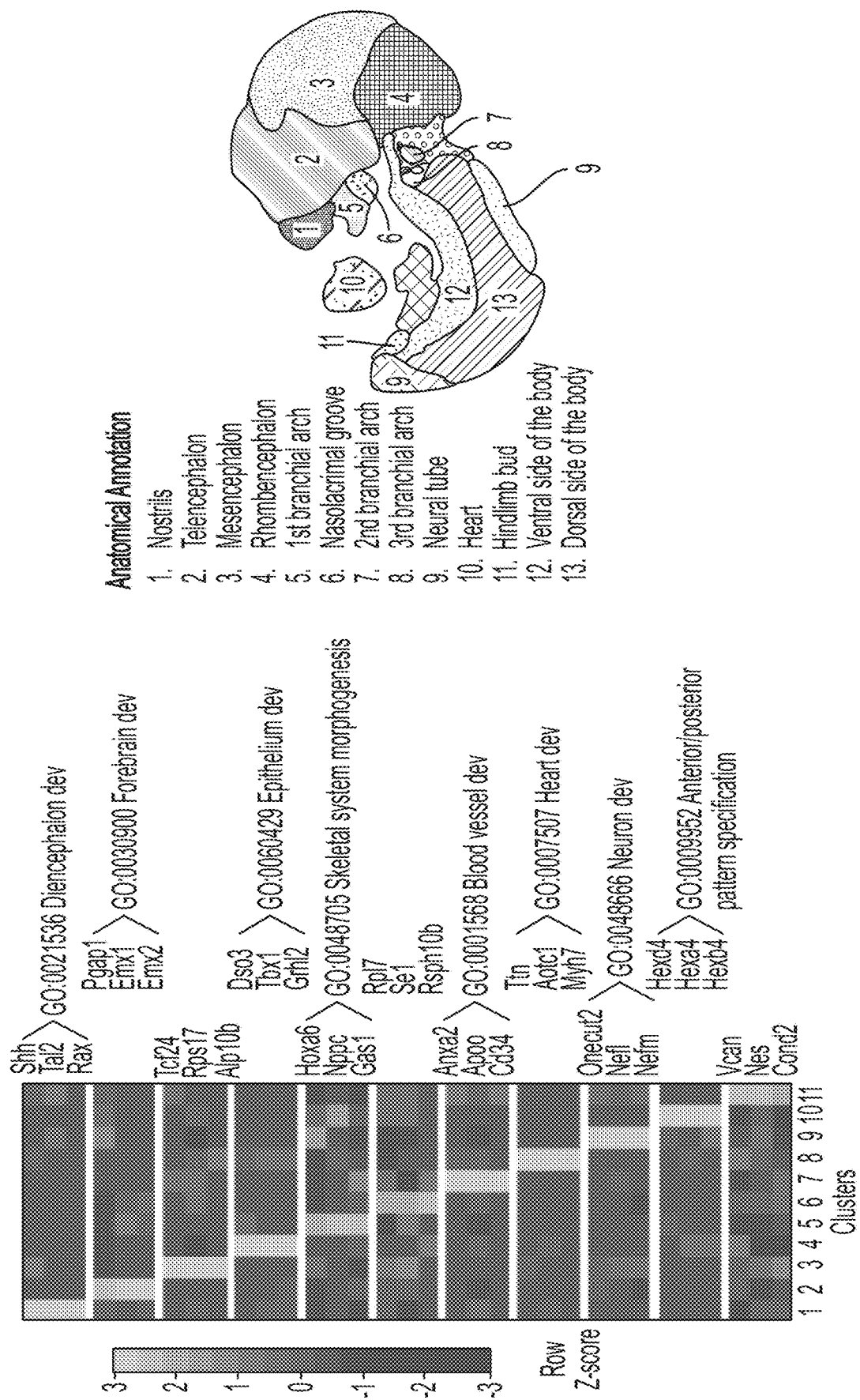
Figure 8F:
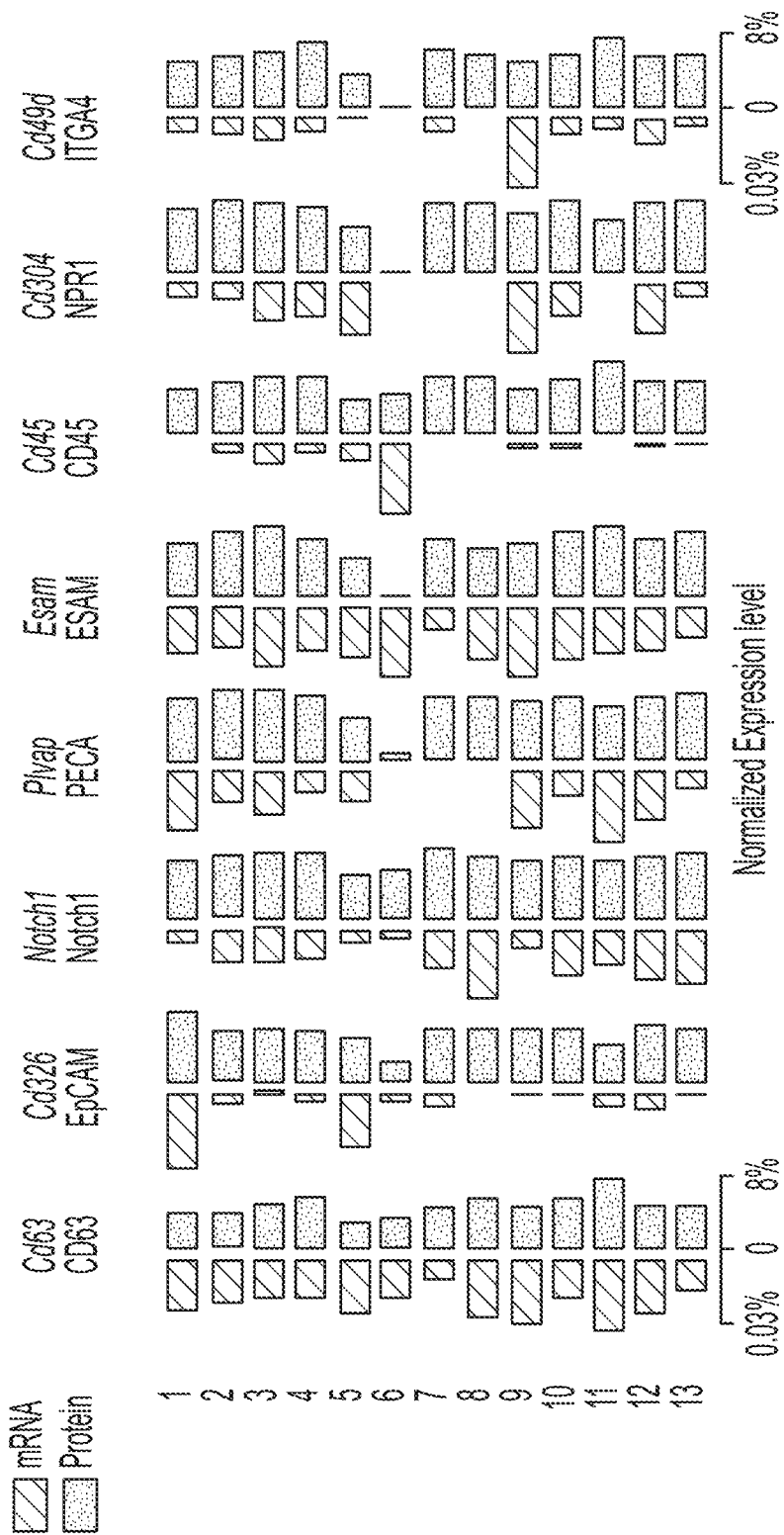

The dynamics of embryonic development, in particular, the formation of different organs (organogenesis) at the early stages, is intricately controlled spatiotemporally. The results from a large number of laboratories around the world and obtained using a range of techniques such as FISH, immunohistochemistry (IHC), and RNAseq, have been integrated to generate a relatively complete mouse embryo gene expression database such as eMouseAtlas (Armit et al., 2017). Thus, the developing mouse embryos are well suited for validation of a new spatial omics technology by providing known reference data for comparison. We applied DBiT-seq to a E.10 whole mouse embryo tissue slide at a pixel size of 50 μm to computationally construct a spatial multi-omics atlas. The tissue histology image from an adjacent section was stained for H&E (Haemotoxylin and Eosin) (FIG. 8A left). The read counts of mRNA transcripts in individual pixels, equivalent to pan-mRNA detection, are shown as a spatial heatmap (FIG. 8A middle), which is found to correlate well with tissue density and H&E morphology. The total read counts from a panel of 22 protein markers (see Table 1) combined in each pixel appear to be more uniform and less dependent on tissue density and morphology (FIG. 8A right). The quality of sequencing data is excellent with an average of ~4500 genes detected per pixel, which is higher than that in the 10 μm-pixel DBiT-seq data (FIG. 7G), due in part to the larger pixel size and subsequent increased cell type diversity per pixel. To benchmark DBiT-seq data, we aggregated the mRNA expression profiles of all pixels for each E10 embryo sample to generate "pseudo-bulk" data, which were compared to the "pseudo-bulk" data generated from scRNA-seq of E9.5 to E13.5 mouse embryos (Cao et al., 2019) using un-supervised clustering (FIG. 8B). We observed consistent temporal developmental classification visualized in UMAP with four E10 DBiT-seq samples localized between E9.5 and E10.5 data from the reference (Cao et al., 2019). Unsupervised clustering of all pixels based on mRNA transcriptomes reveals eleven major clusters (FIG. 8C) as shown in a tSNE plot that, once mapped back to the spatial atlas, are found to correlate with the major tissue types at this stage including telencephalon (forebrain), mesencephalon (midbrain), rhombencephalon (hindbrain), branchial arches, spinal neural tube, heart, limb bud, and ventral and dorsal side of main body for early internal organ development (FIG. 8D). We anticipate more tissue subtypes to be identified using higher resolution DBiT-seq. Based upon literature database and the classical Kaufman's Atlas of Mouse Development (Baldock and Armit, 2017), we performed anatomical annotations of 13 major tissue types (FIG. 8E), among which 9 were identified by unsupervised clustering. Interestingly, even at this resolution (pixel size=50 µm), some fine features identified by clustering—such as the small clusters in the middle of the brain and a distinct stripe of pixels between the dorsal and ventral layers of the body—are not readily distinguishable in H&E. The former is indicative of early eye and ear development and the latter is less clear but may correlate with the dorsal aorta.

Figure 8G:
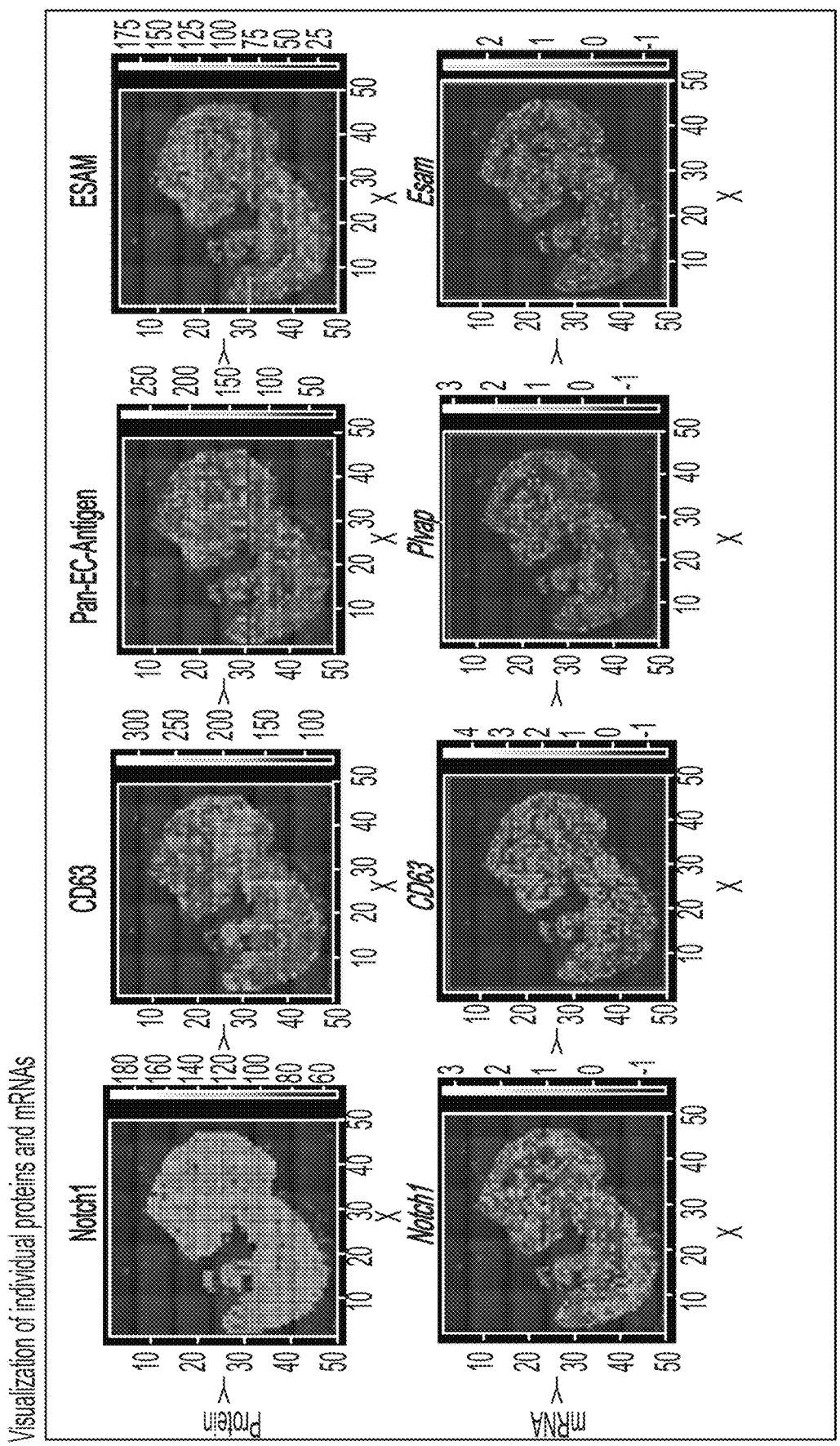
Figure 8G:
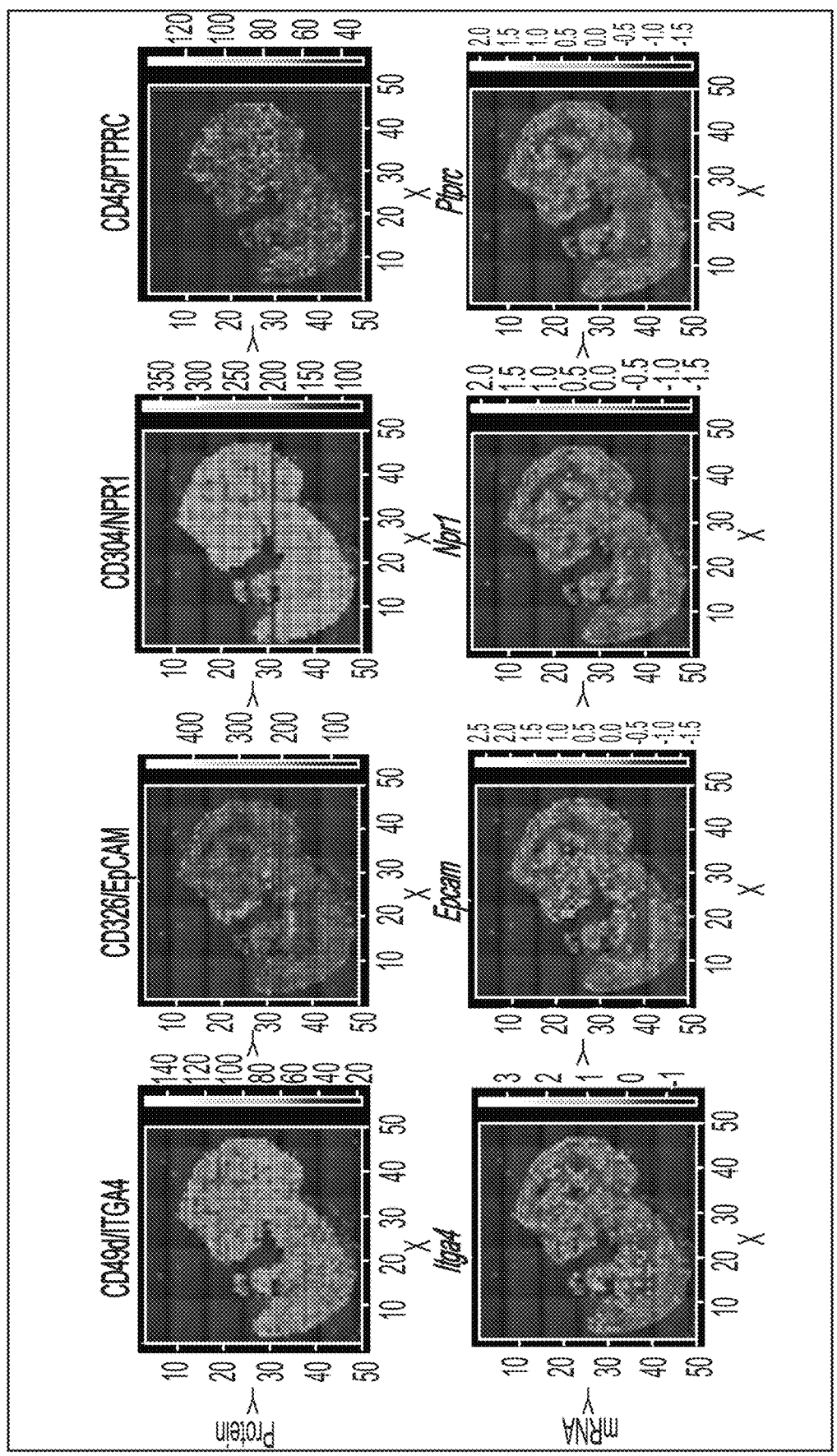
Figure 8I:
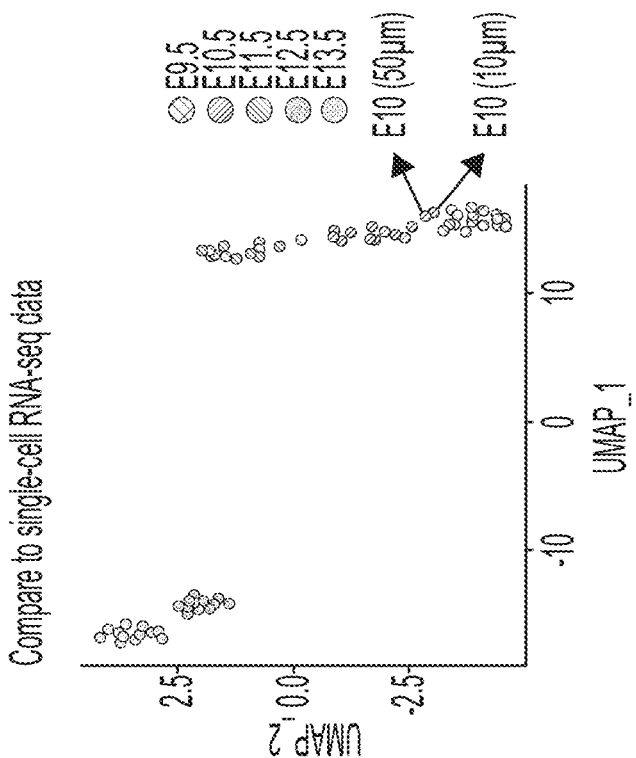
Figure 8H:
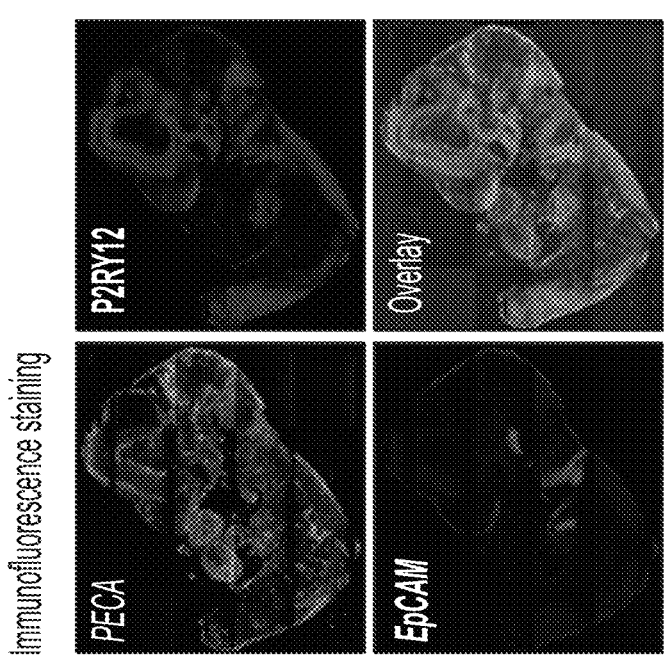

Example 8. Correlation Between Proteins and mRNAs in Spatial Expression Patterns While single-cell RNA/protein co-sequencing such as CITE-seq can directly compare the expression level of individual proteins to cognate mRNAs in a cell, the correlation between their spatial expression patterns in the tissue context are missing. Herein, high quality spatial multi-omics data allows for head-to-head comparison between individual proteins and mRNA transcripts pixel-by-pixel in a tissue. As such, all 22 proteins analyzed are compared with their corresponding mRNAs (data not shown). Selected mRNA/protein pairs are discussed below (FIG. 8G). Notch signaling plays a crucial role in regulating a vast array of embryonic developmental processes. Notch1 protein is found to be highly expressed throughout the whole embryo, which is consistent with the observation of extensive Notch/mRNA expression although it appears to mirror the tissue density. CD63 is an essential player in controlling cell development, growth, proliferation, and motility. Its mRNA transcript is indeed expressed extensively in the whole embryo with a higher expression in hindbrain and heart. Pan-EC-Antigen (PECA) or MECA-32, as a pan-endothelial marker, is expressed in many tissue regions, but the spatial pattern is difficult to identify at this resolution. The expression of EpCAM, a pan-epithelial marker, is highly localized in terms of both mRNA and protein, the expression patterns of which are also highly consistent. Several other genes are discussed as below. Integrin subunit alpha 4 (ITGA4), known to be critical in epicardial development, is indeed highly expressed in embryonic epicardium but also observed in many other tissue regions. Its protein expression is seen throughout the whole embryo. Many genes show strong discordance between mRNA and protein such as NPR1. A pan-leukocyte protein marker CD45 is seen extensively but apparently enriched in the dorsal aorta region and brain, although the expression level of its cognate mRNA Ptprc is low. We further generate a comprehensive chart of tissue region-specific mRNAs and proteins by calculating the average expression in each of 13 anatomically annotated tissue regions (FIG. 8H). Next, to validate the DBiT-seq data, immunofluorescence was performed using antibodies to stain for P2RY12 (microglia in central nerve system) PECA (endothelium), and EpCAM (epithelium). We observed a highly consistent pattern of EpCAM between immunostaining and DBiT-seq (FIG. 8I). Spatial transcriptome sequencing (without ADTs) was repeated with a separate E.10 embryo tissue slide and the results are consistent (data not shown). Finally, a "bulk" transcriptional profile could be derived from spatial DBiT-seq data and compared to scRNA-seq of mouse embryos E9.5-E13.5, which revealed that our data are correctly positioned in the UMap when compared to literature data (Cao et al., 2019).

Example 9. Spatial Multi-Omics Mapping of an Embryonic Brain

Figure 9D:
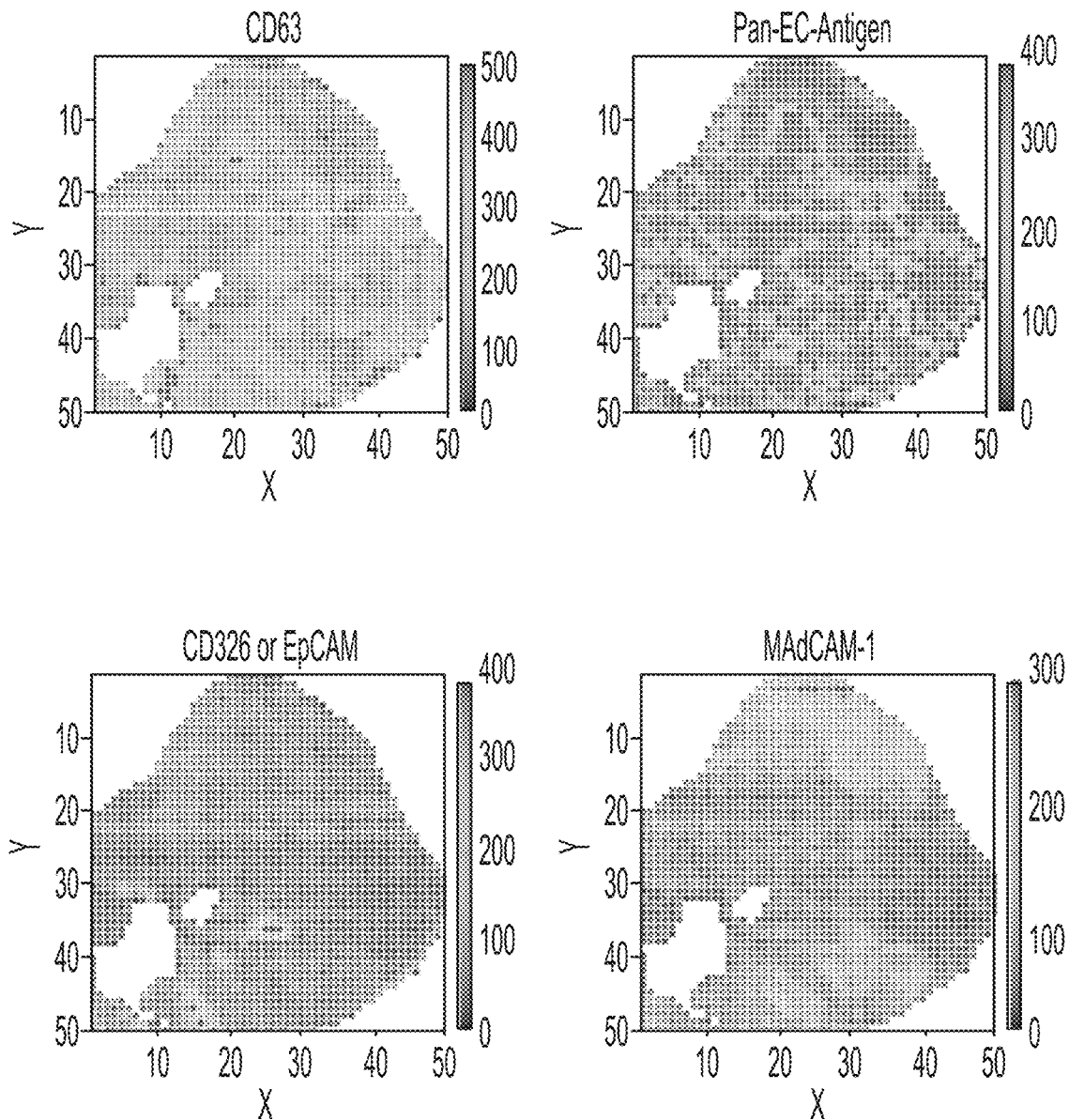
Figure 9E:
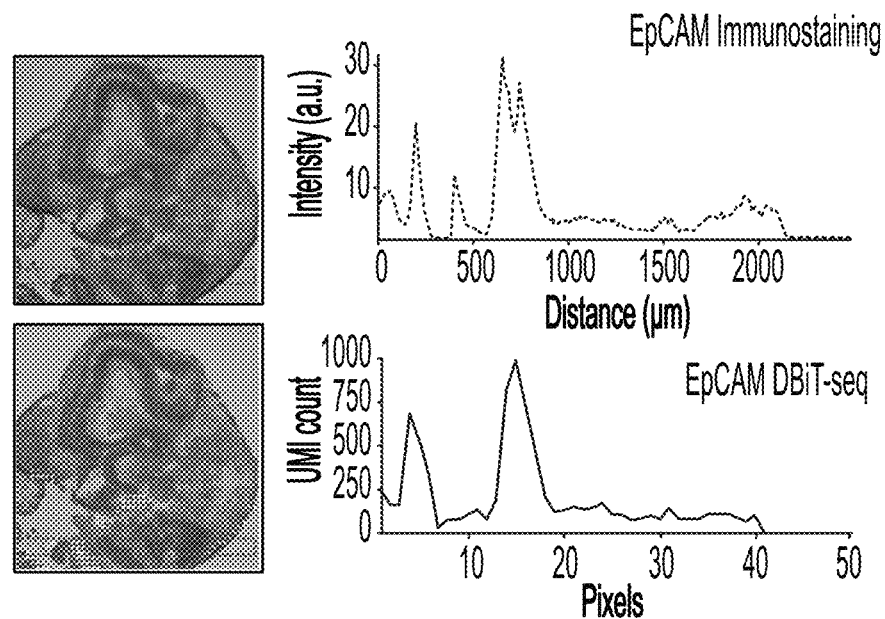
Figure 9E:
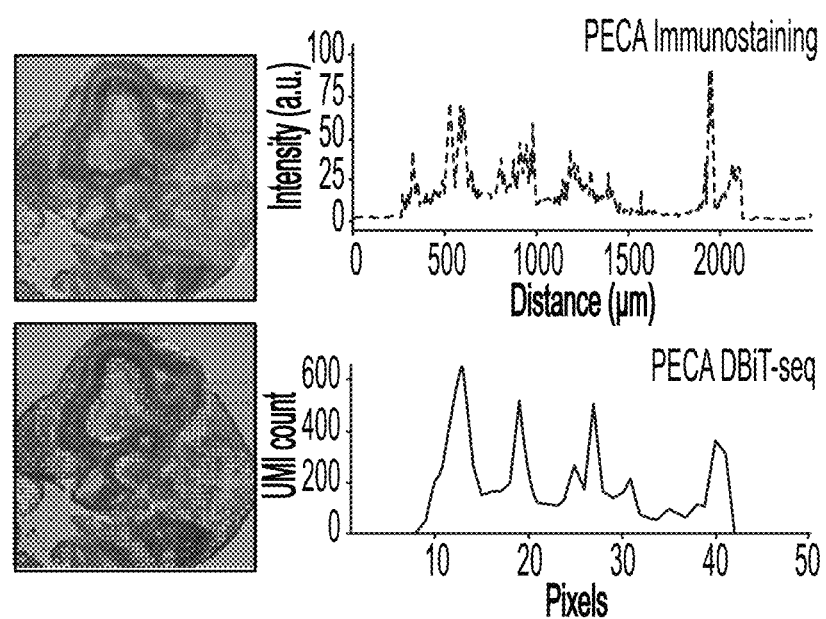
Figure 9F:
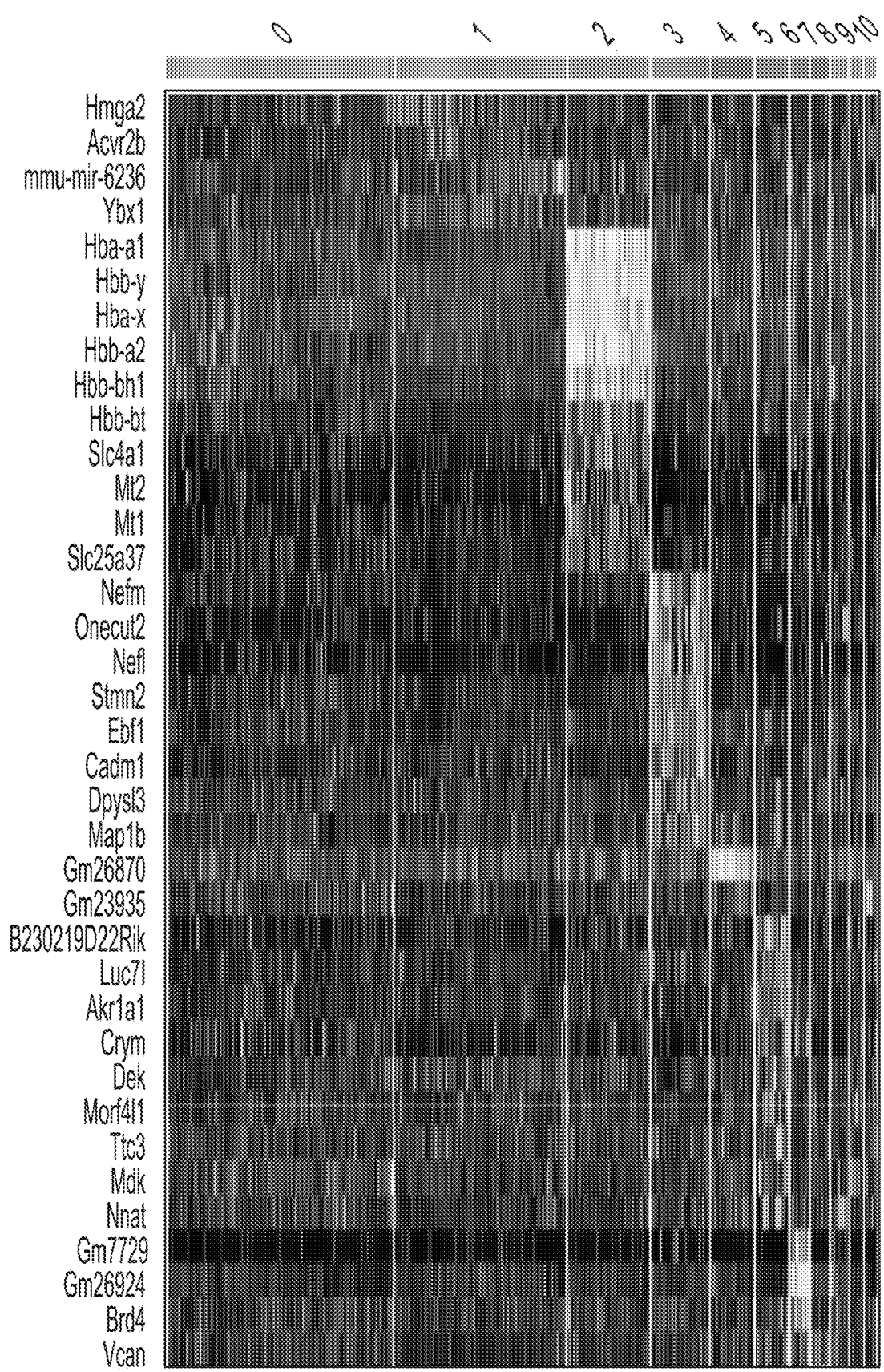
Figure 9F:
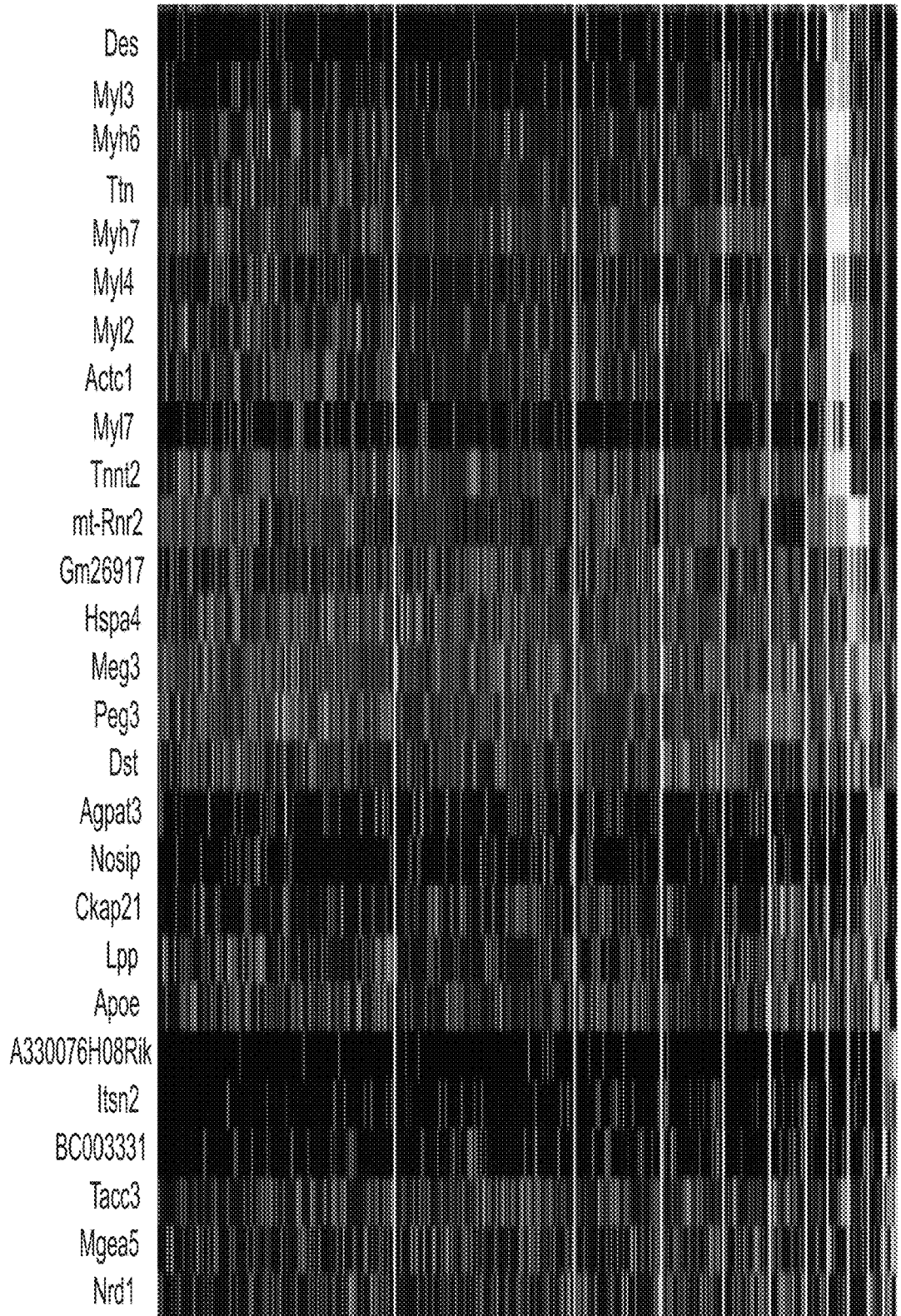
Figure 9G:
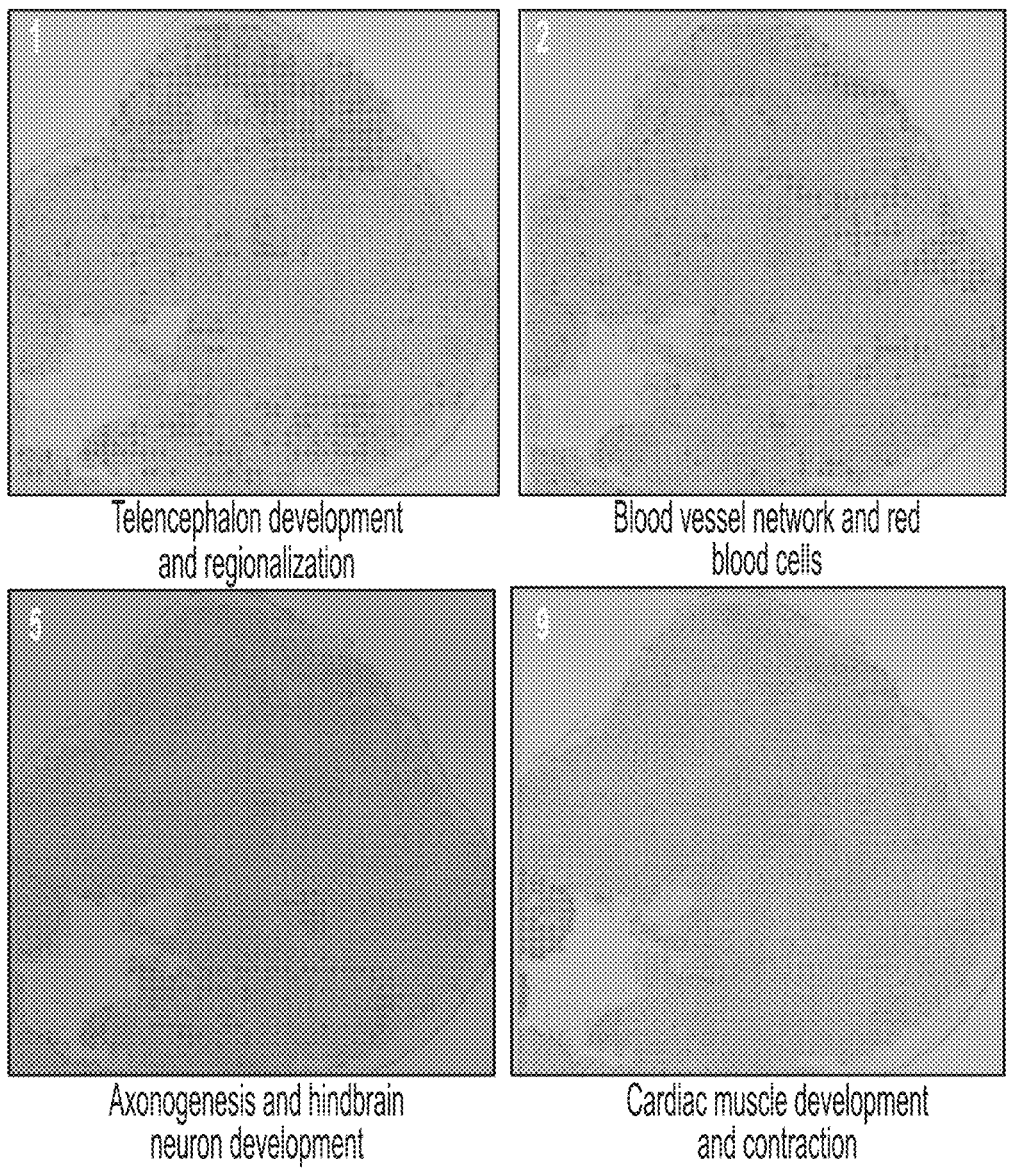

We conducted DBiT-seq with 25 µm pixel size to analyze the brain region of an E10 mouse embryo (FIGS. 9A-9G). As compared to the 50 µm experiment (FIG. 8A-8F), pan-mRNA and pan-protein UMI count maps (FIG. 9C) showed finer structures that correlated with tissue morphology (FIG. 9B). We surveyed all 22 individual proteins and observed distinct expression patterns in at least 12 proteins with four shown in FIG. 9D. CD63 was expressed extensively except in a portion of the forebrain. PECA, a pan-endothelial cell marker, was unambiguously detected in brain microvasculature, which was not readily distinguishable in tissue histology. EpCAM was localized in highly defined regions as thin as a single line of pixels (~25 µm) with high signal-to-noise ratio. MAdCAM was differentially expressed in a sub-region of the forebrain with distinct gene expression signatures (data not shown). To validate these observations, we performed immunofluorescence staining using nearby tissue sections from the same embryo to detect EpCAM and PECA. Spatial expression maps obtained by DBiT-seq and immunofluorescence staining were superimposed onto a H&E image and their line profiles were drawn for quantitative comparison (FIG. 9E). The major peaks agreed with each other although some discordance in exact peak positions was observed because different tissue sections were used for DBiT-seq and immunofluorescence. Finally, we performed unsupervised clustering of all the pixels using their mRNA expression profiles and identified 10 distinct clusters, characterized by specific marker genes (FIG. 9F). We then plotted the spatial distribution of pixels in four representative clusters against the H&E image (FIG. 9G) Pathway analysis of marker genes revealed that cluster 1 was mainly involved in telencephalon development, cluster 2 associated with erythrocytes in blood vessels, clusters 3 implicated in axonogenesis, and clusters 4 corresponding to cardiac muscle development, in good agreement with anatomical annotations. Cluster 2, enriched for hemoglobulin genes in red blood cells, coincided with PECA protein expression that delineated endothelial microvasculature. We further demonstrated that high-quality spatial protein mapping data can be used to guide genome-wide spatial gene expression analysis.

Example 10. High-Spatial-Resolution Mapping of Early Eye Development

Figure 10D:
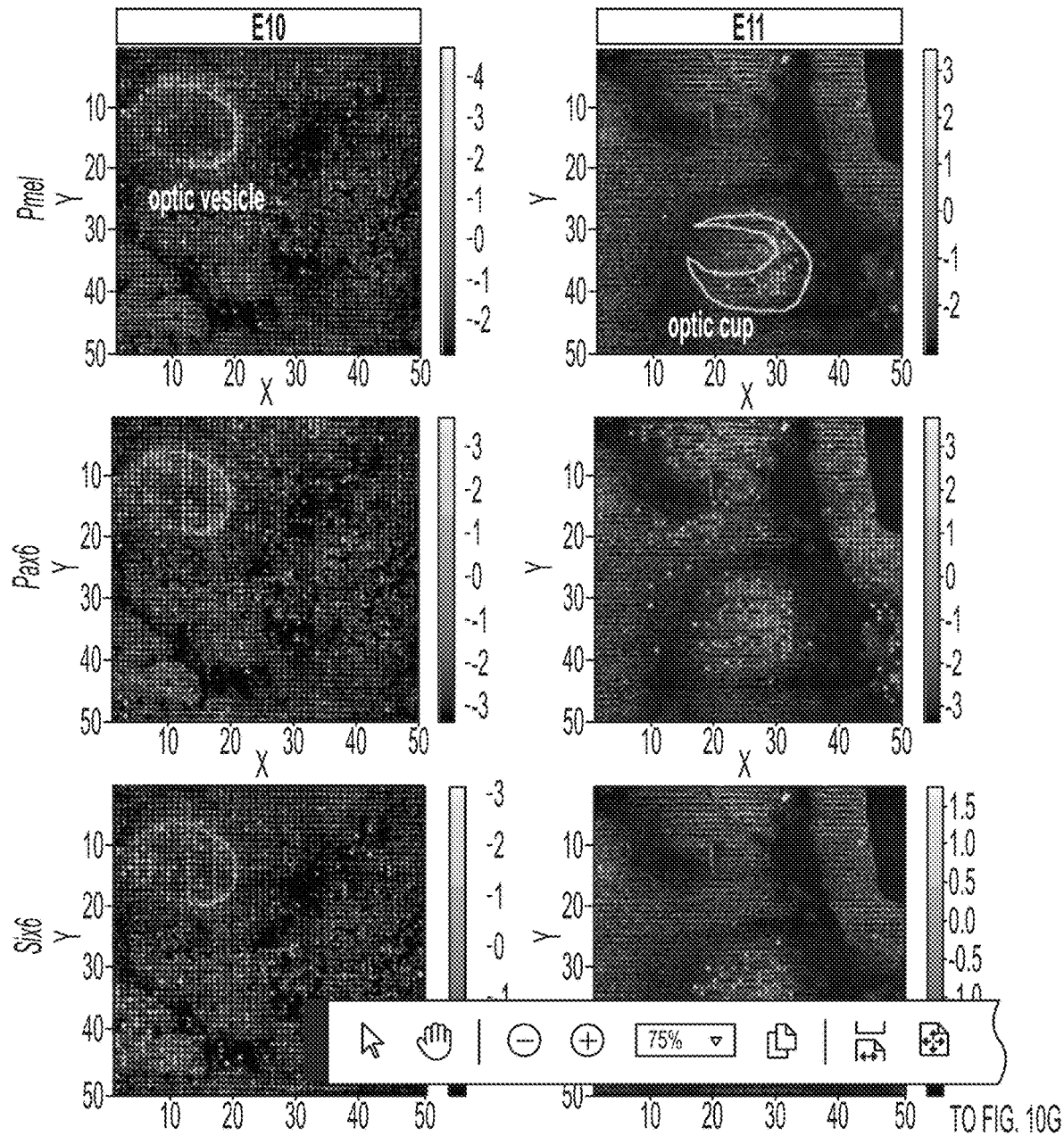
(FIG. 10D) Pmel, Pax6 and Six6 spatial expression superimposed onto the darkfield tissue images of the mouse embryo samples E10 and E11 (pixel size 10 µm). These genes are implicated in early stage embryonic eye development. Pmel was detected in a layer of melanocytes lining the optical vesicle. Pax6 and Six6 were mainly detected inside the optical vesicle but also seen in other regions mapped in this data.
Figure 10E:
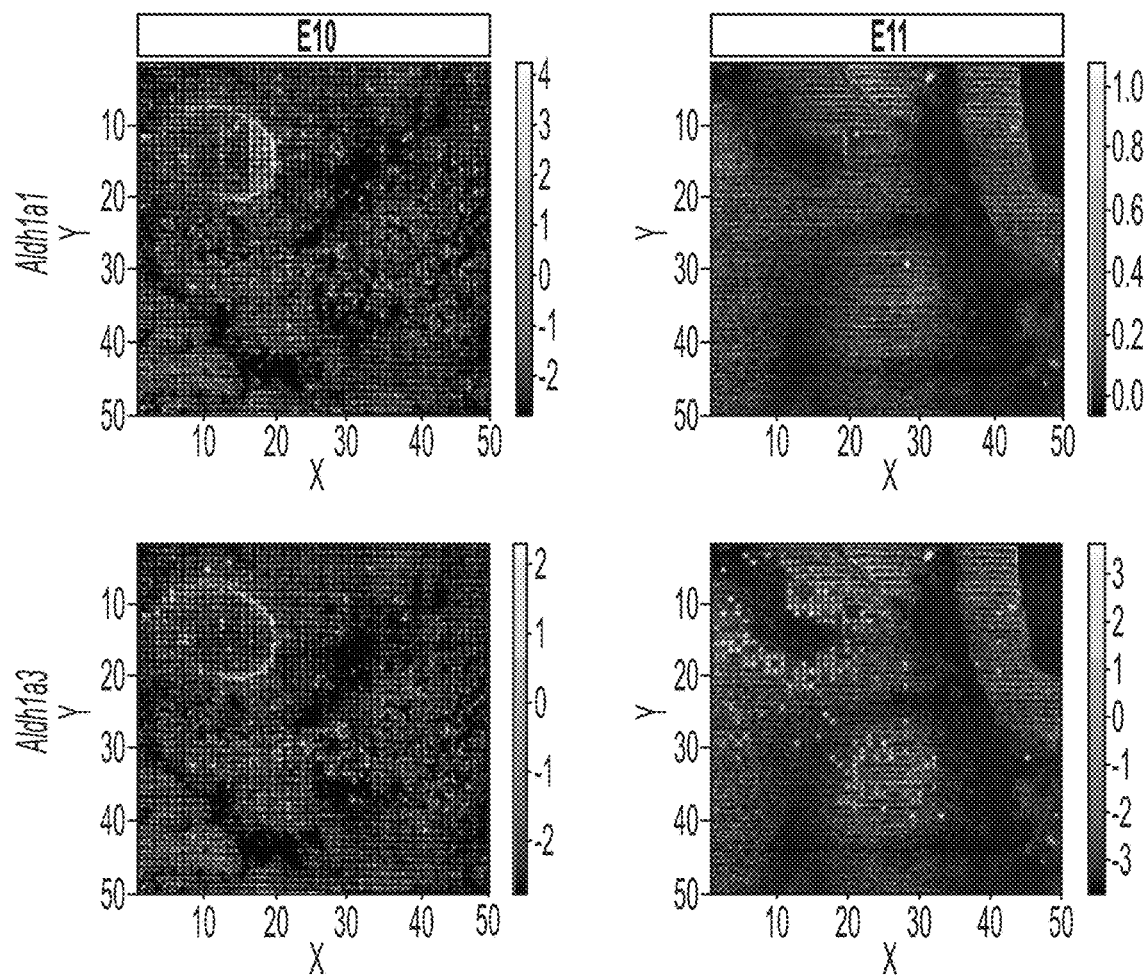
(FIG. 10E) Spatial expression of Aldh1a1 and Aldh1a3. Aldh1a1 is expressed in dorsal retina of early embryo, and meanwhile, Adlh1a3 is mainly expressed in retinal pigmented epithelium and in ventral retina.
Figure 10F:
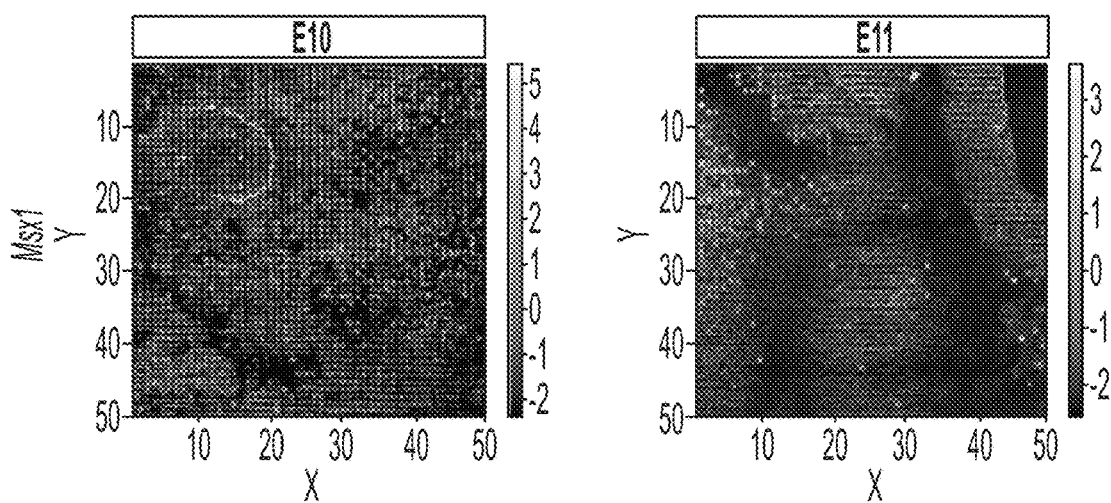
(FIG. 10F) Spatial expression of Msx1. It is mainly enriched in the ciliary body of an eye, including the ciliary muscle and the ciliary epithelium, which produces the aqueous humor.
Figure 10G:
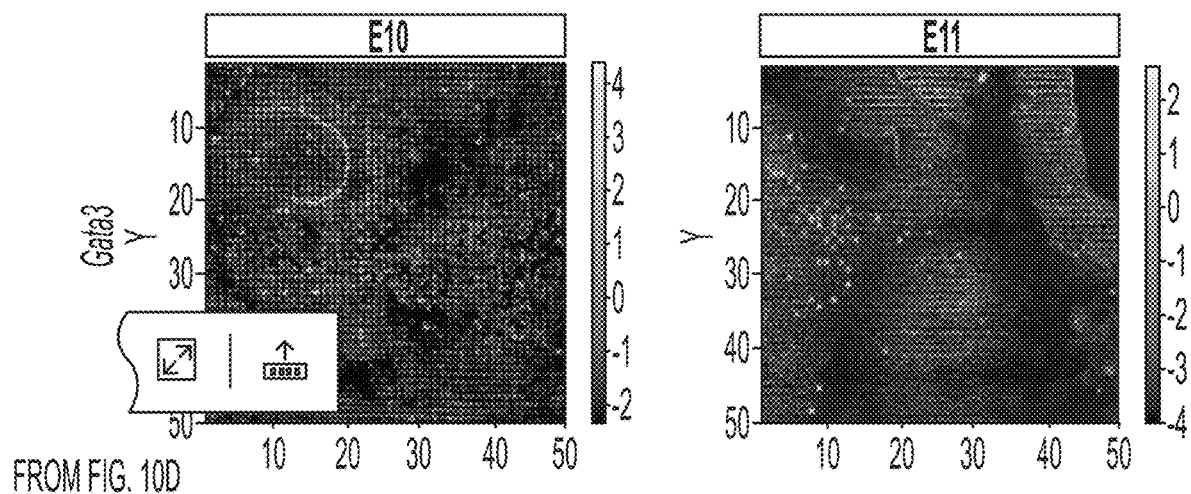
(FIG. 10G) Spatial expression of Gata3. It is essential for lens development and mainly expressed in posterior lens fiber cells during embryogenesis (FIG. 10H) Integration of scRNA-seq (Cao et al., 2019) and DBIT-seq data (10 µm pixel size). The combined data were analyzed with unsupervised clustering and visualized with different colors for different samples. It revealed that DBiT-seq pixels conformed into the clusters of scRNA-seq data (FIG. 10I) Clustering analysis of the combined dataset (scRNA-seq and DBIT-seq) revealed 25 major clusters.

We conducted further spatial transcriptome mapping of the developing eye field in a E10 mouse embryo using 10 µm microfluidic channels and the resultant pan-mRNA UMI heatmap was superimposed onto the whole mouse embryo tissue image (FIG. 10A). An enlarged view of the mapped region showed the imprinted morphology and individual pixels. An adjacent tissue section was stained for H&E (FIG. 10B). At this stage (E10), the eye development likely reaches a late optic vesicle stage. Four genes were identified within the optic vesicle with distinct but spatially correlated expression patterns (FIG. 10C and data not shown). Pax6 was expressed in the optic vesicle and stalk (Heavner and Pevny, 2012; Smith et al., 2009). Pmel, a pigment cell-specific gene (Kwon et al., 1991) involved in developing fibrillar sheets, was observed around the optic vesicle. Six6, a gene known for specification and proliferation of retinal cells in vertebrate embryos, was mainly localized within the optical vesicle but not the optic stalk (Heavner and Pevny, 2012). Trpm1 lined the optic vesicle showing minimal overlap with Six6. It is known that the retinal pigment epithelium (RPE) consists of a single-cell-layer of melabocytes lining around an optic vesicle, which was successfully detected by DBiT-seq with markers like Pmel and Trpm1 (Mort et al., 2015). We further performed GO analysis to identify major pathways and signature genes (data not shown). Eye development and melanin pathways emerged as the two major categories. Additionally, we performed 10 μm DBiT-seq on an E11 mouse embryo and compared it with E10 side-by-side for the eye field region (FIG. 10D). The expression patterns of Pmel, Pax6 and Six6 around the eye were similar between E10 and E11 embryo, but showed spatial changes as the optic cup started to form in E11 (Yun et al. 2009). Additionally, we analyzed other genes known to be involved in early eye formation (FIGS. 10E, 10F and 10G). Aldh1a1, a gene encoding Aldehyde Dehydrogenase 1 Family Member A1, was observed in the dorsal retina whereas Aldh1a3 was mainly located at the ventral side and RPE. The spatial patterning of Aldh1a1 and Aldh1a3 within the eye field and the changes from E10 to E11 were in agreement with literature, showing that the Aldh1a family genes differentially control the dorsal-ventral polarization in embryonic eye development (Matt et al., 2005). We noticed that Msx1, a gene highly expressed in both ciliary muscle and ciliary epithelium as the structural support of eye (Zhao et al., 2002), was mainly surrounding the eye field in both E10 and E11 embryos. Gata3, a gene pivotal for eye closure, was enriched at the front end of the eye field to control the shape of eye during development. Our data allowed for high-spatial-resolution visualization of genome-wide gene expression in early stage eye field development.

Example 11. Direct Integration with Single-Cell RNA Sequencing Data

Figure 10H:
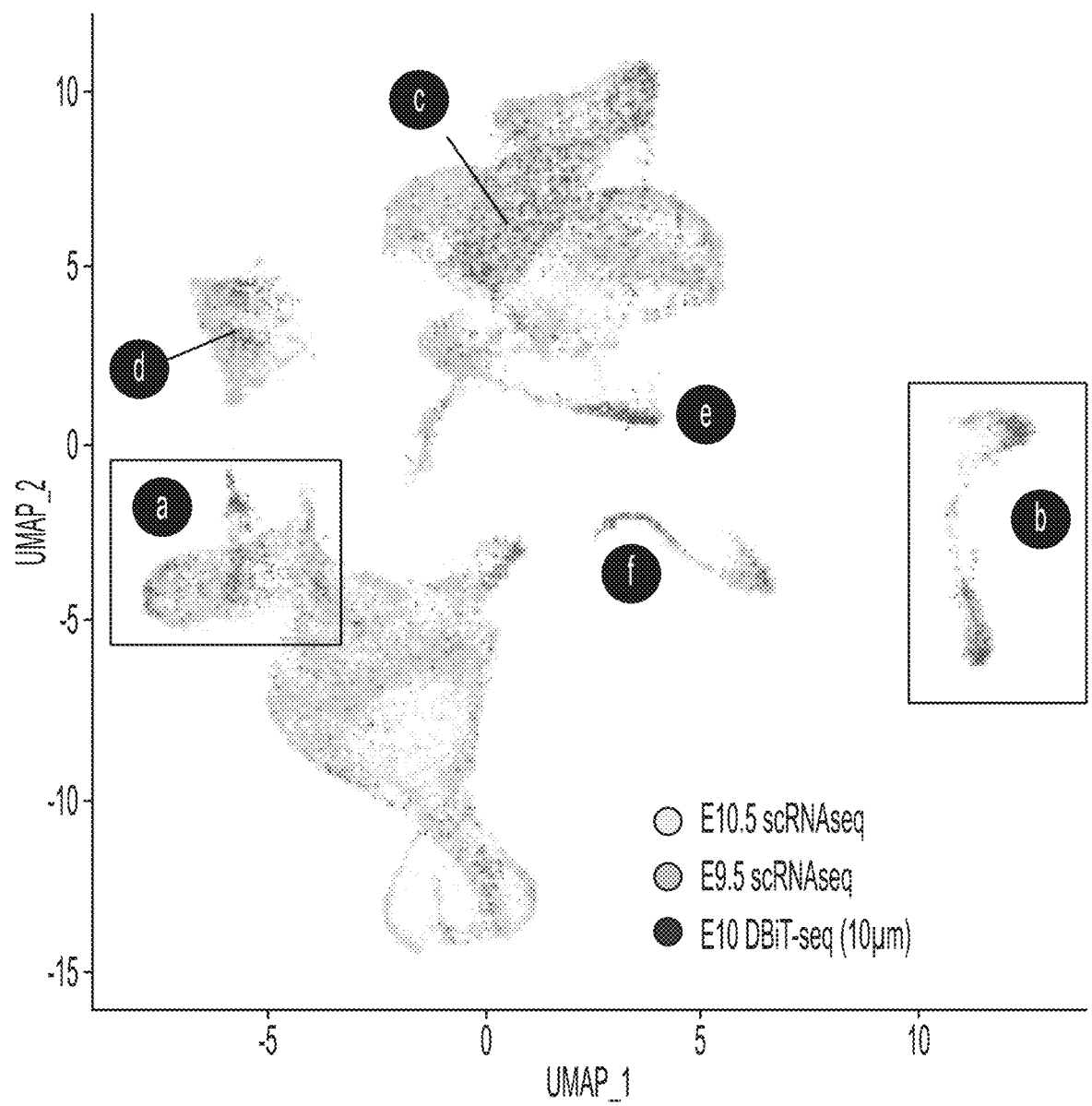
FIGS. 10A-10N. Mapping gene expression in early eye development at the single-cell-layer resolution.
(FIG. 10B) H&E staining performed on an adjacent tissue section. Scale bar=200 µm.
(FIG. 10C) Overlay of spatial expression maps for selected genes. It revealed spatial correlation of different genes with high accuracy. For example, Pax6 is expressed in whole optic vesicle including a single-cell-layer of melanocytes marked by Pmel and the optical nerve fiber bundle on the left. Six6 is expressed within the optic vesicle but does not overlap significantly with the melanocyte layer although they are in proximity. Scale bar=100 µm.
(FIG. 10J) Spatial pattern of select clusters (0, 2, 4, 6, 7, 8, 14, 19, 20, 22) identified in UMAP (FIG. 10I).
(FIG. 10K) Cell types (different colors) identified by scRNA-seq and comparison with DBIT-seq pixels (black) (FIG. 10L), (FIG. 10M) & (FIG. 10N) Spatial expression pattern of DBIT-seq pixels from select clusters (FIG. 10I) in relation to cell types identified (FIG. 10K).
Figure 10I:
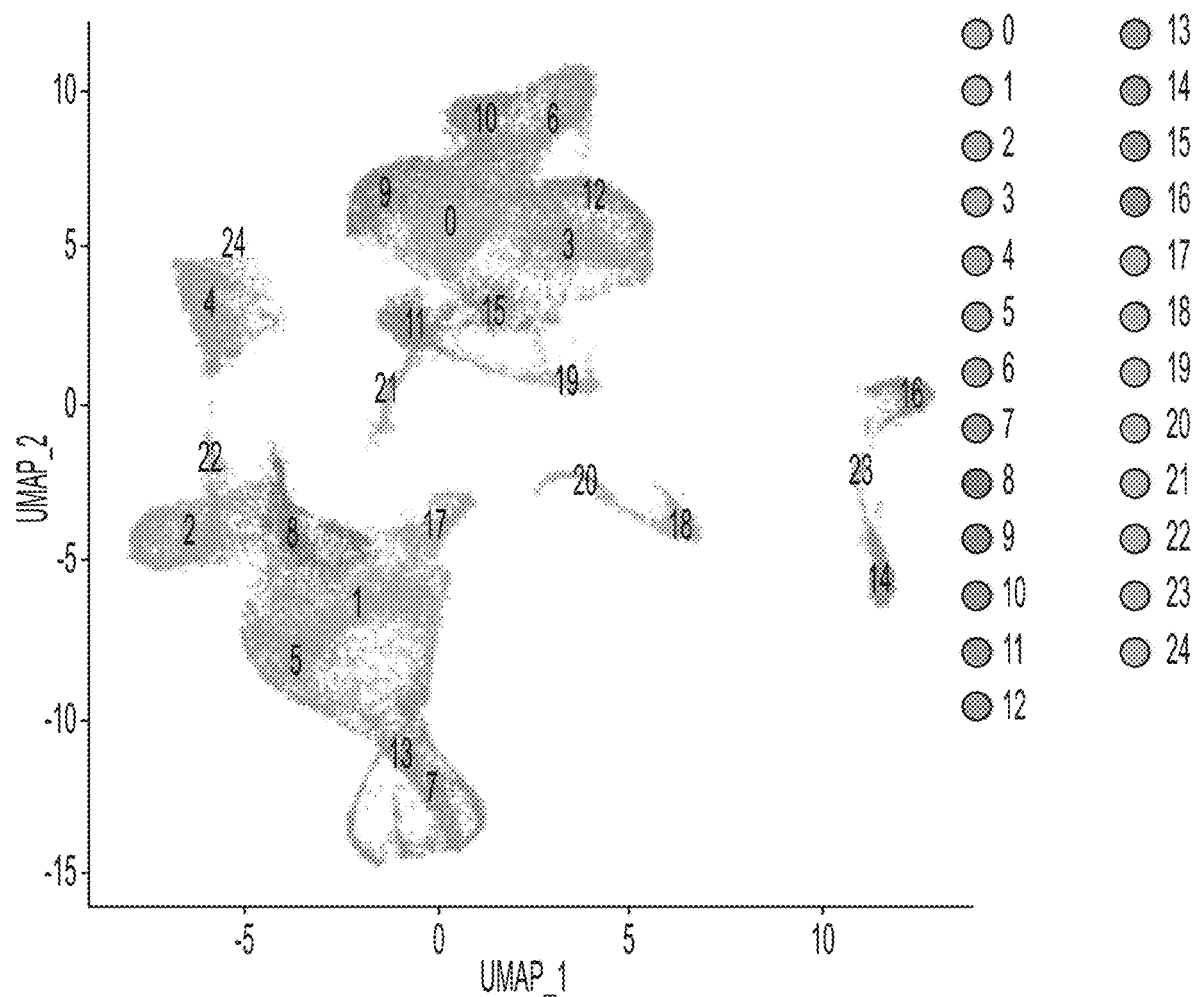
Figure 10J:
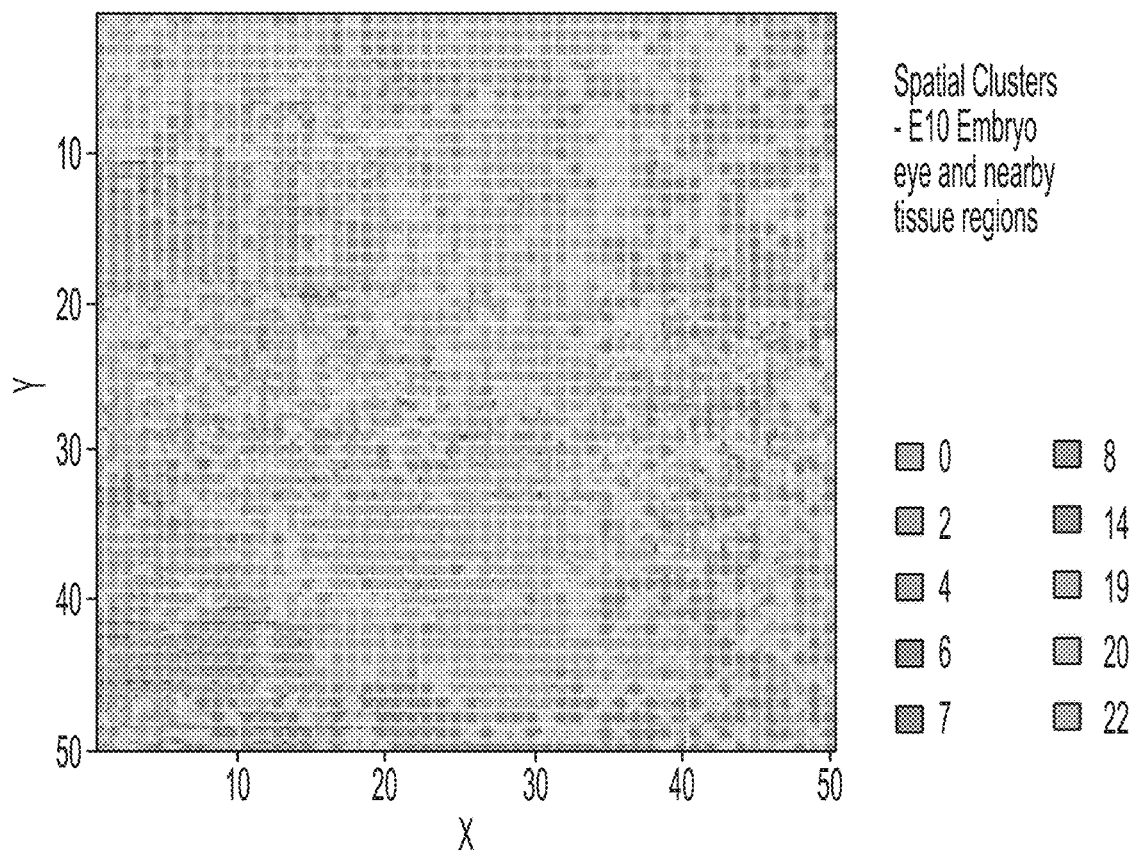
Figure 10K:
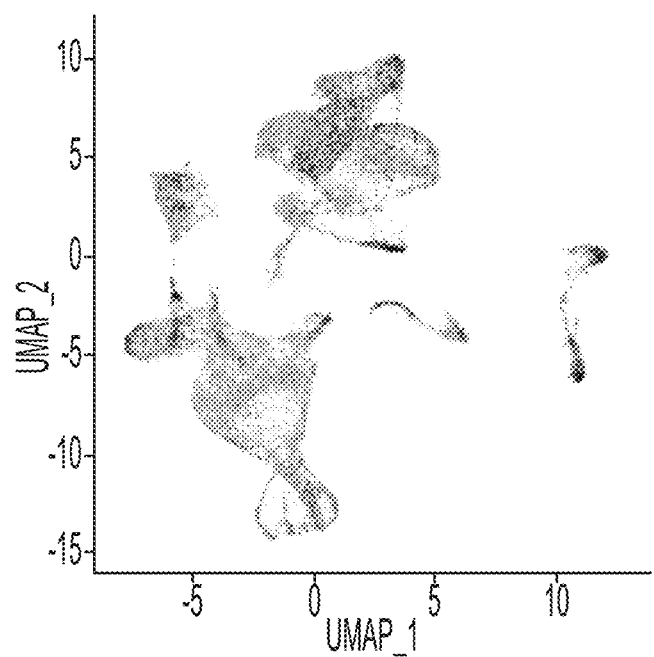
Figure 10L:
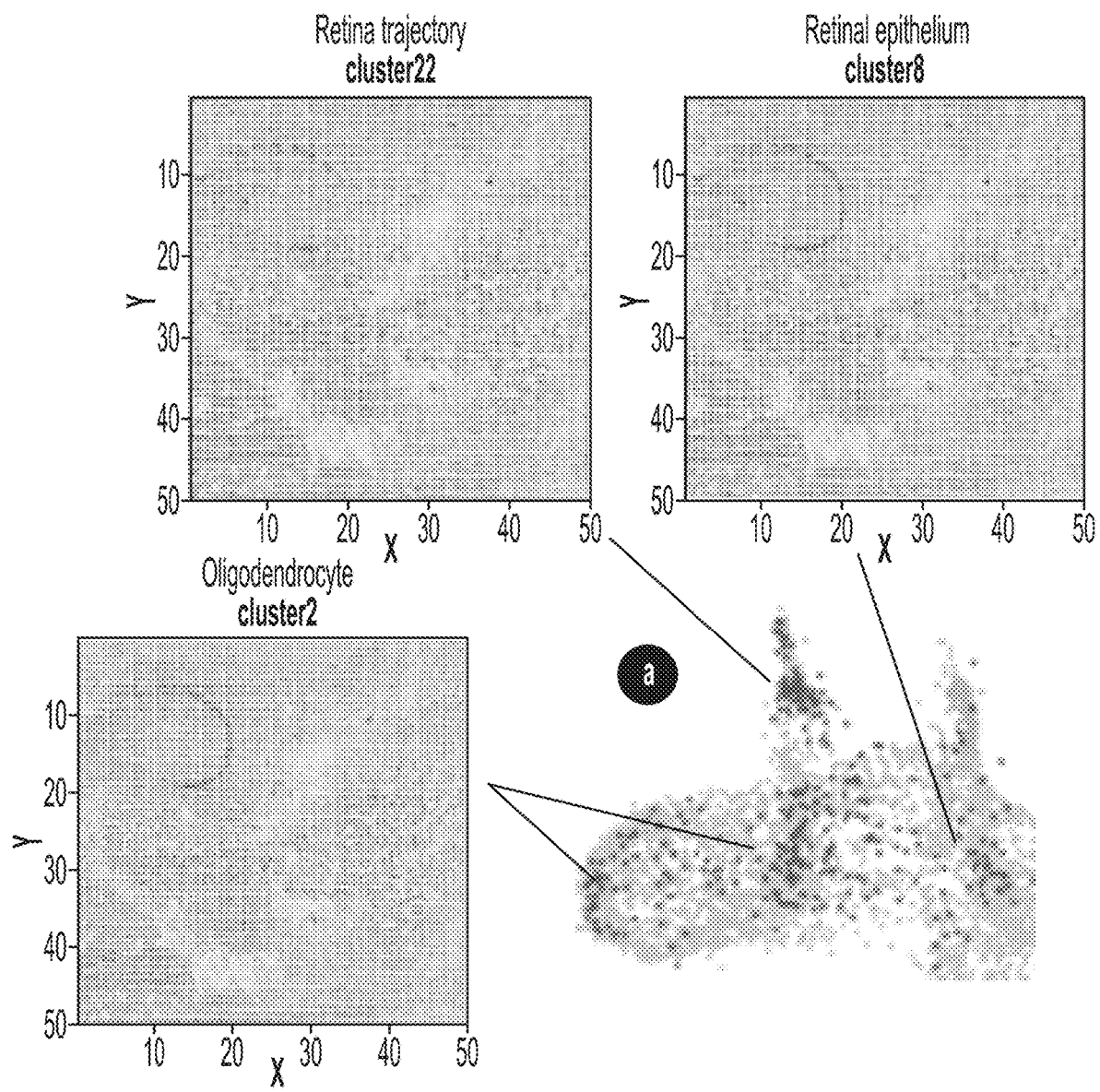
Figure 10M:
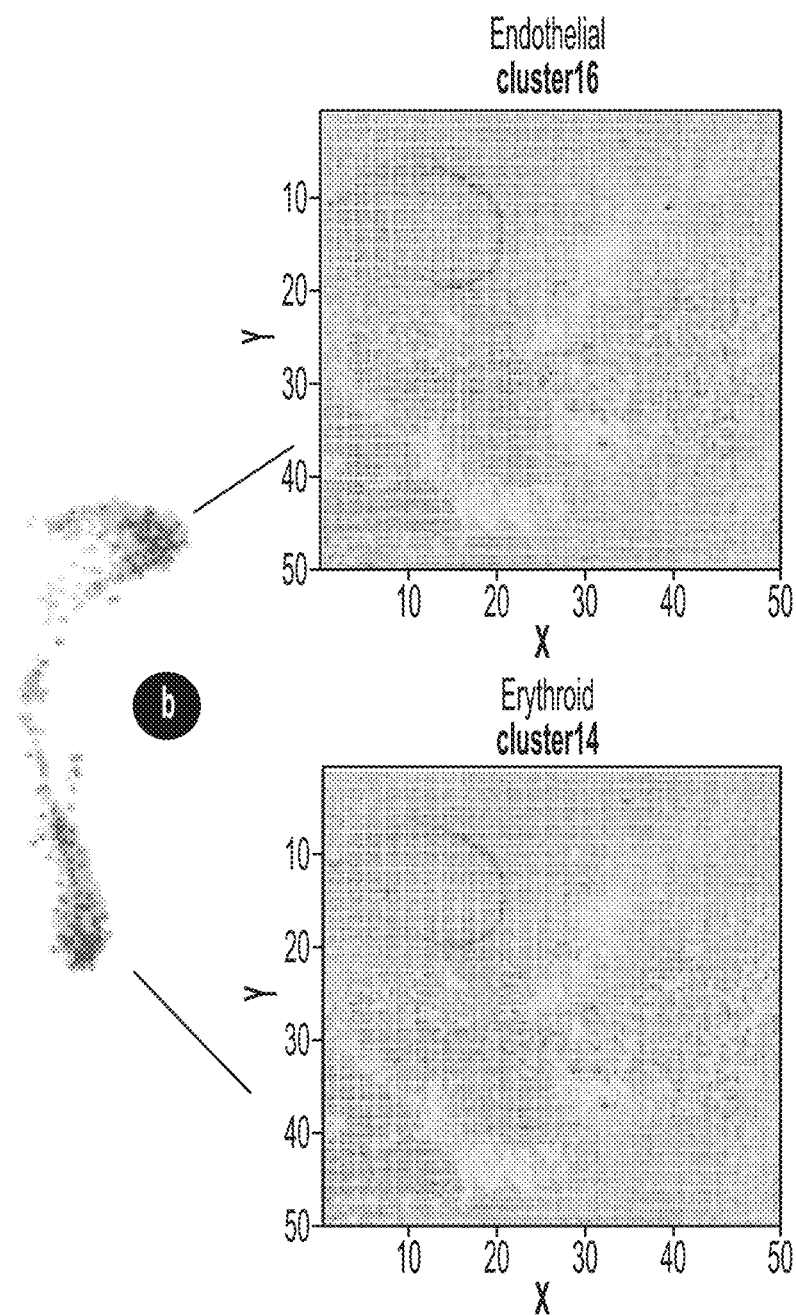
Figure 10N:
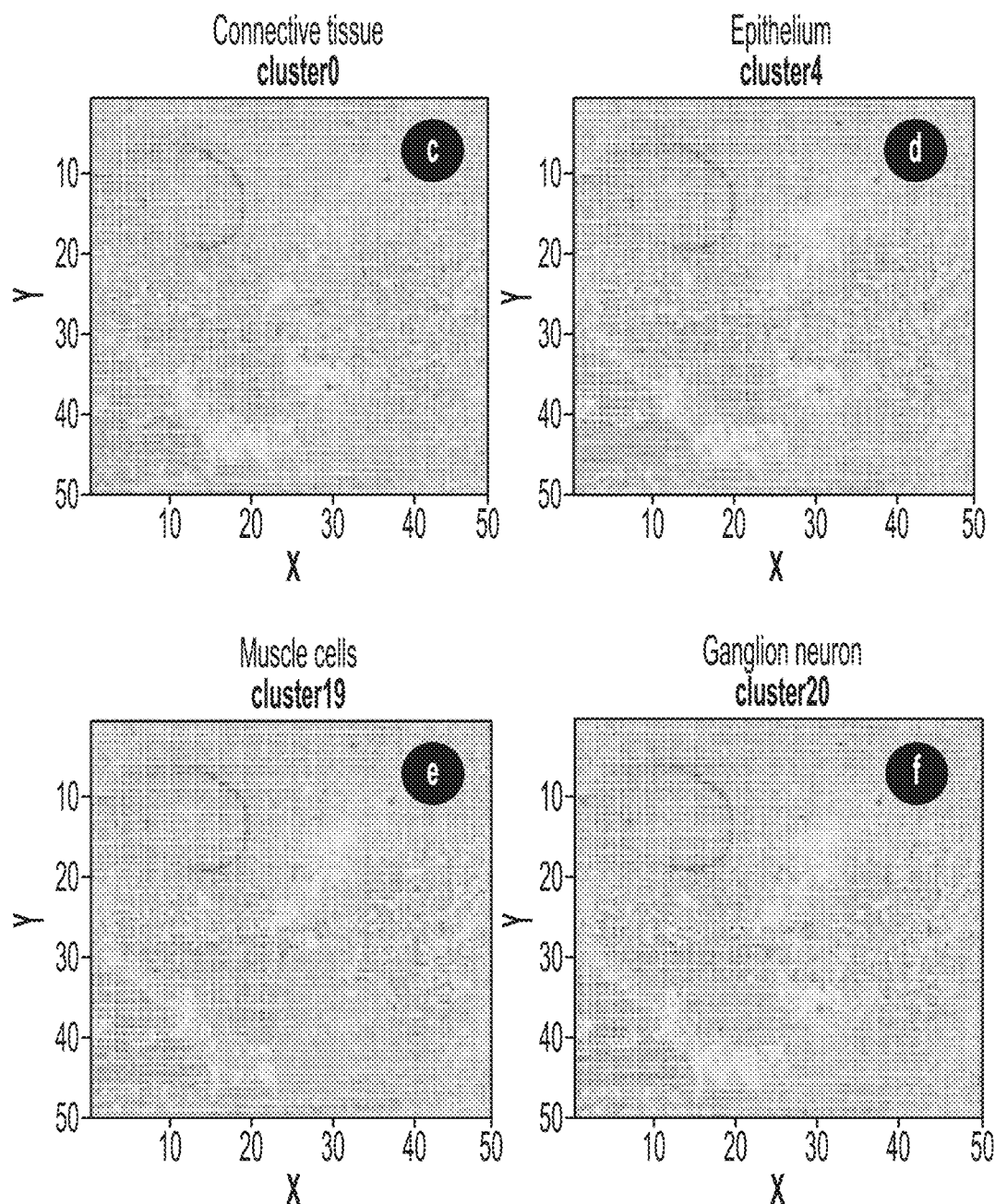

We observed additional tissue features based on the spatial expression pattern of 19 top ranked genes (data not shown) but the cell types could not be readily identified. Since the pixel size (10 μm) in this experiment was approaching cellular level, we speculated that it is possible to directly integrate data from scRNA-seq and DBIT-seq to infer cell types and visualize spatial distribution, scRNA-seq data from E9.5 and E10.5 mouse embryos (Cao et al., 2019) were combined with DBIT-seq data (10 μm pixel size) from an E10 mouse embryo to perform unsupervised clustering (FIG. 10H). We found that the spatial pixels conformed well into single cell transcriptomes and together identified 24 clusters in the combined dataset (FIG. 10I). Each cluster was mapped back to its spatial distribution in tissue (8 clusters are shown in FIG. 10J). We further used scRNA-seq data as a reference for cell type annotation (FIG. 10K) and the reported 53 cell types were directly compared to DBiT-seq data (black) in UMAP, allowing for detecting the dominant cell type in each pixel (10 μm). Then, we could link scRNA-seq-annotated cell types to corresponding spatial pixels and visualize cell type distribution on the tissue. First, we examined spatial pixels in clusters 2, 8 and 22 (see a in FIG. JOH) and the dominant cell types were found to be retina trajectory, retina epithelium, and oligodendrocyte. Mapping cell type-annotated pixels to the tissue image showed that retina trajectory and retina epithelium cells were indeed localized within the optic vesicle while oligodendrocytes were localized in three tissue regions with one corresponding to optic stalk right next to optic vesicle, in agreement with the observation that multiple sub-clusters of oligodendrocyte pixels were present (FIG. 10L). Second, spatial pixels in the region b of FIG. 10H were detected only in clusters 14 and 16, which were found to be dominated by erythroid and endothelial cells. Mapping them back to the tissue image revealed microvessels (endothelial) and blood clots (erythroid) at the upper right corner (FIG. 10M). Third, we also analyzed spatial pixels in c-f of FIG. JOH and the corresponding clusters 0, 4, 19, and 20, respectively Linking spatial pixels to cell types revealed (c) connective tissues as the structural support of eye formation, (d) epithelial cells forming the pituitary gland, muscle cells (e) surrounding the trigeminal sensory nerve for facial touch sensing, and ganglion neurons (f) in the trigeminal sensor itself (FIG. 10N). Thus, DBiT-seq with 10 μm pixel size can be directly integrated with scRNA-seq to infer cell types and visualize spatial distribution in the tissue context.

Example 12. Clustering Analysis of 11 Embryo Samples Across Different Stages (E10-12)

Figure 11A:
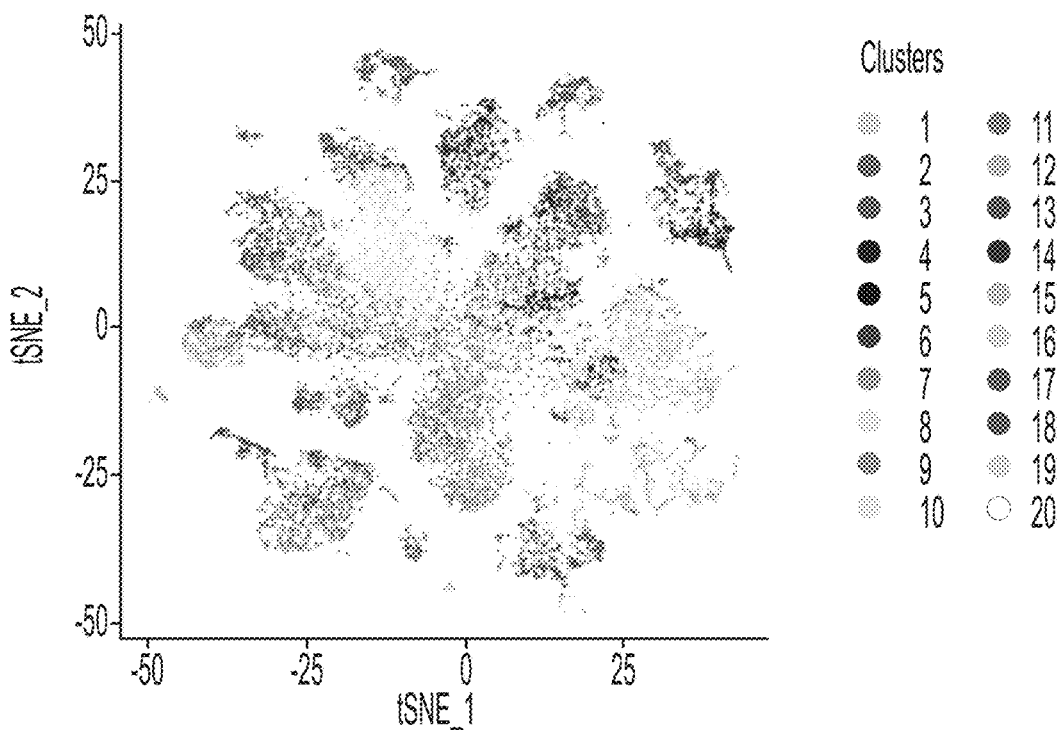
FIGS. 11A-11D. Global clustering analysis of 11 mouse embryos from E10, E11 to E12.
Figure 11B:
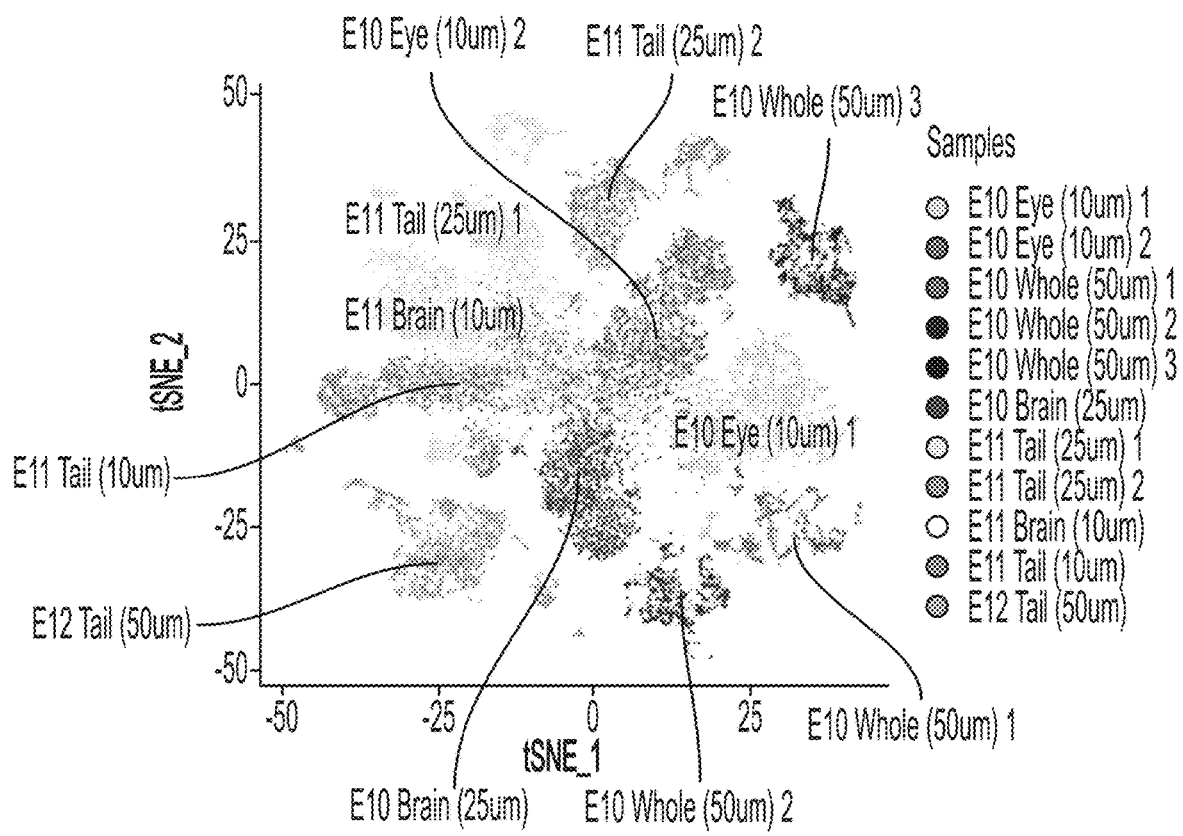
Figure 11C:
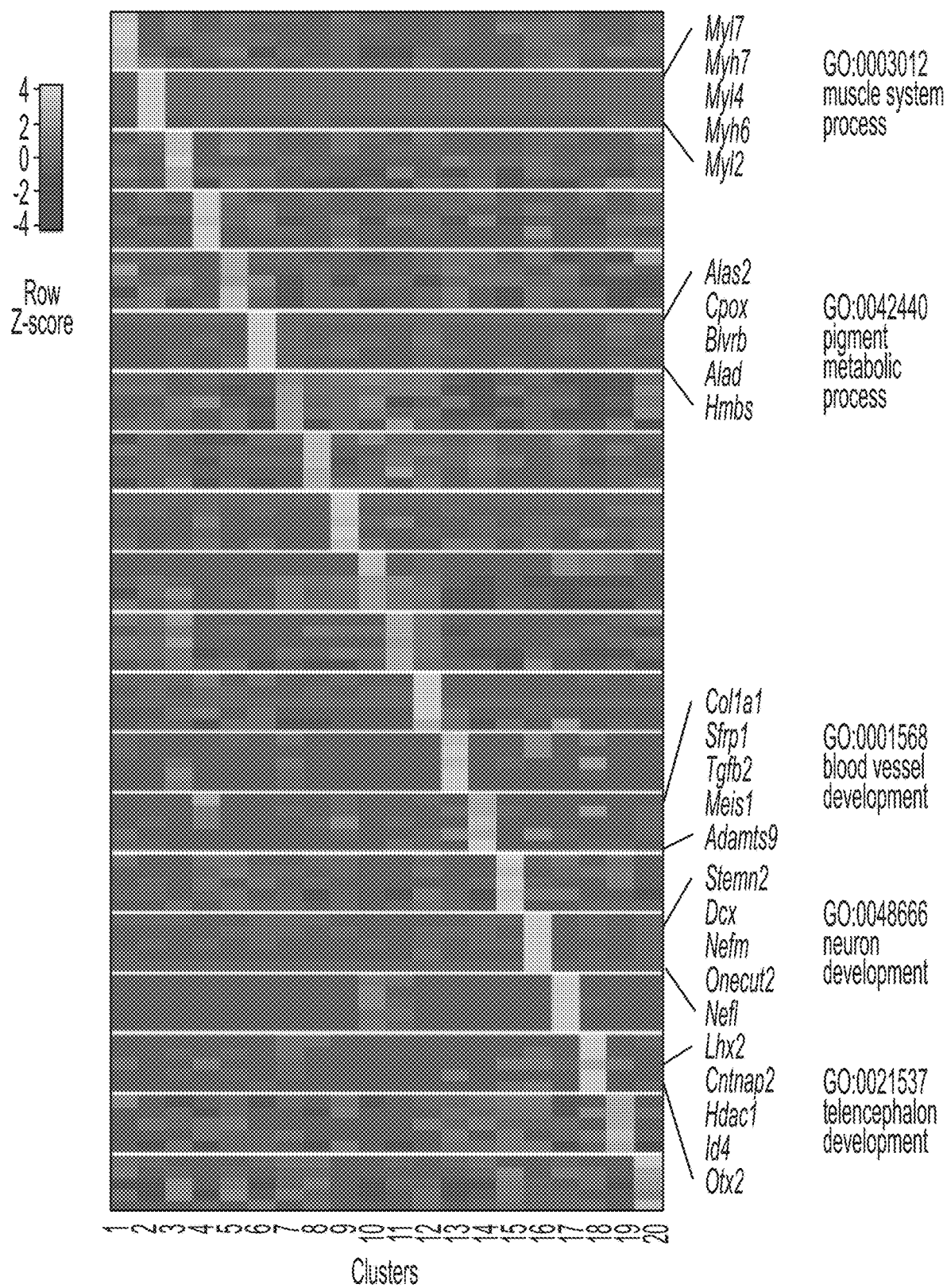
Figure 11D:
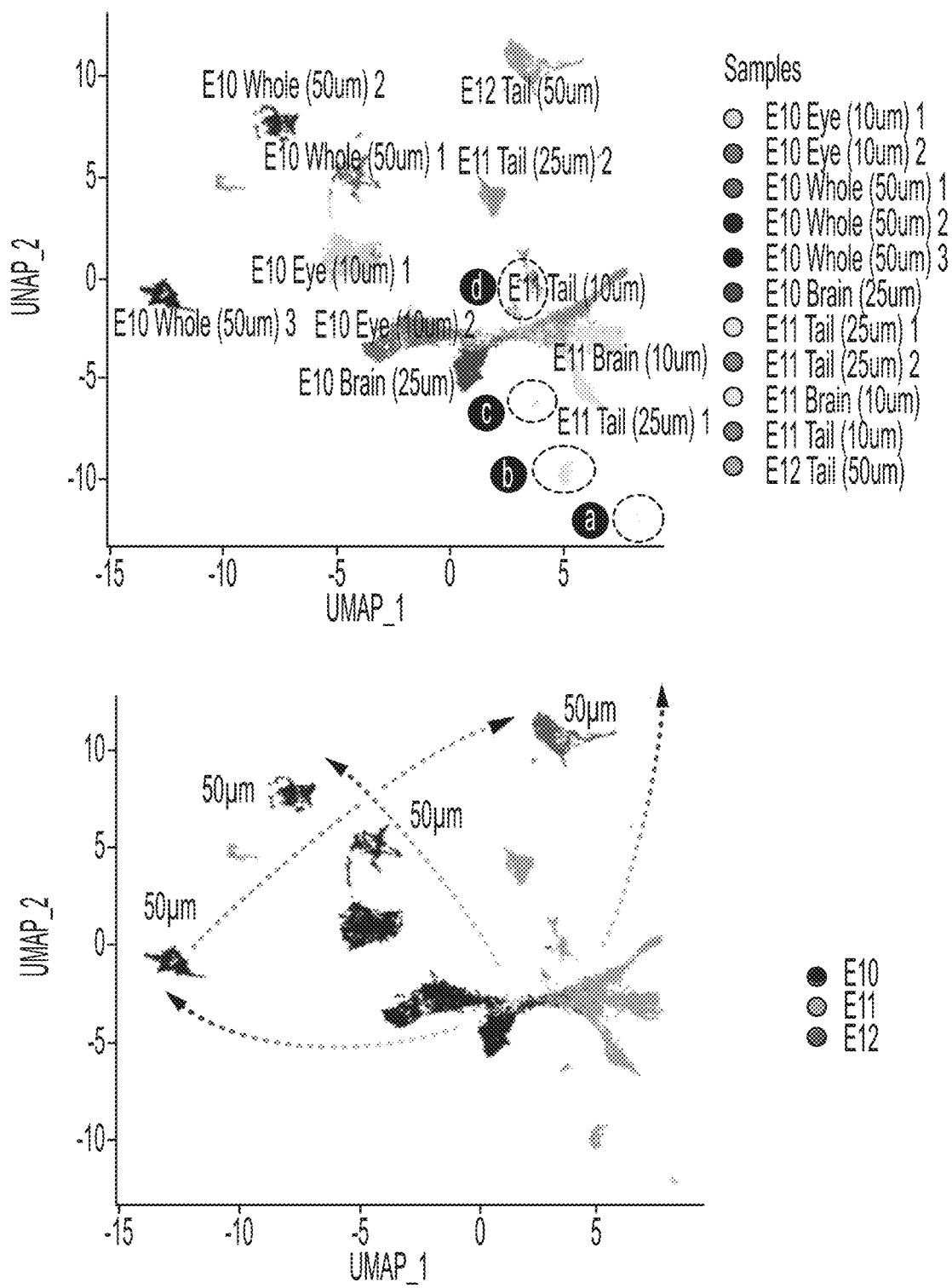

To further understand the early development of mouse embryo over time, we integrated the DBiT-seq data of 11 mouse embryo tissue samples from three stages, E10. E11 and E12 (FIGS. 11A-11D) and conducted unsupervised clustering, which showed 20 clusters visualized by t-distributed stochastic neighbor embedding (t-SNE) (FIGS. 11A and 11B) and the top differentially expressed genes (FIG. 11C). Cluster 2 was associated with muscle system processes with the Myl gene family preferentially expressed and the pixels in this cluster were mainly from three E11 tail samples (see FIG. 11A). Although the pixels from the same sample were clustered together without batch normalization, some samples like "E11 Tail (25 μm) 1" showed multiple distant clusters (FIG. 11D left panel), indicating significant difference of tissue types in this sample. The large pixels (50 μm) tend to locate away from the origin of the UMAP presumably because they covered many more cells and possessed a higher degree of cell diversity within a pixel. In contrast, the 10 μm pixels were clustered around the center of the UMAP, indicating a convergence to single-cell-level gene expression. E10. E11 and E12 pixels were spaced out along the same trajectory (left to right) consistent with the development stages although these samples were hugely different, so that they were mapped for different tissue regions (head vs tail) and of different pixel sizes (10, 25 vs 50 μm) (FIG. 11D right panel).

Examples 13. Spatial Mapping of Internal Organ Development

Figures 12E, 12F:
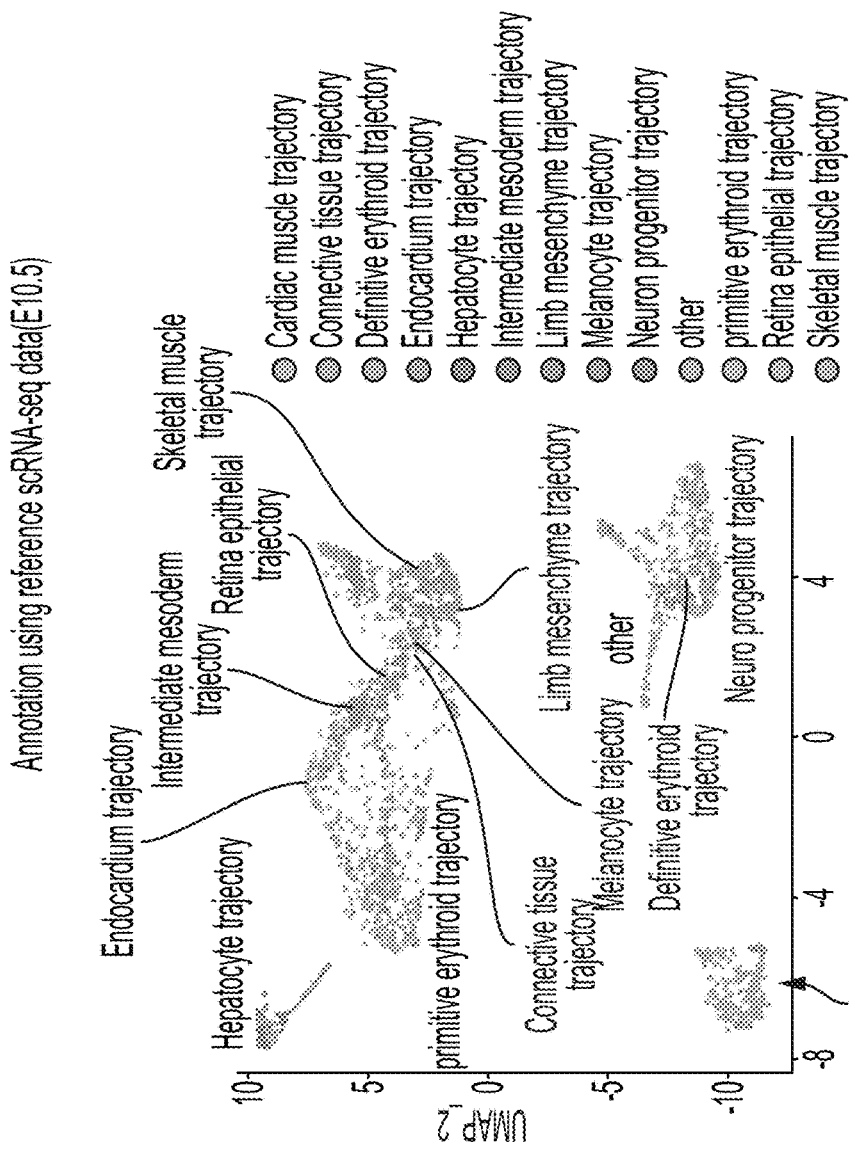
Figure 12G:
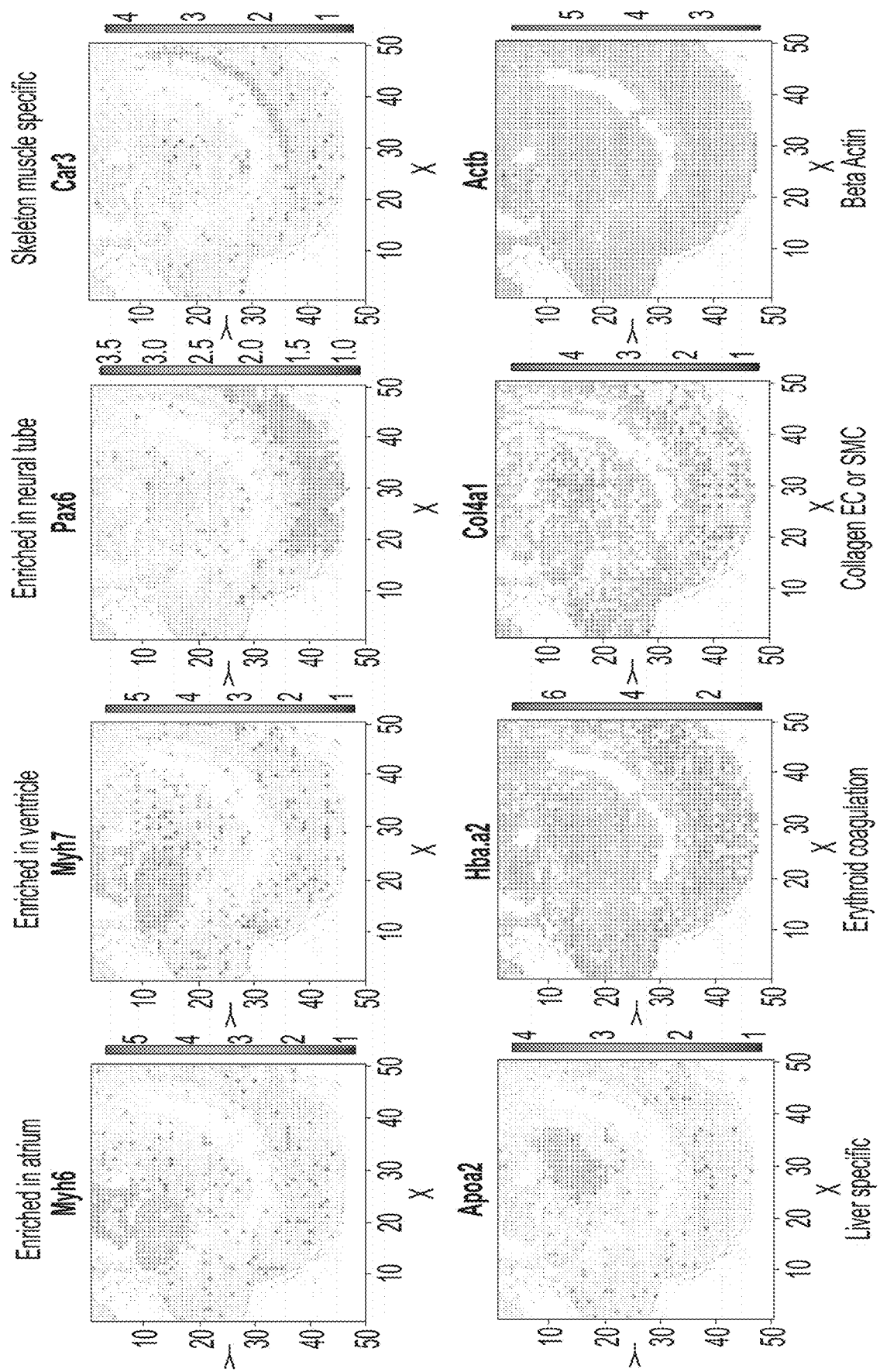

Sample "E11 Tail (25 μm) 1" showed multiple distinct sub-clusters in the global UMAP (FIG. 11D left panel) which made us wonder what cell types constitute these clusters (see enlarged view in FIG. 12A). Four subclusters (a, b, c and d) were mapped back to the tissue image, which revealed distinct spatial patterns for all of them (FIG. 12B). Clustering analysis of all pixels in this sample identified 13 clusters visualized in both UMAP (FIG. 12C) and spatial map (FIG. 12D). To unveil the identities of these spatial patterns, we again use scRNA-seq as reference (Cao et al., 2019) to perform automated cell type annotations (FIG. 12E) with SingleR (Aran et al., 2019) The dominant cell types in these spatial clusters (a, b, c, and d) were associated with different internal organs such as liver (cluster a), neutral tube (cluster b), heart (cluster c), and blood vessels containing coagulated erythrocytes (cluster d) (FIG. 12G). We further visualized the spatial expression of 8 representative marker genes (FIG. 12F). Myh6, a gene encoding Myosin heavy chain a, was highly expressed in atria, while Myh7 (encoding myosin heavy chain B) was the predominant isoform expressed in ventricular muscle, allowing for not only detecting cardiac muscle cells but also differentiating between atria vs ventricle of an embryonic heart. Pax6 was expressed in region-specific neural progenitors in the neural tube. Car3, which encodes carbonic anhydrase III and expressed in slow twitch skeletal muscles, specifically delineated the formation of notochord. Apoa2, which encodes apolipoprotein E, is liver specific. Hemoglobin a encoding gene. Hba.a2, normally found in red blood cells, indicated the coagulated erythrocytes in both large vessels like dorsal aorta and microvessels in multiple organs. It was also found in the blood clots inside atria. Col4a1, which encodes a specific collagen, the type IV alpha1, produced by endothelial cells to form the basement membrane, precisely lined the inner surface of the dorsal aorta, which supposedly consisted of a single layer of endothelial cells. It was also expressed in heart presumably at endocardium and coronary arties. Actb, which encodes β-actin, a widely used reference or housekeeping gene, was expressed extensively throughout the embryo but showed lower expression in, for example, nervous tissues. We also compiled the "pseudo bulk" expression data by aggregating pixels in three major organs (heart, liver and neutral tube) and compared with the ENCODE bulk RNA-seq data side-by-side, which revealed excellent concordance (Pearson Correlation Coefficient=~0.8) (data not shown).

Example 14. Automated Feature Identification with spatialDE

Figure 13A:
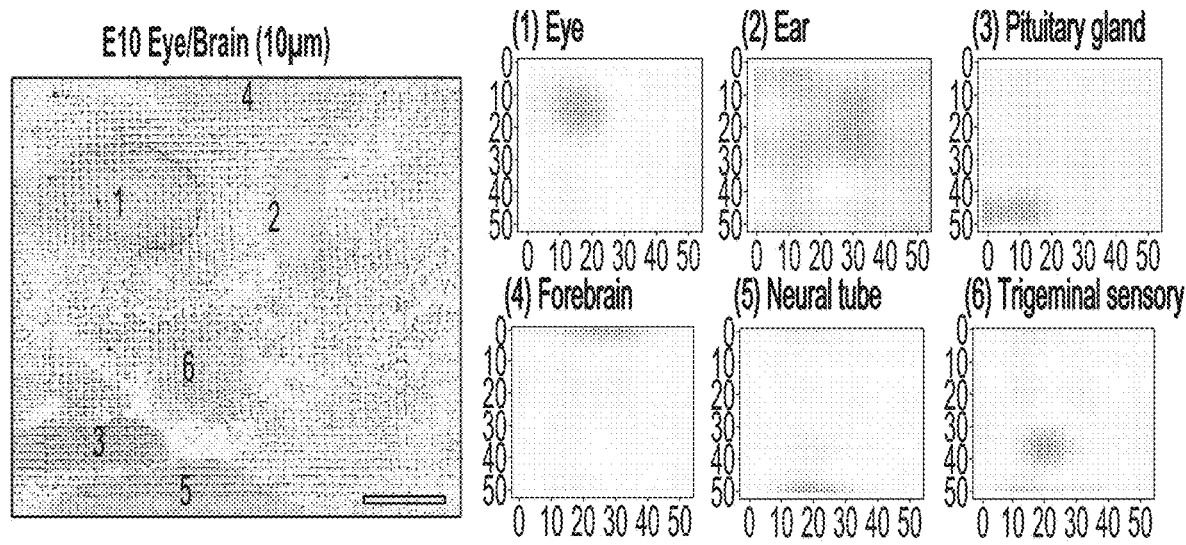
FIGS. 13A-13C. SpatialDE for automated feature identification.
Figure 13B:
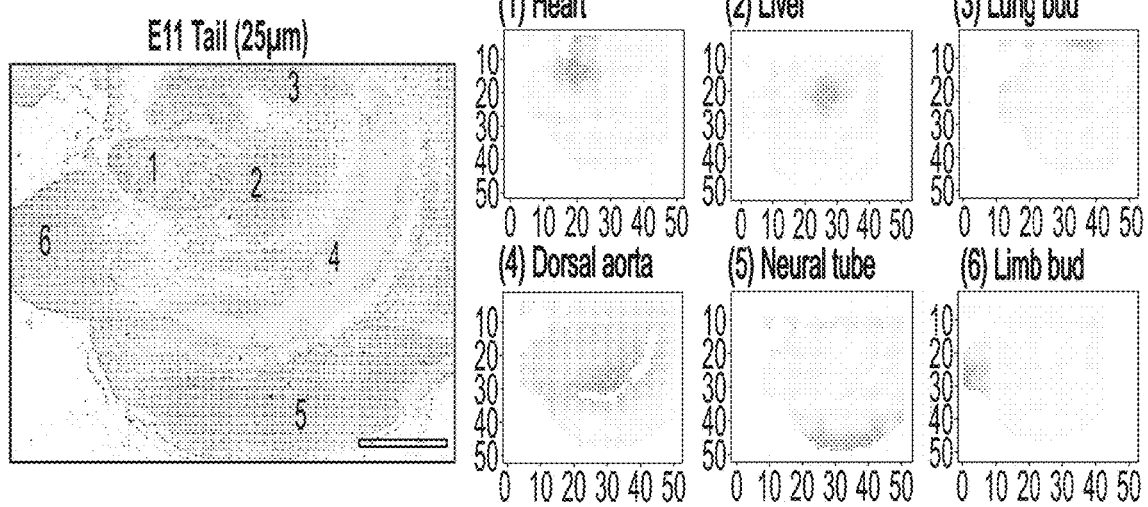
Figure 13C:
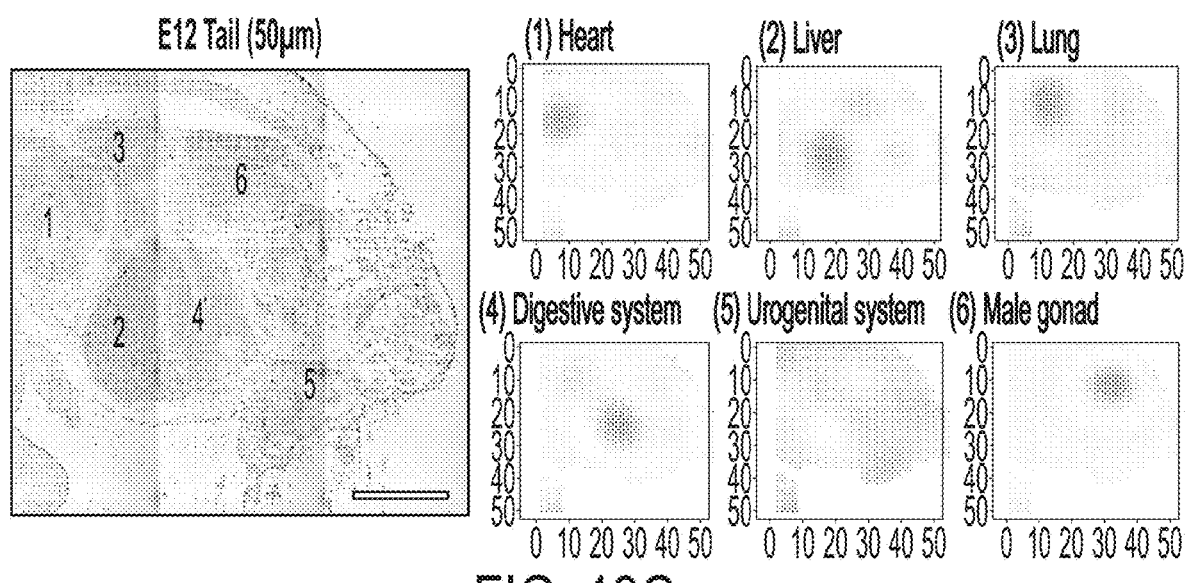

Spatial differential expression (spatialDE) pipeline (Svensson et al., 2018a) previously developed for ST data analysis was evaluated in our study for automated discovery of spatial tissue features without using scRNA-seq for cell type annotation. In addition to the major pathways associated with eye development in FIGS. 10A-10E, spatialDE identified 20 features (FIG. 13A) including eye, ear, muscle, forebrain, and epithelium, which are in agreement with scRNA-seq based cell type identification. In contrast, some features were hardly distinguishable in the corresponding tissue image such as ear (presumably due to too early stage in the developmental process) and forebrain (barely covered in the mapped tissue region). SpatialDE was applied to the data in FIGS. 12A-12G and detected not only heart, liver, dorsal aorta, and neural tube as previously discussed but also a small fraction of lung bud covered in the mapped tissue region. Many internal organs begin to develop at the stage of E10 but barely distinguishable. To further evaluate the potential for spatialDE to detect more distinct organs or tissues, an E12 mouse embryo was analyzed using DBiT-seq. Interestingly, in only ⅓ of the whole embryo tissue section, spatialDE identified 40 distinct features including heart, lung, urogenital system, digestive system, and male gonad (testis) (see FIG. 12C). Many of these features were still too early to identify based on tissue morphology. We also revisited the E10 whole mouse embryo (FIGS. 8A-8F) and E11 lower body DBIT-seq data (FIGS. 12A-12G), and identified ~20 and ~25 distinct features, respectively (data not shown), which were less than that from the E12 sample, indicating that the features newly identified in E12 were associated with the developmental process and the emergence of internal organs at this stage.

Figure 14C:
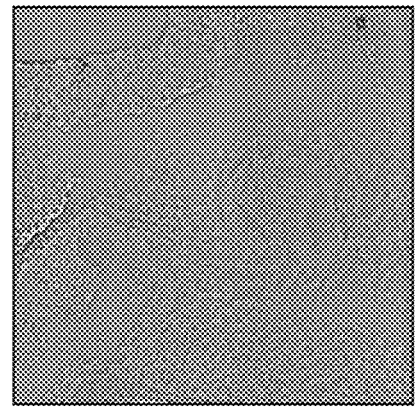
FIGS. 14A-14H. DBiT-seq on a fluorescent IHC-stained tissue sample.
Figure 14F:
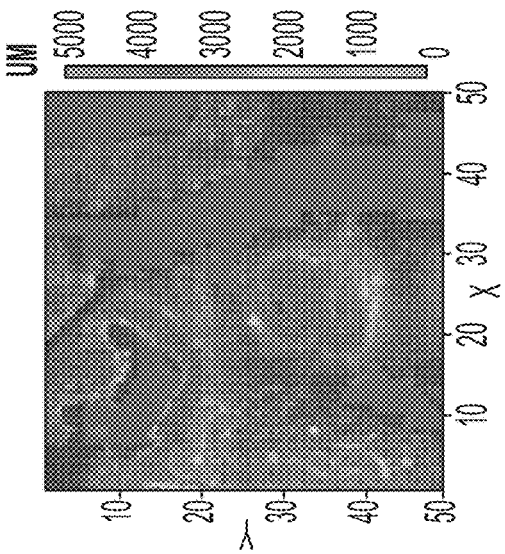
Figure 14B:
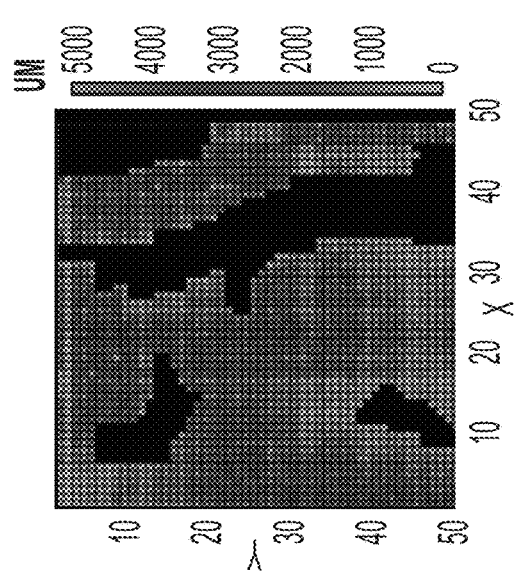
Figure 14E:
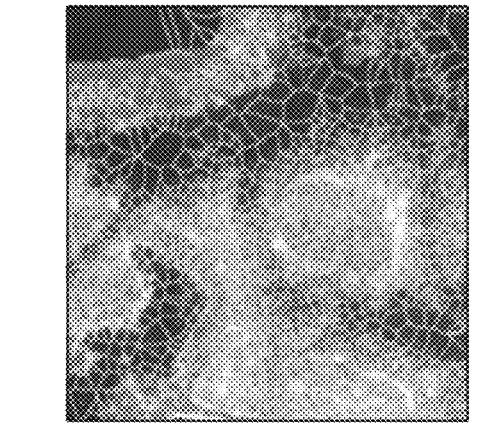
Figure 14A:
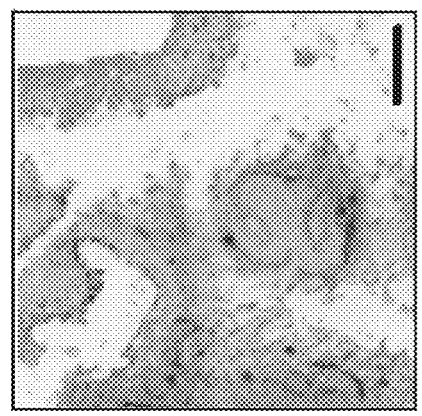
Figure 14D:
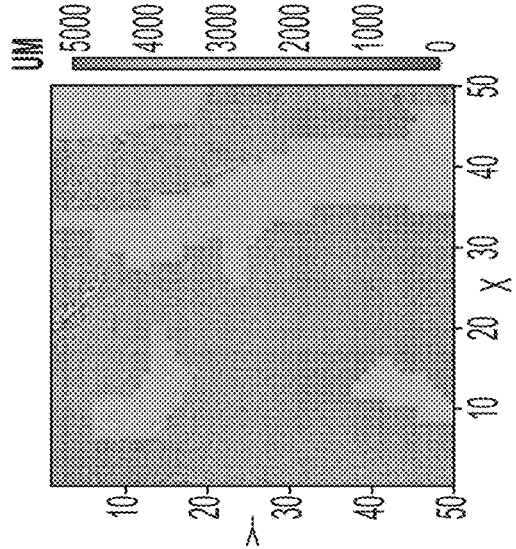
Figure 14G:
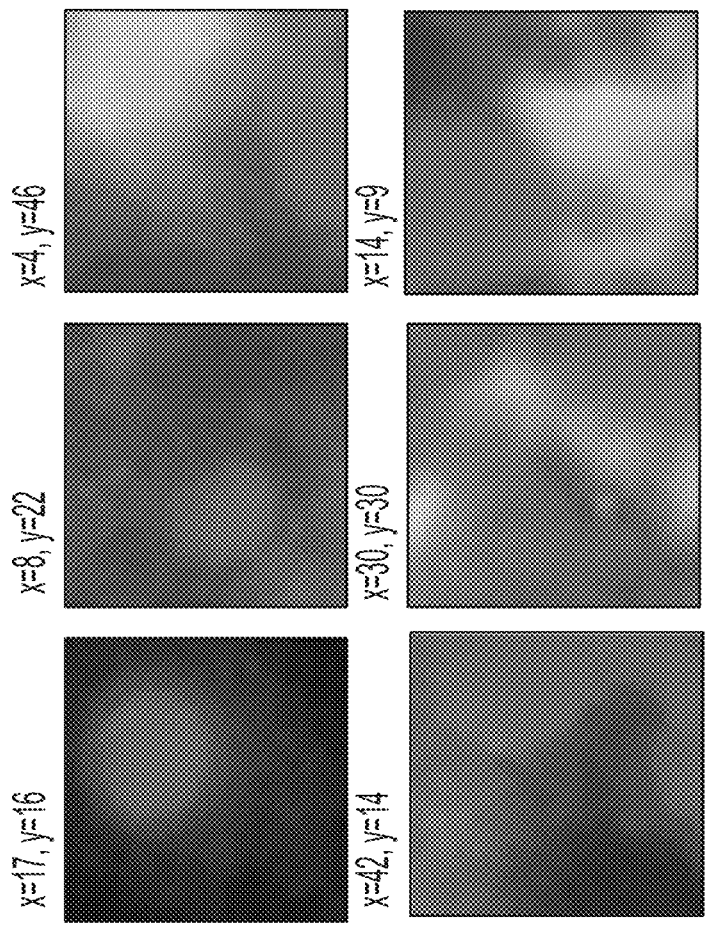
Figure 14H:
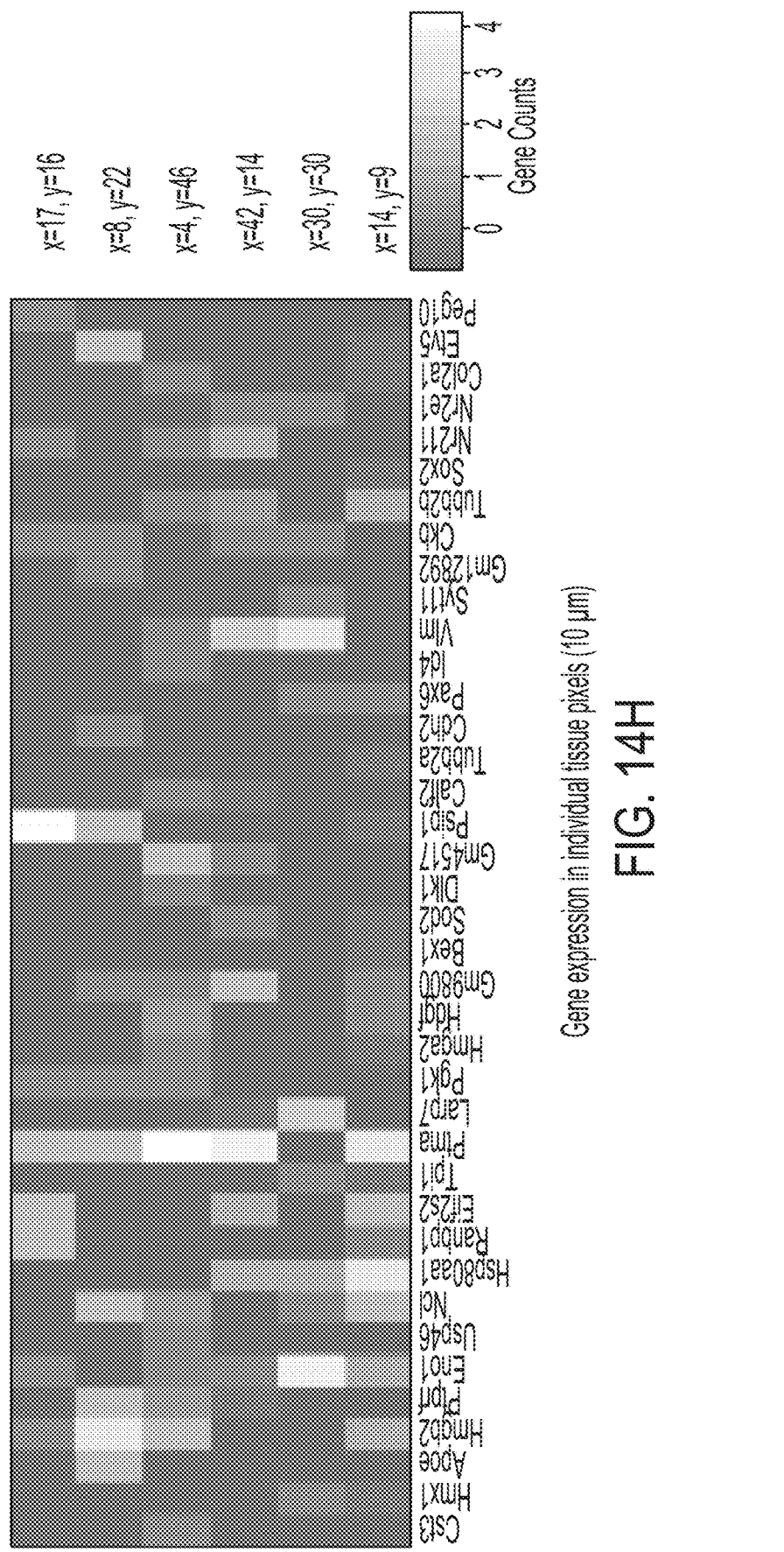
Figure 15:
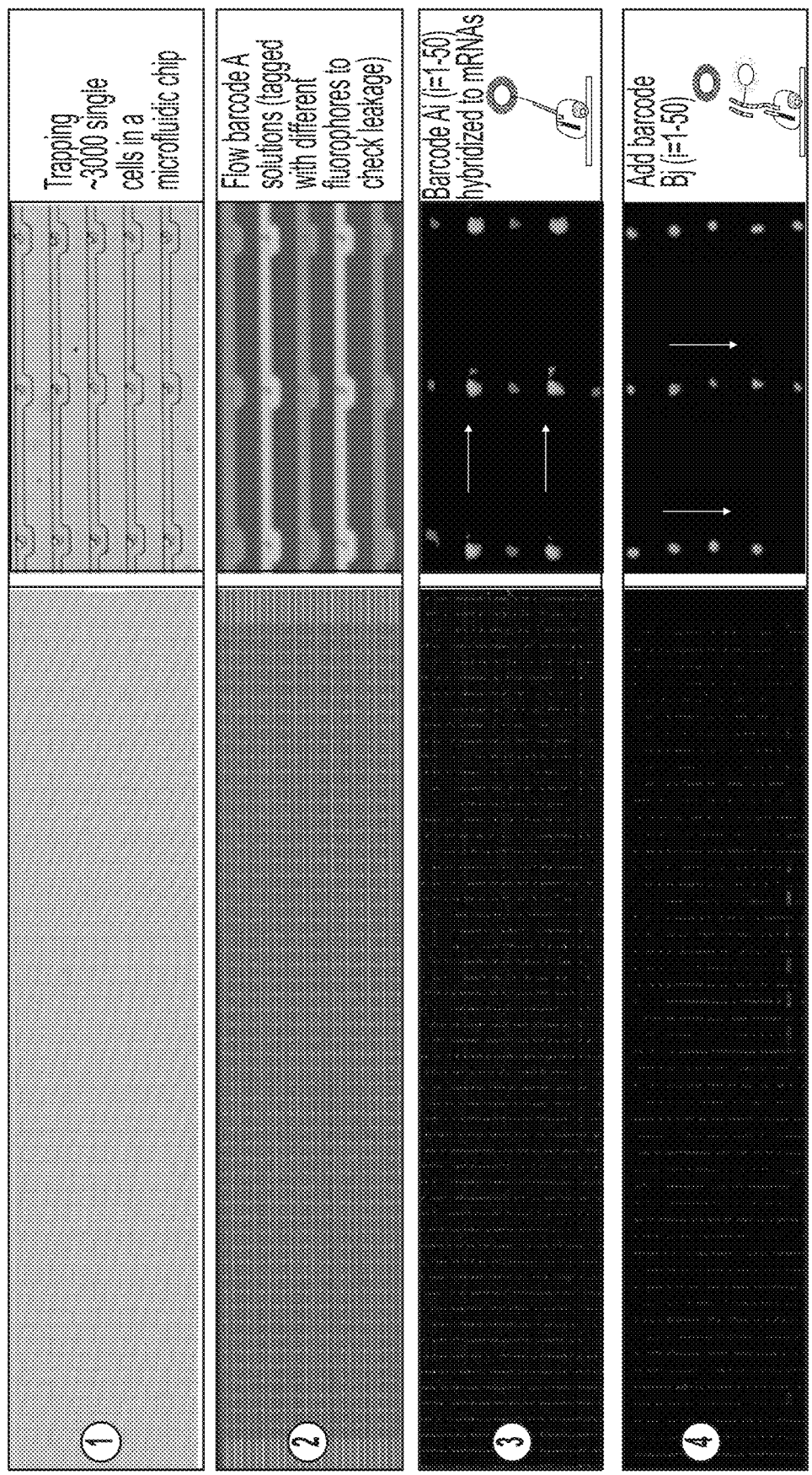
FIG. 15. Single-cell deterministic barcoding.
Figure 16A:
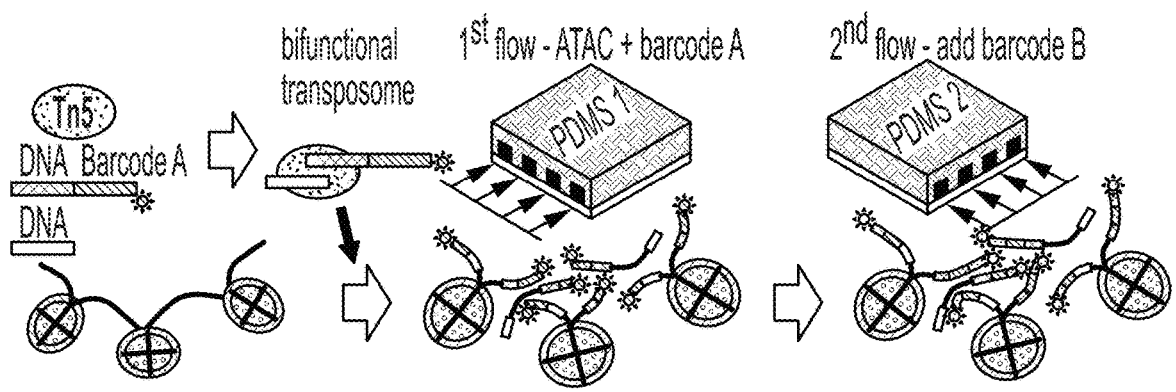
FIGS. 16A-16B. Deterministic barcoding in tissue for chromatin accessibility assay.
Figure 16B:
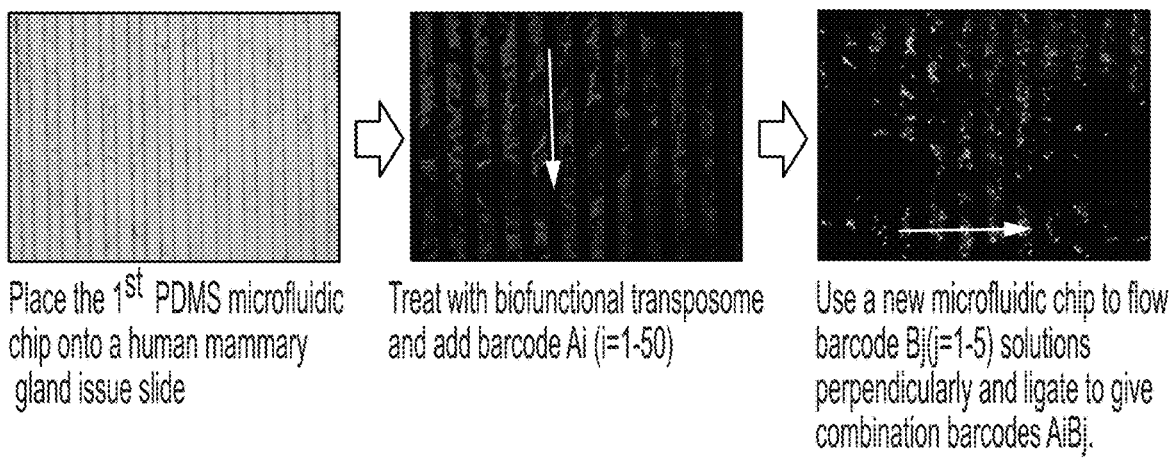

Example 15. Combing Immunofluorescence Staining and DBIT-Seq on the Same Tissue Section Lastly, we demonstrated DBIT-seq with immunofluorescence stained tissue sections. A E11 mouse embryo tissue slide was stained with DAPI, phalloidin and red fluorescent labelled P2RY12 antibody (a G protein-coupled receptor) (FIG. 14A-14H). Then, we performed DBiT-seq. When the microfluidic chip was still on the tissue slide, we imaged the microfluidic channels and the tissue immunofluorescence With DAPI staining for nucleus, we could conduct cell segmentation using ImageJ (FIG. 14E). The immunostaining also enabled us to select the pixels of interest such as those containing single cells or those showing specific protein expression to study the association between morphological characteristics, protein expression, and transcriptome (FIGS. 14G and 14H). Immunofluorescence staining is widely used in tissue pathology to measure spatial protein expression at the cellular or sub-cellular level. Combining immunofluorescence with DBIT-seq at the cellular level (10 μm pixel size) on the same tissue slide could improve the mapping of spatial omics data to specific cell types.

Example 16

In clinic, tissue samples are routinely prepared as formalin fixed paraffin embedded (FFPE) tissue blocks instead of fresh frozen format due to the easiness of tissue handling, storage, and transportation. Meanwhile, for diagnostic purpose, tissue morphology of FFPE sample is well preserved, especially after prolonged storage. Consequently, there are a large number of banked clinical FFPE tissue samples readily available in hospitals and research institutions, which could serve as exploitable source for molecular studies[1]. However, during the sample preparation and storage, the RNA of FFPE tissue often lose its integrity and become partially degraded and fragmented[2]. The most common practice for transcriptome study is through bulk extraction and sequencing, but detailed and important cellular level and spatial information of tissue are lost[3,4]. The formalin fixation procedure also hampered the applications of traditional microfluidic based seRNA-seq techniques in this field.

Spatial transcriptome techniques, needless of general tissue digestion process, emerged recently to study gene expression in tissue sections. Until now, dozens of elegant spatial RNA-seq technique have been reported, either through hybridization with fluorescent probes[5-8] or reverse transcription-based next generation sequencing[9-12]. However, the main focus to date is still on fresh frozen (FF) samples, which bare high quality and non-cross-linked RNA.

Above, we show DBIT-seq as a high spatial resolution multi-omics tool to analyze PFA-fixed frozen tissue sections. In this Example, we demonstrate that DBIT-seq can also be applied to FFPE tissue sections with some protocol modifications. We first demonstrated the whole transcriptomic analysis of an E10.5 mouse embryo. Results show that the gene numbers identified per pixel were sufficient for downstream analysis. The new protocol faithfully detected the major tissue types in early mouse brain and midbody. Integration analysis with publicly available scRNA-seq datasets showed major cell types in each of the organs. We then applied the new protocol to tissue sections of the adult mouse heart and circulatory system (aorta, atrium and ventricle) and obtained the cell distribution maps.

Results

Workflow of DBIT-Seq with FFPE Sample

Figure 17A:
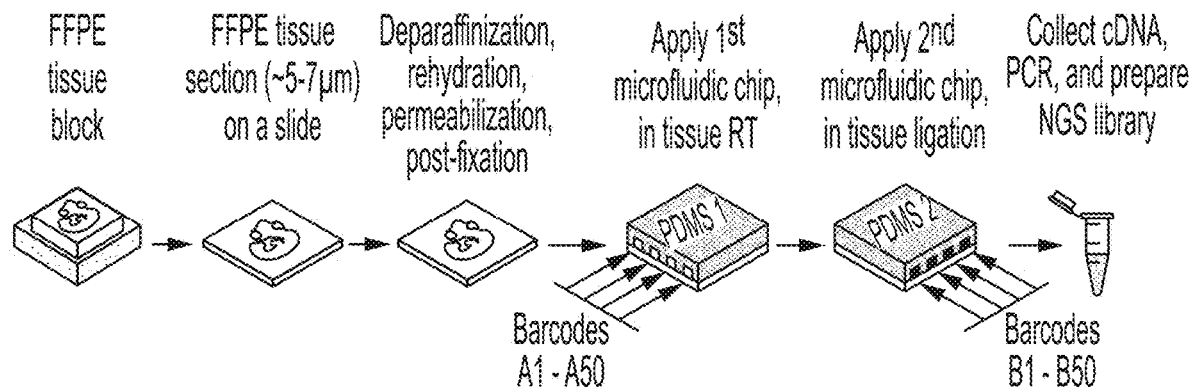
FIGS. 17A-17D. Workflow of DBIT-seq on FFPE samples.
Figure 17B:
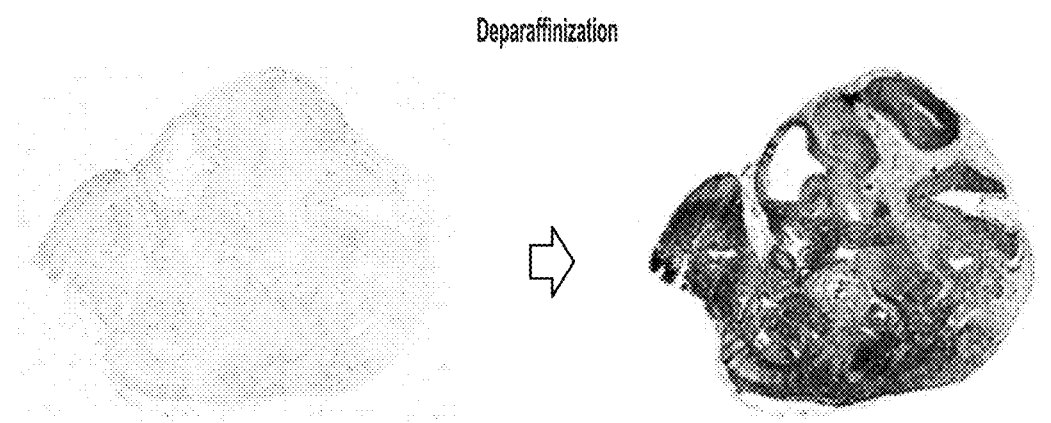

The main workflow for FFPE samples were shown in FIG. 17A. The banked FFPE tissue block was first microtomed into sections of 5-7 µm thickness and placed onto a poly-L-lysine slide. To reduce further RNA oxidative degradation by air exposure, the FFPE sections were stored at −80° C. prior to use. The deparaffinization was carried out using xylene wash. Afterwards, the tissue section was rehydrated and permeabilized by proteinase K, and then post-fixed again by formalin. The deparaffinized tissue section showing a darkened color (FIG. 17B) was then ready for DBiT-seq. Briefly, the $1^{st}$ PDMS chip with 50 parallel channels was attached onto the section and a set of DNA barcode A oligos were flowed through the channels along with reverse transcription reagents. In-tissue reverse transcription would produce cDNAs with barcode A incorporated at the 3' end. After removing the $1^{st}$ chip, a $2^{nd}$ PDMS chip with another 50 channels perpendicular to the first PDMS chip was placed on top of the tissue. Ligation was then performed in each of the channels with the flowing of 50 distinct barcode B oligos plus a universal ligation linker, which matched with a piece of linker sequence of barcode A. The ligation would only occur at the intersections of the two flows. Afterwards, the tissue was imaged and digested completely. The digest was collected and the downstream procedures, including cDNA extraction, template switch, PCR, tagmentation were performed before next generation sequencing.

DBIT-Seq Data Quality

Figure 17C:
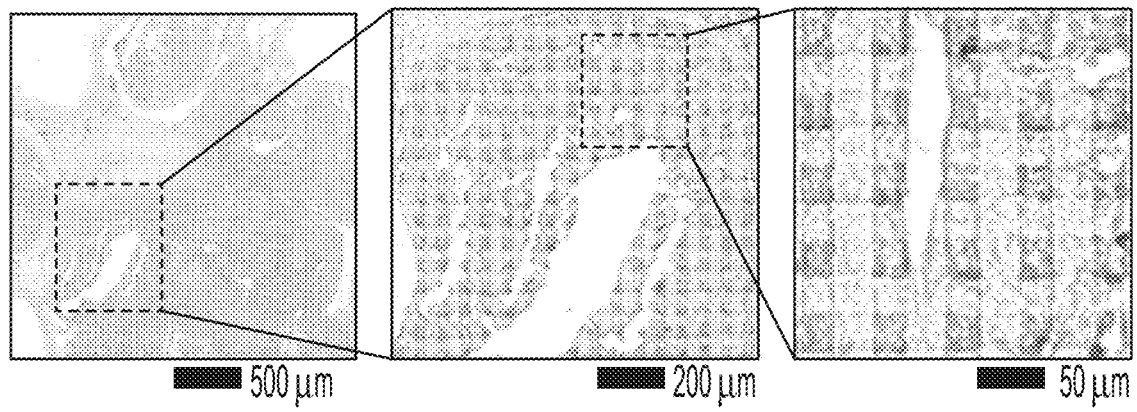
Figure 17D:
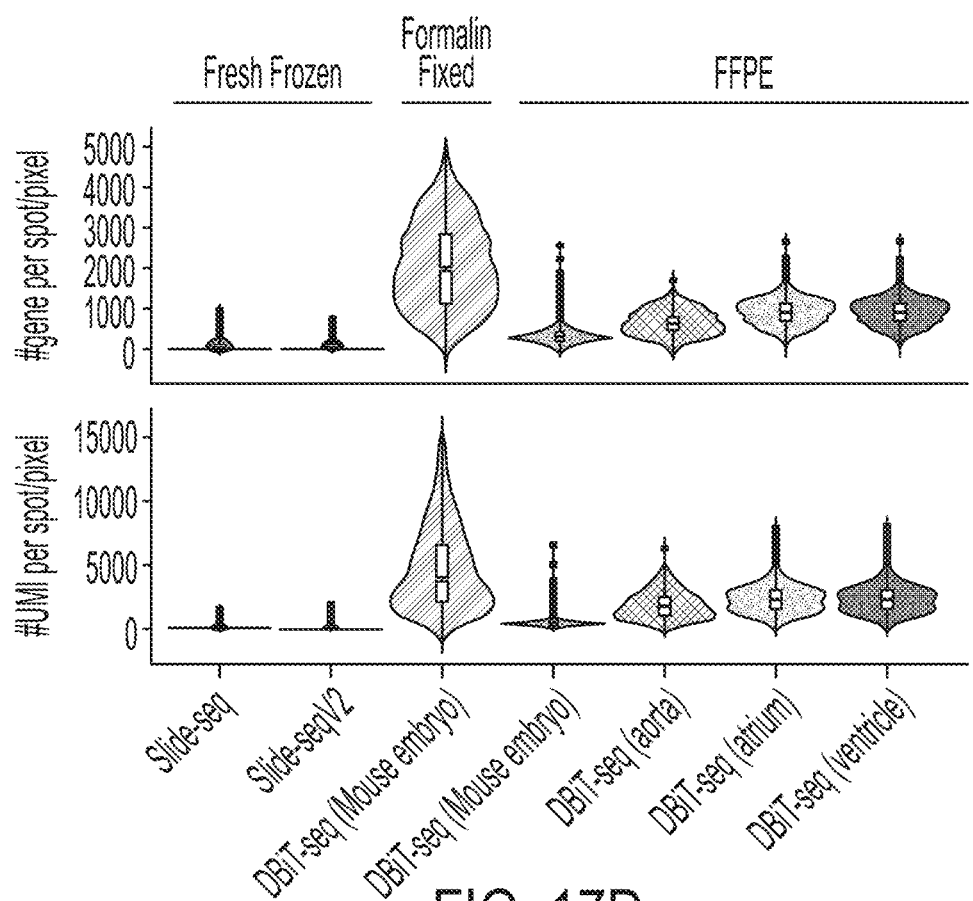

The attachment of PDMS chip to the "soft" tissue sections were enforced by clumps, and the clumping would cause the deformation of tissue sections under the channel walls. As a consequence, after two sequential PDMS chip attachments and flowing, we observed the appearance of an orderly array of squares on the tissue section (FIG. 17C), which allows the precise identification of location and topography of tissue pixels. We first analyzed the cDNA size for a FFPE mouse embryo sample and compared with a Fresh Frozen sample (FF data not shown). We noticed that the size of FFPE sample peaked between 400 and 500 bps, much shorter than the fresh frozen sample with peaks over 1000 bps. The average size is also case, with ~600 bps for FFPE and over 1,400 bps for fresh frozen. Apparently, overtime degradation indeed affected the integrity of RNAs. Next, we calculated the total genes and unique molecular identifiers (UMIs) per pixel (FIG. 17D). For FFPE samples, we found the results were quite diverse among different sample types. For mouse embryo, there are on average 520 UMIs and 355 genes identified per pixel. While for mouse aorta, the average numbers per pixel increased to 1830 UMIs and 663 genes. The average UMIs and genes per pixel in FFPE mouse atrium and ventricle were even higher, showing 3014 UMIs and 1040 genes for atrium and 2140 UMIs and 832 genes for ventricle. In comparison, we revisited the dataset of a fresh frozen mouse embryo sample analyzed by DBiT-seq, which showed an average of 4688 UMIs and 2100 genes. The comparison between FFPE sample and fresh frozen samples clearly showed that FFPE sample was showing around ⅑ of the UMIs or ⅙ of the genes per pixel of a fresh frozen sample. We calculated the Pearson correlation coefficient between the "pseudo bulk" dataset of FFPE and fresh frozen sample and found the r value is ~0.88 (data not shown), which shows a high correlation between the two types of sample despite the high variances from tissue origins or lineage. We also compared with fresh frozen coronal hippocampus sample analyzed by the recent 10 µm spot size techniques Slide-seq and Slide-seqV2, which both have fewer than or around 280 UMIs and 200 genes per spot.

E10.5 Mouse Embryo Spatial Transcriptome Mapping

Figure 18A:
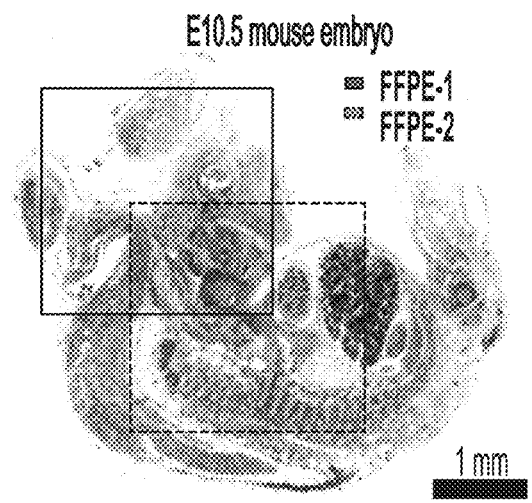
FIGS. 18A-18E. Spatial transcriptome analysis of FFPE tissue sections from an E10.5 mouse embryo.
Figure 18B:
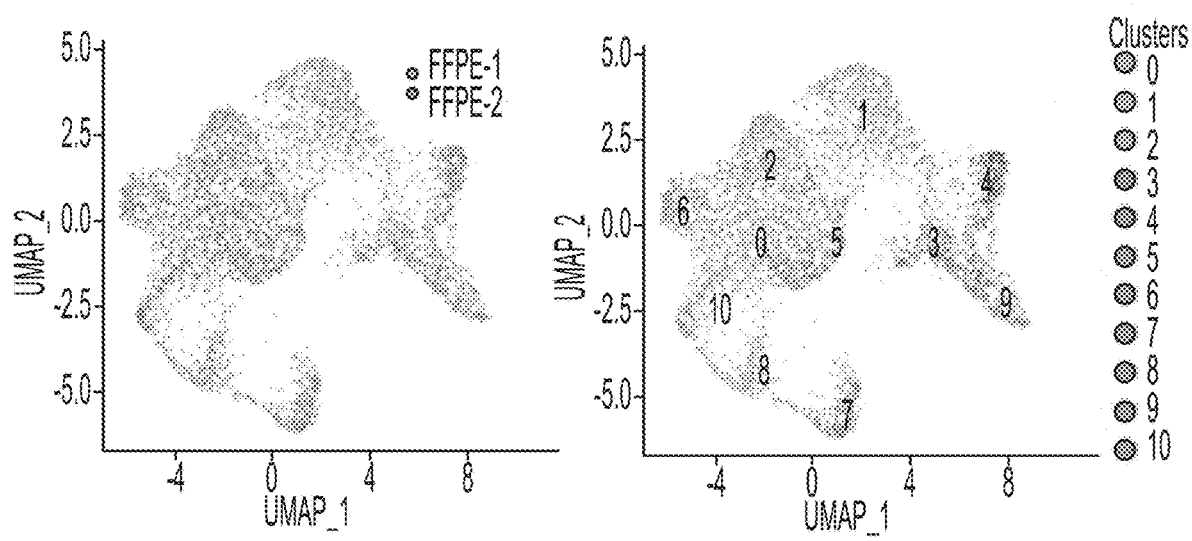
Figure 18C:
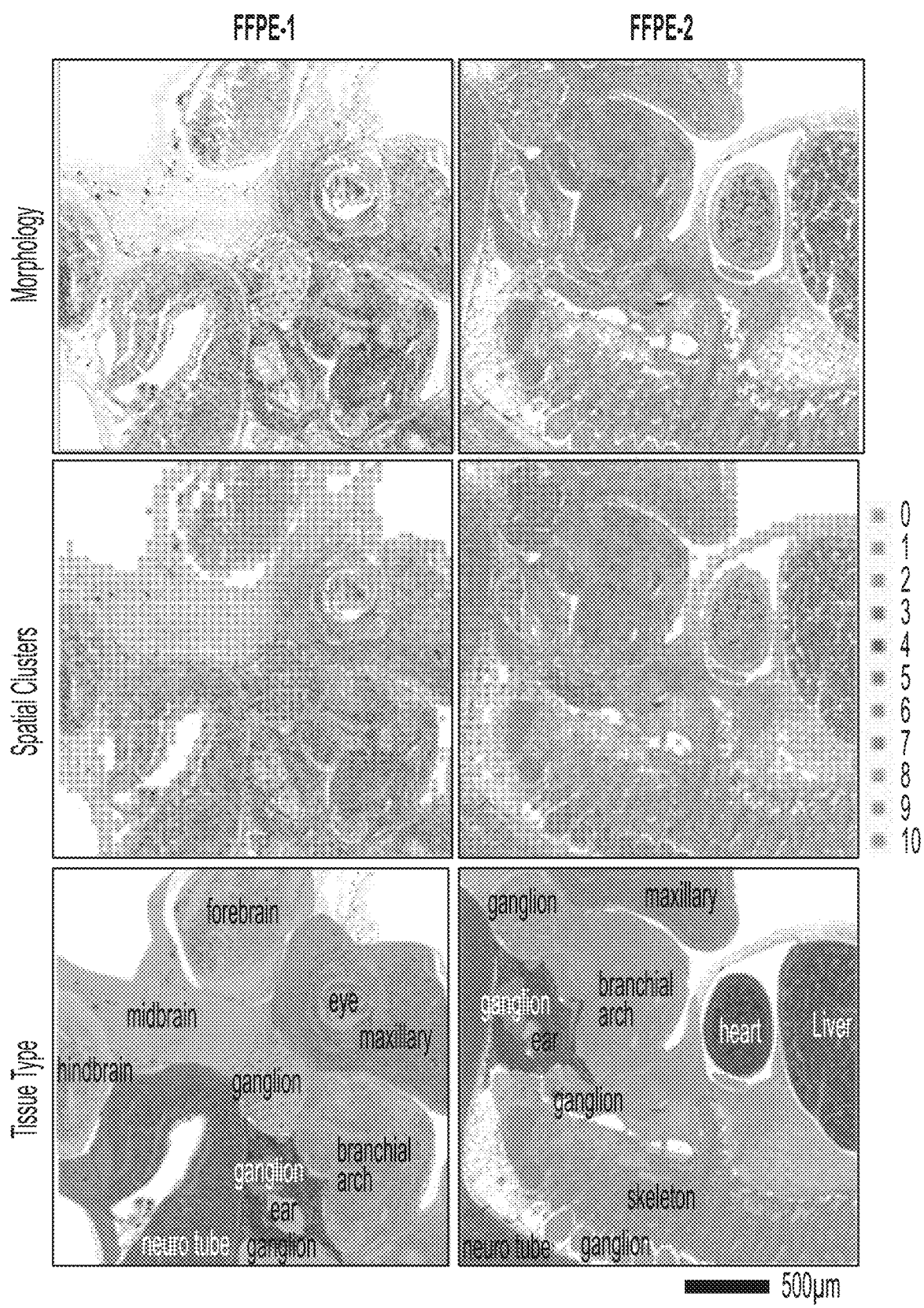
Figure 18D:

Using E10.5 mouse embryo as a demonstration (FIG. 18A), we conducted DBIT-seq on two nearby sections from the same mouse, focusing on two different regions: head (FFPE-1) and midbody (FFPE-2). Integrated clustering analysis of the two datasets using Seurat resulted in 10 distinct clusters (FIG. 18B). Mapping the clusters back to their spatial location, we identified very strong spatially distinct patterns that are matching with tissue anatomical annotations (FIG. 18C). Cluster 0 mainly represents the muscle structures in the embryo. Cluster 3 covers the neural tube, forehead and related nervous system. Cluster 4 is specific for ganglions, which cover the both the ganglions in brain (FIG. 18C left) and dorsal root ganglions (FIG. 18C right). The high resolution also enabled us to see the individual bone pieces in the backbone (cluster 6). Liver is largely shown as cluster 7, whereas heart showed of two layers, with cluster 8 showing the myocardium and cluster 10 showing the epicardium. Cluster 9 is also interesting, it is embedded inside neural tube, which could be a special type of neurons. The spatial clustering demonstrates the high resolution of DBiT-seq, which could resolve very fine structures. We further conducted GO analysis (FIG. 18D) for each cluster, the results matched well with the anatomical annotations. The top 10 differentially expressed genes (DEG) were also shown as heatmap (data not shown). We also conducted similar analysis for each tissue separately and found consistent patterns (data not shown). DEG for each cluster can be analyzed directly (data not shown). For example, Stmn2 and Mapt2, which encode microtubule associated proteins and are important for neuron development, mainly expressed in forebrain and neuro tube. Fabp7, a brain fatty acid binding protein encoding gene, expressed mainly at the hindbrain. Myosin associated genes, Myl2, Myh7 and Myl3 were exclusively expressed in heart. Slc-4a1, a gene related to blood coagulation, was highly expressed in liver, where most coagulation factors were produced. Copx, a heme biosynthetic enzyme encoding gene, was also produced in liver. Afp, a highly expressed gene in liver during the embryo development, was also observed exclusively in liver.

We then applied SpatialDE, an unsupervised spatial pattern identification tool, to study the DBiT-seq data[14]. With default settings, we identified 30 features for each of the two FFPE embryo tissue (data not shown). GO analysis of the gene sets for each pattern reviewed very meaningful results. For example, for FFPE-1, pattern 0 representing neural precursor cell proliferation, whereas pattern 7 is correlated with eye morphogenesis. For FFPE-2, cluster 20 is specific for heme metabolic process, and cluster 26 is for cardiac muscle contractions.

Integration with scRNA-Seq Reference

Figure 18E:
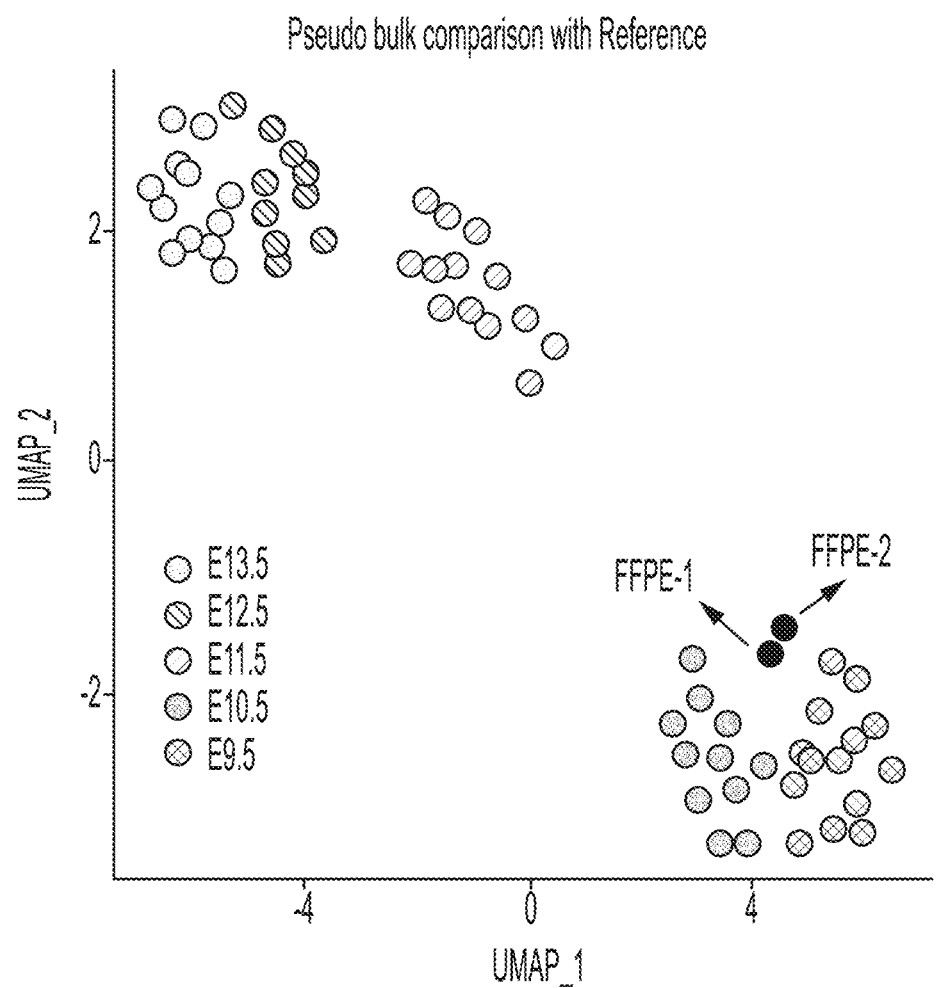
Figure 19B:
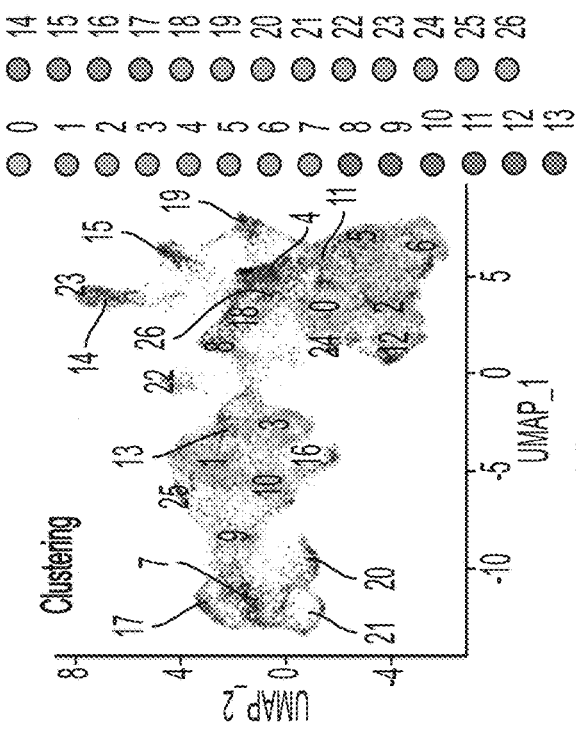
FIGS. 19A-19E. Integration of FFPE mouse embryo DBiT-seq data with scRNA-seq data.
Figure 19C:
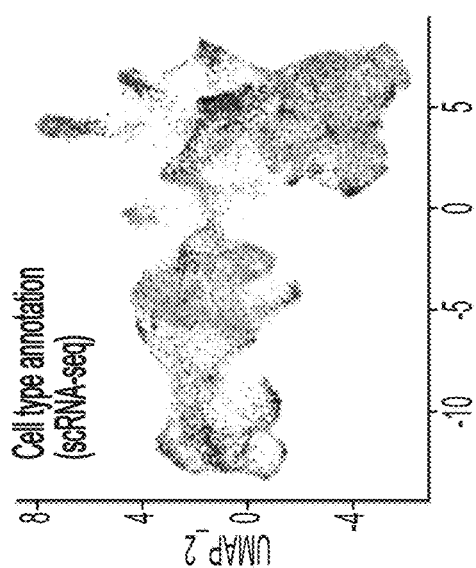
Figure 19A:
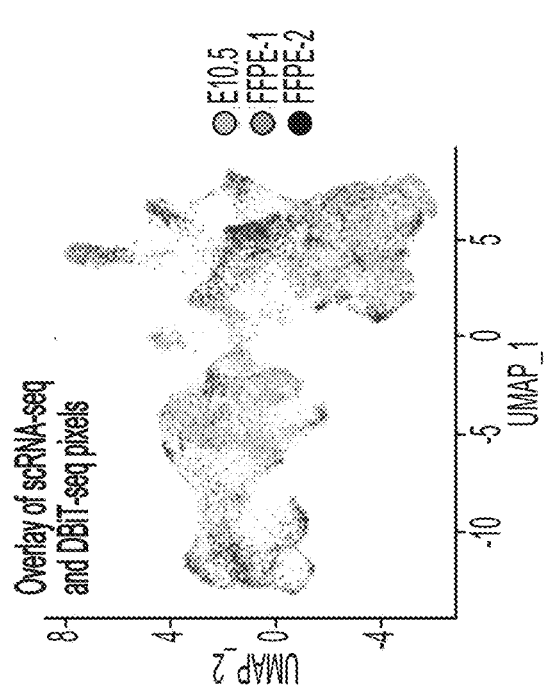
Figure 19D:
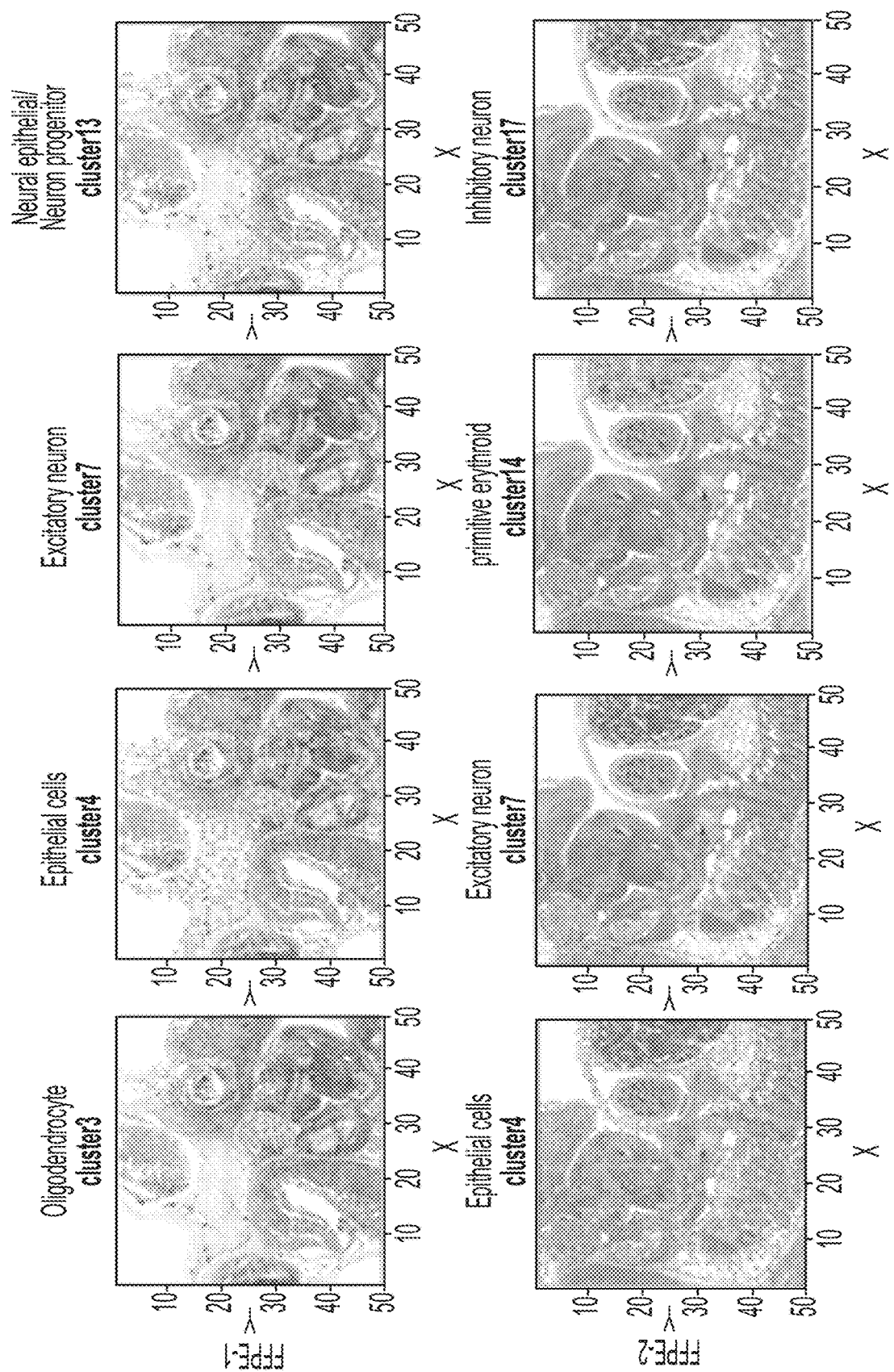
Figures 19D, 19E:
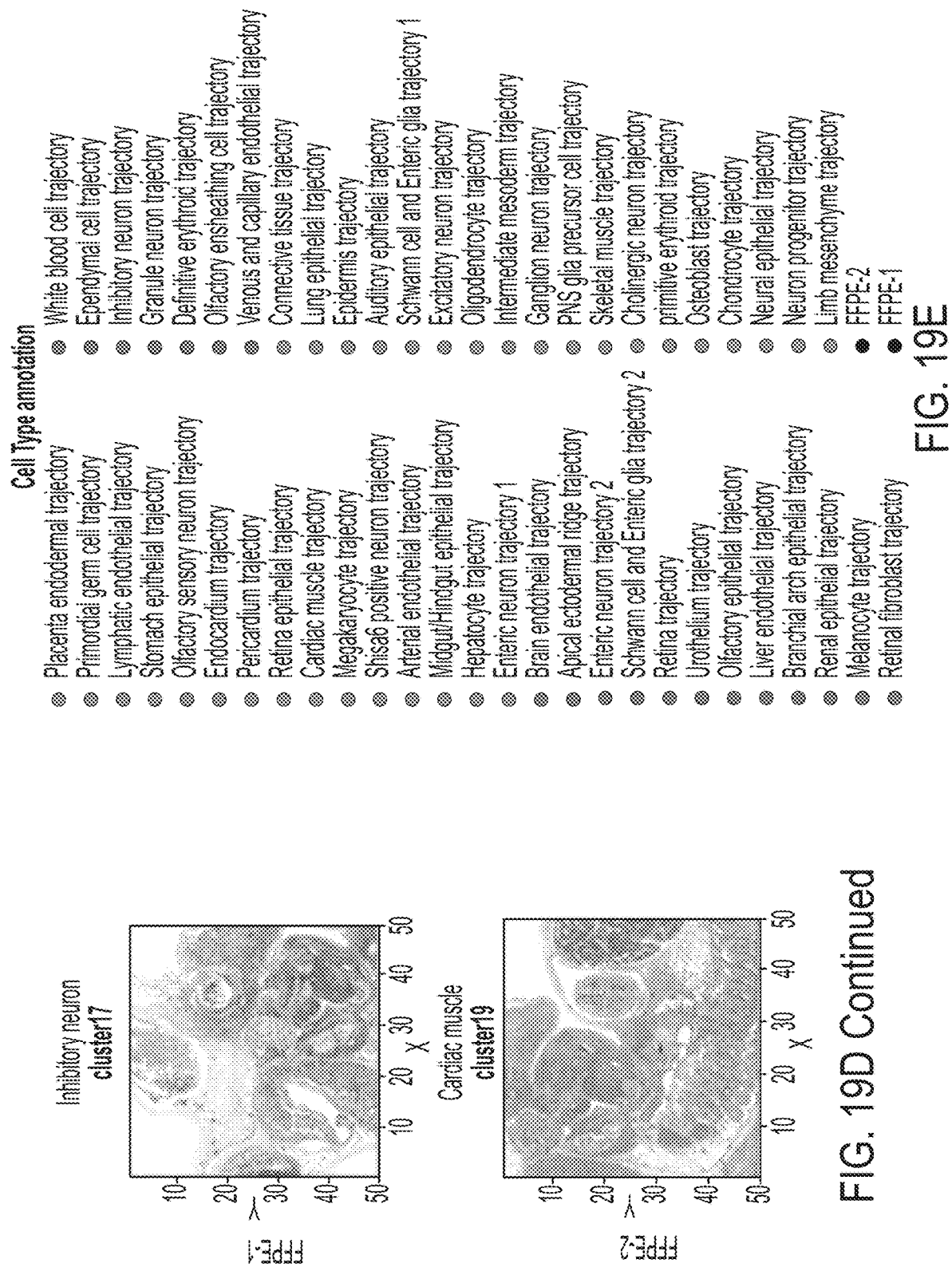

To annotate the cell type for each pixel, we performed integrated analysis of our DBIT-seq mouse E10.5 embryo data with published scRNA-seq reference[15]. We first compared the aggregated "pseudo bulk" data with reference by doing unsupervised clustering (FIG. 18E). The DBiT-seq pixel data for both FFPE-1 and FFPE-2 lie closely with clusters of E10.5 scRNA-seq data, which proved that FFPE sample can show the correct embryonic age even with diminished gene numbers. We then performed the integrated analysis of FFPE spatial transcriptome data with scRNA-seq reference using Seurat, with variation from technical factors removed using SCTransform[16]. The DBIT-seq pixels conformed quite well with scRNA-seq data (FIG. 19A), enabling the transferring of cell type annotations from scRNA-seq data to our spatial pixels. The spatial mapping of the cell types was shown in FIG. 19D. In FFPE-1, cells in cluster 3 are mainly oligodendrocytes. Epithelial cells (cluster 4) and neural epithelial cells (cluster 13) were distributed widely around the tissue. The distributions of excitatory neuron and inhibitory neurons are quite alike, which is meaningful since they are both neurons only functionally different with neurotransmitters. In addition, cluster 14, the primitive erythroid cells that are crucial for the transition from embryo to fetus in developing mammals, mainly appeared in liver region of FFPE-2 appeared 17. Cardiac muscle cells were also identified correctly in heart region. The integration analysis with published scRNA-seq data could provide more detailed biological identity information than general GO analysis, which would be preferred when quality references are available.

Spatial Transcriptome Analysis of Adult Mouse Aorta

Figures 20A, 20B:
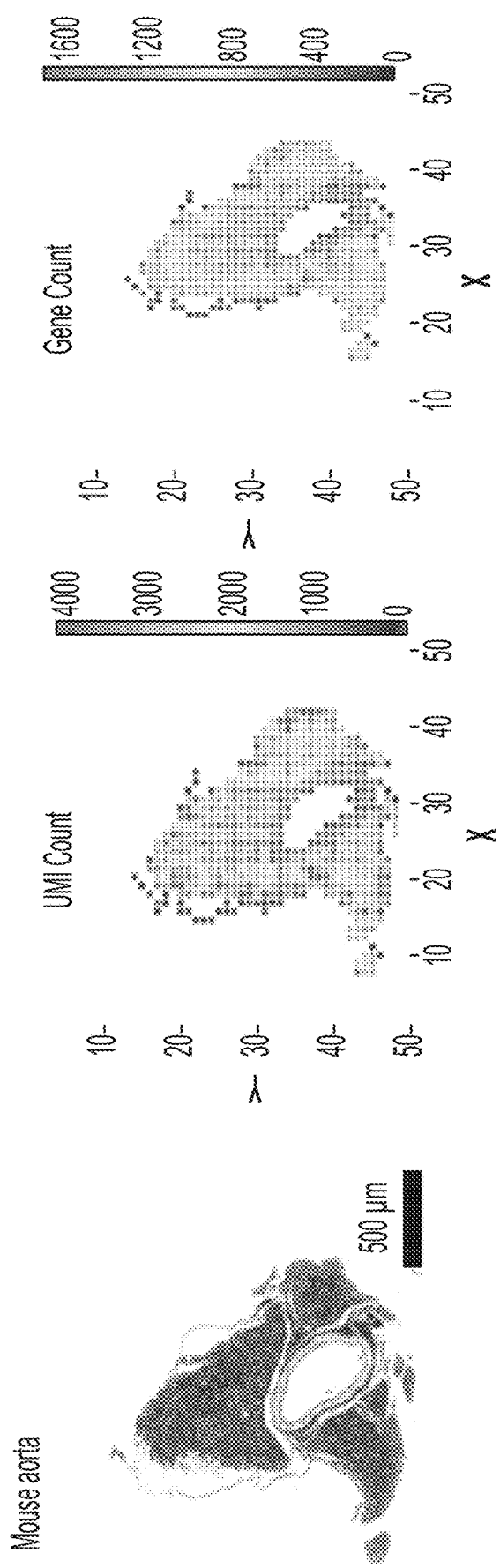
FIGS. 20A-20E. Spatial transcriptome analysis of the FFPE tissue sections from an adult mouse aorta.
Figure 20D:
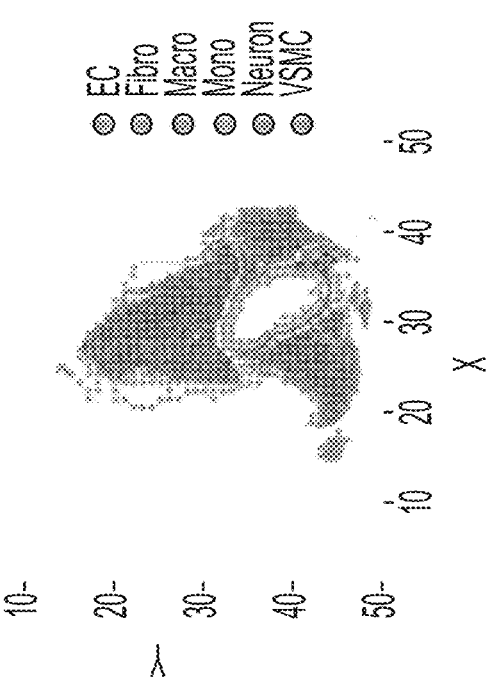
Figure 20C:
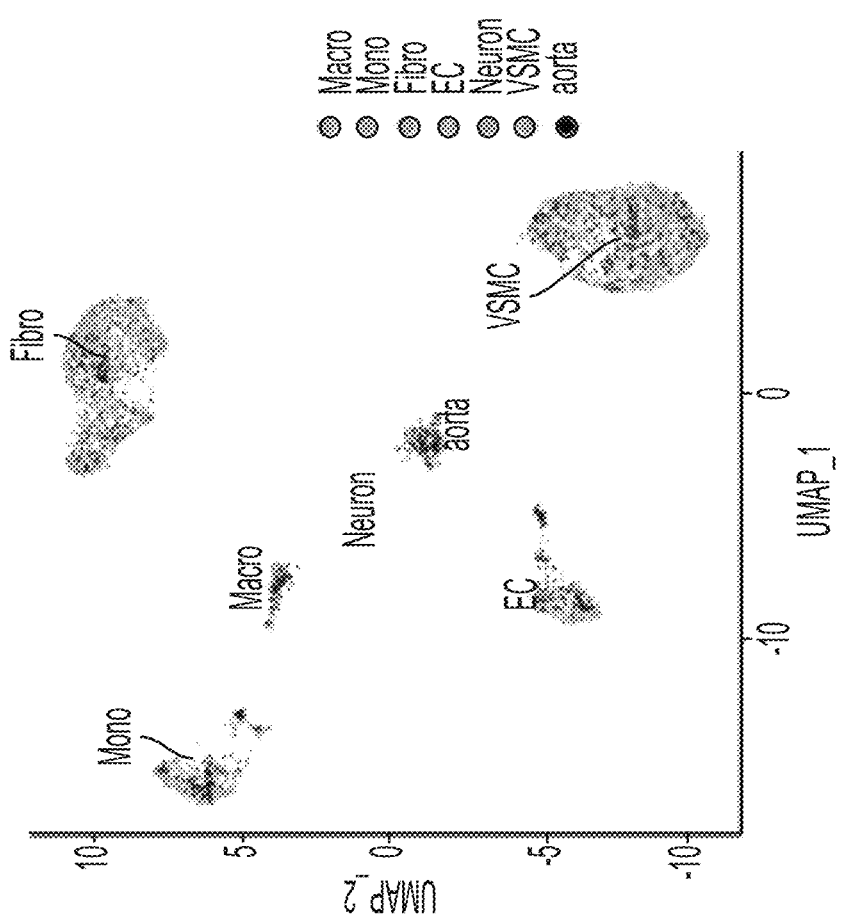
Figure 20E:
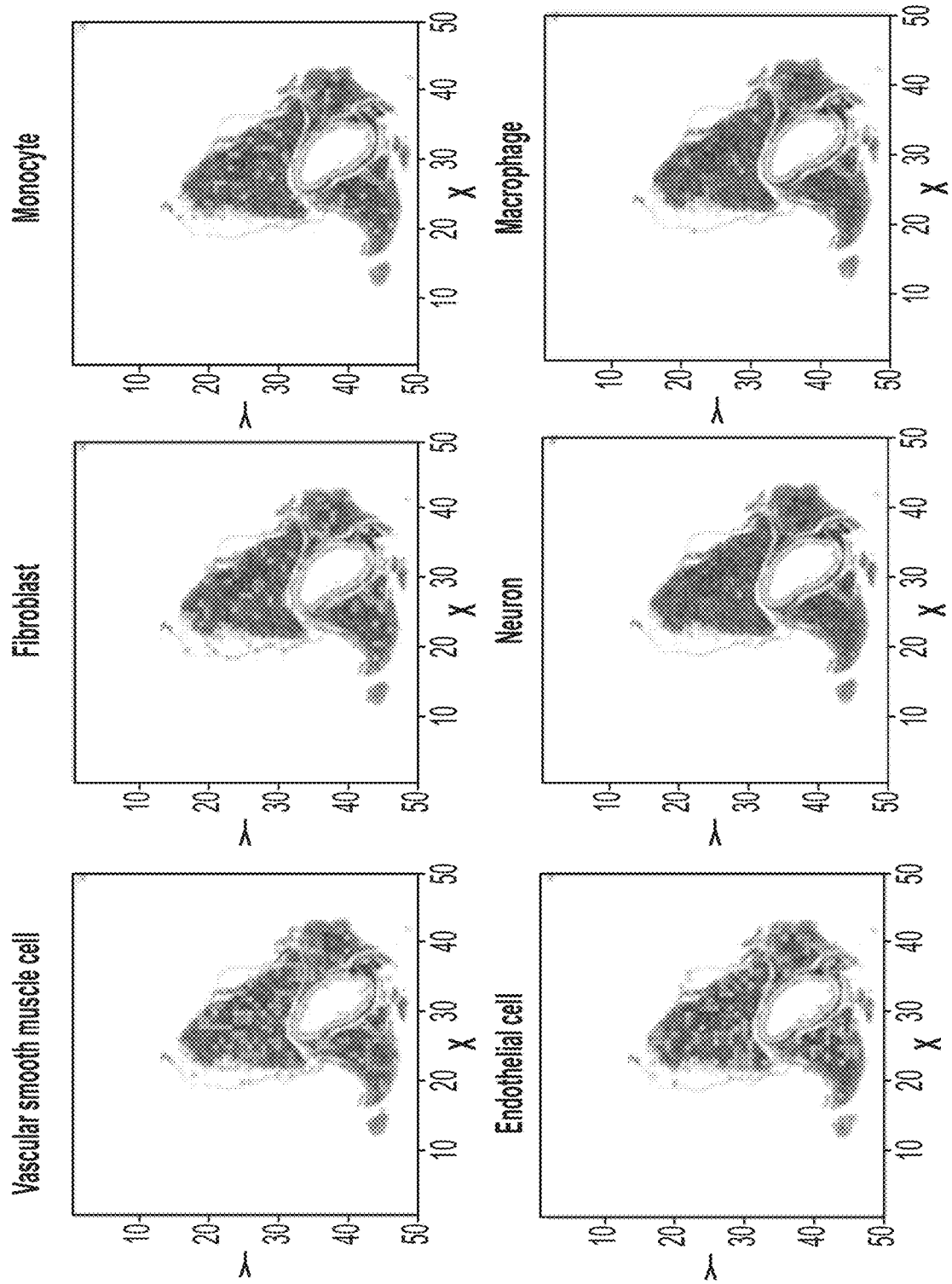

We next examined the FFPE aorta tissue section from an adult mouse (FIG. 20A). The aorta is cross-sectioned, showing a thin wall of the artery along with the supporting tissue. The gene and UMI counts heatmap were shown as FIG. 20B. Unsupervised clustering did not provide rich information due to the lack of distinct tissue features and dominance of cell types such as smooth muscle cells (data not shown). However, when integrated with aorta sc-RNAseq data from reference[18], we can clearly identify six distinct cell types, including endothelial cells (ECs), arterial fibroblasts (Fibro), macrophages (Macro), monocytes (Mono), neurons and vascular smooth muscle cells (VSMCs). The majority of cells are ECs, VSMCs and Fibros. We also noticed that there was a layer of enriched smooth muscle cells in the artery wall, which reported to be the main cell types in vascular tissue[19]. We also run the automatic cell annotation package SingleR briefly for the aorta sample with the built-in reference for mouse single cell data (data not shown). It worth pointing out that adipocytes that normally exist in the supporting tissue around the artery can be readily identified. Meanwhile, the adipocytes specific genes Adipoq and Aoc3 were also found to express at a high level (data not shown).

Spatial Mapping of Atrium and Ventricle with DBIT-Seq

Figure 21A:
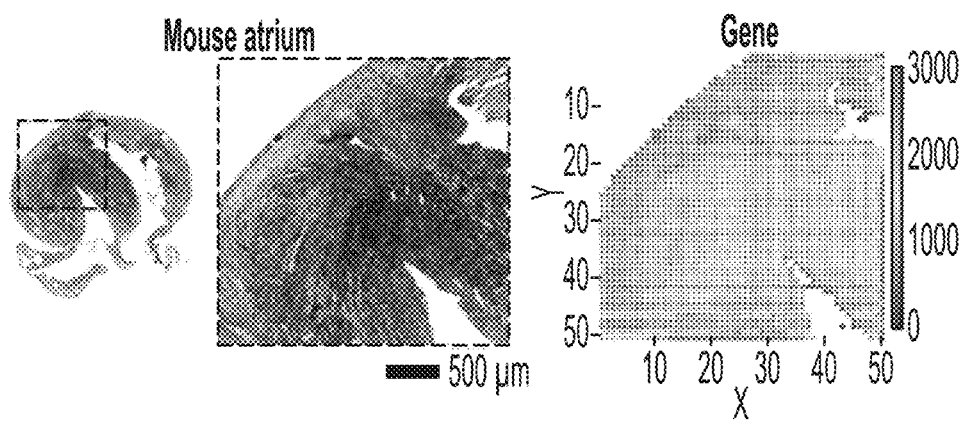
FIGS. 21A-21F. Spatial transcriptome mapping of the FFPE tissue sections from a mouse heart (atrium and ventricle).
Figure 21B:
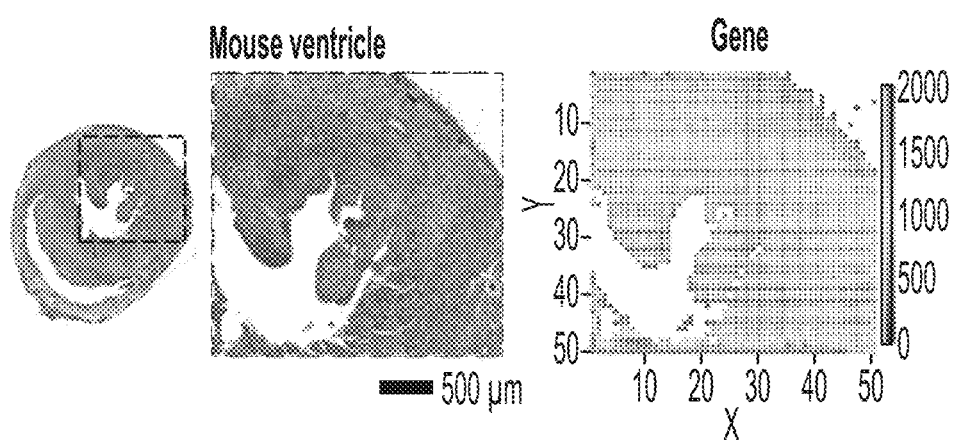
Figure 21C:
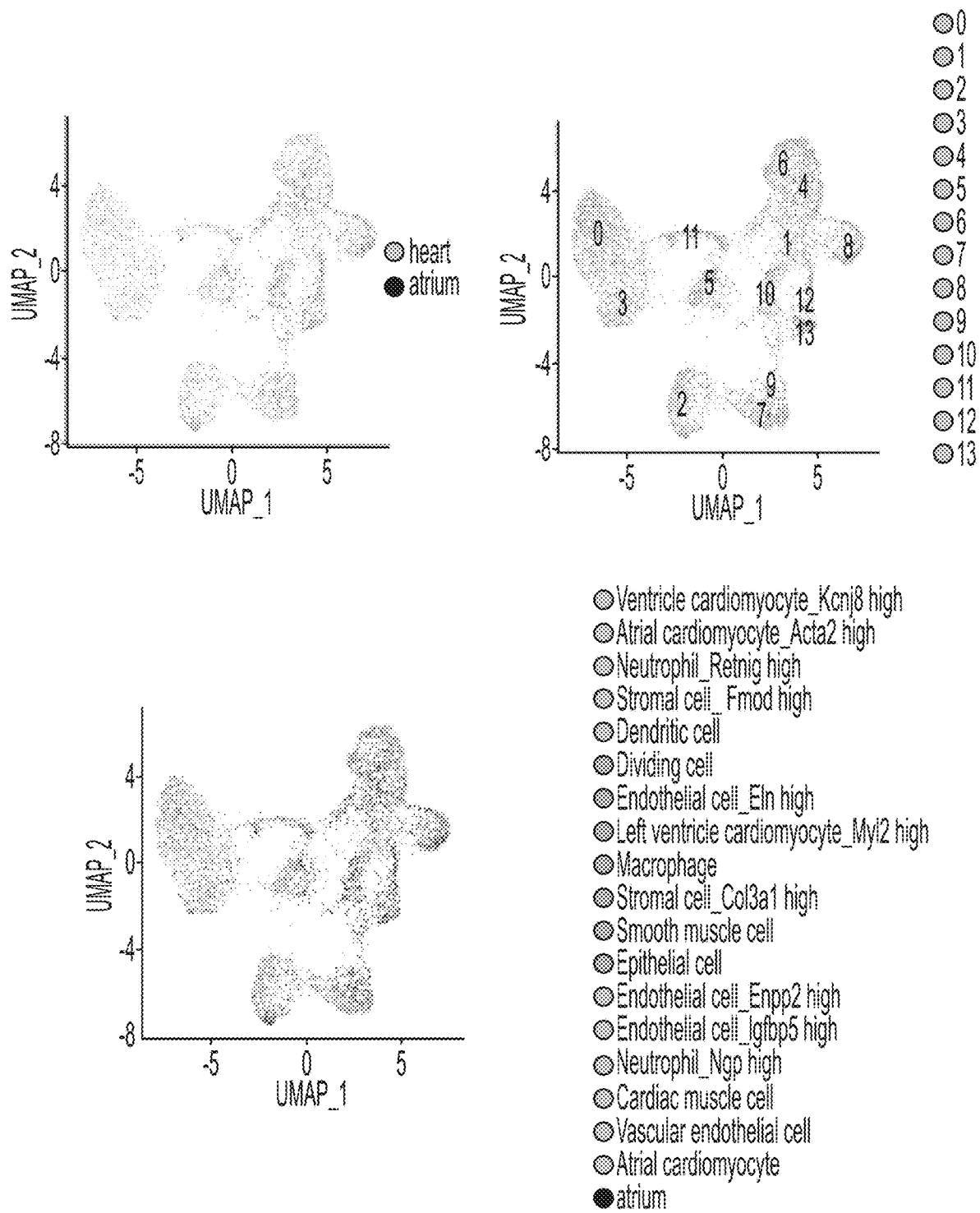
Figure 21D:
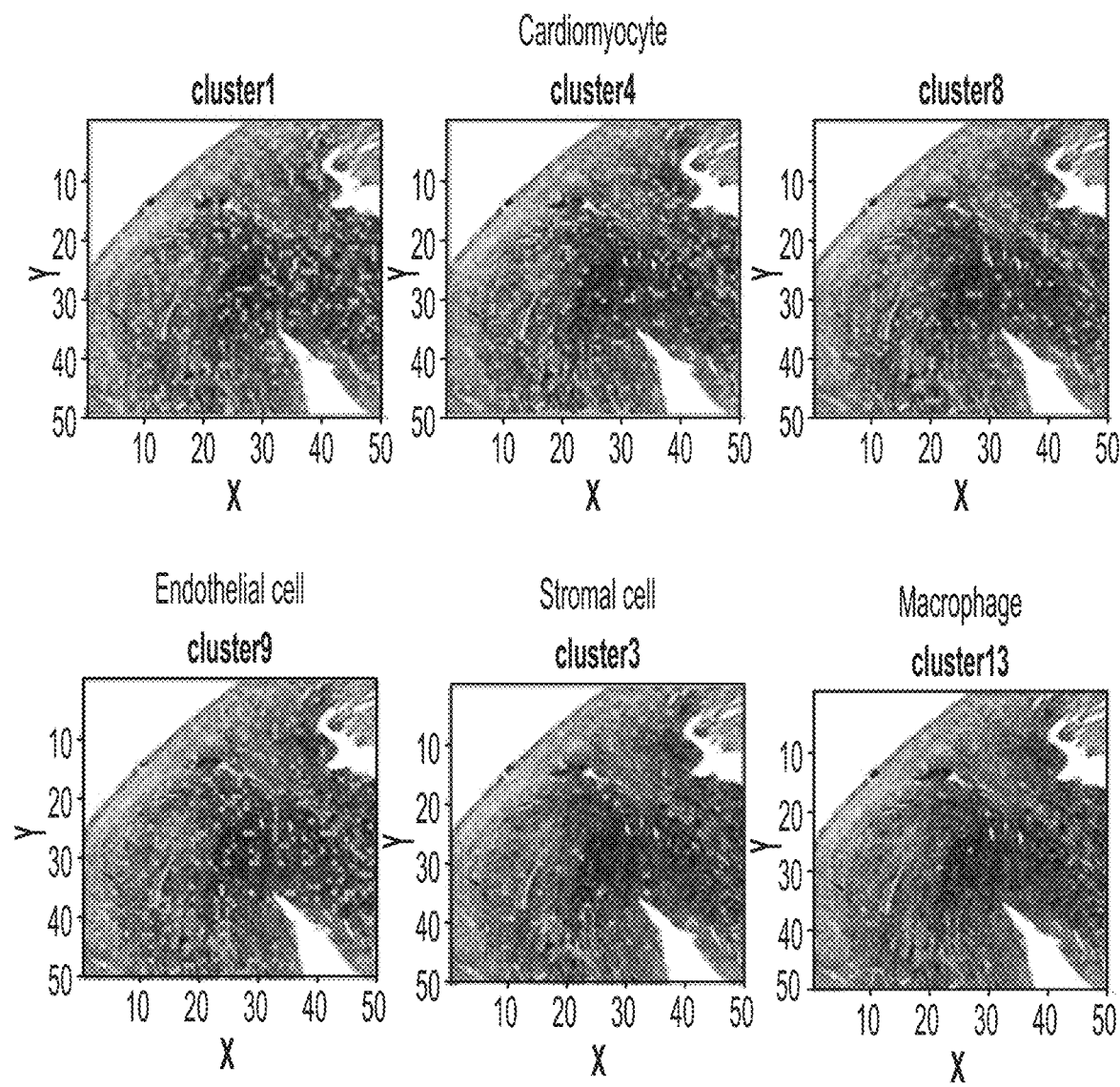
Figure 21E:
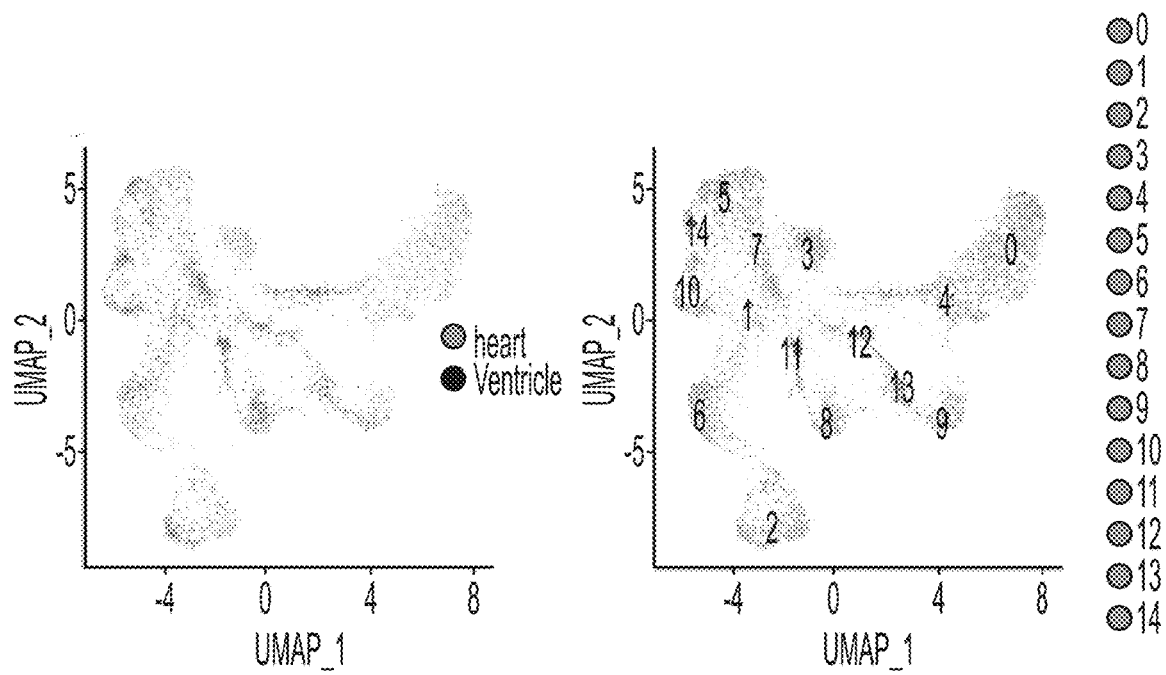
Figure 21E:
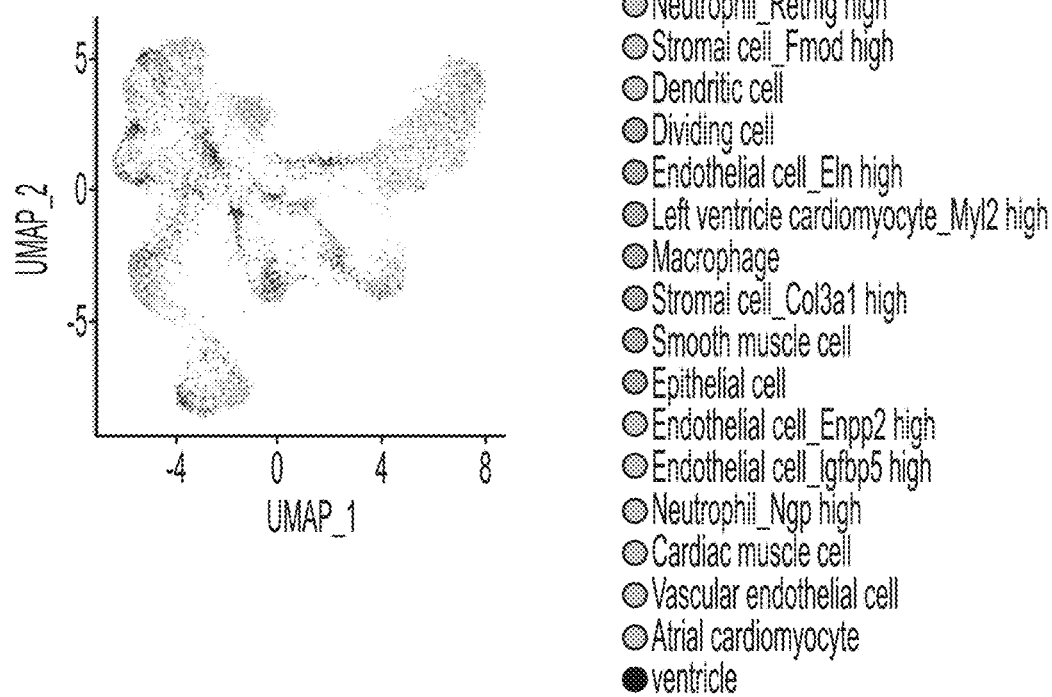
Figure 21F:
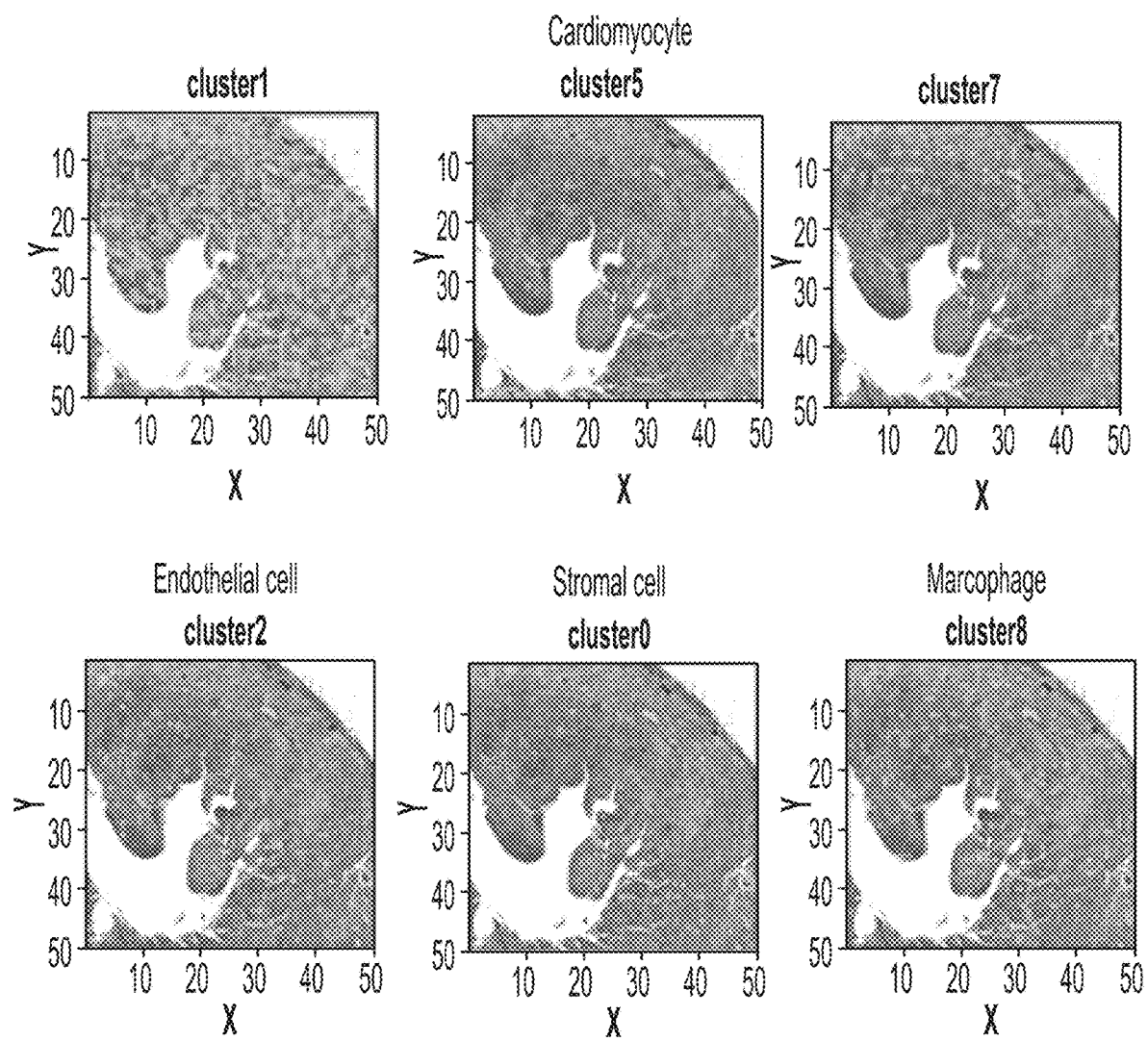

Lastly, we analyzed the cross sections of FFPE block of adult mouse atrium and ventricle using DBiT-seq (FIGS. 21A-21B). Although cardiomyocytes only account for 30-40% of the total cell numbers in heart, the volume fractions of cardiomyocytes can reach to 70-80% 20 Indeed, we observed the universal presence of muscle related Myh6 gene (data not shown), which encodes a protein known as the cardiac alpha ($\alpha$)-myosin heavy chain. This high volume of cardiomyocytes will pose challenges for spatial transcriptome analysis by masking other cell types. As is the case, unsupervised clustering of atrium and ventricle pixels using Seurat could not resolve distinct clusters (data not shown). However, when integrated with scRNA-seq references for mouse heart[21]. DBiT-seq pixels of atrium and ventricle conformed rather well with the reference, which showed a total of 14 clusters (FIGS. 21C, 21E). The clusters were then annotated using the scRNA-seq cell type information (data not shown). After annotation, we noticed that cardiomyocytes were still the main cell types found across multiple clusters (FIGS. 21D, 21F), for example, cluster 1, cluster 4 and cluster 8 in atrium. There are also a good number of endothelial cells. Other cell types, like stromal cells and macrophage were much less presented.

Conclusion

To conclude, we demonstrated DBiT-seq as a high-resolution tool for the spatial transcriptome analysis of FFPE tissue sections. It generates useful transcriptome data out of the highly degraded mRNAs. Applying it to mouse embryo tissue samples resulted in clear spatial patterns that are matching well with anatomical patterns. Integration with published scRNA-seq data greatly improved our understanding of the tissue by providing cell type information. Aorta, atrium and ventricle samples were also successfully profiled using DBiT-seq, providing detailed cell type information. As FFPE sample are easily available and more commonly used in clinic, we envision that, with DBiT-seq, more in-depth understanding and analysis of clinically important samples would be feasible.

Methods for Examples 1-15

Microfluidic Device Fabrication and Assembly

The microfluidic device was fabricated with polydimethylsiloxane (PDMS) using soft lithography. The chrome photomasks with 10 µm, 25 µm and 50 µm channel width were ordered from the company Front Range Photomasks (Lake Havasu City, AZ). The molds were fabricated using SU-8 negative photoresist according to the following microfabrication process. A thin layer of SU-8 resist (SU-8 2010, SU-8 2025 and SU-8 2050, Microchem) was spin-coated on a clean silicon wafer following manufacturer's guidelines. The thickness of the resistant was ~50 µm for the 50-µm-wide microfluidic channel device, ~28 µm for 25-µm-wide device, and ~20 µm for 10-µm-wide device. A protocol to perform SU-8 photo lithography, development, and hard baking was followed based on the manufacturer's (MicroChem) recommendations to yield the silicon molds for PDMS replication.

PDMS microfluidic chips were then fabricated via a replication molding process. The PDMS precursor was prepared by combining GE RTV PDMS part A and part B at a 10:1 ratio. After stir mixing, degassing, this mixture was poured to the mold described above, degassed again for 30 min, and cured at 75° C. for ~2 hours or overnight. The solidified PDMS slab was cut out, peeled off, and the inlet and outlet holes were punched to complete the fabrication. The inlet holes were ~2 mm in diameter, which can hold up to 13 µL of solution. A pair of microfluidic chips with the same location of inlets and outlets but orthogonal microfluidic channels in the center were fabricated as a complete set of devices for flow barcoding a tissue slide. To do that, the PDMS slab was attached to the tissue section glass slides and a custom-designed acrylic clamp was used to firmly hold the PDMS against the tissue specimen to prevent leakage across microfluidic channels without the need for harsh bonding processed such as thermal bonding or plasma bonding (Temiz et al., 2015).

DNA Barcodes and Other Key Reagents

Oligos used were listed in Table 3 and Table 4. All other key reagents used were listed as Table 2.

Tissue Handling

Formaldehyde fixed tissue or frozen tissue slides were obtained from a commercial source Zyagen (San Diego, CA). The protocol Zyagen used to prepare the embryonic tissue slides is the following. The pregnant mice (C57BL/6NCrl) were bred and maintained by Charles River Laboratories. More information can be found in the information sheet. The time-pregnant mice (day 10 or day 12) were shipped to Zyagen (San Diego, CA) the same day. The mice were sacrificed at the day of arrival for embryos collection. The embryo sagittal frozen sections were prepared by Zyagen (San Diego, CA) as following: the freshly dissected embryos were immersed into OCT and snapped frozen with liquid nitrogen. Before sectioning, the frozen tissue block was warmed to the temperature of cryotome cryostat (−20° C.). Tissue block was then sectioned into thickness of ~7 μm and placed in the center of a poly-L-lysine coated glass slide (CatLog no. 63478-AS, electron microscopy sciences). The frozen slides were then fixed with 4% formaldehyde or directly kept at −80° C. if a long-time storage is needed.

Tissue Slides and Fixation

To thaw the tissue slides, they were taken out of the freezer, placed on a bench at room temperature for 10 minutes, and then cleaned with 1× phosphate buffer saline (PBS) supplemented with RNase inhibitor (0.05 U/μL, Enzymatics). If the tissue slides were frozen sections, they were first fixed by immersing in 4% formaldehyde (Sigma) for 20 minutes. Afterwards, the tissue slides were dried with forced nitrogen air and then ready to use for spatial barcoding.

Tissue Histology and H&E Staining

An adjacent tissue section was also requested from the same commercial resource which could be used to perform tissue histology examination using H&E staining. Basically, the fixed tissue slide was first cleaned by DI water, and the nuclei were stained with the alum hematoxylin (Sigma) for 2 minutes. Afterwards, the slides were cleaned in DI water again and incubated in a bluing reagent (0.3% acid alcohol. Sigma) for 45 seconds at room temperature. Finally, the slides were stained with eosin for 2 more minutes. The stained embryo slide was examined immediately or stored at −80° C. fridge for future analysis.

Immunofluorescence Staining

Immunofluorescence staining was performed either on the same tissue slide or an adjacent slide to yield validation data. Three fluorescent-labelled antibodies listed below were used for visualizing the expression of three target proteins: Alexa Fluor 647 anti-mouse CD326 (EpCAM) Antibody. Alexa Fluor 488 anti-mouse Panendothelial Cell Antigen Antibody, PE anti-P2RY12 Antibody. The procedure to stain the mouse embryo tissue slide is as follows. (1) Fix the fresh frozen tissue sections with 4% Formaldehyde for 20 mins, wash three times with PBS. (2) Add 1% bovine serum albumin (BSA) in PBS to block the tissue and incubate for 30 mins at RT. (3) Wash the tissue with PBS for three times. (4) Add the mixture of three antibodies (final concentration 25 μg/mL in 1% BSA, PBS) to the tissue, need around 50 μL. Incubate for 1 hour in dark at RT. (5) Wash the tissue with PBS for three times, with 5 mins washing each time. (6) Dip the tissue in water shortly and air dry the tissue. (7) Image the tissue using EVOS (Thermo Fisher EVOS fl), at a magnification of 10 ×. Filters used are Cy5, RFP and GFP.

Application of DNA-Antibody Conjugates to the Tissue Slide

In order to obtain spatial proteomic information, we incubated the fixed tissue slide with a cocktail of DNA-antibody conjugates prior to microfluidic spatial barcoding. The cocktail was prepared by combining 0.1 μg of each DNA-antibody conjugates. The tissue slide was first blocked with 1% BSA/PBS plus RNase inhibitor, and then incubated with the cocktail for 30 minutes at 4° C. Afterwards, the tissue slide was washed 3 times with a washing buffer containing 1% BSA+0.01% Tween 20 in 1×PBS and one time with DI water prior to attaching the first PDMS microfluidic chip.

Adding the First Set of Barcodes and Reverse Transcription

To perform spatial barcoding of mRNAs for transcriptomic mapping, the slides were blocked by 1% BSA plus RNase inhibitor (0.05 U/μL, Enzymatics) for 30 minutes at room temperature. After cleaning with 1× PBS and quickly with DI water, the first PDMS microfluidic chip was roughly aligned and placed on the tissue glass slide such that the center of the flow barcoding region covered the tissue of interest. This tissue section was then permeabilized by loading 0.5% Triton X-100 in PBS into each of the 50 channels followed by incubation for 20 minutes and finally were cleaned thoroughly by flowing through 20 μL of 1×PBS. A vial of RT mix was made from 50 μL of RT buffer (5×, Maxima H Minus kit), 32.8 μL of RNase free water, 1.6 μL of RNase Inhibitor (Enzymatics), 3.1 μL of SuperaseIn RNase Inhibitor (Ambion), 12.5 μL of dNTPs (10 mM, Thermo Fisher), 25 μL of Reverse Transcriptase (Thermo Fisher), 100 μL of 0.5× PBS with Inhibitor (0.05 U/μL, Enzymatics). To perform the $1^{st}$ microfluidic flow barcoding, we added to each inset a 5 μL of solution containing 4.5 μL of the RT mix described and 0.5 μL of one of the 50 DNA barcodes (A1-A50) solution (25 μM), and then pulled in using a house vacuum for <3 minutes depending on channel width. Afterwards, the binding of DNA oligomers to mRNAs fixed in tissue was allowed to occur at room temperature for 30 minutes and then incubated at 42° C. for 1.5 hours for in situ reverse transcription. To prevent the evaporation of solution inside the channels, the whole device was kept inside a sealed wet chamber (Gervais and Delamarche, 2009). Finally, the channels were rinsed by flowing NEB buffer 3.1 (1×, New England Biolabs) supplemented with 1% RNase inhibitor (Enzymatics) continuously for 10 minutes. During the flow barcoding step, optical images could be taken to record the exact positions of these microfluidic channels in relation to the tissue section subjected to spatial barcoding. It was done using an EVOS microscope (Thermo Fisher EVOS fl) in a light or dark field mode. Then the clamp was removed and the PDMS chip was detached from the tissue slide, which was subsequently dipped into a 50 mL Eppendorf tube containing RNase free water to rinse off remaining salts.

Adding the Second Set of Barcodes and Ligation

After drying the tissue slides, the second PDMS chip with the microfluidic channels perpendicular to the direction of the first PDMS chip in the tissue barcoding region was carefully aligned and attached to the tissue slide such that the microfluidic channels cover the tissue region of interest. The ligation mix was prepared as follows: 69.5 μL of RNase free water, 27 μL of T4 DNA ligase buffer (10×, New England Biolabs), 11 μL T4 DNA ligase (400 U/μL. New England Biolabs), 2.2 μL RNase inhibitor (40 U/μL. Enzymatics), 0.7 μL SuperaseIn RNase Inhibitor (20 U/μL, Ambion), 5.4 μL of Triton X-100 (5%). To perform the second flow barcoding, we added to each channel a total of 5 μL of solution consisting of 2 μL of the aforementioned ligation mix, 2 μL of NEB buffer 3.1 (1×, New England Biolabs) and 1 μL of DNA barcode B (25 μM). Reaction was allowed to occur at 37° C. for 30 minutes and then the microfluidic channels were washed by flowing IX PBS supplemented with 0.1% Triton X-100 and 0.25% SUPERase In RNase Inhibitor for 10 minutes. Again, the images showing the location of the microfluidic channels on the tissue slide could be taken during the flow step under the light or dark field optical microscope (Thermo Fisher EVOS fl) before peeling off the second PDMS chip.

cDNA Collection and Purification

We devised a square well PDMS gasket, which could be aligned and placed on the tissue slide, creating an open reservoir to load lysis buffer specifically to the flow barcoded tissue region to collect cDNAs of interest. Depending on the area of this region, the typical amount of buffer is 10-100 µL of Proteinase K lysis solution, which contains 2 mg/mL proteinase K (Thermo Fisher), 10 mM Tris (pH=8.0), 200 mM NaCl, 50 mM EDTA and 2% SDS. Lysis was carried out at 55° C. for 2 hours. The lysate was then collected and stored at −80° C. prior to use. The cDNAs in the lysate were purified using streptavidin beads (Dynabeads MyOne Streptavidin C1 beads, Thermo Fisher). The beads (40 µL) were first washed three times with 1× B&W buffer (Ref to manufacturer's manual) with 0.05% Tween-20, and then stored in 100 µL of 2× B&W buffer (with 2 µL of SUPERase In Rnase Inhibitor). To perform purification from stored tissue lysate, it was allowed to thaw, and the volume was brought up to 100 µL by RNase free water. Then, 5 µL of PMSF (100 µM, Sigma) was added to the lysate and incubated for 10 minutes at room temperature to inhibit the activity of Proteinase K. Next, 100 µL of the cleaned streptavidin bead suspension was added to the lysate and incubated for 60 minutes with gentle rotating. The beads with cDNA were further cleaned with 1× B&W buffer for two times and then with 1× Tris buffer (with 0.1% Tween-20) once.

Template Switch and PCR Amplification

The cDNAs bound to beads were cleaned and resuspended into the template switch solution. The template switch reaction mix contains 44 µL of 5× Maxima RT buffer (Thermo Fisher), 44 µL of 20% Ficoll PM-400 solution (Sigma), 22 µL of 10 mM dNTPs each (Thermo Fisher), 5.5 µL of RNase Inhibitor (Enzymatics), 11 µL of Maxima H Minus Reverse Transcriptase (Thermo Fisher), and 5.5 µL of a template switch primer (100 µM). The reaction was conducted at room temperature for 30 minutes followed by an additional incubation at 42° C. for 90 minutes. The beads were rinsed once with a buffer containing 10 mM Tris and 0.1% Tween-20 and then rinsed again with RNase free water using a magnetic separation process. PCR was conducted following these two steps. In the first step, a mixture of 110 µL Kapa HiFi HotStart Master Mix (Kapa Biosystems), 8.8 µL of 10 µM stocks of primers 1 and 2, and 92.4 µL of water was added to the cleaned beads. If the protein detection was conducted in conjunction using a process similar to CITE-seq, a primer 3 solution (1.1 µL, 10 µM) was also added at this step. PCR reaction was then done using the following conditions: first incubate at 95° C. for 3 mins, then cycle five times at 98° C.' for 20 seconds, 65° C. for 45 seconds, 72° C. for 3 minutes and then the beads were removed from the solution by magnet. Evagreen (20×, Biotium) was added to the supernatant with 1:20 ratio, and a vial of the resultant solution was loaded into a qPCR machine (BioRad) to perform a second PCR step with an initial incubation at 95° C. for 3 minutes, then cycled at 98° C. for 20 seconds, 65° C. for 20 seconds, and finally 72° C. for 3 minutes. The reaction was stopped when the fluorescence signal just reached the plateau.

Amplicon Purification, Sequencing Library Preparation and Quality Assessment

The PCR product was then purified by Ampure XP beads (Beckman Coulter) at 0.6×ratio. The mRNA-derived cDNAs (>300 bp) were then collected from the beads. If the cDNAs were less than 300 bp, they remained in the supernatant fraction. If the protein detection was conducted like CITE-seq, this fraction was used instead. For sequencing antibody-DNA conjugate-derived cDNAs, we further purified the supernatant using 2× Ampure XP beads. The purified cDNA was then amplified using a PCR reaction mix containing 45 µL purified cDNA fraction, 50 µL 2× KAPA Hifi PCR Master Mix (Kapa Biosystems), 2.5 µl P7 primer of 10 UM and 2.5 µL P5 cite primer at 10 µM. PCR was performed in the following conditions: first incubated at 95° C. for 3 minutes, then cycled at 95° C. for 20 seconds, 60° C. for 30 seconds and 72° C. for 20 seconds, for 10 cycles, lastly 72° C. for 5 minutes. The PCR product was further purified by 1.6× Ampure XP beads. For sequencing mRNA-derived cDNAs, the quality of amplicon was analyzed firstly using Qubit (Life Technologies) and then using an Agilent Bioanalyzer High Sensitivity Chip. The sequencing library was then built with a Nextera XT kit (Illumina) and sequenced using a HiSeq 4000 sequencer using a pair-end 100×100 mode. To conduct joint profiling of proteins and mRNAs, the DNA-antibody conjugate-derived sequencing library was combined with mRNA-derived cDNA library at a 1:9 ratio, which is sufficient to detect the finite set of proteins and minimally affects the sequencing depth required for mRNAs.

Tissue Fluorescent Staining Before DBIT-Seq

Fluorescent staining of tissue sections with either common nucleus staining dyes or fluorescent labelled antibodies can be performed before the DBIT-seq to facilitate the identification of tissue region of interest. After the DBiT-seq fixation procedure with formaldehyde, the whole tissue was permeabilized with 0.5% Triton X-100 in PBS for 20 minutes and cleaned with 1×PBS for three times. Working solution mixture of DAPI and phalloidin (FITC labelled) were added on top of the tissue and then incubate at room temperature for 20 minutes. After washing thrice with 1×PBS, tissue sections were blocked with 1% BSA for 30 minutes. Finally, antibody with fluorescent labels (here we use P2RY12) were added and incubated at room temperature for 1 hour. Images of the tissue were taken using EVOS microscope (Thermo Fisher EVOS fl), using 10 × objective. Filters used were DAPI, GFP and RFP. DBIT-seq barcoding procedure could be continued after staining.

smFISH and Comparison with DBIT-Seq

Single molecular fish (smFISH) was performed using HCR v3.0 kit (Molecular Instruments, Inc) following manufacture protocols. Probes used in current study included Ttn, sfrp2, Trf and Dlk1, smFISH z-stack images were taken using a ZEISS LSM 880 confocal microscope with a 60× oil immersion objective. The smFISH quantitation was performed using FISH-quant (biii.eu/fish-quant). mRNA transcript count was an average of three fields of view with each having a size of 306×306 µm. The sum of DBIT-seq transcript counts in the same locations were also calculated and compared side by side with smFISH counts.

Cell Number Counting in Each Pixel

Cell numbers for each pixel were counted manually using DAPI and ethidium homodimer-1 stained tissue images. The total cell counts were obtained by summing the nucleus numbers in each of the pixels. If a nucleus appeared at the edge of a pixel, we would count it as 1 if more than half of the nucleus lied within the pixel and as 0 if otherwise. A total of 50 pixels were counted and the averaged numbers were reported.

QUANTIFICATION AND STATISTICAL ANALYSIS

Sequence Alignment and Generation of Gene Expression Matrix

To obtain transcriptomics data, the Read 2 was processed by extracting the UMI, Barcode A and Barcode B. The processed read 1 was trimmed, mapped against the mouse genome (GRCh38), demultiplexed and annotated (Gencode release M11) using the ST pipeline v1.7.2 (Navarro et al., 2017), which generated the digital gene expression matrix for down-stream analysis. The rows of the gene matrix correspond to pixels, defined by their location info (barcode A×barcode B) and columns correspond to genes.

For proteomics data, the Read 2 was processed by extracting the antibody-derived barcode spatial Barcode A and Barcode B. The processed read was trimmed, demultiplexed using the ST pipeline v1.7.2 (Navarro et al., 2017), which generated the gene protein matrix for down-stream analysis. Similar to the gene expression matrix, the rows correspond to pixels, defined by (barcode A×barcode B) and columns correspond to proteins.

The pan-mRNA and pan-protein heatmap plots in FIG. 2A were generated using raw UMI counts without normalization.

Data Normalization and Integration

Normalization and variance stabilization of transcriptome data for each pixel with regularized negative binomial regression was performed using "SCTransform", a module in Seurat V3.2. The process is similar to that widely used for scRNA-seq data normalization, with each "pixel" treated as a "single cell". The expression matrix of all pixels was SCTransformed ("NormalizeData", "ScaleData", and "FindVariableFeatures"). The integration of scRNA-seq reference data and spatial transcriptome data was conducted using Seurat V3.2 with the "SCTransform" module. Normalization of gene data was completed through Scran (V3.11) following a standard protocol as recommended in Seurat package.

Clustering Analysis

Spatially variable genes were identified by SpatialDE (Svensson et al., 2018b). The resulting list of differentially expressed genes was submitted to ToppGene (Chen et al., 2009) for GO and Pathway enrichment analysis. Spatially variable genes generated by SpatialDE were used to conduct the clustering analysis. Non-negative matrix factorization (NMF) was performed using the NNLM packages in R, after the raw expression values were log-transformed. We chose k of 11 for the mouse embryo DBiT-seq transcriptome data obtained at a 50 μm pixel size. For each pixel, the largest factor loading from NMF was used to assign cluster membership. NMF clustering of pixels was plotted by tSNE using the package "Rtsne" in R.

Comparison with ENCODE Bulk Sequencing Data

Public bulk RNA-Seq datasets were downloaded from ENCODE (liver, heart and neural tube from mouse embryo E11.5) and the raw expression counts were normalized with FPKM. For DBiT-seq data, "pseudo-bulk" gene expression profiles were obtained by summing counts for each gene in each tissue region and divided by the sum of total UMI counts in this specific region, and further multiplied by 1 million. The scatter plots were plotted using $\log_{10}$(FPKM+1) value for bulk data and log 10 (pseudo gene expression+1)) for DBiT-seq data. Pairwise Pearson correlation coefficients were calculated. Good correlations (r>0.784) were observed between the two different sets of data.

Gene Length Bias Analysis

Gene length bias is well understood in bulk RNA-seq data. We further analyzed our DBiT-seq data and ST data using reference package GeneLengthBias for RNAseq data (Phipson et al., 2019) following standard protocols.

Data Analysis with Single-Cell RNA-Seq Analysis Workflow

The data analysis of E10-E12 tissue sections was carried out with Seurat V3.2 (Butler et al., 2018; Stuart et al., 2019) following standard procedures. In short, data normalization, transformation, and selection of variable genes were performed using the SCTransform function with default settings. Principal component analysis (PCA) was performed on the top 3,000 variable genes using the RunPCA function, and the first 30 principal components were used for Shared Nearest Neighbor (SNN) graph construction using the FindNeighbors function. Clusters were then identified using the FindClusters function. We used Uniform Manifold Approximation and Projection (UMAP) to visualize DBIT-seq data in a reduced two-dimensional space (McInnes et al., 2018). To identify differentially expressed genes for every cluster, pair-wise comparisons of cells in individual clusters against all remaining cells were performed using the FindAllMarkers function (settings: min.pct=0.25, logfc.threshold=0.25). Expression heatmap was then generated using top 10 differentially expressed genes in each cluster.

Integrative Data Analysis and Cell Type Identification

Automatic cell type identification for E11 mouse tail region was achieved with SingleR (version 1.2.3) (Aran et al., 2019) following standard procedure. Single cell RNA-seq data E10.5 from (Cao et al., 2019) was used as the reference. The 12 most frequent cell types were shown in the UMAP, and cell types with small size were shown as "other".

Cell type identification for E10 Eye region was performed through integration with scRNA-seq reference data. We combined DBIT-seq data with scRNA-seq data of mouse embryo E9.5 and E10.5 (Cao et al., 2019) using Seurat V3.2 and did the clustering after "SCTransform" procedure. DBiT-seq data showed a similar distribution as scRNA-seq reference data. We then assign each cluster with a cell type using cell type information from the reference data (if two cell types presented in one cluster, the major cell types were assigned). The cell type of each pixel was then assigned by their cluster number.

REFERENCES FOR EXAMPLES 1-15

Aran, D., Looney, A. P., Liu, L., Wu, E., Fong, V., Hsu, A., Chak, S., Naikawadi, R. P., Wolters, P. J., Abate, A. R., et al. (2019). Reference-based analysis of lung single-cell sequencing reveals a transitional profibrotic macrophage. Nat Immunol 20, 163-172.

Armit, C., Richardson, L., Venkataraman, S., Graham, L., Burton, N., Hill, B., Yang, Y., and Baldock, R. A. (2017). eMouse Atlas: An atlas-based resource for understanding mammalian embryogenesis. Dev Biol 423, 1-11.

Baldock, R. A., and Armit, C. (2017). eHistology image and annotation data from the Kaufman Atlas of Mouse Development. Gigascience 7.

Burgess, D. J. (2019). Spatial transcriptomics coming of age. Nat Rev Genet 20, 317.

Cao, J. Y., Spielmann, M., Qiu, X. J., Huang, X. F., Ibrahim, D. M., Hill, A. J., Zhang. F., Mundlos, S., Christiansen, L., Steemers, F. J., et al. (2019). The single-cell transcriptional landscape of mammalian organogenesis. Nature 566, 496-+.

Chen, J., Bardes, E. E., Aronow, B. J., and Jegga, A. G. (2009). ToppGene Suite for gene list enrichment analysis and candidate gene prioritization. Nucleic Acids Res 37, W305-W311.

Chen, K. H., Boettiger, A. N., Moffitt, J. R., Wang, S. Y., and Zhuang, X. W. (2015). Spatially resolved, highly multiplexed RNA profiling in single cells. Science 348.

de Bruin, E. C., McGranahan, N., Mitter, R., Salm, M., Wedge, D. C., Yates, L., Jamal-Hanjani, M., Shafi, S., Murugaesu, N., Rowan, A. J., et al. (2014). Spatial and temporal diversity in genomic instability processes defines lung cancer evolution. Science 346, 251-256.

de Sousa Abreu, R., Penalva, L. O., Marcotte, E. M., and Vogel. C. (2009). Global signatures of protein and mRNA expression levels. Molecular BioSystems 5, 1512-1526.

Deschamps, J., and Duboule, D. (2017). Embryonic timing, axial stem cells, chromatin dynamics, and the Hox clock. Genes Dev 31, 1406-1416.

Eng, C. L., Lawson, M., Zhu, Q., Dries, R., Koulena, N., Takei, Y., Yun, J., Cronin, C., Karp. C., Yuan, G. C., et al. (2019). Transcriptome-scale super-resolved imaging in tissues by RNA seqFISH. Nature 568, 235-239.

Fuchs, E., Tumbar, T., and Guasch, G. (2004). Socializing with the neighbors: stem cells and their niche. Cell 116, 769-778.

Gervais, L., and Delamarche, E. (2009). Toward one-step point-of-care immunodiagnostics using capillary-driven microfluidics and PDMS substrates. Lab Chip 9, 3330-3337.

Heavner, W., and Pevny, L. (2012). Eye development and retinogenesis. Cold Spring Harb Perspect Biol 4.

Ivanovs, A., Rybtsov, S., Ng, E. S., Stanley, E. G., Elefanty, A. G., and Medvinsky, A (2017). Human haematopoietic stem cell development: from the embryo to the dish. Development 144, 2323-2337.

Klein, A. M., Mazutis, L., Akartuna, I., Tallapragada, N., Veres, A., Li, V., Peshkin, L., Weitz, D. A., and Kirschner, M. W. (2015). Droplet barcoding for single-cell transcriptomics applied to embryonic stem cells. Cell 167, 1187-1201.

Knipple, D. C., Seifert, E., Rosenberg, U. B., Preiss, A., and Jackle, H. (1985). Spatial and temporal patterns of Kruppel gene expression in early *Drosophila* embryos. Nature 377, 40-44.

Kwon, B. S., Chintamaneni, C., Kozak, C. A., Copeland, N. G., Gilbert, D. J., Jenkins, N., Barton, D., Francke, U., Kobayashi, Y., and Kim, K. K. (1991). A melanocyte-specific gene. Pmel 17, maps near the silver coat color locus on mouse chromosome 10 and is in a syntenic region on human chromosome 12. Proc Natl Acad Sci USA 88, 9228-9232.

Lee, J. H., Dangharthy, E. R., Scheiman, J., Kalhor, R., Ferrante, T. C., Terry, R., Turczyk, B. M., Yang, J. L., Lee. H. S., Aach, J., et al. (2015). Fluorescent in situ sequencing (FISSEQ) of RNA for gene expression profiling in intact cells and tissues. Nat Protoc 10, 442-458.

Lu, Y., Chen, J. J., Mu, L. Y., Xue, Q., Wu, Y., Wu, P. H., Li, J., Vortmeyer, A. O., Miller-Jensen, K., Wirtz, D., et al. (2013). High-Throughput Secretomic Analysis of Single Cells to Assess Functional Cellular Heterogeneity. Anal Chem 85, 2548-2556.

Lu, Y., Xue, Q., Eisele, M. R., Sulistijo, E. S., Brower, K., Han, L., Amir, E. D., Pe'er, D., Miller-Jensen, K., and Fan, R. (2015). Highly multiplexed profiling of single-cell effector functions reveals deep functional heterogeneity in response to pathogenic ligands. Proc Natl Acad Sci USA 112, E607-E615.

Lubeck, E., Coskun, A. F., Zhiyentayev, T., Ahmad, M., and Cai, L. (2014). Single-cell in situ RNA profiling by sequential hybridization. Nat Methods 11, 360-361.

Macosko, E. Z., Basu, A., Satija, R., Nemesh, J., Shekhar, K., Goldman, M., Tirosh, I., Bialas, A. R., Kamitaki, N., Martersteck, E. M., et al. (2015). Highly Parallel Genome-wide Expression Profiling of Individual Cells Using Nanoliter Droplets. Cell 161, 1202-1214.

Matt, N., Dupe, V. Garnier, J. M., Dennefeld, C., Chambon, P., Mark, M., and Ghyselinck, N. B. (2005). Retinoic acid-dependent eye morphogenesis is orchestrated by neural crest cells. Development 132, 4789-1800.

Mitiku, N., and Baker, J. C. (2007). Genomic analysis of gastrulation and organogenesis in the mouse Dev Cell 13, 897-907.

Mort, R. L., Jackson, I. J., and Patton, E. E. (2015). The melanocyte lineage in development and disease. Development 142, 620-632.

Navarro, J. F., Sjöstrand, J., Salmen, F., Lundeberg, J., and Ståhl, P. L. (2017). ST Pipeline: an automated pipeline for spatial mapping of unique transcripts. Bioinformatics 33, 2591-2593.

Perkel, J. M. (2019). Starfish enterprise: finding RNA patterns in single cells. Nature 572, 549-551.

Pichon, X., Lagha, M., Mueller, F., and Bertrand, E. (2018). A Growing Toolbox to Image Gene Expression in Single Cells: Sensitive Approaches for Demanding Challenges Mol Cell 77, 468-480.

Pijuan-Sala, B., Griffiths, J. A., Guibentif, C., Hiscock, T. W., Jawaid, W., Calero-Nieto, F. J., Mulas, C., Ibarra-Soria, X., Tyser, R. C. V., Ho, D. L. L., et al. (2019). A single-cell molecular map of mouse gastrulation and early organogenesis. Nature 566, 490-495.

Rodriques, S. G., Stickels, R. R., Goeva, A., Martin, C. A., Murray, E., Vanderburg, C. R., Welch, J., Chen, L. M., Chen. F., and Macosko, E. Z. (2019). Slide-seq: A scalable technology for measuring genome-wide expression at high spatial resolution. Science 363, 1463-1467.

Scadden, D. T. (2014). Nice neighborhood: emerging concepts of the stem cell niche. Cell 157, 41-50.

Shahi, P., Kim, S. C., Haliburton, J. R., Gartner, Z. J., and Abate, A. R. (2017). Abseq: Ultrahigh-throughput single cell protein profiling with droplet microfluidic barcoding. Sci Rep 7, 44447.

Slack, J. M. (2008). Origin of stem cells in organogenesis. Science 322, 1498-1501.

Smith, A. N., Miller, L. A., Radice, G., Ashery-Padan, R., and Lang, R. A. (2009). Stage-dependent modes of Pax6-Sox2 epistasis regulate lens development and eye morphogenesis. Development 136, 2977-2985.

Stahl, P. L., Salmen, F., Vickovic, S., Lundmark, A., Navarro, J. F., Magnusson, J., Giacomello, S., Asp, M., Westholm, J. O., Huss, M., et al. (2016). Visualization and analysis of gene expression in tissue sections by spatial transcriptomics. Science 353, 78-82.

Stoeckius, M., Hafemeister, C., Stephenson, W., Houck-Loomis, B., Chattopadhyay, P. K., Swerdlow, H., Satija, R., and Smibert, P. (2017). Simultaneous epitope and transcriptome measurement in single cells. Nat Methods 14, 865-868.

Svensson, V., Teichmann, S. A., and Stegle, O. (2018a). SpatialDE: identification of spatially variable genes. Nat Methods 15, 343-346.

Svensson, V., Teichmann, S. A., and Stegle, O. (2018b). SpatialDE: identification of spatially variable genes. Nature Methods 15, 343.

Temiz, Y., Lovchik, R. D., Kaigala, G. V., and Delamarche, E. (2015) Lab-on-a-chip devices: How to close and plug the lab? Microelectronic Engineering 132, 156-175.

Treek, T., Lionnet, T., Shroff, H., and Lehmann, R. (2017). mRNA quantification using single-molecule FISH in *Drosophila* embryos. Nat Protoc 12, 1326-1348.

van Vliet, S., Dal Co, A., Winkler, A. R., Spriewald, S., Stecher, B., and Ackermann, M. (2018). Spatially Correlated Gene Expression in Bacterial Groups: The Role of Lineage History, Spatial Gradients, and Cell-Cell Interactions. Cell Syst 6, 496-507 e196.

Vickovic, S., Eraslan, G., Salmen, F., Kinghammer, J., Stenbeck, L., Schapiro, D., Aijo, T., Bonneau, R., Bergenstrahle, L., Navarro, J. F., et al. (2019). High-definition spatial transcriptomics for in situ tissue profiling. Nat Methods.

Vogel, C., and Marcotte, E. M. (2012). Insights into the regulation of protein abundance from proteomic and transcriptomic analyses. Nat Rev Genet 13, 227-232

Wang, X., Allen, W. E., Wright, M. A., Sylwestrak, E. L., Samusik, N., Vesuna, S., Evans, K., Liu, C., Ramakrishnan, C., Liu, J., et al. (2018). Three-dimensional intact-tissue sequencing of single-cell transcriptional states. Science 361.

Yudushkin, I. A., Schleifenbaum, A., Kinkhabwala, A., Neel, B. G., Schultz, C., and Bastiaens, P. I. (2007). Live-cell imaging of enzyme-substrate interaction reveals spatial regulation of PTP1B. Science 315, 115-119.

Yun, S., Saijoh, Y., Hirokawa, K. E., Kopinke, D., Murtaugh, L. C., Monuki, E. S., and Levine, E. M. (2009). Lhx2 links the intrinsic and extrinsic factors that control optic cup formation. Development 136, 3895-3906.

Zhao, S., Chen, Q., Hung, F. C., and Overbeck, P. A. (2002). BMP signaling is required for development of the ciliary body. Development 129, 4435-4442.

References for Example 16

1. Hedegaard, J., Thorsen, K., Lund, M. K., Hein, A. M. K., Hamilton-Dutoit, S. J., Vang, S., Nordentoft, I., Birkenkamp-Demtröder, K., Kruhoffer, M., Hager, H., Knudsen, B., Andersen, C. L., Sorensen, K. D., Pedersen, J. S., Ørtoft, T. F. & Dyrskjot, L. Next-Generation Sequencing of RNA and DNA Isolated from Paired Fresh-Frozen and Formalin-Fixed Paraffin-Embedded Samples of Human Cancer and Normal Tissue. *PLoS ONE* 9, e98187 (2014).
2. Xie, R., Chung, J. Y., Ylaya, K., Williams, R. L., Guerrero, N., Nakatsuka, N., Badie, C. & Hewitt, S. M. Factors Influencing the Degradation of Archival Formalin-Fixed Paraffin-Embedded Tissue Sections. *J. Histochem. Cytochem.* 59, 356-365 (2011).
3. Sinicropi, D., Qu, K., Collin, F., Crager, M., Liu, M. L., Pelham, R. J., Pho, M., Rossi, A. D., Jeong, J., Scott, A., Ambannavar, R., Zheng, C., Mena, R., Esteban, J., Stephans, J., Morlan, J. & Baker, J. Whole Transcriptome RNA-Seq Analysis of Breast Cancer Recurrence Risk Using Formalin-Fixed Paraffin-Embedded Tumor Tissue. *PLoS ONE* 7, e40092 (2012)
4. Beck, A. H., Weng, Z., Witten, D. M., Zhu, S., Foley, J. W., Lacroute, P., Smith, C. L., Tibshirani, R., van de Rijn, M., Sidow, A. & West, R. B. 3'-End Sequencing for Expression Quantification (3SEQ) from Archival Tumor Samples. *PLoS ONE* 5, e8768 (2010).
5. Pichon, X., Lagha, M., Mueller, F. & Bertrand, E. A Growing Toolbox to Image Gene Expression in Single Cells: Sensitive Approaches for Demanding Challenges. *Mol Cell* 71, 468-480 (2018).
6. Trek, T., Lionnet, T., Shroff, H. & Lehmann, R. mRNA quantification using single-molecule FISH in *Drosophila* embryos. *Nat Protoc* 12, 1326-1348 (2017).
7. Lubeck, E., Coskun, A. F., Zhiyentayev, T., Ahmad, M. & Cai, L. Single-cell in situ RNA profiling by sequential hybridization. *Nat Methods* 11, 360-361 (2014).
8. Eng, C. L., Lawson, M., Zhu, Q. Dries, R., Koulena, N., Takei, Y., Yun, J., Cronin, C., Karp, C., Yuan, G. C. & Cai, L. Transcriptome-scale super-resolved imaging in tissues by RNA seqFISH. *Nature* 568, 235-239 (2019).
9. Asp, M., Bergenstråhle. J. & Lundeberg, J. Spatially Resolved Transcriptomes—Next Generation Tools for Tissue Exploration. *Bioessays* n/a, 1900221.
10. Rodriques, S. G., Stickels, R. R., Goeva, A., Martin, C. A., Murray, E., Vanderburg, C. R., Welch, J., Chen, L. M., Chen, F. & Macosko, E. Z. Slide-seq: A scalable technology for measuring genome-wide expression at high spatial resolution. *Science* 363, 1463-1467 (2019).
11. Stahl, P. L., Salmen, F., Vickovic. S. et al. Visualization and analysis of gene expression in tissue sections by spatial transcriptomics. *Science* 353, 78-82 (2016).
12. Vickovic, S., Eraslan, G., Salmen, F., Klughammer, J., Stenbeck, L., Schapiro, D., Aijo, T., Bonneau, R., Bergenstrahle, L., Navarro, J. F., Gould, J., Griffin, G. K., Borg, A., Ronaghi, M., Frisen, J., Lundeberg, J., Regev, A. & Stahl, P. L. High-definition spatial transcriptomics for in situ tissue profiling. *Nat Methods* (2019).
13. Liu, Y., Yang, M., Deng, Y., Su, G., Guo, C. C., Zhang, D., Kim, D., Bai, Z., Xiao. Y. & Fan, R. High-Spatial-Resolution Multi-Omics Atlas Sequencing of Mouse Embryos via Deterministic Barcoding in Tissue. *bioRxiv.* 788992 (2019).
14. Svensson, V., Teichmann, S. A. & Stegle, O. SpatialDE: identification of spatially variable genes. *Nat. Meth.* 15, 343-346 (2018).
15. Cao, J., Spielmann, M., Qiu, X., Huang, X., Ibrahim, D. M., Hill, A. J., Zhang, F., Mundlos, S., Christiansen, L., Steemers, F. J., Trapnell, C. & Shendure, J. The single-cell transcriptional landscape of mammalian organogenesis. *Nature* 566, 496-502 (2019).
16. Hafemeister, C. & Satija, R. Normalization and variance stabilization of single-cell RNA-seq data using regularized negative binomial regression. *bioRxiv,* 576827 (2019).
17. Baron, M. H., Isern, J. & Fraser, S. T. The embryonic origins of erythropoiesis in mammals. Blood 119, 4828-4837 (2012).
18. Kalluri, A. S., Vellarikkal, S. K., Edelman, E. R., Nguyen, L., Subramanian. A., Ellinor, P. T., Regev. A., Kathiresan, S. & Gupta, R. M. Single-Cell Analysis of the Normal Mouse Aorta Reveals Functionally Distinct Endothelial Cell Populations. *Circulation* 140, 147-163 (2019).
19. Lynn Ray, J., Leach, R., Herbert, J. M. & Benson, M. Isolation of vascular smooth muscle cells from a single murine aorta. *Methods in Cell Science* 23, 185-188 (2001).
20. Zhou, P. & Pu, W. T. Recounting Cardiac Cellular Composition. *Circ. Res.* 118, 368-370 (2016).
21. Schaum, N., Karkanias, J., Neff, N. F. et al. Single-cell transcriptomics of 20 mouse organs creates a Tabula Muris. *Nature* 562, 367-372 (2018).
22. Navarro, J. F., Sjöstrand, J., Salmén, F., Lundeberg, J. & Stahl, P. L. ST Pipeline: an automated pipeline for spatial mapping of unique transcripts. *Bioinformatics* 33, 2591-2593 (2017).

23. Stuart, T., Butler, A., Hoffman, P., Hafemeister, C., Papalexi, E., Mauck III, W. M., Hao, Y., Stoeckius, M., Smibert, P. & Satija, R. Comprehensive integration of single-cell data. *Cell* 177, 1888-1902, e1821 (2019).

24. Butler, A., Hoffman, P., Smibert, P., Papalexi, E. & Satija, R. Integrating single-cell transcriptomic data across different conditions, technologies, and species. *Nat. Biotechnol.* 36, 411-420 (2018).

25. Aran, D., Looney, A. P., Liu, L., Wu, E., Fong, V., Hsu, A., Chak. S., Naikawadi, R. P., Wolters, P. J., Abate, A. R., Butte, A. J. & Bhattacharya, M. Reference-based analysis of lung single-cell sequencing reveals a transitional pro-fibrotic macrophage. *Nat. Immunol.* 20, 163-172 (2019).

Additional References

Armit, C., Richardson, L., Venkataraman, S., Graham, L., Burton, N., Hill, B., Yang, Y., and Baldock, R. A. (2017). eMouse Atlas: An atlas-based resource for understanding mammalian embryogenesis. Dev Biol 423, 1-11.

Baldock, R. A., and Armit. C. (2017). eHistology image and annotation data from the Kaufman Atlas of Mouse Development. Gigascience 7.

Cao, J. Y., Spielmann, M., Qiu, X. J., Huang, X. F., Ibrahim, D. M., Hill, A. J., Zhang, F., Mundlos, S., Christiansen, L., Steemers, F. J., et al. (2019). The single-cell transcriptional landscape of mammalian organogenesis. Nature 566, 496-+.

Chen, J., Bardes, E. E., Aronow, B. J., and Jegga, A. G. (2009). ToppGene Suite for gene list enrichment analysis and candidate gene prioritization. Nucleic Acids Research 37. W305-W311.

Chen, K. H., Boettiger, A. N., Moffitt, J. R., Wang, S. Y., and Zhuang, X. W. (2015). Spatially resolved, highly multiplexed RNA profiling in single cells. Science 348.

Chen, X., Shen. Y., Draper, W., Buenrostro, J. D., Litzenburger, U., Cho, S. W., Satpathy, A. T., Carter, A. C., Ghosh, R. P., East-Seletsky, A., et al. (2016). ATAC-see reveals the accessible genome by transposase-mediated imaging and sequencing. Nat Methods 13, 1013-1020.

de Bruin, E. C., McGranahan, N., Mitter, R., Salm. M., Wedge. D. C., Yates, L., Jamal-Hanjani, M., Shafi, S., Murugaesu. N., Rowan, A. J., et al. (2014). Spatial and temporal diversity in genomic instability processes defines lung cancer evolution. Science 346, 251-256.

Dura. B., Choi, J. Y., Zhang, K., Damsky, W., Thakral, D., Bosenberg, M., Craft. J., and Fan, R. (2019). scFTD-seq: freeze-thaw lysis based, portable approach toward highly distributed single-cell 3' mRNA profiling. Nucleic Acids Res 47, e16.

Eng, C. L., Lawson, M., Zhu, Q., Dries, R., Koulena, N., Takei, Y., Yun. J., Cronin, C., Karp, C., Yuan, G. C., et al. (2019). Transcriptome-scale super-resolved imaging in tissues by RNA seqFISH. Nature 568, 235-239.

Fuchs, E., Tumbar, T., and Guasch, G. (2004). Socializing with the neighbors: stem cells and their niche. Cell 116, 769-778.

Gervais, L., and Delamarche, E. (2009). Toward one-step point-of-care immunodiagnostics using capillary-driven microfluidics and PDMS substrates. Lab on a chip 9, 3330-3337.

Heavner, W., and Pevny, L. (2012). Eye development and retinogenesis. Cold Spring Harb Perspect Biol 4.

Ivanovs, A., Rybtsov, S., Ng, E. S., Stanley, E. G., Elefanty, A. G., and Medvinsky, A. (2017). Human haematopoietic stem cell development: from the embryo to the dish. Development 144, 2323-2337.

Klein, A. M., Mazutis, L., Akartuna, I., Tallapragada, N., Veres, A., Li, V., Peshkin, L., Weitz, D. A., and Kirschner, M. W. (2015). Droplet barcoding for single-cell transcriptomics applied to embryonic stem cells. Cell 161, 1187-1201.

Knipple, D. C., Seifert. E., Rosenberg, U. B., Preiss, A., and Jackle, H. (1985). Spatial and temporal patterns of Kruppel gene expression in early *Drosophila* embryos. Nature 317, 40-44.

Kwon, B. S., Chintamaneni, C., Kozak, C. A., Copeland, N. G., Gilbert, D. J., Jenkins, N., Barton, D., Francke, U., Kobayashi, Y., and Kim, K. K. (1991). A melanocyte-specific gene, Pmel 17, maps near the silver coat color locus on mouse chromosome 10 and is in a syntenic region on human chromosome 12. Proc Natl Acad Sci USA 88, 9228-9232.

Lee, J. H., Daugharthy, E. R., Scheiman, J., Kalhor, R., Ferrante, T. C., Terry, R., Turczyk, B. M., Yang, J. L., Lee, H. S., Aach, J., et al. (2015). Fluorescent in situ sequencing (FISSEQ) of RNA for gene expression profiling in intact cells and tissues. Nat Protoc 10, 442-458.

Lu, Y., Chen, J. J., Mu, L. Y., Xue, Q., Wu, Y., Wu, P. H., Li, J., Vortmeyer, A. O., Miller-Jensen, K., Wirtz, D., et al. (2013). High-Throughput Secretomic Analysis of Single Cells to Assess Functional Cellular Heterogeneity. Anal Chem 85, 2548-2556.

Lu, Y., Xue, Q., Eisele, M. R., Sulistijo, E. S., Brower, K., Han, L., Antir, E. D., Pe'er, D., Miller-Jensen, K., and Fan, R. (2015). Highly multiplexed profiling of single-cell effector functions reveals deep functional heterogeneity in response to pathogenic ligands. P Natl Acad Sci USA 112, E607-E615

Lubeck, E., Coskun, A. F., Zhiyentayev, T., Ahmad, M., and Cai, L. (2014). Single-cell in situ RNA profiling by sequential hybridization. Nat Methods 17, 360-361.

Macosko, E. Z., Basu, A., Satija, R., Nemesh, J., Shekhar, K., Goldman, M., Tirosh, I., Bialas, A. R., Kamitaki, N., Martersteck, E. M., et al. (2015). Highly Parallel Genome-wide Expression Profiling of Individual Cells Using Nanoliter Droplets. Cell 167, 1202-1214.

Mitiku, N., and Baker, J. C. (2007). Genomic analysis of gastrulation and organogenesis in the mouse. Dev Cell 13, 897-907.

Navarro, J. F., Sjöstrand. J., Salmón, F., Lundeberg, J., and Ståhl, P. L. (2017). ST Pipeline: an automated pipeline for spatial mapping of unique transcripts. Bioinformatics 33, 2591-2593.

Perkel, J. M. (2019). Starfish enterprise: finding RNA patterns in single cells. Nature 572, 549-551.

Pichon, X., Lagha, M., Mueller, F., and Bertrand, E. (2018). A Growing Toolbox to Image Gene Expression in Single Cells: Sensitive Approaches for Demanding Challenges. Mol Cell 77, 468-480.

Pijuan-Sala, B., Griffiths, J. A., Guibentif, C., Hiscock, T. W., Jawaid, W., Calero-Nieto, F. J., Mulas, C., Ibarra-Soria, X., Tyser, R. C. V., Ho. D. L. L., et al. (2019). A single-cell molecular map of mouse gastrulation and early organogenesis. Nature 566, 490-495.

Rodriques, S. G., Stickels, R. R., Goeva, A., Martin, C. A., Murray, E., Vanderburg, C. R., Welch, J., Chen, L. M., Chen, F., and Macosko, E. Z. (2019). Slide-seq: A scalable technology for measuring genome-wide expression at high spatial resolution. Science 363, 1463-1467.

Salmen, F., Stahl, P. L., Mollbrink, A., Navarro, J. F., Vickovic, S., Frisen, J., and Lundeberg, J. (2018). Barcoded solid-phase RNA capture for Spatial Transcriptomics profiling in mammalian tissue sections. Nat Protoc 13, 2501-2534.

Scadden, D. T. (2014). Nice neighborhood: emerging concepts of the stem cell niche. Cell 157, 41-50.

Shahi, P., Kim, S. C., Haliburton, J. R., Gartner, Z. J., and Abate, A. R. (2017). Abseq: Ultrahigh-throughput single cell protein profiling with droplet microfluidic barcoding. Sci Rep 7, 44447.

Skene, P. J., and Henikoff, S. (2017). An efficient targeted nuclease strategy for high-resolution mapping of DNA binding sites. Elife 6.

Slack, J. M. (2008). Origin of stem cells in organogenesis. Science 322, 1498-1501.

Smith, A. N., Miller, L. A., Radice, G., Ashery-Padan, R., and Lang, R. A. (2009). Stage-dependent modes of Pax6-Sox2 epistasis regulate lens development and eye morphogenesis. Development 136, 2977-2985.

Stahl, P. L., Salmen, F., Vickovic, S., Lundmark, A., Navarro, J. F., Magnusson, J., Giacomello, S., Asp, M., Westholm, J. O., Huss, M., et al. (2016). Visualization and analysis of gene expression in tissue sections by spatial transcriptomics. Science 353, 78-82.

Stoeckius, M., Hafemeister, C., Stephenson, W., Houck-Loomis, B., Chattopadhyay, P. K., Swerdlow, H., Satija, R., and Smibert, P. (2017). Simultaneous epitope and transcriptome measurement in single cells. Nat Methods 14, 865-868.

Svensson, V., Teichmann, S. A., and Stegle, O. (2018a). SpatialDE: identification of spatially variable genes. Nat Methods 15, 343-346.

Svensson, V., Teichmann, S. A., and Stegle, O. (2018b). SpatialDE: identification of spatially variable genes. Nature Methods 15, 343

Temiz, Y., Lovchik, R. D., Kaigala, G. V., and Delamarche, E. (2015). Lab-on-a-chip devices: How to close and plug the lab? Microelectronic Engineering 132, 156-175.

Trek, T., Lionnet, T., Shroff, H., and Lehmann, R. (2017). mRNA quantification using single-molecule FISH in *Drosophila* embryos. Nat Protoc 12, 1326-1348.

van Vliet, S., Dal Co, A., Winkler, A. R., Spriewald, S., Stecher, B., and Ackermann, M. (2018). Spatially Correlated Gene Expression in Bacterial Groups: The Role of Lineage History, Spatial Gradients, and Cell-Cell Interactions. Cell Syst 6, 496-507 e496.

Vickovic, S., Eraslan, G., Salmen, F., Kinghammer, J., Stenbeck, L., Schapiro, D., Aijo, T., Bonneau, R., Bergenstrahle, L., Navarro, J. F., et al. (2019). High-definition spatial transcriptomics for in situ tissue profiling. Nat Methods.

Wang, X., Allen, W. E., Wright, M. A., Sylwestrak, E. L., Samusik, N., Vesuna, S., Evans, K., Liu, C., Ramakrishnan, C., Liu, J., et al. (2018). Three-dimensional intact-tissue sequencing of single-cell transcriptional states. Science 361.

Yudushkin, I. A., Schleifenbaum, A., Kinkhabwala, A., Neel, B. G., Schultz, C., and Bastiaens, P. I. (2007). Live-cell imaging of enzyme-substrate interaction reveals spatial regulation of PTP1B. Science 315, 115-119.

TABLE 1

| Barcode | Specificity | Clone | Barcode Sequence | SEQ ID NO: |
|---|---|---|---|---|
| 0012 | CD117 (c-kit) | 2B8 | TGCATGTC ATCGGTG | 1 |
| 0078 | CD49d | R1-2 | CGCTTGGA CGCTTAA | 2 |
| 0096 | CD45 | 30-F11 | TGGCTATG GAGCAGA | 3 |
| 0104 | CD102 | 3C4 (MIC2/4) | GATATTCA GTGCGAC | 4 |
| 0115 | FcεRIα | MAR-1 | AGTCACCT CGAAGCT | 5 |
| 0118 | NK-1.1 | PK136 | GTAACATT ACTCGTC | 6 |
| 0119 | Siglec H | 551 | CCGCACCT ACATTAG | 7 |
| 0122 | TER-119/ Erythroid Cells | TER-119 | GCGCGTTT GTGCTAT | 8 |
| 0130 | Ly-6A/E (Sca-1) | D7 | TTCCTTTC CTACGCA | 9 |
| 0232 | MAdCAM-1 | MECA-367 | TTGGGCGA TTAAGAA | 10 |
| 0381 | Panendothelial Cell Antigen | MECA-32 | CGTCCTAG TCATTGG | 11 |
| 0415 | P2RY12 | S16007D | TTGCTTAT TTCCGCA | 12 |
| 0439 | CD201 (EPCR) | RCR-16 | TATGATCT GCCCTTG | 13 |
| 0442 | Notch 1 | HMN1-12 | TCCGGTCA CTCAGTA | 14 |
| 0443 | CD41 | MWReg30 | ACTTGGAT GGACACT | 15 |
| 0449 | CD326 (Ep-CAM) | G8.8 | ACCCGCGT TAGTATG | 16 |
| 0552 | CD304 (Neuropilin-1) | 3E12 | CCAGCTCA TTCAACG | 17 |
| 0553 | CD309 (VEGFR2, Flk-1) | Avas12 | ATAAGAGC CCACCAT | 18 |
| 0558 | CD55 (DAF) | RIKO-3 | ATTGTTGT CAGACCA | 19 |
| 0559 | CD63 | NVG-2 | ATCCGACA CGTATTA | 20 |
| 0564 | Folate Receptor β (FR-β) | 10/FR2 | CTCAGATG CCCTTTA | 21 |
| 0596 | ESAM | 1G8/ESAM | TATAGTTT CCGCCGT | 22 |

TABLE 2

Reagents and Resources

| REAGENT or RESOURCE | SOURCE | IDENTIFIER |
|---|---|---|
| Antibodies | | |
| Alexa Fluor ® 647 anti-mouse CD326 (Ep-CAM) Antibody | Biolegend | 118212 |
| Alexa Fluor ® 488 anti-mouse Panendothelial Cell Antigen Antibody | Biolegend | 120506 |
| PE anti-P2RY12 Antibody | Biolegend | 848004 |
| TotalSeq antibodies | Biolegend | |
| Biological Samples | | |
| Mouse C57 Embryo Sagittal Frozen Sections, E10 | Zyagen | MF-104-10-C57 |
| Mouse C57 Embryo Sagittal Frozen Sections, E12 | Zyagen | MF-104-12-C57 |
| Chemicals, Peptides, and Recombinant Proteins | | |
| Maxima H Minus Reverse Transcriptase (200 U/L) | Thermo Fisher Scientific | EP0751 |
| dNTP mix | Thermo Fisher Scientific | R0192 |
| RNase Inhibitor | Enzymatics | Y9240L |
| SUPERase• In ™ RNase Inhibitor | Thermo Fisher Scientific | AM2694 |
| T4 DNA Ligase | New England Biolabs | M0202L |
| Ampure XP beads | Beckman Coulter | A63880 |
| Dynabeads MyOne C1 | Thermo Fisher Scientific | 65001 |
| Proteinase K, recombinant, PCR grade | Thermo Fisher Scientific | EO0491 |
| Kapa Hotstart HiFi ReadyMix | Kapa Biosystems | KK2601 |
| Formaldehyde solution | Sigma | F8775-25ML |
| NEBuffer 3.1 | New England Biolabs | B7203S |
| T4 DNA Ligase Reaction Buffer | New England Biolabs | B0202S |
| PMSF | Sigma | 10837091001 |
| Evagreen Dye, 20X in water | Biotium | 31000-T |
| Critical Commercial Assays | | |
| Nextera XT DNA Preparation Kit | FC-131-1024 | Illumina |
| Deposited Data | | |
| Oligonucleotides | | |
| Primers, Ligation linkers, DNA barcodes | IDT | See Tables 3 and 4 |
| Software and Algorithms | | |

TABLE 3

DNA oligos used for PCR and preparation of sequencing library.
SEQ ID NOS: 23-31 (top to bottom)

| Oligo Name | Sequence |
|---|---|
| PCR Primer 1 | CAAGCGTTGGCTTCTCGCATCT |
| PCR Primer 2 | AAGCAGTGGTATCAACGCAGAGT |
| Ligation Linker | CGAATGCTCTGGCCTCTCAAGCACGTGGAT |
| Template Switch Oligo | AAGCAGTGGTATCAACGCAGAGTGAATrGrG + G |
| P5 oligo | AATGATACGGCGACCACCGAGATCTACACTAGATCGCTCGTCGGCAGCGTCAGATGTGTATAAGAGACAG |
| P7 oligo (701) | CAAGCAGAAGACGGCATACGAGATTCGCCTTAGTCTCGTGGGCTCGGAGATGTGTATAAGAGACAGCAAGCGTTGGCTTCTCGCATCT |
| P7 oligo (702) | CAAGCAGAAGACGGCATACGAGATCTAGTACGGTCTCGTGGGCTCGGAGATGTGTATAAGAGACAGCAAGCGTTGGCTTCTCGCATCT |
| P7 oligo (703) | CAAGCAGAAGACGGCATACGAGATTTCTGCCTGTCTCGTGGGCTCGGAGATGTGTATAAGAGACAGCAAGCGTTGGCTTCTCGCATCT |
| P7 oligo (704) | CAAGCAGAAGACGGCATACGAGATGCTCAGGAGTCTCGTGGGCTCGGAGATGTGTATAAGAGACAGCAAGCGTTGGCTTCTCGCATCT |

TABLE 4

DNA barcode sequences.
SEQ ID NOS: 32-131 (top to bottom)

| | Sequence |
|---|---|
| 1st Barcode | |
| Barcode A-1 | /5Phos/AGGCCAGAGCATTCGAACGTGATTTTTTTTTTTTTTVN |
| Barcode A-2 | /5Phos/AGGCCAGAGCATTCGAAACATCGTTTTTTTTTTTTTTVN |
| Barcode A-3 | /5Phos/AGGCCAGAGCATTCGATGCCTAATTTTTTTTTTTTTTVN |

TABLE 4-continued

DNA barcode sequences.
SEQ ID NOS: 32-131 (top to bottom)

| | Sequence |
|---|---|
| Barcode A-4 | /5Phos/AGGCCAGAGCATTCGAGTGGTCATTTTTTTTTTTTTVN |
| Barcode A-5 | /5Phos/AGGCCAGAGCATTCGACCACTGTTTTTTTTTTTTTTVN |
| Barcode A-6 | /5Phos/AGGCCAGAGCATTCGACATTGGCTTTTTTTTTTTTTTVN |
| Barcode A-7 | /5Phos/AGGCCAGAGCATTCGCAGATCTGTTTTTTTTTTTTTTVN |
| Barcode A-8 | /5Phos/AGGCCAGAGCATTCGCATCAAGTTTTTTTTTTTTTTTVN |
| Barcode A-9 | /5Phos/AGGCCAGAGCATTCGCGCTGATCTTTTTTTTTTTTTTVN |
| Barcode A-10 | /5Phos/AGGCCAGAGCATTCGACAAGCTATTTTTTTTTTTTTTVN |
| Barcode A-11 | /5Phos/AGGCCAGAGCATTCGCTGTAGCCTTTTTTTTTTTTTTVN |
| Barcode A-12 | /5Phos/AGGCCAGAGCATTCGAGTACAAGTTTTTTTTTTTTTTVN |
| Barcode A-13 | /5Phos/AGGCCAGAGCATTCGAACAACCATTTTTTTTTTTTTTVN |
| Barcode A-14 | /5Phos/AGGCCAGAGCATTCGAACCGAGATTTTTTTTTTTTTTVN |
| Barcode A-15 | /5Phos/AGGCCAGAGCATTCGAACGCTTATTTTTTTTTTTTTTVN |
| Barcode A-16 | /5Phos/AGGCCAGAGCATTCGAAGACGGATTTTTTTTTTTTTTVN |
| Barcode A-17 | /5Phos/AGGCCAGAGCATTCGAAGGTACATTTTTTTTTTTTTTVN |
| Barcode A-18 | /5Phos/AGGCCAGAGCATTCGACACAGAATTTTTTTTTTTTTTVN |
| Barcode A-19 | /5Phos/AGGCCAGAGCATTCGACAGCAGATTTTTTTTTTTTTTVN |
| Barcode A-20 | /5Phos/AGGCCAGAGCATTCGACCTCCAATTTTTTTTTTTTTTVN |
| Barcode A-21 | /5Phos/AGGCCAGAGCATTCGACGCTCGATTTTTTTTTTTTTTVN |
| Barcode A-22 | /5Phos/AGGCCAGAGCATTCGACGTATCATTTTTTTTTTTTTTVN |
| Barcode A-23 | /5Phos/AGGCCAGAGCATTCGACTATGCATTTTTTTTTTTTTTVN |
| Barcode A-24 | /5Phos/AGGCCAGAGCATTCGAGAGTCAATTTTTTTTTTTTTTVN |
| Barcode A-25 | /5Phos/AGGCCAGAGCATTCGAGATCGCATTTTTTTTTTTTTTVN |
| Barcode A-26 | /5Phos/AGGCCAGAGCATTCGAGCAGGAATTTTTTTTTTTTTTVN |
| Barcode A-27 | /5Phos/AGGCCAGAGCATTCGAGTCACTATTTTTTTTTTTTTTVN |
| Barcode A-28 | /5Phos/AGGCCAGAGCATTCGATCCTGTATTTTTTTTTTTTTTTVN |
| Barcode A-29 | /5Phos/AGGCCAGAGCATTCGATTGAGGATTTTTTTTTTTTTTVN |

TABLE 4-continued

DNA barcode sequences.
SEQ ID NOS: 32-131 (top to bottom)

| | Sequence |
|---|---|
| Barcode A-30 | /5Phos/AGGCCAGAGCATTCGCAACCACATTTTTTTTTTTTTVN |
| Barcode A-31 | /5Phos/AGGCCAGAGCATTCGGACTAGTATTTTTTTTTTTTTVN |
| Barcode A-32 | /5Phos/AGGCCAGAGCATTCGCAATGGAATTTTTTTTTTTTTVN |
| Barcode A-33 | /5Phos/AGGCCAGAGCATTCGCACTTCGATTTTTTTTTTTTTVN |
| Barcode A-34 | /5Phos/AGGCCAGAGCATTCGCAGCGTTATTTTTTTTTTTTTVN |
| Barcode A-35 | /5Phos/AGGCCAGAGCATTCGCATACCAATTTTTTTTTTTTTVN |
| Barcode A-36 | /5Phos/AGGCCAGAGCATTCGCCAGTTCATTTTTTTTTTTTTVN |
| Barcode A-37 | /5Phos/AGGCCAGAGCATTCGCCGAAGTATTTTTTTTTTTTTVN |
| Barcode A-38 | /5Phos/AGGCCAGAGCATTCGCCGTGAGATTTTTTTTTTTTTVN |
| Barcode A-39 | /5Phos/AGGCCAGAGCATTCGCCTCCTGATTTTTTTTTTTTTVN |
| Barcode A-40 | /5Phos/AGGCCAGAGCATTCGCGAACTTATTTTTTTTTTTTTVN |
| Barcode A-41 | /5Phos/AGGCCAGAGCATTCGCGACTGGATTTTTTTTTTTTTVN |
| Barcode A-42 | /5Phos/AGGCCAGAGCATTCGCGCATACATTTTTTTTTTTTTVN |
| Barcode A-43 | /5Phos/AGGCCAGAGCATTCGCTCAATGATTTTTTTTTTTTTVN |
| Barcode A-44 | /5Phos/AGGCCAGAGCATTCGCTGAGCCATTTTTTTTTTTTTVN |
| Barcode A-45 | /5Phos/AGGCCAGAGCATTCGCTGGCATATTTTTTTTTTTTTVN |
| Barcode A-46 | /5Phos/AGGCCAGAGCATTCGGAATCTGATTTTTTTTTTTTTVN |
| Barcode A-47 | /5Phos/AGGCCAGAGCATTCGCAAGACTATTTTTTTTTTTTTVN |
| Barcode A-48 | /5Phos/AGGCCAGAGCATTCGGAGCTGAATTTTTTTTTTTTTVN |
| Barcode A-49 | /5Phos/AGGCCAGAGCATTCGGATAGACATTTTTTTTTTTTTVN |
| Barcode A-50 | /5Phos/AGGCCAGAGCATTCGGCCACATATTTTTTTTTTTTTVN |
| 2nd Barcode | |
| Barcode B-1 | /5Biosg/CAAGCGTTGGCTTCTCGCATCTNNNNNNNNNNAACGTGATATCCACGTGCTTGAG |
| Barcode B-2 | /5Biosg/CAAGCGTTGGCTTCTCGCATCTNNNNNNNNNNAAACATCGATCCACGTGCTTGAG |
| Barcode B-3 | /5Biosg/CAAGCGTTGGCTTCTCGCATCTNNNNNNNNNNATGCCTAAATCCACGTGCTTGAG |
| Barcode B-4 | /5Biosg/CAAGCGTTGGCTTCTCGCATCTNNNNNNNNNNAGTGGTCAATCCACGTGCTTGAG |

TABLE 4-continued

DNA barcode sequences.
SEQ ID NOS: 32-131 (top to bottom)

| | Sequence |
|---|---|
| Barcode B-5 | /5Biosg/CAAGCGTTGGCTTCTCGCATCTNNNNNNNNNNACCACTGTATCCACGTGCTTGAG |
| Barcode B-6 | /5Biosg/CAAGCGTTGGCTTCTCGCATCTNNNNNNNNNNACATTGGCATCCACGTGCTTGAG |
| Barcode B-7 | /5Biosg/CAAGCGTTGGCTTCTCGCATCTNNNNNNNNNNCAGATCTGATCCACGTGCTTGAG |
| Barcode B-8 | /5Biosg/CAAGCGTTGGCTTCTCGCATCTNNNNNNNNNNCATCAAGTATCCACGTGCTTGAG |
| Barcode B-9 | /5Biosg/CAAGCGTTGGCTTCTCGCATCTNNNNNNNNNNCGCTGATCATCCACGTGCTTGAG |
| Barcode B-10 | /5Biosg/CAAGCGTTGGCTTCTCGCATCTNNNNNNNNNNACAAGCTAATCCACGTGCTTGAG |
| Barcode B-11 | /5Biosg/CAAGCGTTGGCTTCTCGCATCTNNNNNNNNNNCTGTAGCCATCCACGTGCTTGAG |
| Barcode B-12 | /5Biosg/CAAGCGTTGGCTTCTCGCATCTNNNNNNNNNNAGTACAAGATCCACGTGCTTGAG |
| Barcode B-13 | /5Biosg/CAAGCGTTGGCTTCTCGCATCTNNNNNNNNNNACAACCAATCCACGTGCTTGAG |
| Barcode B-14 | /5Biosg/CAAGCGTTGGCTTCTCGCATCTNNNNNNNNNNACCGAGAATCCACGTGCTTGAG |
| Barcode B-15 | /5Biosg/CAAGCGTTGGCTTCTCGCATCTNNNNNNNNNNACGCTTAATCCACGTGCTTGAG |
| Barcode B-16 | /5Biosg/CAAGCGTTGGCTTCTCGCATCTNNNNNNNNNNAGACGGAATCCACGTGCTTGAG |
| Barcode B-17 | /5Biosg/CAAGCGTTGGCTTCTCGCATCTNNNNNNNNNNAGGTACAATCCACGTGCTTGAG |
| Barcode B-18 | /5Biosg/CAAGCGTTGGCTTCTCGCATCTNNNNNNNNNNACACAGAAATCCACGTGCTTGAG |
| Barcode B-19 | /5Biosg/CAAGCGTTGGCTTCTCGCATCTNNNNNNNNNNACAGCAGAATCCACGTGCTTGAG |
| Barcode B-20 | /5Biosg/CAAGCGTTGGCTTCTCGCATCTNNNNNNNNNNACCTCCAAATCCACGTGCTTGAG |
| Barcode B-21 | /5Biosg/CAAGCGTTGGCTTCTCGCATCTNNNNNNNNNNACGCTCGAATCCACGTGCTTGAG |
| Barcode B-22 | /5Biosg/CAAGCGTTGGCTTCTCGCATCTNNNNNNNNNNACGTATCAATCCACGTGCTTGAG |
| Barcode B-23 | /5Biosg/CAAGCGTTGGCTTCTCGCATCTNNNNNNNNNNACTATGCAATCCACGTGCTTGAG |
| Barcode B-24 | /5Biosg/CAAGCGTTGGCTTCTCGCATCTNNNNNNNNNNAGAGTCAAATCCACGTGCTTGAG |
| Barcode B-25 | /5Biosg/CAAGCGTTGGCTTCTCGCATCTNNNNNNNNNNAGATCGCAATCCACGTGCTTGAG |
| Barcode B-26 | /5Biosg/CAAGCGTTGGCTTCTCGCATCTNNNNNNNNNNAGCAGGAAATCCACGTGCTTGAG |
| Barcode B-27 | /5Biosg/CAAGCGTTGGCTTCTCGCATCTNNNNNNNNNNAGTCACTAATCCACGTGCTTGAG |
| Barcode B-28 | /5Biosg/CAAGCGTTGGCTTCTCGCATCTNNNNNNNNNNATCCTGTAATCCACGTGCTTGAG |
| Barcode B-29 | /5Biosg/CAAGCGTTGGCTTCTCGCATCTNNNNNNNNNNATTGAGGAATCCACGTGCTTGAG |

TABLE 4-continued

DNA barcode sequences.
SEQ ID NOS: 32-131 (top to bottom)

| | Sequence |
|---|---|
| Barcode B-30 | /5Biosg/CAAGCGTTGGCTTCTCGCATCTNNNNNNNNNNCAACC ACAATCCACGTGCTTGAG |
| Barcode B-31 | /5Biosg/CAAGCGTTGGCTTCTCGCATCTNNNNNNNNNNGACTA GTAATCCACGTGCTTGAG |
| Barcode B-32 | /5Biosg/CAAGCGTTGGCTTCTCGCATCTNNNNNNNNNNCAATG GAAATCCACGTGCTTGAG |
| Barcode B-33 | /5Biosg/CAAGCGTTGGCTTCTCGCATCTNNNNNNNNNNCACTTC GAATCCACGTGCTTGAG |
| Barcode B-34 | /5Biosg/CAAGCGTTGGCTTCTCGCATCTNNNNNNNNNNCAGCG TTAATCCACGTGCTTGAG |
| Barcode B-35 | /5Biosg/CAAGCGTTGGCTTCTCGCATCTNNNNNNNNNNCATACC AAATCCACGTGCTTGAG |
| Barcode B-36 | /5Biosg/CAAGCGTTGGCTTCTCGCATCTNNNNNNNNNNCCAGTT CAATCCACGTGCTTGAG |
| Barcode B-37 | /5Biosg/CAAGCGTTGGCTTCTCGCATCTNNNNNNNNNNCCGAA GTAATCCACGTGCTTGAG |
| Barcode B-38 | /5Biosg/CAAGCGTTGGCTTCTCGCATCTNNNNNNNNNNCCGTG AGAATCCACGTGCTTGAG |
| Barcode B-39 | /5Biosg/CAAGCGTTGGCTTCTCGCATCTNNNNNNNNNNCCTCCT GAATCCACGTGCTTGAG |
| Barcode B-40 | /5Biosg/CAAGCGTTGGCTTCTCGCATCTNNNNNNNNNNCGAAC TTAATCCACGTGCTTGAG |
| Barcode B-41 | /5Biosg/CAAGCGTTGGCTTCTCGCATCTNNNNNNNNNNCGACT GGAATCCACGTGCTTGAG |
| Barcode B-42 | /5Biosg/CAAGCGTTGGCTTCTCGCATCTNNNNNNNNNNCGCAT ACAATCCACGTGCTTGAG |
| Barcode B-43 | /5Biosg/CAAGCGTTGGCTTCTCGCATCTNNNNNNNNNNCTCAAT GAATCCACGTGCTTGAG |
| Barcode B-44 | /5Biosg/CAAGCGTTGGCTTCTCGCATCTNNNNNNNNNNCTGAG CCAATCCACGTGCTTGAG |
| Barcode B-45 | /5Biosg/CAAGCGTTGGCTTCTCGCATCTNNNNNNNNNNCTGGC ATAATCCACGTGCTTGAG |
| Barcode B-46 | /5Biosg/CAAGCGTTGGCTTCTCGCATCTNNNNNNNNNNGAATCT GAATCCACGTGCTTGAG |
| Barcode B-47 | /5Biosg/CAAGCGTTGGCTTCTCGCATCTNNNNNNNNNNCAAGA CTAATCCACGTGCTTGAG |
| Barcode B-48 | /5Biosg/CAAGCGTTGGCTTCTCGCATCTNNNNNNNNNNGAGCT GAAATCCACGTGCTTGAG |
| Barcode B-49 | /5Biosg/CAAGCGTTGGCTTCTCGCATCTNNNNNNNNNNGATAG ACAATCCACGTGCTTGAG |
| Barcode B-50 | /5Biosg/CAAGCGTTGGCTTCTCGCATCTNNNNNNNNNNGCCAC ATAATCCACGTGCTTGAG |

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "about" and "substantially" preceding a numerical value mean±10% of the recited numerical value.

Where a range of values is provided, each value between the upper and lower ends of the range are specifically contemplated and described herein.

What is claimed is:

1. A method, comprising:
   (a) delivering to a region of interest in a fixed section of a mammalian tissue mounted on a substrate a first set of barcoded polynucleotides that bind to nucleic acids of the fixed tissue section, wherein the first set of barcoded polynucleotides is delivered through a first microfluidic device clamped to the region of interest, wherein the first microfluidic device comprises variable width microchannels, each having (i) an inlet port and an outlet port, (ii) a width of 50-150 µm at the inlet port and at the outlet port, and (iii) a width of 10-50 µm at the region of interest;
   (b) delivering to the region of interest reverse transcription reagents to produce cDNAs linked to barcoded polynucleotides of the first set;
   (c) delivering to the region of interest a second set of barcoded polynucleotides, wherein the second set of barcoded polynucleotides is delivered through a second microfluidic device clamped to the region of interest, wherein the second microfluidic device comprises variable width microchannels, each having (i) an inlet port and an outlet port, (ii) a width of 50-150 µm at the inlet port and at the outlet port, and (iii) a width of 10-50 µm at the region of interest, wherein the microchannels of the second microfluidic device are perpendicular to the microchannels of the first microfluidic device;
   (d) delivering to the region of interest ligation reagents to join barcoded polynucleotides of the first set to barcoded polynucleotides of the second set;
   (e) imaging the region of interest to produce a sample image;
   (f) delivering to the region of interest lysis buffer or denaturation reagents to produce a lysed or denatured tissue sample; and
   (g) extracting cDNA from the lysed or denatured tissue sample.

2. The method of claim 1 further comprising sequencing the cDNA to produce cDNA reads.

3. The method of claim 1, wherein the first and/or second microfluidic device is fabricated from polydimethylsiloxane (PDMS).

4. The method of claim 1, wherein each microchannel of the first and second microfluidic device has a width of 10 µm and a height of 12-15 µm, a width of 25 µm and height of 17-22 µm, or a width of 50 µm and a height of 20-100 µm at the region of interest.

5. The method of claim 1, wherein delivery of the first set of barcoded polynucleotides is delivered through the first microfluidic device using a negative pressure system and/or delivery of the second set of barcoded polynucleotides is delivered through the second microfluidic device using a negative pressure system.

6. The method of claim 1, wherein the lysis buffer or denaturation reagents are delivered directly to the tissue section.

7. The method of claim 1, wherein the barcoded polynucleotides of the first set comprise a ligation linker sequence, a spatial barcode sequence, and a polyT sequence.

8. The method of claim 7, wherein the barcoded polynucleotides of the second set comprise a ligation linker sequence, a spatial barcode sequence, a unique molecular identifier (UMI) sequence, and a first PCR handle end sequence.

9. The method of claim 8, wherein (i) the barcoded polynucleotides of the second set are bound to a universal ligation linker, or (ii) the method further comprises delivering to the fixed tissue section a universal ligation linker sequence, wherein the universal ligation linker comprises a sequence complementary to the ligation linker sequence of the barcoded polynucleotides of the first set and comprises a sequence complementary to the ligation linker sequence of the barcoded polynucleotides of the second set.

10. The method of claim 1, wherein the first and/or second set of barcoded polynucleotides comprises at least 50 barcoded polynucleotides.

11. The method of claim 1, wherein the nucleic acids of the fixed tissue section are selected from (i) ribonucleic acids (RNAs), and (ii) deoxyribonucleic acids (DNAs).

12. The method of claim 11, wherein the nucleic acids of the fixed tissue section are messenger RNAs.

13. The method of claim 11, wherein the nucleic acids of the fixed tissue section are genomic DNAs.

14. The method of claim 1, wherein the imaging is with an optical or fluorescence microscope.

15. The method of claim 1, wherein the first microfluidic device comprises at least 5 variable width microchannels and the second microfluidic device comprises at least 5 variable width microchannels.

16. The method of claim 15, wherein the first microfluidic device comprises 5-100 variable width microchannels and the second microfluidic device comprises 5-100 variable width microchannels.

17. A method, comprising:
(a) delivering to a region of interest in a fixed section of a mammalian tissue mounted on a substrate binder-DNA tag conjugates that comprise (i) a binder molecule that specifically binds to a protein of interest and (ii) a DNA tag, wherein the DNA tag comprises a binder barcode and a polyA sequence;
(b) delivering to the region of interest a first set of barcoded polynucleotides that bind to nucleic acids of the fixed tissue section, wherein the first set of barcoded polynucleotides is delivered through a first microfluidic device clamped to the region of interest, wherein the first microfluidic device comprises variable width microchannels, each having (i) an inlet port and an outlet port, (ii) a width of 50-150 µm at the inlet port and at the outlet port, and (iii) a width of 10-50 µm at the region of interest;
(c) delivering to the region of interest reverse transcription reagents to produce cDNAs linked to barcoded polynucleotides of the first set;
(d) delivering to the region of interest a second set of barcoded polynucleotides, wherein the second set of barcoded polynucleotides is delivered through a second microfluidic device clamped to the region of interest, wherein the second microfluidic device comprises variable width microchannels, each having (i) an inlet port and an outlet port, (ii) a width of 50-150 µm at the inlet port and at the outlet port, and (iii) a width of 10-50 µm at the region of interest, wherein the microchannels of the second microfluidic device are perpendicular to the microchannels of the first microfluidic device;
(e) delivering to the region of interest ligation reagents to join barcoded polynucleotides of the first set to barcoded polynucleotides of the second set;
(f) imaging the region of interest to produce a sample image;
(g) delivering to the region of interest lysis buffer or denaturation reagents to produce a lysed or denatured tissue sample; and
(h) extracting cDNA from the lysed or denatured tissue sample.

18. The method of claim 17 further comprising sequencing the cDNA to produce cDNA reads, and constructing a spatial molecular expression map of the fixed tissue section by matching the binder-DNA tag conjugates to corresponding cDNA reads.

19. The method of claim 18 further comprising identifying the anatomical location of the nucleic acids by correlating the spatial molecular expression map to the sample image.

20. The method of claim 17, wherein the binder molecule is an antibody.

21. The method of claim 20, wherein the antibody is selected from the group consisting of: whole antibodies, Fab antibody fragments, F(ab')$_2$ antibody fragments, monospecific Fab$_2$ fragments, bispecific Fab$_2$ fragments, trispecific Fab$_3$ fragments, single chain variable fragments (scFvs), bispecific diabodies, trispecific diabodies, scFv-Fc molecules, and minibodies.

22. The method of claim 17, wherein the first microfluidic device comprises at least 5 variable width microchannels and the second microfluidic device comprises at least 5 variable width microchannels.

23. The method of claim 22, wherein the first microfluidic device comprises 5-100 variable width microchannels and the second microfluidic device comprises 5-100 variable width microchannels.

* * * * *